US010793607B2

(12) United States Patent
Rutten et al.

(10) Patent No.: US 10,793,607 B2
(45) Date of Patent: Oct. 6, 2020

(54) TRIMER STABILIZING HIV ENVELOPE PROTEIN MUTATIONS

(71) Applicant: Janssen Vaccines & Prevention B.V., Leiden (NL)

(72) Inventors: Lucy Rutten, Gouda (NL); Daphné Truan, Haarlem (NL); Nika Mindy Strokappe, Utrecht (NL); Johannes Petrus Maria Langedijk, Amsterdam (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 193 days.

(21) Appl. No.: 15/704,651

(22) Filed: Sep. 14, 2017

(65) Prior Publication Data
US 2018/0072777 A1   Mar. 15, 2018

(30) Foreign Application Priority Data

Sep. 15, 2016 (EP) ..................... 16188866

(51) Int. Cl.
C07K 14/15    (2006.01)
A61K 39/21    (2006.01)
C07K 14/16    (2006.01)
A61K 39/12    (2006.01)
C07K 14/005   (2006.01)
A61K 39/00    (2006.01)
C12N 7/02     (2006.01)

(52) U.S. Cl.
CPC ............ *C07K 14/162* (2013.01); *A61K 39/12* (2013.01); *A61K 39/21* (2013.01); *C07K 14/005* (2013.01); *A61K 2039/53* (2013.01); *C12N 7/02* (2013.01); *C12N 2740/16122* (2013.01); *C12N 2740/16134* (2013.01)

(58) Field of Classification Search
CPC .. C07K 14/162; C07K 14/15; C07K 2039/53; C07K 16/1063; A64K 39/12; A64K 39/21; C12N 7/02; C12N 2740/16122; C12N 2740/16134; A61K 39/21; A61K 39/00
See application file for complete search history.

(56) References Cited

U.S. PATENT DOCUMENTS

| | | | |
|---|---|---|---|
| 4,603,112 A | 7/1986 | Paoletti et al. |
| 5,185,146 A | 2/1993 | Altenburger |
| 5,639,649 A | 6/1997 | Almond et al. |
| 5,643,576 A | 7/1997 | Johnston et al. |
| 6,761,893 B2 | 7/2004 | Chaplin et al. |
| 6,911,205 B2 | 6/2005 | Sodroski et al. |
| 7,592,014 B2 | 9/2009 | Binley et al. |
| 7,901,690 B2 | 3/2011 | Lu et al. |
| 7,939,083 B2 | 5/2011 | Dey et al. |
| 8,197,825 B2 | 6/2012 | Sutter et al. |
| 9,017,691 B2 | 4/2015 | Barouch et al. |
| 2003/0206926 A1 | 11/2003 | Chaplin et al. |
| 2003/0207287 A1 | 11/2003 | Short |
| 2006/0159699 A1 | 7/2006 | Howley et al. |
| 2007/0166784 A1 | 7/2007 | Barnett et al. |
| 2007/0298051 A1 | 12/2007 | Barouch et al. |
| 2008/0199939 A1 | 8/2008 | Havenga et al. |
| 2008/0279879 A1 | 11/2008 | Zolla-Pazner |
| 2011/0159036 A1 | 6/2011 | Moss et al. |
| 2011/0250220 A1 | 10/2011 | Dey et al. |
| 2012/0045472 A1 | 2/2012 | Harrison et al. |
| 2012/0076812 A1 | 3/2012 | Barouch et al. |
| 2013/0189754 A1 | 7/2013 | Parks et al. |
| 2014/0302080 A1 | 10/2014 | Barouch et al. |
| 2014/0348791 A1 | 11/2014 | Barouch et al. |
| 2015/0291935 A1 | 10/2015 | Barouch et al. |
| 2016/0024156 A1 | 1/2016 | Barouch et al. |
| 2016/0122392 A1 | 5/2016 | Baker et al. |
| 2017/0165355 A1 | 6/2017 | Langedijk |
| 2017/0362280 A1 | 12/2017 | Nguyen et al. |
| 2018/0064803 A1 | 3/2018 | Tomaka et al. |
| 2018/0072777 A1 | 3/2018 | Rutten et al. |

FOREIGN PATENT DOCUMENTS

| | | |
|---|---|---|
| CN | 102282175 A | 12/2011 |
| WO | 0119958 | 3/2001 |
| WO | 200242480 A2 | 5/2002 |
| WO | 2003048184 A2 | 6/2003 |
| WO | 2003/104467 A1 | 12/2003 |

(Continued)

OTHER PUBLICATIONS

"Endogenous Retrovirus Group K Member 25 Env Polyprotein", Database UNIPROT, Accession No. Q5GI17, 2 pages (Mar. 1, 2005).
"GCN4 Fusion Linker Peptide, SEQ ID No. 3," Database Geneseq, Accession No. AEN61500, 1 page (Mar. 8, 2007).
"Recombinant Protein gp41 Heterologous Transmembrane Region, SEQ ID1," Database Geneseq, Accession No. AUR74751, 1 page, (Mar. 19, 2009).
"Transmembrane Domain Peptide, SEQ ID 14," Database Geneseq, Accession No. AEF06609, 1 page (Mar. 23, 2006).

(Continued)

Primary Examiner — Bao Q Li
(74) Attorney, Agent, or Firm — Ice Miller LLP

(57) ABSTRACT

Human immunodeficiency virus (HIV) envelope proteins having mutations that stabilize the trimeric form of the envelope protein are provided. The HIV envelope proteins have certain amino acid substitutions at specified positions in the envelope protein sequence. The HIV envelope proteins described herein have an improved percentage of trimer formation and/or an improved trimer yield as compared to an HIV envelope protein that does not have one or more of the indicated amino acid substitutions. Also provided are nucleic acid molecules and vectors encoding the HIV envelope proteins, as well as compositions containing the HIV envelope proteins, nucleic acid, and vectors.

23 Claims, 23 Drawing Sheets
Specification includes a Sequence Listing.

(56) References Cited

FOREIGN PATENT DOCUMENTS

| WO | 2004/0044155 |    | 5/2004  |          |
|----|--------------|----|---------|----------|
| WO | 2006002079   |    | 1/2006  |          |
| WO | 2006020071   |    | 2/2006  |          |
| WO | 2006/040330  |    | 4/2006  |          |
| WO | 2007005934   |    | 1/2007  |          |
| WO | 2007/024941  | A2 | 3/2007  |          |
| WO | 2007/104792  | A2 | 9/2007  |          |
| WO | 2007/149491  |    | 12/2007 |          |
| WO | 2008063331   |    | 5/2008  |          |
| WO | WO 2008/063331 | A2 * | 5/2008 | ...... C07K 14/162 |
| WO | 2008107370   | A1 | 9/2008  |          |
| WO | 2010/042942  | A2 | 4/2010  |          |
| WO | 2010/059732  | A1 | 5/2010  |          |
| WO | 2010096561   | A1 | 8/2010  |          |
| WO | 2011/082087  | A2 | 7/2011  |          |
| WO | 2011/092029  | A1 | 8/2011  |          |
| WO | 2012/030904  |    | 3/2012  |          |
| WO | 2013055908   |    | 4/2013  |          |
| WO | 2014/047261  |    | 3/2014  |          |
| WO | 2014107744   | A1 | 7/2014  |          |
| WO | 2014/124301  | A1 | 8/2014  |          |
| WO | 2015/048770  |    | 4/2015  |          |
| WO | 2016037154   | A1 | 3/2016  |          |
| WO | 2016049287   | A1 | 3/2016  |          |
| WO | 2017102929   | A1 | 6/2017  |          |

OTHER PUBLICATIONS

Abrahams et al, "Quantitating the Multiplicity of Infection with Human Immunodeficiency Virus Type 1 Subtype C Reveals a Non-Poisson Distribution of Transmitted Variants," Journal of Virology, vol. 83, No. 8, pp. 3556-3567 (Apr. 2009).

Abrahamyan et al, "The Cytoplasmic Tail Slows the Folding of Human Immunodeficiency Virus Type 1 Env from a late Prebundle Configuration into the Six-Helix Bundle", Journal of Virology, vol. 79, No. 1, pp. 106-115 (2005).

Achenbach et al., "Effect of Therapeutic Intensification Followed by HIV DNA Prime and rAd5 Boost Vaccination on HIV-specific Immunity and HIV Reservoir (EraMune 02): a Multicentre Randomised Clinical Trial", The Lancet, vol. 2, No. 3, pp. e82-e91 (Mar. 2015).

Amanna et al, "Contributions of Humoral and Cellular Immunity to Vaccine-Induced Protection in Humans," Virology, vol. 411, No. 2, pp. 206-215 (2011).

Ambrosini et al., "Gene Transfer in Astrocytes: Comparison Between Different Delivering Methods and Expression of the HIV-1 Protein Nef.", J. Neurosci. Res., vol. 55, p. 569 (1999) (Abstract Only).

Baba et al, "Human Neutralizing Monoclonal Antibodies of the IgG1 Subtype Protect Against Mucosal Simian-Human Immunodeficiency Virus Infection," Nature Medicine, vol. 6, No. 2, pp. 200-206 (2000).

Baden et al., "First-in-human Evaluation of the Safety and Immunogenicity of a Recombinant Adenovirus Serotype 26 HIV-1 Env Vaccine (IPCAVD 001)", J. Infect. Dis., vol. 207, No. 2, pp. 240-7 (2013).

Baicu et al., "Acid-base Buffering in Organ Preservation Solutions as a Function of Temperature: New Parameters for Comparing Buffer Capacity and Efficiency", Cryobiology, vol. 45, pp. 33-48 (2002).

Bangari et al., "Development of Nonhuman Adenoviruses as Vaccine Vectors", Vaccine, vol. 24, No. 7, pp. 849-26 (2006).

Barnett et al, "Development of V2-deleted trimeric envelope vaccine candidates from human immunodeficiency virus type 1 (HIV-1) subtypes B and C," Microbes Infect., vol. 7, vol. 14, pp. 1386-1391 (2005).

Barouch et al., "Accelerating HIV-1 Vaccine Efficacy Trials", Cell, vol. 159, No. 5, pp. 969-792 (Nov. 2014).

Barouch et al., "Characterization of Humoral and Cellular Immune Responses Elicited by a Recombinant Adenovirus Serotype 26 HIV-1 Env Vaccine in Healthy Adults (IPCAVD 001)", J. Infect. Dis, vol. 207, No. 2, pp. 248-56 (2013).

Barouch et al., "International Seroepidemiology of Adenovirus Serotypes 5, 36, 35 and 48 in Pediatric and Adult Populations", Vaccine, vol. 29: pp. 5203-5209 (2011).

Barouch et al., "Protective Efficacy of a Global HIV-1 Mosaic Vaccine against Heterologous SHIV Challenges in Rhesus Monkeys", Cell, vol. 155, pp. 531-539 (Oct. 2013).

Barouch et al., "Protective Efficacy of Adenovirus/Protein Vaccines Against SIV Challenges in Rhesus Monkeys", Science, vol. 349, No. 6245, pp. 320-324 (Jul. 2015).

Barouch, "Challenges in the Development of an HIV-1 Vaccine", Nature, vol. 455, No. 2, pp. 613-19 (2008).

Beddows et al, "A Comparative Immunogenicity Study in Rabbits of Disulfide-Stablized, Proteolytically Cleaved, Soluble Trimeric Human Immunodeficiency Virus Type 1 gp140, Trimeric Cleavage-Defective gp140 and Monomeric gp120," Virology, vol. 360, pp. 329-340 (2007).

Berger et al, "Chemokine Receptors as HIV-1 Coreceptors: Roles in Viral Entry, Tropism and Disease," Annu. Rev. Immunol., vol. 17, pp. 657-700 (1999).

Berman et al, "Comparison of the Immune Response to Recombinant gp120 in Humans and Chimpanzees," AIDS, vol. 8, pp. 591-601 (1994).

Binley et al "A Recombinant Human Immunodeficiency Virus Type 1 Envelope Glycoprotein Complex Stabilized by 6 an Intermolecular Disulfide Bond Between the gp120 and gp41 Subunits is an Antigenic Mimic of the Trimeric Virion-Associated Structure," Journal of Virology, vol. 74, No. 2, pp. 627-643 (Jan. 2000).

Blanchard et al., "Modified Vaccinia Virus Ankara Undergoes Limited Replication in Human Cells and Lacks Several Immunomodulatory Proteins: Implications for Use as a Human Vaccine", Journ. of Gen. Viro., vol. 79, pp. 1159-1167 (1998).

Blondelle et al., "Immunogenically Optimized Peptides Derived from Natural Mutants of HIV CTL Epitopes and Peptide Combinational Libraries", Biopolymers, vol. 90(5), pp. 683-694 (2008).

Bower et al, "Elicitation of Neutralizing Antibodies with DNA Vaccines Expressing Soluble Stabilized Human Immunodefiency Virus Type 1 Envelope Glycoprotein Trimers Conjugated to C3d", Journ. of Viro., vol. 78, No. 9, pp. 4710-4719 (May 2004).

Bower et al, "HIV-1 ENV gp 140 Trimers Elicit Neutralizing Antibodies Without Efficient Induction of Conformational Antibodies," Vaccine, vol. 24, pp. 5442-5451 (2006).

Buchbinder et al., Efficacy Assessment of a Cell-Mediated Immunity HIV-1 Vaccine (The Step Study): A Double-Blind, Randomised, Placebo-Controlled, Test-of-Concept Trial, Lancet, vol. 372 No. 9653, pp. 1881-93 (2008).

Burke et al. "Neutralizing Antibody Responses to Subtype B and C Adjuvanted HIV Envelope Protein Vaccination in Rabbits," Virology, vol. 387, No. 1, pp. 147-156 (Apr. 2009).

Burton et al, "HIV Vaccine Design and the Neutralizing Antibody Problem," Nature Immunology, vol. 5, No. 3, pp. 233-236 (Mar. 2004).

Calarese et al, "Antibody Domain Exchange is an Immunological Solution to Carbohydrate Cluster Recognition," Science, vol. 300, No. 5628, pp. 2065-2071 (2003).

Carcelain et al., "Immune Interventions in HIV Infection", Immunol Rev., vol. 254, No. 1, pp. 355-71 (2013).

Cardoso et al, "Broadly Neutralizing Anti-HIV Antibody 4E10 Recognizes a Helical Conformation of a Highly Conserved Fusion-Associated Motif in gp41," Immunity, vol. 22, No. 2, pp. 163-173 (Feb. 2005).

Cardoso et al, "Structural Basis of Enhanced Binding of Extended and Helically Constrained Peptide Epitopes of the Broadly Neutralizing HIV-1 Antibody 4E1 0," Journal of Molecular Biology, vol. 365, No. 5, pp. 1533-1544 (2007).

Carroll et al., "Host Range and Cytopathogenicity of the Highly Attenuated MVA Strain of Vaccinia Virus: Propagation and Generation of Recombinant Viruses in a Nonhuman Mammalian Cell Line", Virology, vol. 238, pp. 198-211 (1997).

Carrow et al, "High Prevalance of Antibodies to the gp120 V3 Regional Principal Neutralizing Determinant of HIV-1 MN in Sera

(56) References Cited

OTHER PUBLICATIONS from Africa and the Americas," Aids Research and Human Retroviruses, vol. 7, No. 10, pp. 831-838 (1991).
Catanzaro et al, "Phase I Clinical Evaluation of a Six-Plasmid Multiclade HIV-1 DNA Candidate Vaccine," Vaccine, vol. 25, No. 20, pp. 4085-4092 (2007).
Centlivre et al., "In HIV-1 Pathogenesis the Die is Cast During Primary Infections", AIDS, vol. 21, No. 1, pp. 1-11 (2007).
Checkley et al, "HIV-1 Envelope Glycoprotein Biosynthesis, Trafficking, and Incorporation," Journal of Molecular Biology, vol. 410, No. 4, pp. 582-608 (2011).
Chen et al, "Expression, Purification, and Characterization of gp160e, the Soluble, Trimeric Ectodomain of the Simian Immunodeficiency Virus Envelope Glycoprotein, gp160," The Journal of Biological Chemistry, vol. 275, No. 45, pp. 34946-34953 (Nov. 10, 2000).
Chen et al., A Chimeric Protein of Simian Immunodeficiency Virus Envelope Glycoprotein gp140 and *Escherichia coli* Asparatate Transcarbamoylase, J. Virol, vol. 78, No. 9, pp. 4508-16 (2004).
Chen et al., "Adenovirus-Based Vaccines: Comparison of Vectors from Three Species of Adenoviridae", J. Virol, vol. 84, No. 20, pp. 10522-32 (2010).
Chen et al., "Protection of Rhesus Macaques Against Disease Progression from Pathogenic SHIV-89.6PD by Vaccination with Phage-Displayed HIV-1 Epitopes", Nat. Med., vol. 7, No. 11, pp. 1225-31 (2001).
Cho et al, "Polyvalent Envelope Glycoprotein Vaccine Elicits a Broader Neutralizing Antibody Response But is Unable to Provide Sterilizing Protection Against Heterologous Simian/Human Immunodeficiency Virus Infection in Pigtailed Macaques," Journal of Virology, vol. 75, No. 5, pp. 2224-2234 (Mar. 2001).
Clapp et al. "Vaccines with Aluminum-Containing Adjuvants: Optimizing Vaccine Efficacy and Thermal Stability", J. Pharm. Sci. vol. 100, No. 2: pp. 388-401 (2011).
Cohen et al, "Chimpanzee Adenovirus CV-68 Adapted as a Gene Delivery Vector Interacts with the Coxsackievirus and Adenovirus Receptor", J. Gen. Virol., vol. 83, pp. 151-55 (2002).
Cohen, "Did Merck's Failed HIV Vaccine Cause Harm?" Science, vol. 318, pp. 1048-1049 (2007).
Cohen, "Naked DNA Points Way to Vaccines," Science, vol. 259, pp. 1691-1692 (Mar. 1993).
Crooks et al, "A Comparative Immunogenicity Study of HIV-1 Virus-Like Particles Bearing Various Forms of Envelope Proteins, Particles Bearing No Envelope and Soluble Monomeric gp120," ScienceDirect, Virology vol. 366, pp. 245-262 (2007).
Davenport et al, "Binding Interactions Between Soluble HIV Envelope Glycoproteins and Quaternary-Structure-Specific Monoclonal Antibodies PG9 and PG16," Journal of Virology, vol. 85, No. 14, pp. 7095-7107 (Jul. 2011).
Int'l Preliminary Report on Patentability and Written Opinion dated May 24, 2011 in Int'L Application No. PCT/US2009/064999.
Int'l Preliminary Report on Patentability dated Jan. 26, 2017 in Int'l Application No. PCT/US2015/51891.
Int'l Preliminary Report on Patentability dated Apr. 5, 2016 in Int'l Application No. PCT/US2014/059093.
Sarzotti-Kelsoe et al, "Optimization and Validation of the TZM-bl Assay for Standardized Assessments of Neutralizing Antibodies Against HIV-1," Journal of Immunological Methods, vol. 409, pp. 131-146 (2014).
Sattentau, "Envelope Glycoprotein Trimers as HIV-1 Vaccine Immunogens", Vaccines, vol. 1, pp. 497-512 (2013).
Scheid et al, "Broad Diversity of Neutralizing Antibodies Isolated From Memory B Cells in HIV-Infected Individuals," D Nature, vol. 458, pp. 636-640 (Apr. 2, 2009).
Scheid et al, "Sequence and Structural Convergence of Broad and Potent HIV Antibodies That Mimic CD4 Binding," Science, vol. 333, pp. 1633-1637 (2011).
Schnierle et al, "Pseudotyping of Murine Leukemia Virus with the Envelope Glycoproteins of HIV Generates a Retroviral Vector with Specificity of infection for CD4-Expressing Cells," Proceedings of the National Academy of Sciences of the United States of America, vol. 94, pp. 8640-8645 (Aug. 1997).
Seaman et al, "Multiclade Human Immunodeficiency Virus Type 1 Envelope Immunogens Elicit Broad Cellular and Humoral Immunity in Rhesus Monkeys," Journal of Virology, vol. 79, No. 5, pp. 2956-2963 (2005).
Seaman et al, "Standardized Assessment of NAb Responses Elicited in Rhesus Monkeys Immunized with Single- or Multi-Clade HIV-1 Envelope Immunogens," Virology, vol. 367, pp. 175-186 (2007).
Shu et al., "Efficient Boosting After Plasmid DNA or Recombinant Adenovirus Immunization with HIV-1 Vaccine Constructs", Vaccine, vol. 25, No. 8, pp. 1398-1408 (2007).
Simek et al, "Human Immunodeficiency Virus Type 1 Elite Neutralizers: Individuals With Broad and Potent Neutralizing Activity Identified by Using a High-Throughput Neutralization Assay Together With an Analytical Selection Algorithm," Journal of Virology, vol. 83, No. 14, pp. 7337-7748 (2009).
Sok et al, "Promiscuous Glycan Site Recognition by Antibodies to the High-Mannose Patch of gp120 Broadens Neutralization of HIV," Science Translational Medicine, vol. 6, No. 236, pp. 236ra63 (May 14, 2014).
Spranger et al., "Quantifying Adenovirus-Neutralizing Antibodies by Luciferase Transgene Detection: Addressing Preexisting Immunity to Vaccine and Gene Therapy Vectors", J. Clin. Microbiol, vol. 41, No. 11, pp. 5046-52 (2003).
Stamatatos et al, "Neutralizing Antibodies Generated During Natural HIV-1 Infection: Good News for an HIV-1 Vaccine?," Nature Medicine, vol. 15, No. 8, pp. 866-870 (2009).
Stickl, "Smallpox Vaccination and it's Consequences: First Experiences with the Highly Attenuated Smallpox Vaccine MVA", Preventive Medicine, vol. 3, pp. 97-101 (1974).
Tatsis et al., "A CD46-binding Chimpanzee Adenovirus Vector as a Vaccine Carrier", Molecular Therapy, vol. 15, No. 3, pp. 608-17 (2007).
Thompson et al., "DNA/MVA Vaccination of HIV-1 Infected Participants with Viral Suppression on Antiretroviral Therapy, Followed by Treatment Interruption: Elicitation of Immune Responses without Control of Re-Emergent Virus", PLOS ONE, vol. 11, No. 10, pp. 25 (Oct. 2016).
Thorner et al., "Age Dependence of Adenovirus-Specific Neutralizing Antibody Titer in Individuals From Sub-Saharan Africa", J. Clin. Microbiol, vol. 44, No. 10, pp. 3781-3 (2006).
Thurmond et al., "Web-Based Design and Evaluation of T-cell Vaccine Candidates," Bioinformatics, vol. 24, No. 14, pp. 1639-1640 (2008).
Uchiyama, "Liquid Formulation for Antibody Drugs", Biochimica Biophysica, vol. 1844, pp. 2041-52 (2014).
Unaids, "Report on the Global AIDS Epidemic", 198 pgs (2013).
Vaine et al, "Antibody Responses Elicited through Homologous or Heterologous Prime-Boost DNA and Protein Vaccinations Differ in Functional Activity and Avidity," Vaccine, vol. 28, No. 17, pp. 2999-3007 (2010).
Vaine et al, "Improved Induction of Antibodies Against Key Neutralizing Epitopes by Human Immunodeficiency Virus Type 1 gp120 DNA Prime-Protein Boost Vaccination Compared to gp120 Protein-Only Vaccination," Journal of Virology, vol. 82, No. 15, pp. 7369-7378 (Aug. 2008).
Vaine et al, "Profiles of Human Serum Antibody Responses Elicited by Three Leading HIV Vaccines Focusing on the Induction of Env-Specific Antibodies," PLoS One, vol. 5, No. 11, pp. e13916 (Nov. 2010).
Vogel et al, "The Majority of Neutralizing Abs in HIV-1-Infected Patients Recognize Linear V3 Loop Sequences," The Journal of Immunology, vol. 153, pp. 1895-1904 (1994).
Vogels et al., "Replication-Deficient Human Adenovirus Type 35 Vecotrs for Gene Transfer and Vaccination: Efficient Human Cell Infection and Bypass of Preexisting Adenovirus Immunity", J. Virol, vol. 77, No. 15, pp. 8263-71 (2003).
Walker et al, "Broad and Potent Neutralizing Antibodies from an African Donor Reveal a New HIV-1 Vaccine Target," Science, vol. 326, No. 5950, pp. 285-289 (Oct. 9, 2009).

(56) References Cited

OTHER PUBLICATIONS

Walker et al, "Broad Neutralization Coverage of HIV by Multiple Highly Potent Antibodies," Nature, vol. 477, No. 7365, pp. 466-470 (Sep. 22, 2011).
Walker et al, "Toward an AIDS Vaccine," Science, vol. 320, pp. 760-764 (May 9, 2008).
Wang et al, "Cross-Subtype Antibody and Cellular Immune Responses Induced by a Polyvalent DNA Prime-Protein Boost HIV-1 Vaccine in Healthy Human Volunteers," Vaccine, vol. 26, No. 31, pp. 3947-3957 (Jul. 23, 2008).
Wang et al, "Enhanced Immunogenicity of gp120 Protein when Combined with Recombinant DNA Priming to Generate Antibodies that Neutralize the JR-FL Primary Isolate of Human Immunodeficiency Virus Type 1," Journal of Virology, vol. 79, No. 12, pp. 7933-7937 (Jun. 2005).
Wang et al, "Polyvalent HIV-1 Env Vaccine Formulations Delivered by the DNA Priming Plus Protein Boosting Approach are Effective in Generating Neutralizing Antibodies Against Primary Human Immunodeficiency Virus Type 1 Isolates from Subtypes A, B, C, D and E," Virology, vol. 350, No. 1, pp. 34-47 (2006).
Watkins et al, "Immune Escape by Human Immunodeficiency Virus Type 1 from Neutralizing Antibodies: Evidence for Multiple Pathways," Journal of Virology, vol. 67, No. 12, pp. 7493-7500 (Dec. 1993).
Wattanapitayakul et al, "Recent Developments in Gene Therapy for Cardiac Disease," Biomed & Pharmacother, vol. 54, No. 1, pp. 487-504 (2000).
Wiggan et al. "Novel Formulations Enhance the Thermal Stability of Live-Attenuated Flavivirus Vaccines," Vaccine, vol. 29, pp. 7456-7462 (2011).
Williams et al., "HIV-1 DNA Predicts Disease Progression and Post-Treatment Virological Control", eLIfe, vol. 3, 16 pgs (2014).
Wiznerowicz et al, "Harnessing HIV for Therapy, Basic Research and Biotechnology," Trends in Biotechnology, vol. 23, No. 1, pp. 42-47 (Jan. 2005).
Written Opinion dated Mar. 21, 2014 in Int'l Application No. PCT/US2014/010543.
Wu et al, "Rational Design of Envelope Identifies Broadly Neutralizing Human Monoclonal Antibodies to HIV-1," Science, vol. 329, No. 5993, pp. 856-861 (Aug. 13, 2010).
Wyatt et al, "The Antigenic Structure of the HIV gp120 Envelope Glycoprotein," Nature, vol. 393, pp. 705-711 (Jun. 18, 1998).
Yang et al, "Improved Elicitation of Neutralizing Antibodies Against Primary Human Immunodeficiency Viruses by Soluble Stabilized Envelope Glycoprotein Trimers," Journal of Virology, vol. 75, No. 3, pp. 1165-1171 (Feb. 2001).
Yang et al, "Modifications That Stabilize Human Immunodeficiency Virus Envelope Glycoprotein Trimers in Solution," Journal of Virology, vol. 74, No. 10, pp. 4746-4754 (2000).
Yang et al., "Highly Stable Trimers Formed by Human Immunodeficiency Virus Type 1 Envelope Glycoproteins Fused with the Trimeric Motif of T4 Bacteriophage Fibritin", J. Virol., vol. 76, No. 9, pp. 4634-42 (2002).
Yasmeen et al, "Differential Binding of Neutralizing and Non-Neutralizing Antibodies to Native-Like Soluble HIV-1 Env Trimers, Uncleaved Env Proteins, and Monomeric Subunits," Retrovirology, vol. 11, No. 41 (2014).
Zhang et al, "Extensively Cross-Reactive Anti-HIV-1 Neutralizing Antibodies Induced by gp140 Immunization," PNAS, vol. 104, No. 24, pp. 10193-10198 (2007).
Zhou et al, "Structural Basis for Broad and Potent Neutralization of HIV-1 by Antibody VRC01," Science, vol. 329, No. 5993, pp. 811-817 (Aug. 13, 2010).
Zigler et al., "Analysis of the Cytotoxic Effects of Light-Exposed Hepes-Containing Culture Medium", In Vitro Cell Dev. Biol., vol. 21, No. 5, pp. 282-287 (1985).
Zolla-Pazner et al, "Focusing the Immune Response on the V3 Loop, a Neutralizing Epitope of the HIV-1 gp210 Envelope," Virology, vol. 372, pp. 233-246 (2008).

Lynch et al, "The Development of CD4 Binding Site Antibodies During HIV-1 Infection," Journal of Virology, vol. 86, No. 14, pp. 7588-7595 (Jul. 2012).
Malherbe et al, "Sequential Immunization with a Subtype B HIV-1 Envelope Quasispecies Partially Mimics the In Vivo Development of Neutralizing Antibodies," Journal of Virology, vol. 85, No. 11, pp. 5262-5274 (Jun. 2011).
Mangeat et al, "Lentiviral Vectors and Antiretroviral Intrinsic Immunity," Human Gene Therapy, vol. 16, No. 8, pp. 913-920 (Aug. 2005).
Mascola et al, "Protection of Macaques Against Pathogenic Simian/Human Immunodeficiency Virus 89.6PD by Passive Transfer of Neutralizing Antibodies," Journal of Virology, vol. 73, No. 5, pp. 4009-4018 (May 1999).
Mascola et al, "Protection of Macaques Against Vaginal Transmission of a Pathogenic HIV-1/SIV Chimeric Virus by Passive Infusion of Neutralizing Antibodies," Nature Medicine, vol. 6, No. 2, pp. 207-210 (Feb. 2000).
Masopust et al., "Hidden Memories: Frontline Memory T Cells and Early Pathogen Interception", J. Immunol., vol. 188, No. 12, pp. 5811-7 (2012).
Mast et al., "International Epidemiology of Human Pre-Existing Adenovirus (Ad) Type-5, Type-6, Type-26 and Type-36 Neutralizing Antibodies: Correlates of High Ad5 Titers and Implications for Potential HIV Vaccine Trials", Vaccine, vol. 28: pp. 950-957 (2010).
Mayr et al., "The Small Pox Vaccination Strain MVA: Marker, Genetic Structure, Experience Gained with the Parenteral Vaccination and Behavior in Organisms with a Debilitated Defence Mechanism," Zentralbl Bacteriol. vol. 167, pp. 375-390 (1978) (Abstract Only).
Mcburney et al, "Evaluation of Heterologous Vaginal SHIV SF162p4 Infection Following Vaccination with a Polyvalent Clade B Virus-Like Particle Vaccine," AIDS Research and Humam Retroviruses, vol. 28, No. 9, pp. 863-872 (2012).
Mcburney et al, "Human Immunodeficiency Virus-Like Particles with Consensus Envelopes Elicited Broader Cell-Mediated Peripheral and Mucosal Immune Responses than Polyvalent and Monovalent Env Vaccines," Vaccine, vol. 27, No. 32, pp. 4337-4349 (2009).
Mccoy et al, "Potent and Broad Neutralization of HIV-1 by a Llama Antibody Elicited by Immunization," The Journal of Experimental Medicine, vol. 209, No. 6, pp. 1091-1103 (2012).
Mcelrath et al, "Induction of Immunity to Human Immunodeficiency Virus Type-1 by Vaccination," Immunity, vol. 33, pp. 542-554 (Oct. 29, 2010).
McElrath et al., "HIV-1 Vaccine-Induced Immunity in the Test-of-Concept Step Study: A Case-Cohort Analysis", Lancet, vol. 372, No. 9653, pp. 1894-905 (2008).
Mcguire et al, "Engineering HIV Envelope Protein to Activate Germline B Cell Receptors of Broadly Neutralizing Anti-CD4 Binding Site Antibodies," The Journal of Experimental Medicine, vol. 210, No. 4, pp. 655-663 (2013).
Mclellan et al, "Structure of HIV-1 gp120 V1/V2 Domain with Broadly Neutralizing Antibody PG9," Nature, vol. 480, No. 7377, pp. 336-43 (2011).
Montefiori et al, "Antibody-Based HIV-1 Vaccines: Recent Developments and Future Directions," PLOS Medicine, vol. 4, No. 12, pp. e348 (2007).
Montefiori, "Evaluating Neutralizing Antibodies Against HIV, SIV, and SHIV in Luciferase Reporter Gene Assays," Current Protocols in Immunology, vol. 12, No. 11, pp. 1-17 (2004).
Montefiori, "Measuring HIV Neutralization in a Luciferase Reporter Gene Assay," HIV Protocols Second 25 Edition, vol. 485, pp. 395-405 (2009).
Morner et al, "Human Immunodeficiency Virus Type 1 ENV Trimer Immunization of Macaques and Impact of D Priming with Viral Vector or Stabilized Core Protein," Journal of Virology, vol. 83, No. 2, pp. 540-551 (Jan. 2009).
Mouquet et al, "Complex-Type N-Glycan Recognition by Potent Broadly Neutralizing HIV Antibodies," Proceedings of the National Academy of Sciences of the United States of America, vol. 109, No. 47, pp. E3268-E3277 (2012).

(56) References Cited

OTHER PUBLICATIONS

Muthumani et al., "HIV-1 Env DNA Vaccine plus PRotein Boost Delivered by EP Expands B- and T-Cell Responses and Neutralizing Phenotype In Vivo", PLOS One, vol. 8, No. 12, 12 pgs (Dec. 2013).
Nara et al, "Purified Envelope Glycoproteins from Human Immunodeficiency Virus Type 1 Variants Induce Individual, Type-Specific Neutralizing Antibodies," Journal of Virology, vol. 62, No. 8, pp. 2622-2628 (Aug. 1988).
Ncbi Blast for GenBank AAY23526.1, Jul. 2016, "Envelope glycoprotein Human immunodeficiency virus 1", downloaded from web page: http://www.ncbi.nlm.nih.gov/protein/62956393, Download date: Feb. 8, 2018 (2 pages).
Nkolola et al, "Stability and Neutralization Capacity of a Novel Mosaic HIV-1 gp140 trimer in a Guinea Pig Model" AIDS Vaccine Poster, Ragon Institute, 1 pg. (2012).
Nkolola et al, "Stability and Neutralization Capacity of a Novel Mosaic HIV-1 gp140 Trimer in a Guinea Pig Model," Retrovirology, vol. 9, Supp. 2, pp. 299 (2012).
Nkolola et al., "Breadth of Neutralizing Antibodies Elicited by Stable, Homogeneous Clade A and Clade C HIV-1 gp140 Envelope Trimers in Guinea Pigs", Journ. of Viro., vol. 84. No. 7, pp. 3270-3279 (Apr. 2010).
Nkolola et al., "Characterization and Immunogenicity of a Novel Mosaic M HIV-1 gp140 Trimer", Journ. of Virology, vol. 88, No. 17, pp. 9538-9552 (Sep. 2014).
Ofek et al, "Structure and Mechanistic Analysis of the Anti-Human Immunodeficiency Virus Type 1 Antibody 2F5 in Complex with Its gp41 Epitope," Journal of Virology, vol. 78, No. 19, pp. 10724-10737 (Oct. 2004).
Page et al, "Studies on the Immunogenicity of Chinese Hamster Ovary Cell-Derived Recombinant gp120 (HIV-1111B), " Vaccine, vol. 9, pp. 47-52 (Jan. 1991).
Pancera et al, "Crystal Structure of PG16 and Chimeric Dissection with Somatically Related PG9: Structure-Function Analysis of Two Quaternary-Specific Antibodies That Effectively Neutralize HIV-1," Journal of Virology, vol. 84, No. 16, pp. 8098-8110 (Aug. 2010).
Pancera et al, "Structure of HIV-1 gp120 with gp41-Interactive Region Reveals Layered Envelope Architecture and Basis of Conformational Mobility," Procedures of the National Academy of Sciences of the United States of America, vol. 107, No. 3, pp. 1166-1171 (2010).
Pantophlet et al, "GP120: Target for Neutralizing HIV-1 Antibodies," Annu. Rev. Immunol., vol. 24, pp. 739-69 (2006).
Patterson et al. "Protection Against Mucosal Simian Immunodeficiency Virus SIVmac251 Challenge by Using Replicating Adenovirus-SIV Multigene Vaccine Priming and Subunit Boosting," Journal of Virology, vol. 78, No. 5, pp. 2212-2221 (Mar. 2004).
Pejchal et al, "A Potent and Broad Neutralizing Antibody Recognizes and Penetrates the HIV Glycan Shield," Science, vol. 334, No. 6059, pp. 1097-1103 (2011).
Pejchal et al, "Structure and Function of Broadly Reactive Antibody PG16 Reveal an H3 Subdomain that Mediates Potent Neutralization of HIV-1," Proceedings of the National Academy of Sciences of the United States of America, vol. 107, No. 25, pp. 11483-11488 (2010).
Peng et al. "Replicating Rather than Nonreplicating Adenovirus-Human Immunodeficiency Virus Recombinant Vaccines Are Better at Eliciting Potent Cellular Immunity and Priming High-Titer Antibodies," Journal of Virology, vol. 79, No. 16, pp. 10200-10209 (Aug. 2005).
Pinter, "Roles of HIV-1 Env Variable Regions in Viral Neutralization and Vaccine Development", Current HIV Research, vol. 5, No. 6, pp. 542-553 (2007).
Pitisuttihum et al., "Randomized, Double-Blind, Placebo-Controlled Efficacy Trial of a Bivalent Recombinant Glycoprotein 120 HIV-1 Vaccine Among Injection Drug Users in Bangkok, Thailand", J. Infect. Dis., vol. 194, No. 12, pp. 1661-71 (2006).
Plotkin et al, "Postscript Relating to New Allegations Made by Edward Hooper at The Royal Society Discussion Meeting on Sep. 11, 2000," Philosophical Transactions of the Royal Society of London B: Biological Sciences, vol. 356, No. 1410, pp. 825-829 (2001).
Plotkin, "Correlates of Protection Induced by Vaccination," Clinical and Vaccine Immunology, vol. 17, No. 7, pp. 1055-1065 (Jul. 2010).
PLOTKIN, "Immunologic Correlates of Protection Induced by Vaccination," Pediatric Infectious Disease Journal, vol. 20, No. 1, pp. 63-75 (2001).
Plotkin, "The RV144 Thai HIV Vaccine Trial," Human Vaccines, vol. 6, No. 2, p. 159 (Feb. 2010).
Polonis et al, "Recent Advances in the Characterization of HIV-1 Neutralization Assays for Standardized Evaluation of the Antibody Response to Infection and Vaccination," Virology, vol. 375, pp. 315-320 (2008).
Rerks-Ngarm et al.", Vaccination with ALVAC and AIDSVAX to Prevent HIV-1 Infection in Thailand", N. Engl J Med., vol. 361, No. 23, pp. 2209-20 (2009).
Rodenburg et al, "Near Full-Length Clones and Reference Sequences for Subtype C Isolates of HIV Type 1 from Three Different Continents," AIDS Research and Human Retroviruses, vol. 17, No. 2, pp. 161-168 (2001).
Saez-Cirion et al., "Post-Treatment HIV-1 Controllers with a Long-Term Virological Remission after the Interruption of Early Initiated Antiretroviral Therapy ANRS VISCONTI Study", PLOS Pathogens, vol. 9, No. 3, 12 pgs (Mar. 2013).
Salminen et al, "Full-length Sequence of an Ethiopian Human Immunodeficiency Virus Type 1 (HIV-1) Isolate of Genetic Subtype C," AIDS Res. Human Retroviruses, vol. 12, No. 14, pp. 1329-39 (1996).
Sanders et al., "Brunenders: A Partially Attenuated Historic Poliovirus Type 1 Vaccine Strain", Journ. of General Viro., vol. 96, pp. 2614-2622 (2015).
Santra et al., "Mosaic Vaccines Elicit CD8+ T Lymphocyte Responses That Confer Enhanced Immune Coverage of Diverse HIV Strains in Monkeys", Nat Med., vol. 16, No. 3, pp. 324-8 (2010).
Saphire et al, "Crystal Structure of a Neutralizing Human IgG Against HIV-1: A Template for Vaccine Design," Science, vol. 293, No. 5532, pp. 1155-1159 (2001).
Extended Search Report dated Nov. 22, 2016 in EP Application No. 16188866.
De Taeye et al, "Immunogenicity of Stabilized HIV-1 Envelope Trimers With Reduced Exposure of Non-Neutralizing Epitopes," Cell, vol. 163, pp. 1702-1715 (2015).
Julien et al, "Design and Structure of Two HIV-1 Clade C SOSIP. 664 Trimers That Increase The Arsenal of Native-Like Env Immunogens," PNAS, vol. 112, No. 38, pp. 11947-11952 (2015).
Kwon et al, "Crystal Structure, Conformational Fixation and Entry-Related Interactions of Mature Ligand-Free HIV-1 ENV," Nature Structural & Molecular Biology, vol. 22, No. 7, pp. 522-531 (2015).
Pugach et al, "A Native-Like SOSIP.664 Trimer Based on an HIV-I Subtype B Env Gene," Journal of Virology, vol. 89, No. 6, pp. 3380-3395 (2015).
Altschul et al, "Gapped BLAST and PSI-BLAST: A New Generation of Protein Database Search Programs," Nucleic Acids Research, vol. 25, No. 17, pp. 3389-3402 (1997).
Eglen et al, "The Use of AlphaScreen Technology in HTS: Current Status," Current Chemical Genomics, vol. 1, pp. 2-10 (2008).
Abbink et al, "Comparative Seroprevalence and Immunogenicity of Six Rare Serotype Recombinant Adenovirus Vaccine Vectors From Subgroups B and D," Journal of Virology, vol. 81, No. 9, pp. 4654-4663 (2007).
Barouch et al, "Mosaic HIV-1 Vaccines Expand the Breadth and Depth of Cellular Immune Responses in Rhesus Monkeys," Nat. Med., vol. 16, No. 3, pp. 319-323 (2010).
Georgiev et al, "Single-Chain Soluble BG505.SOSIP gp140 Trimers as Structural and Antigenic Mimics of Mature closed HIV-1 ENV," Journal of Virology, vol. 89, pp. 5318-5329.
Bale et al, "Covalent Linkage of HIV-1 Trimers to Synthetic Liposomes Elicits Improved B Cell and Antibody Responses," Journal of Virology, vol. 91, No. 16, pp. e00443-17 (2017).

(56) References Cited

OTHER PUBLICATIONS

Harris et al, "Trimeric HIV-1 Glycoprotein gp140 Immunogens and Native HIV-1 Envelope Glycoproteins Display the Same Closed and Open Quaternary Molecular Architectures," PNAS, vol. 108, No. 28, pp. 11440-11445 (2011).

Guenaga et al, "Glycine Substitution at Helix-To-Coil Transitions Facilitates the Structural Determination of a Stabilized Subtype C HIV Envelope Glycoprotein," Immunity, vol. 46, pp. 792-803.

Lopez-Sagaseta et al, "Self-Assembling Protein Nanoparticles in the Design of Vaccines," Computational and Structural Biotechnology Journal, vol. 14, pp. 58-68 (2016).

Kesavardhana et al, "Stabilizing the Native Trimer of HIV-1 Env by Destabilizing the Heterodimeric Interface of the gp41 Postfusion Six-Helix Bundle," Journal of Virology, vol. 88, No. 17, pp. 9590-9604.

He et al, "Presenting Native-Like Trimeric HIV-1 Antigens With Self-Assembling Nanoparticles," Nature Communications, vol. 7, No. 1, pp. doi:10.1038/ncomms12041. http://dx.doi.org/10.1038/ncomms12041 (2016).

Sanders et al, "Stabilization of the Solubale, Cleaved, Trimeric Form of the Envelope Glycoprotein Complex of Human Immunodeficiency Virus Type 1," Journal of Virology, vol. 76, No. 17, pp. 8875-8889 (2002).

Kong et al, "Uncleaved Prefusion-Optimized gp140 Trimers Derived From Analysis of HIV-1 Envelope Metastability," Nature Communications, vol. 7, No. 1, pp. doi:10.1038/ncomms12040. http://dx.doi.org/10.1038/ncomms12040 (2016).

Zhang et al, "Expression, Purification, and Characterization of Recombinant HIV gp140," Journal of Biological Chemistry, vol. 276, No. 43, pp. 39577-39585 (2001).

Sanders et al, "HIV-1 Neutralizing Antibodies Induced by Native-Like Envelope Trimers," Science, vol. 349, Issue 6244, pp. 10.1126/science.aac4223 (2015).

Zhao et al, "Nanoparticle Vaccines," Vaccines, vol. 32, pp. 327-337 (2014).

Sharma et al, "Cleavage-Independent HIV-1 Env Trimers Engineered as Soluble Native Spike Mimetics for Vaccines Design," Cell Reports, vol. 11, pp. 1-12 (2015).

Kushnir et al, "Virus-Like Particles as a Highly Efficient Vaccine Platform: Diversity of Targets and Production Systems and Advances in Clinical Development," Vaccine, vol. 31, pp. 58-83 (2012).

Davenport et al, "Binding Interactions Between Soluble HIV Envelope Glycoproteins and Quatemary-Structure-Specific Monoclonal Antibodies PG9 and PG16," Journal of Virology, vol. 85, No. 14, pp. 7095-7107 (Jul. 2011).

De Gruijl et al., "Intradermal Delivery of Adenoviral Type-35 Vectors Leads to High Efficiency Transduction of Mature, CD8+ T Cell-Stimulating Skin-Emigrated Dendritic Cells, J. Immunol, vol. 177, No. 4, pp. 2208-15 (2006).

Derby et al, "Isolation and Characterization of Monoclonal Antibodies Elicited by Trimeric HIV-1 ENV gp140 Protein 14 Immunogens," Virology, vol. 366, pp. 433-445 (2007).

Desrosiers, "Prospects for an AIDS Vaccine", Nature Medicine, vol. 10, No. 3, pp. 221-223 (2004).

Dey et al, "Characterization of Human Immunodeficiency Virus Type 1 Monomeric and Trimeric gp120 Glycoproteins Stabilized in the CD4-Bound State: Antigenicity, Biophysics, and Immunogenicity," Journal of Virology, vol. 81, No. 11, pp. 5579-5593 (Jun. 2007).

Doores et al, "Antibody 2G12 Recognizes Di-Mannose Equivalently in Domain- and Nondomain-Exchanged Forms but Only Binds the HIV-1 Glycan Shield if Domain Exchanged," Journal of Virology, vol. 84, No. 20, pp. 10690-10699 (2010).

Doria-Rose et al, "Frequency and Phenotype of Human Immunodeficiency Virus Envelope-Specific B Cells from Patients with Broadly Cross-Neutralizing Antibodies," Journal of Virology, vol. 83, No. 1, pp. 188-199 (Jan. 2009).

Engelhardt et al, "Ablation of E2A in Recombinant Adenoviruses Improves Transgene Persistence and Decreases Inflammatory Response in Mouse Liver," Proceedings of the National Academy of Sciences of the United States of America, vol. 91, No. 13, pp. 6196-6200 (Jun. 1994).

Falkowska et al, "PGV04, an HIV-1 gp120 CD4 Binding Site Antibody, is Broad and Potent in Neutralization but Does Not Induce Conformational Changes Characteristic of CD4," Journal of Virology, vol. 86, No. 8, pp. 4394-4403 (2012).

Farina et al., "Replication-defective Vector Based on a Chimpanzee Adenovirus", J. Virol, vol. 75, No. 23, pp. 11603-13 (2001).

Fiebig et al, "Neutralizing Antibodies Against Conserved Domains of p15E of Porcine Endogenous Retroviruses: Basis for a Vaccine for Xenotransplantation?" Virology, vol. 307, No. 2, pp. 406-413 (2003).

Fischer et al, "Identification of a Peptide Mimicking the Binding Pattern of an Antiphospholipid Antibody," Immunobiology, vol. 211, No. 9, pp. 695-699 (2006).

Fischer et al., "Coping with Viral Diversity in HIV vaccine Design: A Response to Nickle et al.," PLoS Comput Bioi., vol. 4, No. 1, pp. 175-179 (2008).

Fischer et al., "Polyvalent Vaccines for Optimal Coverage of Potential T-Cell Epitopes in Global HIV-1 Variants", Nat. Med., vol. 13, No. 1, pp. 100-106 (Jan. 2007).

Flynn et al., "Placebo-controlled phase 3 trial of a recombinant glycoprotein 120 vaccine to prevent HIV-1 infection",. J. Infect Dis, vol. 191, No. 5, pp. 654-65 (2005).

Freeman et al, "Crystal Structure of HIV-1 Primary Receptor CD4 in Complex with a Potent Antiviral Antibody," Structure, vol. 18, No. 12, pp. 1632-1641 (Dec. 8, 2010).

Frey et al, "A Fusion-Intermediate State of HIV-1 gp41 Targeted by Broadly Neutralizing Antibodies," Proceedings of the National Academy of Sciences of the United States of America, vol. 105, No. 10, pp. 3739-3744 (Mar. 11, 2008).

Fynan et al, "DNA Vaccines: Protective Immunizations by Parenteral, Mucosal, and Gene-Gun Inoculations," Proceedings of the National Academy of Sciences of the United States of America, vol. 90, No. 24, pp. 11478-11482 (Dec. 1993).

Gach et al., "HIV-1-Specific Antibody Response and Function after DNA Prime and Recombinant Adenovirus 5 Boost HIV Vaccine in HIV-Infected Subjects", PLOS One, vol. 11, No. 8, pp. 17 (Aug. 2016).

Gallo et al, "The HIV Env-mediated Fusion Reaction," Biochemics et Biophysica Acta, pp. 36-50 (2003).

Gallo, "The End or the Beginning of the Drive to an HIV-Preventive Vaccine: A View from over 20 Years", The Lancet, vol. 366, No. 9500, pp. 1894-1898 (Nov. 2005).

Gao et al, "A Comprehensive Panel of Near-Full-Length Clones and Reference Sequences for Non-Subtype B Isolates of Human Immunodeficiency Virus Type 1, "Journal of Virology, vol. 72, No. 7, pp. 5680-5698 (1998).

Gao et al, "Antigenicity and Immunogenicity of a Synthetic Human Immunodeficiency Virus Type 1 Group M Consensus Envelope Glycoprotein," Journal of Virology, vol. 79, No. 2, pp. 1154-1163 (Jan. 2005).

Gao et al, "Centralized HIV-1 Envelope Immunogens and Neutralizing Antibodies," Current HIV Research, vol. 5, No. 6, pp. 572-577 (2007).

Gao et al, "Molecular Cloning and Analysis of Functional Envelope Genes from Human Immunodeficiency Virus Type 1 Sequence Subtypes A through G" Journal of Virology, vol. 70, No. 3, pp. 1651-1667 (Mar. 1996).

Gaschen et al, "Diversity Consideration in HIV-1 Vaccine Selection," Science, vol. 296, No. 5577, pp. 2354-2360 (Jun. 28, 2002).

Genbank Accession No. AF286227.1, "HIV-1 strain 97Za012 from South Africa, complete genome." Accessed Jan. 6, 2016.

GenBank Accession No. KC769514. Retrieved on Dec. 30, 2014 (2 pages).

Georgiev et al, "Delineating Antibody Recognition in Polyclonal Sera from Patterns of HIV-1 Isolate Neutralization," Science, vol. 340, No. 6133, pp. 751-756 (2013).

Gianella et al., "Effect of Early Antiretroviral Therapy During Primary HIV-1 Infection on Cell-Associated HIV-1 DNA and Plasma HIV-1 RNA", Antiviral Therapy, vol. 16, No. 4, pp. 535-45 (2011).

(56) References Cited

OTHER PUBLICATIONS

Girard et al., A Review of Vaccine Research and Development: The Human Immunodeficiency Virus (HIV), Vaccine, vol. 24, pp. 4062-4081 (2006).
Gomez-Roman et al., "An Adenovirus-Based HIV Subtype B Prime/Boost Vaccine Regimen Elicits Antibodies Mediating Broad Antibody-Dependent Cellular Cytotoxicity Against Non-Subtype B HIV Strains", J. Acquir. Immune Defic. Syndr., vol. 43, No. 3, pp. 270-277 (Nov. 2006).
Gotch et al., "Candidate Vaccines for Immunotherapy in HIV", HIV Medicine, vol. 2, pp. 260-265 (2001).
Goujard et al., "HIV-1 Control After Transient Antiretroviral Treatment Initiated in Primary Infection: Role of Patient Characteristics and Effect of Therapy", Antiviral Therapy, vol. 17, No. 6, pp. 1001-9 (2012).
Graham et al, "Phase 1 Safety and Immunogenicity Evaluation of a Multiclade HIV-1 DNA Candidate Vaccine," The Journal of Infectious Diseases, vol. 194, No. 12, pp. 1650-1660 (Dec. 15, 2006).
Gray et al, "Isolation of a Monoclonal Antibody That Targets the Alpha-2 Helix of gp120 and Represents the Initial Autologous Neutralizing-Antibody Response in an HIV-1 Subtype C-Infected Individual," Journal of Virology, vol. 85, No. 15, pp. 7719-7729 (Aug. 2011).
Gray et al., "Safety and Efficacy of the HVTN 503/Phambili Study of a Clade-B-based HIV-1 Vaccine in South Africa: A Double-Blind, Randomised, Placebo-Controlled Test-of-Concept Phase 2b Study", Lancet Infect Dis, vol. 11, No. 7, pp. 507-15 (2011).
Grundner et al, "Analysis of the Neutralizing Antibody Response Elicited in Rabbits by Repeated Inoculation with Trimeric HIV-1 Envelope Glycoproteins," Virology, vol. 331, No. 1, pp. 33-46 (2005).
Gurwith et al, "Safety and Immunogenicity of an Oral, Replicating Adenovirus Serotype 4 Vector Vaccine for H5N1 Influenza: A Randomised, Double-Blind, Placebo-Controlled, Phase 1 Study", Lancet Infect Dis, vol. 13, No. 3, pp. 238-50 (2013).
Hamlyn et al., "Plasma HIV Viral Rebound Following Protocol-Indicated Cessation of ART Commenced in Primary and Chronic HIV Infection", PLOS ONE, vol. 7, No. 8, 8 pgs (Aug. 2012).
Hammer et al, "Efficacy Trial of a DNA/rAd5 HIV-1 Preventive Vaccine," The New England Journal of Medicine, vol. 369, No. 22, pp. 2083-2092 (Nov. 28, 2013).
Haslett et al., "Strong Human Immunodeficiency Virus (HIV)-Specific CD4+ T Cell Responses in a Cohort of Chronically Infected Patients are Associated with Interruptions in Anti-HIV Chemotherapy, "J. Infect. Dis, vol. 81, No. 4, pp. 1264-72 (2000).
Havenga et al., "Novel Replication-Incompetent Adenoviral B-Group Vectors: High Vector Stability and Yield in PER. C6 Cells", Journ. of Gen Viro., vol. 87, pp. 2135-2143 (2006).
Haynes et al., "Immune-Correlates Analysis of an HIV-1 Vaccine Efficacy Trial," The New England Journal of Medicine, vol. 366, No. 14, pp. 1275-1286 (2012).
Hierholzer et al., "Adenoviruses from Patients with AIDS: A Plethora of Serotypes and a Description of Five New Serotypes of Subgenus D (types 43-47).", J. Infect. Dis., vol. 158, No. 4 pp. 804-13 (1988) (Abstract Only).
Hoganson et al., "Development of a Stable Adenoviral Vector Formulation", BioProcessing Journ., pp. 43-48 (Mar. 2002).
Huang et al, "Broad and Potent Neutralization of HIV-1 by a gp41-Specific Human Antibody," Nature, vol. 491, No. 7424, pp. 406-412 (2012).
Janes et al., "MRKAd5 HIV-1 Gag/Pol/Nef Vaccine-Induced T-cell Responses Inadequately Predict Distance of Breakthrough HIV-1 Sequences to the Vaccine or Viral Load", PLoS One, vol. 7, No. 8, pp. e43396 (2012).
Jeffs et al, "Expression and Characterization of Recombinant Oligomeric Envelope Glycoproteins Derived From Primary Isolates of HIV-1," Vaccine, vol. 22, No. 8, pp. 1032-1046 (2004).
Jin et al., "Stabilizing Formulations for Inhalable Powders of an Adenovirus 35-Vectored Tuberculosis (TB) Vaccine (AERAS-402)", Vaccine, vol. 28, No. 27, pp. 4369-75 (2010).

Julien et al, "Asymmetric Recognition of the HIV-1 Trimer by Broadly Neutralizing Antibody PG9," Proceedings of the National Academy of Sciences of the United States of America, vol. 110, No. 11, pp. 4351-4356 (Mar. 12, 2013).
Julien et al, "Broadly Neutralizing Antibody PGT121 Allosterically Modulates CD4 Binding via Recognition of the HIV-1 gp120 V3 Base and Multiple Surrounding Glycans," PLOS Pathogens, vol. 9, No. 5, pp. e1003342 (May 2013).
Kamerzell et al., "Protein-Excipient Interactions: Mechanisms and Biophysical Characterization Applied to Protein Formulation Development", Advanced Drug Delivery Review, vol. 63, pp. 1118-1159 (2011).
Kang et al, "Structural and Immunogenicity Studies of a Cleaved, Stabilized Envelope Trimer Derived from Subtype A HIV-1," Vaccine, vol. 27, pp. 5120-5132 (2009).
Katlama et al., "Barriers to a Cure for HIV: New Ways to Target and Eradicate HIV-1 Reservoirs", The Lancet, vol. 381, No. 988., pp. 2109-2117 (Jun. 2013).
Khoo et al., "Adenovirus Infections in Human Immunodeficiency Virus-Positive Patients: Clinical Features and Molecular Epidemiology", J. Infect. Dis, vol. 172, No. 3, pp. 629-37 (1995) (Abstract Only).
Kim et al, "Comparison of HIV Type 1 ADA gp120 Monomers Versus gp140 Trimers as Immunogens for the Induction of Neutralizing Antibodies," AIDS Research and Human Retroviruses, vol. 21, No. 1, pp. 58-67 (2005).
Kobinger et al, "Chimpanzee Adenovirus Vaccine Protects Against Zaire Ebola Virus", Virology, vol. 346, pp. 394-401 (2006).
Kochanek et al, "A New Adenoviral Vector. Replacement of All Viral Coding Sequences with 28 kb of DNA Independently Expressing Both Full-Length Dystrophin and Beta-Galactosidase," Proceedings of the National Academy of Sciences of the United States of America, vol. 93, No. 12, pp. 5731-5736 (Jun. 1996).
Kong et al., "Expanded Breadth of the T -Cell Response to Mosaic Human Immunodeficiency Virus Type 1 Envelope DNA Vaccination," J. Viral., vol. 83, No. 5, pp. 2201-2215 (2009).
Korber et al., "T-Cell Vaccine Strategies for Human Immunodeficiency Virus, The Virus with a Thousand Faces," J. Viral., vol. 83, No. 17, pp. 8300-8314 (2009).
Kothe et al, "Ancestral and Consensus Envelope Immunogens for HIV-1 Subtype C," Virology, vol. 352, No. 2, pp. 438-449 (2006).
Kothe et al, "Antigenicity and Immunogenicity of HIV-1 Consensus Subtype B Envelope Glycoproteins," Virology, vol. 360, No. 1, pp. 218-234 (Mar. 30, 2007).
Kovacs et al., "HIV-1 Envelope Trimer Elicits more Potent Neutralizing Antibody Responses than Monomeric gp120", Proc. Natl. Acac. Sci., vol. 109, No. 30, pp. 12111-12116 (2012).
Kuschner et al., "A Phase 3, Randomized, Double-Blind, Placebo-Controlled Study of the Safety and Efficacy of the Live, Oral Adenovirus Type 4 and Type 7 Vaccine, in U.S. Military Recruits", Vaccine, vol. 31(28), pp. 2963-71 (2013).
Kwong et al, "Structure of an HIV gp120 Envelope Glycoprotein in Complex with the CD4 Receptor and a Neutralizing Human Antibody," Nature, vol. 393, No. 6686, pp. 648-659 (Jun. 18, 1998).
Lasaro et al., "New Insights on Adenovirus as Vaccine Vectors", Mol. Ther., vol. 17, No. 8, pp. 1333-39 (2009).
Lee et al, "A Single Point Mutation in HIV-1 V3 Loop Alters the Immunogenic Properties of rgp120," Archives of Virology, vol. 145, pp. 2087-2103 (2000).
Lepe-Zuniga et al., "Toxicity of Light-Exposed Hepes Media", Journ. of Immun. Methods, vol. 103, pp. 145 (1987).
Letvin et al., "Potent, Protective Anti-HIV Immune Responses Generated by Bimodal HIV Envelope DNA Plus Protein Vaccination", Proc. Natl. Acad. Sci., vol. 94, pp. 9378-9383 (1997).
Levine, "Why Do We Not Yet Have a Human Immunodfciency Virus Vaccine," J. Virol., vol. 82, No. 24, pp. 11998-12000 (Dec. 2008).
Li et al, "Broad HIV-1 Neutralization Mediated by CD4-Binding Site Antibodies," Nature Medicine, vol. 13, No. 9, pp. 1032-1039 (Sep. 2007).
Li et al, "Characterization of Antibody Responses Elicited by Human Immunodeficiency Virus Type 1 Primary Isolate Trimeric

(56) References Cited

OTHER PUBLICATIONS and Monomeric Envelope Glycoproteins in Selected Adjuvants," Journal of Virology, vol. 80, No. 3, pp. 1414-1426 (Feb. 2006).

Li et al, "Evidence for Potent Autologous Neutralizing Antibody Titers and Compact Envelopes in Early Infection with Subtype C Human Immunodeficiency Virus Type 1," Journal of Virology, vol. 80, No. 11, pp. 5211-5218 (Jun. 2006).

Li et al, "Human Immunodeficiency Virus Type 1 env Clones from Acute and Early Subtype B Infections for Standardized Assessments of Vaccine-Elicited Neutralizing Antibodies," Journal of Virology, vol. 79, No. 16, pp. 10108-10125 (Aug. 2005).

Li et al, "Removal of a Single N-Linked Glycan in Human Immunodeficiency Virus Type 1 gp120 Results in an Enhanced Ability to Induce Neutralizing Antibody Responses," Journal of Virology, vol. 82, No. 2, pp. 638-651 (Jan. 2008).

Li et al., "Visuatizing Antigen-Specific and Infected Cells in Situ Predicts Outcomes in Early Viral Infection", Science, vol. 323, No. 5922, pp. 1726-9 (2009).

Lian et al., "Evaluation of Envelope Vaccines Derived from the South African Subtype C Human Immunodeficiency Virus Type 1 TV1 Strain," Journal of Virology, vol. 79, No. 21, pp. 13338-13349 (Nov. 2005).

Liao et al., "A Group M Consensus Envelope Glycoprotein Induces Antibodies That Neutralize Subsets of Subtype B and C HIV-1 Primary Viruses," Virology, vol. 353, No. 2, pp. 268-282 (Sep. 30, 2006).

Liao et al, "Antigenicity and Immunogenicity of Transmitted/Founder, Consensus, and Chronic Envelope Glycoproteins of Human Immunodeficiency Virus Type 1," Journal of Virology, vol. 87, No. 8, pp. 4185-4201 (Apr. 2013).

Liao et al, "Co-Evolution of a Broadly Neutralizing HIV-1 Antibody and Founder Virus," Nature, vol. 496, No. 7446, pp. 469-76 (Apr. 25, 2013).

Lin et al, "Designing Immunogens to Elicit Broadly Neutralizing Antibodies to the HIV-1 Envelope Glycoprotein," Current HIV Research, vol. 5, No. 6, pp. 514-541 (2007).

Liu et al., "Magnitude and Phenotype of Cellular Immune Responses Elicited by Recombinant Adenovirus Vectors and Heterologous Prime-Boost Regimens in Rhesus Monkeys", J. Viol,, vol. 82, No. 10, pp. 4844-52 (2008).

Liu et al., Immune Control of an SIV Challenge by a T-Cell-Based Vaccine in Rhesus Monkeys, Nature, vol. 457, No. 7225, pp. 87-91(2009).

Li et al., "Genetic and Neutralization Properties of Subtype C Human Immunodeficiency Virus Type 1 Molecular env Clones From Acute Early Heterosexually Acquired Infections in Southern Africa," Journal of Virology, vol. 80, No. 23, 11776-11790 (Dec. 2006).

Li et al, "Human Immunodeficiency Vins Type 1 env Clones from Acute and Early Subtype B Infections for Standardized Assessments of Vaccine-Elicited Neutralizing Antibodies," Journal of Virology, vol. 79, No. 16, pp. 10108-10125 (Aug. 2005).

Lodi et al., "Immunovirologic Control 24 Months After Interruption of Antiretroviral Therapy Initiated Close to HIV Seroconversion", Archives of Internal Medicine, vol. 172, No. 16, pp. 1252-5 (2012).

Lore et al., "Myeloid and Plasmacytoid Dendritic Cells are Susceptible to Recombinant Adenovirus Vectors and Stimulate Polyfunctional Memory T Cell Responses", J. Immunol, vol. 179, No. 3, pp. 1721-9 (2007).

\* cited by examiner

FIG. 13

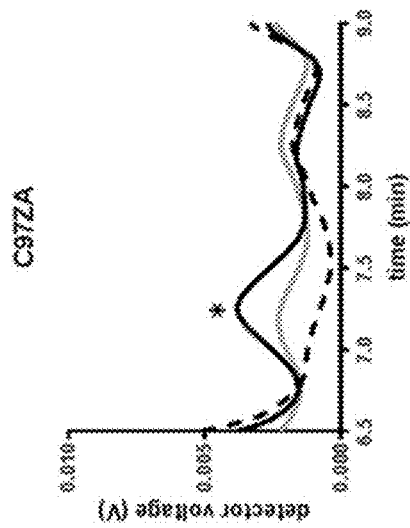
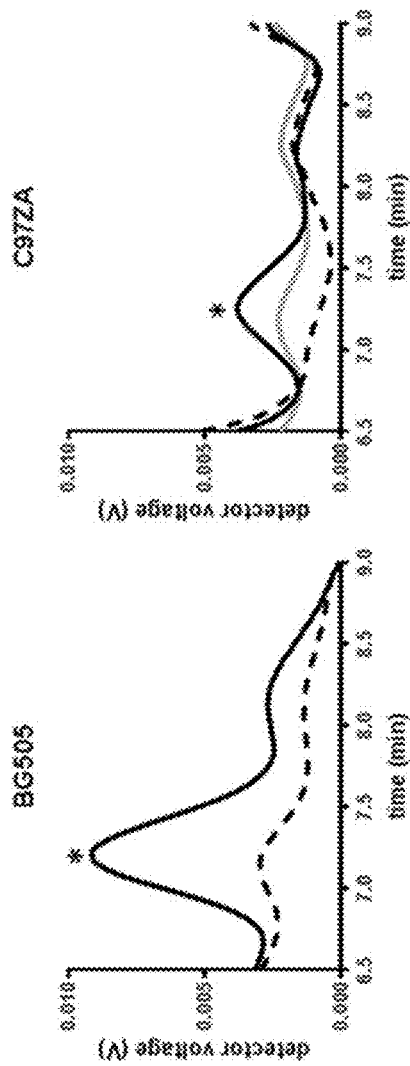
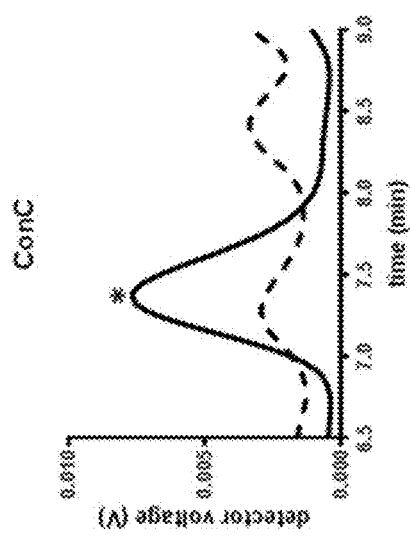
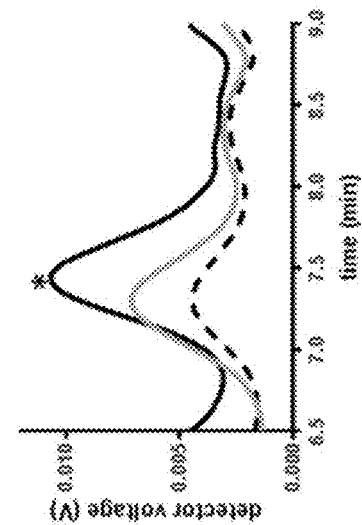
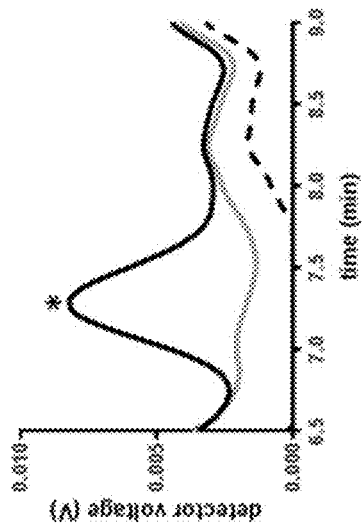
FIG. 14A ConC
FIG. 14B BG505
FIG. 14C C97ZA
FIG. 14D Du422
FIG. 14E sC4
Backbone SOSIP
Repaired
Repaired and stabilized

TRIMER STABILIZING HIV ENVELOPE PROTEIN MUTATIONS

CROSS REFERENCE TO RELATED APPLICATIONS

This application claims priority to EP Application 16 188 866.4, filed on Sep. 15, 2016, the disclosure of which is herein incorporated by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "688097-131US Sequence Listing" and a creation date of Sep. 14, 2017, and having a size of 123 kb. The sequence listing submitted via EFS-Web is part of the specification and is herein incorporated by reference in its entirety.

BACKGROUND OF THE INVENTION

Human Immunodeficiency Virus (HIV) affects millions of people worldwide, and the prevention of HIV through an efficacious vaccine remains a very high priority, even in an era of widespread antiretroviral treatment. Antigenic diversity between different strains and clades of the HIV virus renders it difficult to develop vaccines with broad efficacy. HIV-1 is the most common and pathogenic strain of the virus, with more than 90% of HIV/AIDS cases deriving from infection with HIV-1 group M. The M group is subdivided further into clades or subtypes, of which clade C is the largest. An efficacious vaccine ideally would be capable of eliciting both potent cellular responses and broadly neutralizing antibodies capable of neutralizing HIV-1 strains from different clades.

The envelope protein spike (Env) on the HIV surface is composed of a trimer of heterodimers of glycoproteins gp120 and gp41 (FIG. 1A). The precursor protein gp160 is cleaved by furin into gp120, which is the head of the spike and contains the CD4 receptor binding site as well as the large hypervariable loops (V1 to V5), and gp41, which is the membrane-anchored stem of the envelope protein spike. Like other class I fusogenic proteins, gp41 contains an N-terminal fusion peptide (FP), a C-terminal transmembrane (TM) domain, and a cytoplasmic domain. Membrane fusion between HIV and target cell membranes requires a series of conformational changes in the envelope protein. HIV vaccines can be developed based upon the envelope protein.

However, various factors make the development of an HIV vaccine based upon the envelope protein challenging, including the high genetic variability of HIV-1, the dense carbohydrate coat of the envelope protein, and the relatively dynamic and labile nature of the envelope protein spike structure. The wild-type envelope protein is unstable due to its function. Therefore, stabilizing modifications are sometimes introduced into the envelope structure for generating vaccine candidates. The envelope protein is a target for neutralizing antibodies and is highly glycosylated, which reduces the immunogenicity by shielding protein epitopes. All known broadly neutralizing antibodies (bNAbs) do accommodate these glycans.

For vaccine development, it is preferred to use envelope proteins that can induce bNAbs. However, most bNAbs only recognize the native envelope protein conformation before it undergoes any conformation changes. Therefore, developing a stable envelope protein in its native-like compact and closed conformation, while minimizing the presentation of non-native and thus non-neutralizing epitopes, could improve the efficiency of generating such bNAbs. Previous efforts to produce an HIV vaccine have focused on developing vaccines that contain the pre-fusion ectodomain of the trimeric HIV envelope protein, gp140. Gp140 does not have the transmembrane (TM) and cytoplasmic domains, but unlike gp120, it can form trimer structures. Moreover, these previous efforts have mainly focused on clade A. However, the breadth of the neutralizing antibody response that has been induced is still limited. Therefore, it would also be beneficial if stabilized native envelope trimers against multiple HIV clades were available.

For more than two decades, attempts have been made to develop a stable envelope protein in its pre-fusion trimer conformation with only limited success in producing soluble, stable trimers of the envelope protein capable of inducing a broadly neutralizing antibody response. For example, the so-called SOSIP mutations (501C, 605C and 559P) have been introduced into the envelope protein sequence to improve the formation of a soluble gp140 trimer fraction (Sanders et al., (2002), *J. Virol.* 76(17): 8875-89). The so-called SOSIP mutations include cysteine residues at positions 501 and 605, and a proline residue at position 559 according to the numbering in gp160 of HIV-1 isolate HXB2, which is the conventional numbering scheme used in the field. The introduction of the two cysteine residues at positions 501 and 605, which are close to one another in the three-dimensional protein structure results in a disulfide bridge. SOSIP mutant envelope proteins, such as BG505_SOSIP and B41_SOSIP (envelope proteins from HIV strains BG505 and B41 (i.e. 9032-08.A1.4685) strains with SOSIP mutations), have been used in vaccine studies and shown to induce tier 2 autologous neutralizing Abs (Sanders et al., *Science* (2015), 349(6224): 139-140).

However, even though the so-called SOSIP mutations are capable of stabilizing the trimer form of the envelope protein, the trimer fraction of such SOSIP mutants is usually below 10%, with large amounts of monomer and aggregates still produced. Even the SOSIP mutant BG505_SOSIP, which is one of the most promising SOSIP mutant envelope proteins known to date in terms of its ability to stabilize the trimer form typically yields up to only 25% of the trimer form (Julien et al., *Proc. Nat. Acad. Sci.* (2015), 112(38), 11947-52). Moreover, in this trimer fraction the trimers are not completely stable as they breathe at the apex. Thus, in addition to the SOSIP mutations, several additional substitutions, such as E64K, A316W, and 201C-433C, have been designed to stabilize the apex and prevent it from breathing (de Taeye et al., *Cell* (2015), 163(7), 1702-15; Kwon et al., (2015) *Nat. Struct. Mol. Biol.* 22(7) 522-31).

Accordingly, there is a need for stabilized trimers of HIV envelope proteins that have improved percentage of trimer formation, improved trimer yield, and/or improved trimer stability. Preferably, such stabilized trimers of HIV envelope proteins would also display good binding with broadly neutralizing antibodies (bNAbs), and relatively limited binding to non-broadly neutralizing Abs (non-bNAbs). It is an object of the invention to provide HIV Env proteins that have improved trimer percentages, and preferably also improved trimer yields.

BRIEF SUMMARY OF THE INVENTION

The invention relates to recombinant HIV envelope proteins from different clades that have improved percentage of trimer formation and/or improved trimer yields as compared to previously described HIV envelope trimers. Env folding is optimized, strain-specific features are repaired, and regions of the prefusion-closed conformation important for the fusion process are stabilized by mutations described herein. This provides a universal approach to optimize the folding and stability of prefusion-closed HIV-1 envelope trimers. The resulting stable and well-folded HIV Env trimers are useful for immunization purposes, e.g. to improve chances of inducing broadly neutralizing antibodies and reducing induction of non-neutralizing and weakly neutralizing antibodies upon administration of the recombinant HIV Env trimers. The invention also relates to isolated nucleic acid molecules and vectors encoding the recombinant HIV envelope proteins, cells comprising the same, and compositions of the recombinant HIV envelope protein, nucleic acid molecule, vector, and/or cells.

In one general aspect, the invention relates to recombinant human immunodeficiency virus (HIV) envelope proteins having particular amino acid residues at identified positions in the envelope protein sequence that stabilize the formation of trimers.

In certain embodiments, a recombinant HIV envelope (Env) protein of the invention comprises the amino acid sequence of an HIV Env protein having the indicated amino acid residues at at least two of the indicated positions selected from the group consisting of:
 (i) Phe, Leu, Met, or Trp at position 651;
 (ii) Phe, Ile, Met, or Trp at position 655;
 (iii) Asn or Gln at position 535;
 (iv) Val, Ile or Ala at position 589;
 (v) Phe or Trp at position 573;
 (vi) Ile at position 204; and
 (vii) Phe, Met, or Ile at position 647,
wherein the numbering of the positions is according to the numbering in gp160 of HIV-1 isolate HXB2. In certain preferred embodiments, the indicated amino acid residue at position 651 is Phe; the indicated amino acid residue at position 655 is Ile; the indicated amino acid residue at position 535 is Asn; and/or the indicated amino acid residue at position 573 is Phe.

In certain embodiments, a recombinant HIV Env protein of the invention comprises the amino acid sequence of an HIV Env protein and an amino acid substitution by the indicated amino acid residue at at least one of the indicated positions selected from the group consisting of:
 (i) Phe, Leu, Met, or Trp at position 651;
 (ii) Phe, Ile, Met, or Trp at position 655;
 (iii) Asn or Gln at position 535;
 (iv) Val, Ile or Ala at position 589;
 (v) Phe or Trp at position 573;
 (vi) Ile at position 204; and
 (vii) Phe, Met, or Ile at position 647,
wherein the HIV Env protein is selected from the group consisting of:
 (1) an HIV Env consensus amino acid sequence, e.g. from clade C (e.g. comprising the amino acid sequence of SEQ ID NO: 2 or 3) or from clade B (e.g. comprising the amino acid sequence of SEQ ID NO: 4 or 5);
 (2) a synthetic HIV Env protein, e.g. comprising (a): the amino acid sequence of SEQ ID NO: 6, or (b): SEQ ID NO: 6 with a mutation of Glu to Arg at position 166, or (c): (a) or (b) with a mutation of the amino acids at positions 501 and 605 into Cys residues and a mutation of the amino acid at position 559 into a Pro residue, or (d): (a), (b) or (c) having a further furin cleavage site mutation, e.g. replacement of the amino acids at positions 508-511 by RRRRRR (SEQ ID NO: 10), or (e) SEQ ID NO: 7, or (f) a mosaic Env sequence such as Env comprising the amino acid sequence of SEQ ID NO: 8 or 9; and
 (3) a parent HIV Env protein, which preferably is a wild-type HIV Env protein, preferably of clade C, comprising at least one repair mutation at an amino acid residue that is found at the corresponding position at a frequency of less than 7.5%, preferably less than 2%, of HIV Env sequences in a collection of at least 100, preferably at least 1000, preferably at least 10000, wild-type HIV Env sequences, wherein the repair mutation is a substitution by an amino acid residue that is found at the corresponding position at a frequency of at least 10% of HIV Env sequences in said collection and preferably the repair mutation is a substitution by the amino acid residue that is found at the corresponding position most frequently in said collection;
and the numbering of the positions is according to the numbering in gp160 of HIV-1 isolate HXB2. In certain preferred embodiments, the indicated amino acid residue at position 651 is Phe; the indicated amino acid residue at position 655 is Ile; the indicated amino acid residue at position 535 is Asn; and/or the indicated amino acid residue at position 573 is Phe.

In certain embodiments, a recombinant HIV Env protein of the invention comprises the amino acid sequence of an HIV Env protein and an amino acid substitution by the indicated amino acid residue at at least one of the indicated positions selected from the group consisting of:
 (i) Phe, Leu, Met, or Trp at position 651;
 (ii) Phe, Ile, Met, or Trp at position 655;
 (iii) Asn or Gln at position 535;
 (iv) Val, Ile or Ala at position 589;
 (v) Phe or Trp at position 573;
 (vi) Ile at position 204; and
 (vii) Phe, Met, or Ile at position 647,
wherein the HIV Env protein is a SOSIP mutant HIV Env protein comprising at least one mutation resulting in the indicated amino acid residue(s) at the indicated positions selected from the group consisting of:
 (a) Cys at positions 501 and 605;
 (b) Pro at position 559; and
 (c) Cys at positions 501 and 605 and Pro at position 559; and
the numbering of the positions is according to the numbering in gp160 of HIV-1 isolate HXB2. In certain preferred embodiments, the indicated amino acid residue at position 651 is Phe; the indicated amino acid residue at position 655 is Ile; the indicated amino acid residue at position 535 is Asn; and the indicated amino acid residue at position 573 is Phe.

In other embodiments, a recombinant HIV Env protein of the invention further comprises an indicated amino acid residue at at least one of the indicated positions selected from the group consisting of:
 (viii) Gln, Glu, Ile, Met, Val, Trp or Phe, preferably Gln or Glu, at position 588;
 (ix) Lys at position 64, or Arg at position 66, or Lys at position 64 and Arg at position 66;
 (x) Trp at position 316;
 (xi) Cys at both positions 201 and 433;
 (xii) Pro at position 556, or Pro at position 558, or Pro at positions 556 and 558;
 (xiii) replacement of the loop at amino acid positions 548-568 (HR1-loop) by a loop having 7-10 amino acids, preferably a loop of 8 amino acids, e.g. having a sequence chosen from any one of (SEQ ID NOs: 12-17);

(xiv) Gly at position 568, or Gly at position 569, or Gly at position 636, or Gly at both positions 568 and 636, or Gly at both positions 569 and 636; and/or (xv) Tyr at position 302, or Arg at position 519, or Arg at position 520, or Tyr at position 302 and Arg at position 519, or Tyr at position 302 and Arg at position 520, or Tyr at position 302 and Arg at both positions 519 and 520.

In certain embodiments, a recombinant HIV Env protein of the invention further comprises a mutation in the furin cleavage sequence of the HIV Env protein, such as a replacement at positions 508-511 by RRRRRR (SEQ ID NO: 10).

In one embodiment, the recombinant HIV Env protein is a gp140 protein.

In another embodiment, the recombinant HIV Env protein is a gp160 protein.

In certain embodiments, the recombinant HIV Env protein is truncated in the cytoplasmic region, e.g. after 7 amino acids of the cytoplasmic region.

In another general aspect, the invention relates to a trimeric complex comprising a noncovalent oligomer of three of any of the recombinant HIV Env proteins described herein.

It is another general aspect of the invention to provide a method to improve the folding and stability (measured as increased trimer percentage and/or trimer yield) of a parent HIV Env protein, the method comprising repairing the amino acid sequence of the parent HIV Env protein by introducing at least one repair mutation, preferably at least 3 repair mutations in the parent HIV Env protein, wherein a repair mutation is an amino acid substitution at an amino acid residue that is present at the corresponding position at a frequency of less than 7.5%, preferably less than 2%, of HIV Env sequences in a collection of at least 100, preferably at least 500, preferably at least 1000, preferably at least 10000, wild-type HIV Env sequences, wherein the substitution is by an amino acid residue that is present at the corresponding position at a frequency of at least 10% of HIV Env sequences in said collection and preferably the substitution is by the amino acid residue that is present at the corresponding position most frequently in said collection. The invention also provides a repaired HIV Env protein that is obtainable by said method of the invention for improving the folding and stability (measured as trimer percentage and/or trimer yield) of a HIV Env protein. The invention also provides a pharmaceutical composition comprising said repaired HIV Env protein. The invention also provides a method for producing a HIV Env protein, comprising the method for repairing the HIV Env protein described herein, and expressing nucleic acid encoding the repaired stabilized HIV Env protein in a recombinant host cell.

In another general aspect, the invention relates to a recombinant HIV Env protein comprising an amino acid sequence that is at least 95%, 96%, 97%, 98%, 99% or 100% identical to SEQ ID NO: 2, wherein preferably positions 204, 535, 573, 589, 647, 651, and 655, and preferably further positions 64, 66, 201, 316, 433, 501, 508-511, 556, 558, 559, 588, 548-568 and 605 are not taken into account when determining the % identity, and wherein numbering is according to numbering in gp160 of HIV-1 isolate HXB2. In certain embodiments thereof, the recombinant HIV Env protein comprises an amino acid sequence that is at least 98%, 99% or 100% identical to SEQ ID NO: 3, wherein preferably positions 204, 535, 573, 589, 647, 651, and 655, and preferably further positions 64, 66, 201, 316, 433, 508-511, 556, 558, 588, and 548-568 are not taken into account when determining the % identity, and wherein numbering is according to numbering in gp160 of HIV-1 isolate HXB2.

In another general aspect, the invention relates to a recombinant HIV Env protein comprising an amino acid sequence that is at least 95%, 96%, 97%, 98%, 99% or 100% identical to SEQ ID NO: 4, wherein preferably positions 204, 535, 573, 589, 647, 651, and 655, and preferably further positions 64, 66, 201, 316, 433, 501, 508-511, 556, 558, 559, 588, 548-568 and 605 are not taken into account when determining the % identity, and wherein numbering is according to numbering in gp160 of HIV-1 isolate HXB2. In certain embodiments thereof, the recombinant HIV Env protein comprises an amino acid sequence that is at least 98%, 99% or 100% identical to SEQ ID NO: 5, wherein preferably positions 204, 535, 573, 589, 647, 651, and 655, and preferably further positions 64, 66, 201, 316, 433, 508-511, 556, 558, 588, and 548-568 are not taken into account when determining the % identity, and wherein numbering is according to numbering in gp160 of HIV-1 isolate HXB2.

In these aspects and embodiments, one or more of the amino acids at the indicated positions that are not taken into account for determining the % identity, are preferably chosen from the amino acids indicated as being preferred herein, e.g. Ile at position 204; Phe, Ala, Leu, or Trp at position 651; etc (see Tables 1 and 2 below).

In another general aspect, the invention relates to a recombinant HIV Env protein comprising an amino acid sequence that is at least 95%, 96%, 97%, 98%, 99% or 100% identical to any one of SEQ ID NOs: 2, 3, 4, 5, 20, 22, 24, 26, 27, 28, 29, 30, 31, or 32, wherein SEQ ID NOs: 20, 22, 24, 26, 27, 28, 29, 30, 31, or 32 are particularly preferred. In this aspect, preferably positions 204, 535, 573, 589, 647, 651, 655, and 658 and preferably further positions 64, 66, 201, 316, 433, 508-511, 556, 558, 588, and 548-568 are not taken into account when determining the % identity, and wherein numbering is according to numbering in gp160 of HIV-1 isolate HXB2. Also in this aspect, one or more of the amino acids at the indicated positions that are not taken into account for determining the % identity, are preferably chosen from the amino acids indicated as being preferred herein in (i)-(vii) of Table 1, (viii)-(xv) of Table 2, and/or (xvi) of Table 1, e.g. Ile at position 204; Phe, Leu, Met, or Trp at position 651; etc.

In another general aspect, the invention relates to a particle, preferably a liposome or nanoparticle, e.g. a self-assembling nanoparticle, displaying on its surface a recombinant HIV Env protein of the invention.

In another general aspect, the invention relates to an isolated nucleic acid molecule encoding a recombinant HIV Env protein of the invention and vectors comprising the isolated nucleic acid molecule operably linked to a promoter. In one embodiment, the vector is a viral vector. In another embodiment, the vector is an expression vector. In one preferred embodiment, the viral vector is an adenovirus vector.

Another general aspect relates to a host cell comprising the isolated nucleic acid molecule or vector encoding the recombinant HIV Env protein of the invention. Such host cells can be used for recombinant protein production, recombinant protein expression, or the production of viral particles.

Another general aspect relates to methods of producing a recombinant HIV Env protein, comprising growing a host cell comprising an isolated nucleic acid molecule or vector encoding the recombinant HIV Env protein of the invention under conditions suitable for production of the recombinant HIV Env protein.

Yet another general aspect relates to a composition comprising a recombinant HIV Env protein, trimeric complex, isolated nucleic acid molecule, vector, or host cell as described herein, and a pharmaceutically acceptable carrier.

BRIEF DESCRIPTION OF THE FIGURES

The foregoing summary, as well as the following detailed description of the invention, will be better understood when read in conjunction with the appended drawings. It should be understood that the invention is not limited to the precise embodiments shown in the drawings.

In the figures:

FIG. 1A shows a full length HIV Env protein; and

FIG. 1B shows a soluble HIV Env protein containing the so-called SOSIP mutations and a C-terminal truncation beginning at residue 664 according to the numbering in gp160 of HIV-1 isolate HXB2 (SOSIP.644 sequence);

In FIG. 10B, the Env sequence was further optimized by additional mutations (21 extra muts) that were added to repair the C97ZA Env sequence according to the conceptual framework described in FIG. 12 and by introduction of additional stabilizing substitutions (K655I, D589V, A204I and K588E). Trimer yield and the percentage of trimer formation were measured by AlphaLISA assay. The signals were normalized to ConC_SOSIP signal that was set at 1. PNGS is potential N-glycosylation site.

FIG. 13 shows prefusion closed HIV ENV_SOSIP trimers through sequence repair and mutational stabilization. AlphaLISA signals in cell culture supernatant for all SOSIP variants normalized to the ConC_SOSIP for broadly neutralizing antibodies.

FIGS. 14A-14E show analytical SEC profile of control Env_SOSIP variants (Backbone SOSIP), repaired Env variants according to the concept described in Example 12 and FIG. 12, and Env variants with additional stabilizing substitutions according to table 3 using cell culture supernatants after transfection (ConC (FIG. 14A); BG505 (FIG. 14B); C97ZA (FIG. 14C); Du422 (FIG. 14D); sC4 (FIG. 14E)). Mock signal of cell culture supernatant was subtracted from all profiles. The trimer peaks are indicated with *.

DETAILED DESCRIPTION OF THE INVENTION

Figures 1A, 1B:
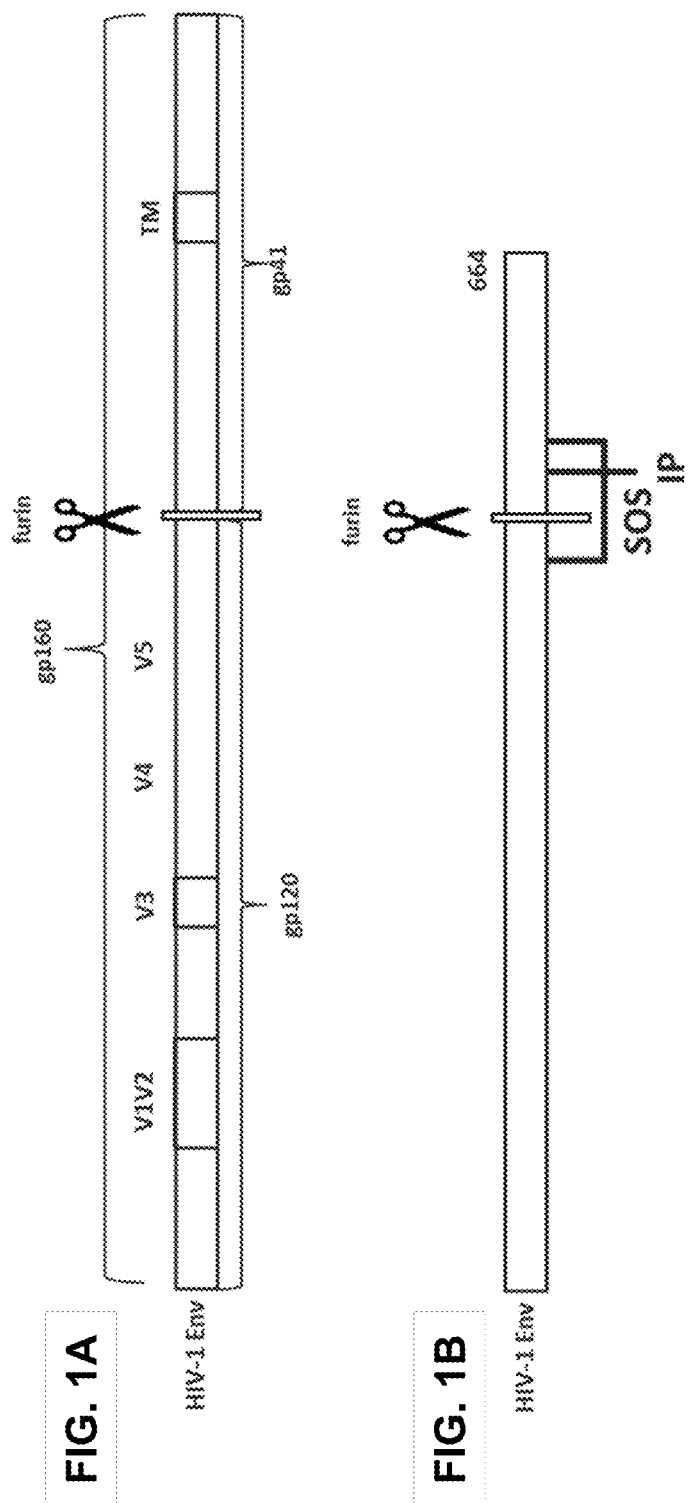
FIGS. 1A and 1B show a schematic representation of the structure of HIV envelope (Env) proteins.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. As used herein, the use of a numerical range expressly includes all possible subranges, all individual numerical values within that range, including integers within such ranges and fractions of the values unless the context clearly indicates otherwise.

Amino acids are referenced throughout the disclosure. There are twenty naturally occurring amino acids, as well as many non-naturally occurring amino acids. Each known amino acid, including both natural and non-natural amino acids, has a full name, an abbreviated one letter code, and an abbreviated three letter code, all of which are well known to those of ordinary skill in the art. For example, the three and one letter abbreviated codes used for the twenty naturally occurring amino acids are as follows: alanine (Ala; A), arginine (Arg; R), aspartic acid (Asp; D), asparagine (Asn; N), cysteine (Cys; C), glycine (Gly; G), glutamic acid (Glu; E), glutamine (Gln; Q), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y) and valine (Val; V). Amino acids can be referred to by their full name, one letter abbreviated code, or three letter abbreviated code.

Unless the context clearly dictates otherwise, the numbering of positions in the amino acid sequence of an HIV envelope protein as used herein is according to the numbering in gp160 of HIV-1 isolate HXB2 as for instance set forth in Korber et al. (Human Retroviruses and AIDS 1998: A Compilation and Analysis of Nucleic Acid and Amino Acid Sequences. Korber et al., Eds. Theoretical Biology and Biophysics Group, Los Alamos National Laboratory, Los Alamos, N. Mex.), which is incorporated by reference herein in its entirety. Numbering according to HXB2 is conventional in the field of HIV Env proteins. The gp160 of HIV-1 isolate HXB2 has the amino acid sequence shown in SEQ ID NO: 1. Alignment of an HIV Env sequence of interest with this sequence can be used to find the corresponding amino acid numbering in the sequence of interest.

The phrases "comprises the amino acid sequence of" an HIV Env protein having the indicated amino acid residue at at least one of the indicated positions selected from the group consisting of and "comprises one or more of the following (amino acid residues)" are used interchangeably herein.

The term "percent (%) sequence identity" or "% identity" describes the number of matches ("hits") of identical amino acids of two or more aligned amino acid sequences as compared to the number of amino acid residues making up the overall length of the amino acid sequences. In other terms, using an alignment, for two or more sequences the percentage of amino acid residues that are the same (e.g. 95%, 97% or 98% identity) may be determined, when the sequences are compared and aligned for maximum correspondence as measured using a sequence comparison algorithm as known in the art, or when manually aligned and visually inspected. The sequences which are compared to determine sequence identity may thus differ by substitution(s), addition(s) or deletion(s) of amino acids. Suitable programs for aligning protein sequences are known to the skilled person. The percentage sequence identity of protein sequences can, for example, be determined with programs such as CLUSTALW, Clustal Omega, FASTA or BLAST, e.g using the NCBI BLAST algorithm (Altschul S F, et al (1997), Nucleic Acids Res. 25:3389-3402).

A 'collection of HIV Env sequences' as used herein is a collection of a representative number (e.g. at least 100, or 500, or 1000, or more) of random sequences of wild-type HIV Env proteins, which may be from the same clade (e.g. clade C) or from different clades (e.g. clades A, B, C, etc). Suitable collections of such sequences are available in databases, or subcollections can be extracted therefrom, e.g. the HIV Sequence Database (Los Alamos National Laboratory). Such a collection comprises preferably at least 100 HIV Env protein sequences, 1000 HIV Env protein sequences, at least 10000 HIV Env protein sequences, at least 50000 HIV Env protein sequences, and may contain more than 90000 HIV Env protein sequences.

A 'corresponding position' in a HIV Env protein refers to position of the amino acid residue when at least two HIV Env sequences are aligned. Unless otherwise indicated, amino acid position numbering for these purposes is according to numbering in gp160 of HIV-1 isolate HXB2, as customary in the field.

A 'stabilizing mutation' as used herein is a mutation as described herein in any of entries (i)-(vii), or (xvi), of Table 1, or (viii)-(xv) of Table 2, which increases the percentage of trimer and/or the trimer yield (which can for instance be measured according to AlphaLISA or SEC-MALS assays described herein) of an HIV Env protein as compared to a parent molecule when the mutation is introduced by substitution of the corresponding amino acid in said parent molecule. The amino acids resulting from such stabilizing mutations typically are rarely, if at all, found in Env proteins of wild-type HIV isolates.

A 'repair mutation' as used herein is a substitution of an amino acid residue in a parent HIV Env protein, which amino acid residue is present in less than 7.5%, preferably less than 2%, at the corresponding position in a collection of HIV Env protein sequences, wherein the substitution is by an amino acid that is present at the corresponding position in said collection more frequently, e.g. in at least 10% of HIV Env proteins in said collection, and preferably is by an amino acid that is present at the corresponding position in said collection in at least 20% of HIV Env proteins or is the most frequently occurring amino acid at the corresponding position in said collection. The amino acids resulting from such repair mutations thus typically are found in a relatively high percentage of Env proteins of wild type HIV isolates, and may in several cases be the same as those at the corresponding position in consensus HIV Env sequences.

A 'repaired and stabilized' HIV Env sequence as used herein typically contains at least one repair mutation and at least one stabilizing mutation, preferably multiple repair mutations and multiple stabilizing mutations as compared to the parent HIV Env sequence.

The terms 'natural' or 'wild-type' are used interchangeably herein when referring to HIV strains (or Env proteins therefrom), and refer to HIV strains (or Env proteins therefrom) as occurring in nature, e.g. such as in HIV-infected patients.

The invention generally relates to recombinant HIV envelope (Env) proteins comprising certain amino acid substitutions at indicated positions in the envelope protein sequence that stabilize the trimer form of the envelope protein. Introducing one or more of the identified amino acid substitutions of the invention into the sequence of an HIV envelope protein can result in an increased percentage of trimer formation and/or an increased trimer yield. This can for instance be measured using trimer-specific antibodies, melting temperature, size exclusion chromatography, and binding to antibodies that bind to correctly folded (stable trimeric) or alternatively to incorrectly folded (non-stable or non-trimeric) Env protein, and increased trimer percentage and/or trimer yield is considered indicative of stable, native, correctly folded Env protein.

Human immunodeficiency virus (HIV) is a member of the genus Lentivirinae, which is part of the family of Retroviridae. Two species of HIV infect humans: HIV-1 and HIV-2. HIV-1 is the most common strain of HIV virus, and is known to be more pathogenic than HIV-2. As used herein, the terms "human immunodeficiency virus" and "HIV" refer to, but are not limited to, HIV-1 and HIV-2. In preferred embodiments, HIV refers to HIV-1.

HIV is categorized into multiple clades with a high degree of genetic divergence. As used herein, the term "HIV clade" or "HIV subtype" refers to related human immunodeficiency viruses classified according to their degree of genetic similarity. The largest group of HIV-1 isolates is called Group M (major strains) and consists of at least ten clades, A through J.

In one general aspect, the invention relates to a recombinant HIV envelope (Env) protein. The term "recombinant" when used with reference to a protein refers to a protein that is produced by a recombinant technique or by chemical synthesis in vitro. According to embodiments of the invention, a "recombinant" protein has an artificial amino acid sequence in that it contains at least one sequence element (e.g., amino acid substitution, deletion, addition, sequence replacement, etc.) that is not found in the corresponding naturally occurring sequence. Preferably, a "recombinant" protein is a non-naturally occurring HIV envelope protein that is optimized to induce an immune response or produce an immunity against one or more naturally occurring HIV strains.

The terms "HIV envelope protein," "HIV Env," and "HIV Env protein" refer to a protein, or a fragment or derivative thereof, that is in nature expressed on the envelope of the HIV virion and enables an HIV to target and attach to the plasma membrane of HIV infected cells. The terms "envelope" and "Env" are used interchangeably throughout the disclosure. The HIV env gene encodes the precursor protein gp160, which is proteolytically cleaved into the two mature envelope glycoproteins gp120 and gp41. The cleavage reaction is mediated by a host cell protease, furin (or by furin-like proteases), at a sequence motif highly conserved in retroviral envelope glycoprotein precursors. More specifically, gp160 trimerizes to $(gp160)_3$ and then undergoes cleavage into the two noncovalently associated mature glycoproteins gp120 and gp41. Viral entry is subsequently mediated by a trimer of gp120/gp41 heterodimers. Gp120 is the receptor binding fragment, and binds to the CD4 receptor (and the co-receptor) on a target cell that has such a receptor, such as, e.g., a T-helper cell. Gp41, which is non-covalently bound to gp120, is the fusion fragment and provides the second step by which HIV enters the cell. Gp41 is originally buried within the viral envelope, but when gp120 binds to a CD4 receptor and co-receptor, gp120 changes its conformation causing gp41 to become exposed, where it can assist in fusion with the host cell. Gp140 is the ectodomain of gp160.

According to embodiments of the invention, an "HIV envelope (Env) protein" can be a gp160 or gp140 protein, or combinations, fusions, truncations, or derivatives thereof. For example, an "HIV envelope protein" can include a gp120 protein noncovalently associated with a gp41 protein. An "HIV envelope protein" can also be a truncated HIV envelope protein including, but not limited to, envelope proteins comprising a C-terminal truncation in the ectodomain (i.e. the domain that extends into the extracellular space), a truncation in the gp41, such as a truncation in the ectodomain of gp41, in the transmembrane domain of gp41, or a truncation in the cytoplasmic domain of gp41. An HIV envelope protein can also be a gp140, corresponding to the gp160 ectodomain, or an extended or truncated version of gp140. Expression of gp140 proteins has been described in several publications (e.g. Zhang et al., 2001; Sanders et al., 2002; Harris et al., 2011), and the protein can also be ordered from service providers, in different variants e.g. based on different HIV strains. A gp140 protein according to the invention can have a cleavage site mutation so that the gp120 domain and gp41 ectodomain are not cleaved and covalently linked, or alternatively the gp120 domain and gp41 ectodomain can be cleaved and covalently linked, e.g. by a disulfide bridge (such as for instance in the SOSIP variants). An "HIV envelope protein" can further be a derivative of a naturally occurring HIV envelope protein having sequence mutations, e.g., in the furin cleavage sites, and/or so-called SOSIP mutations. An HIV envelope protein according to the invention can also have a cleavage site so that the gp120 and gp41 ectodomain can be non-covalently linked.

In preferred embodiments of the invention, the HIV Env protein is a gp140 protein or a gp160 protein, and more preferably a gp140 protein. In other preferred embodiments the Env protein is truncated, e.g. by deletion of the residues after the $7^{th}$ residue of the cytoplasmic region as compared to a natural Env protein.

According to embodiments of the invention, an "HIV envelope protein" can be a trimer or a monomer, and is preferably a trimer. The trimer can be a homotrimer (e.g., trimers comprising three identical polypeptide units) or a heterotrimer (e.g., trimers comprising three polypeptide units that are not all identical). Preferably, the trimer is a homotrimer. In case of a cleaved gp140 or gp160, it is a trimer of polypeptide units that are gp120-gp41 dimers, and in case all three of these dimers are the same, this is considered a homotrimer.

An "HIV envelope protein" can be a soluble protein, or a membrane bound protein. Membrane bound envelope proteins typically comprise a transmembrane domain, such as in the full length HIV envelope protein comprising a transmembrane domain (TM) as shown in FIG. 1A. Membrane bound proteins can have a cytoplasmic domain, but do not require a cytoplasmic domain to be membrane bound. Soluble envelope proteins comprise at least a partial or a complete deletion of the transmembrane domain. For instance, the C-terminal end of a full length HIV envelope protein can be truncated to delete the transmembrane domain, thereby producing a soluble protein, as shown in FIG. 1B. However, the HIV envelope protein can still be soluble with shorter truncations and alternative truncation positions to those shown in FIG. 1B. Truncation can be done at various positions, and non-limiting examples are after amino acid 664, 655, 683, etc. which all result in soluble protein. A membrane-bound Env protein according to the invention may comprise a complete or a partial C-terminal domain (e.g. by partial deletion of the C-terminal cytoplasmic domain, e.g. in certain embodiments after the $7^{th}$ residue of the cytoplasmic region) as compared to a native Env protein.

A signal peptide is typically present at the N-terminus of the HIV Env protein when expressed, but is cleaved off by signal peptidase and thus is not present in the mature protein. The signal peptide can be interchanged with other signal sequences, and some non-limiting examples of signal peptides are provided herein in SEQ ID NOs: 11, 18, 33, and 34.

According to embodiments of the invention, the HIV envelope protein, e.g., gp160, or gp140, can be derived from an HIV envelope protein sequence from any HIV clade (or 'subtype'), e.g., clade A, clade B, clade C, clade D, clade E, clade F, clade G, clade H, etc, or combinations thereof (such as in 'circulating recombinant forms' or CRFs derived from recombination between viruses of different subtypes, e.g BC, AE, AG, BE, BF, ADG, etc). The HIV envelope protein sequence can be a naturally occurring sequence, a mosaic sequence, a consensus sequence, a synthetic sequence, or any derivative or fragment thereof. A "mosaic sequence" contains multiple epitopes derived from at least three HIV envelope sequences of one or more HIV clades, and may be designed by algorithms that optimize the coverage of T-cell epitopes. Examples of sequences of mosaic HIV envelope proteins include those described in, e.g., Barouch et al, *Nat Med* 2010, 16: 319-323; and WO 2010/059732, such as for instance those shown in SEQ ID NOs: 8 and 9. As used herein "consensus sequence" means an artificial sequence of amino acids based on an alignment of amino acid sequences of homologous proteins, e.g. as determined by an alignment (e.g. using Clustal Omega) of amino acid sequences of homologous proteins. It is the calculated order of most frequent amino acid residues, found at each position in a sequence alignment, based upon sequences of Env from at least 1000 natural HIV isolates. A "synthetic sequence" is a non-naturally occurring HIV envelope protein that is optimized to induce an immune response or produce immunity against more than one naturally occurring HIV strains. Mosaic HIV envelope proteins are non-limiting examples of synthetic HIV envelope proteins. In preferred embodiments of the invention, the HIV Env protein is a consensus Env protein, or a synthetic Env protein, having at least one of the indicated amino acids at the indicated positions (i)-(vii) according to the invention. Particularly preferred are consensus Env proteins having at least one, preferably at least two of the indicated amino acid residues at the indicated positions (i)-(vii) according to the invention, preferably having further SOSIP and/or furin cleavage site mutations as described below.

In certain embodiments of the invention, an HIV envelope protein, whether a naturally occurring sequence, mosaic sequence, consensus sequence, synthetic sequence etc., comprises additional sequence mutations e.g., in the furin cleavage sites, and/or so-called SOSIP mutations.

In some embodiments of the invention, an HIV envelope protein is a "SOSIP mutant HIV Env protein." The so-called SOSIP mutations are trimer stabilizing mutations that include the 'SOS mutations' (Cys residues at positions 501 and 605, which results in the introduction of a possible disulfide bridge between the newly created cysteine residues) and the 'IP mutation' (Pro residue at position 559). According to embodiments of the invention, a SOSIP mutant Env protein comprises at least one mutation selected from the group consisting of Cys at positions 501 and 605; Pro at position 559; and preferably Cys at positions 501 and 605 and Pro at position 559. A SOSIP mutant HIV Env protein can further comprise other sequence mutations, e.g., in the furin cleavage site. In addition, in certain embodiments it is possible to further add mutations such that the Env protein comprises Pro at position 556 or position 558 or at positions 556 and 558, which were found herein to be capable of acting not only as alternatives to Pro at position 559 in a SOSIP variant, but also as additional mutations that could further improve trimer formation of a SOSIP variant that already has Pro at position 559.

In certain preferred embodiments of the invention, a SOSIP mutant HIV Env protein comprises Cys at positions 501 and 605, and Pro at position 559.

In certain embodiments, an HIV envelope protein of the invention further comprises a mutation in the furin cleavage site. The mutation in the furin cleavage sequence can be an amino acid substitution, deletion, insertion, or replacement of one sequence with another, or replacement with a linker amino acid sequence. Preferably in the present invention, mutating the furin cleavage site can be used to optimize the cleavage site, so that furin cleavage is improved over wild-type, for instance by a replacement of the sequence at residues 508-511 with RRRRRR (SEQ ID NO: 10) [i.e. replacement of a typical amino acid sequence (e.g. EK) at positions 509-510 with four arginine residues (i.e. two replacements and two additions), while at positions 508 and 511, there are already arginine residues present in most HIV Env proteins, so these typically do not need to be replaced, but since the end result in literature is often referred to as amino acid sequence RRRRRR, we kept this nomenclature herein]. Other mutations that improve furin-cleavage are known and can also be used. Alternatively, it is possible to replace the furin cleavage site with a linker, so that furin cleavage is no longer necessary but the protein will adopt a native-like conformation (e.g. described in (Sharma et al, 2015) and (Georgiev et al, 2015)).

In particular embodiments of the invention, an HIV envelope protein of the invention further comprises both the so-called SOSIP mutations (preferably Cys at positions 501 and 605, and Pro at position 559) and a sequence mutation in the furin cleavage site, preferably a replacement of the sequence at residues 508-511 with RRRRRR (SEQ ID NO: 10). In certain preferred embodiments, the HIV Env comprises both the indicated SOSIP and furin cleavage site mutations, and in addition further comprises a Pro residue at position 556 or 558, most preferably at both positions 556 and 558.

In preferred embodiments of the invention, the amino acid sequence of the HIV envelope protein is a consensus sequence, such as an HIV envelope clade C consensus or an HIV envelope clade B consensus. In a particularly preferred embodiment, the amino acid sequence of the HIV envelope protein is an HIV envelope clade C consensus.

Exemplary HIV envelope proteins that can be used in the invention include HIV envelope clade C consensus (SEQ ID NO: 2) and HIV envelope clade B consensus (SEQ ID NO: 4). These HIV envelope clade C and clade B consensus sequences can comprise additional mutations that, e.g., enhance stability and/or trimer formation, such as for instance the so-called SOSIP mutations and/or a sequence mutation in the furin cleavage site as described above, such as for instance in the ConC_SOSIP sequence shown in SEQ ID NO: 3 and the ConB_SOSIP sequence shown in SEQ ID NO: 5.

Other non-limiting examples of preferred HIV envelope protein sequences that can be used in the invention (as 'background' or 'parent' molecule, wherein then one or more of the mutations of the invention are introduced) include synthetic HIV Env proteins, for instance comprising the amino acid sequence of SEQ ID NO: 6, or SEQ ID NO: 6 with a mutation of Glu to Arg at position 166, either of those optionally having further SOSIP and/or furin cleavage site mutations as described above. Another non-limiting example is SEQ ID NO: 7. Further non-limiting examples are mosaic HIV envelope proteins, such as those having the amino acid sequence of SEQ ID NO: 8 or 9.

In certain embodiments, the parent molecule is a wild-type HIV Env protein, wherein one or preferably more amino acids have been repaired according to methods described herein. Such parent molecules comprise at least one repair mutation at an amino acid residue that is present at the corresponding position at a frequency of less than 7.5%, preferably less than 2%, of HIV Env sequences in a collection of at least 100, preferably at least 500, preferably at least 1000, preferably at least 10000, preferably at least 20000, wild-type HIV Env sequences, wherein the repair mutation is a substitution by an amino acid residue that is present at the corresponding position at a frequency of at least 10% of HIV Env sequences in said collection. Preferably said substitution is by an amino acid residue that is present at the corresponding position at a frequency of at least 15%, at least 20%, at least 25%, of HIV Env sequences in said collection. Preferably, said substitution is by the amino acid residue that is present at the corresponding position most frequently in said collection. In certain preferred embodiments, said parent molecules comprise at least 2, 3, 4, 5, 6, 7, 8, 9, 10, 11, 12, 13, 14, 15, 16, 17, 18, 19, or at least 20 of such repair mutations. Preferably at least 10%, 20%, 30%, 40%, 50%, 60%, 70%, 80%, 90% or all of the amino acid residues that are present at the corresponding positions at a frequency of less than 2% of HIV Env sequences in said collection are repaired in the parent molecule as compared to the wild-type Env protein, In certain embodiments, at least 10%, 20%, 30%, 40%, 50%, 60%, 70%, 80%, 90% or all of the amino acid residues that are present at the corresponding positions at a frequency of less than 7.5% of HIV Env sequences in said collection are repaired in the parent molecule as compared to the wild-type Env protein. In certain embodiments, the wild-type HIV Env protein is from a clade A, B, or C strain, preferably from a clade C strain. As a result of this repairing mutations, the parent molecule will show more resemblance to a HIV Env consensus sequence than the original wild-type strain, hence the repaired amino acid residue is sometimes referred to herein as 'consensus amino acid' or 'consensus residue'. The result of this repair activity is greatly enhanced properties of the resulting parent molecule with respect to folding, trimerization, expression, and/or stability, and the resulting molecule is referred to herein as a 'repaired Env protein'. The addition of the stabilizing mutations of the invention (e.g. one or more of (i)-(vii) (Table 1), and/or (xvi) (Table 1), and/or optionally (viii)-(xv) (Table 2), into such parent molecules leads to an even further improvement in one or more of trimer percentage, trimer yield, stability, broadly neutralizing antibody binding, folding, and the resulting molecules that are derived from wild-type HIV Env proteins are referred to herein as 'repaired and stabilized Env protein'. It will be clear to the skilled person that introduction of the stabilizing mutations actually diverts the resulting sequence a bit from a consensus sequence, so the net result of greatly enhanced properties of repaired and stabilized HIV Env molecules is based on two entirely different concepts.

Mutations resulting in the indicated amino acids at positions (i)-(vii) according to the present invention can also be used in HIV Env proteins wherein no SOSIP mutations are present (e.g. in Env consensus sequences or in Env proteins from wild-type HIV isolates) and are likely to also improve the trimerization thereof, as the mutations of the invention are independent from the SOSIP mutations, and in addition were shown to work in several different HIV Env protein backbones. Indeed, it is shown herein that mutations according to the invention can work in the absence of the SOS-mutations as well as in the absence of the IP-mutation to improve HIV Env trimerization properties.

A recombinant HIV envelope protein according to embodiments of the invention comprises an HIV envelope protein having certain amino acid residue(s) at specified positions in the amino acid sequence of an HIV envelope protein. In particular, seven positions in the envelope protein were identified, as well as the particular amino acid residues to be desirable at each of the identified positions. The identified positions in the envelope protein sequence include (i) position 651, (ii) position 655, (iii) position 535, (iv) position 589, (v) position 573, (vi) position 204, and (vii) position 647, wherein the numbering of the positions is according to the numbering in gp160 of HIV-1 isolate HXB2. An HIV Env protein according to the invention has the specified amino acid residue(s) in at least one of the indicated positions (i)-(vii), preferably at least two of the indicated positions (i)-(vii), more preferably at least three of the indicated positions (i)-(vii). The particular amino acid residues that are desirable to be at each of the identified positions according to embodiments of the invention are shown in Table 1. The preferred positions of these options are (i), (ii), (iii), (iv), (vi), and/or (vii). Particularly preferred positions of these options are (i), (ii), (iii), (iv), and/or (vii). An additional preferred option is (xvi), mentioned in some more detail later herein.

TABLE 1

Desirable Amino Acids at Indicated Positions in the Recombinant HIV Env Proteins According to Embodiments of the Invention

| No. | Position[1] | Desirable Amino Acid Residue |
|---|---|---|
| (i) | 651 | Phe, Leu, Met, or Trp (preferably Phe) |
| (ii) | 655 | Phe, Ile, Met, or Trp (preferably Ile) |
| (iii) | 535 | Asn or Gln (preferably Asn) |
| (iv) | 589 | Val, Ile, or Ala (preferably Val or Ile, most preferably Val) |
| (v) | 573 | Phe or Trp (preferably Phe) |
| (vi) | 204 | Ile |
| (vii) | 647 | Phe, Met, or Ile (preferably Phe) |
| (xvi) | 658 | Val, Ile, Phe, Met, Ala, or Leu (preferably Val or Ile, most preferably Val) |

[1]According to the numbering in gp160 of HIV-1 isolate HXB2

The amino acid sequence of the HIV envelope protein into which one or more desirable amino acid (or indicated amino acid) substitutions at the one or more indicated positions are introduced is referred to as the "backbone HIV envelope sequence" or "parent HIV envelope sequence." For example, if position 651 in the ConC_SOSIP sequence of SEQ ID NO: 3 is mutated to Phe, then the ConC_SOSIP sequence is considered to be the "backbone" or "parent" sequence. Any HIV envelope protein can be used as the "backbone" or "parent" sequence into which a novel stabilizing mutation according to an embodiment of the invention can be introduced, either alone or in combination with other mutations, such as the so-called SOSIP mutations and/or mutations in the furin cleavage site. Non-limiting examples of HIV Env protein that could be used as backbone include HIV Env protein from a natural HIV isolate, a synthetic HIV Env protein, or a consensus HIV Env protein, and in certain non-limiting examples include those comprising SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9.

According to embodiments of the invention, the HIV envelope protein can have the indicated amino acid residue at at least one of the indicated positions selected from the group consisting of positions 651, 655, 535, 589, 573, 204, and 647, such as the indicated amino acid residue at one, two, three, four, five, six, or seven positions. Preferably, the HIV envelope protein is substituted at one, two or three of the indicated positions, and more preferably the HIV envelope protein is substituted at at least two of the indicated positions. Even more preferably, the HIV Env protein is substituted at three of the indicated positions, four of the indicated positions, five of the indicated positions, six of the indicated positions, or all seven of the indicated positions. Preferably, the HIV envelope protein contains the indicated amino acid residues at at least two of the indicated positions. More preferably, the HIV envelope protein contains the indicated amino acid residues at three of the indicated positions. In other preferred embodiments, the HIV envelope protein contains the indicated amino acid residues at four, five, six, or all seven of the indicated positions.

Embodiments of HIV Env proteins having the indicated amino acids at multiple positions are (positions numbered according to numbering in gp160 of HIV-1 isolate HXB2 followed by one letter amino acid code for the residue present on that position, positions within one HIV Env protein embodiment divided by commas [e.g. an embodiment of an Env protein having Phe at position 651 and Ile at position 655 is described as 651F, 655I], while different embodiments (i.e. different HIV Env proteins) are divided by semicolons) include the following. For Env proteins with the indicated amino acids at two positions: 651F, 655I; 651F, 655F; 651F, 655M; 651F, 655W; 651F, 535N; 651F, 535Q; 651F, 589V; 651F, 589I; 651F, 589A; 651F, 573F; 651F, 573W; 651F, 204I; 651F, 647F; 651F, 647I; 651F, 647M; 651L, 655I; 651L, 655F; 651L, 655M; 651L, 655W; 651L, 535N; 651L, 535Q; 651L, 589V; 651L, 589I; 651L, 589A; 651L, 573F; 651L, 573W; 651L, 204I; 651L, 647F; 651L, 647I; 651L, 647M; 651M, 655I; 651M, 655F; 651M, 655A; 651M, 655L; 651M, 655W; 651M, 535N; 651M, 535Q; 651M, 589V; 651M, 589I; 651M, 589A; 651M, 573F; 651M, 573W; 651M, 204I; 651M, 647F; 651M, 647I; 651M, 647M; 651W, 655I; 651W, 655F; 651W, 655M; 651W, 655W; 651W, 535N; 651W, 535Q; 651W, 589V; 651W, 589I; 651W, 589A; 651W, 573F; 651W, 573W; 651W, 204I; 651W, 647F; 651W, 647I; 651W, 647M; 655I, 535N; 655I, 535Q; 655I, 589V; 655I, 589I; 655I, 589A; 655I, 573F; 655I, 573W; 655I, 204I; 655I, 647F; 655I, 647I; 655I, 647M; 655F, 535N; 655F, 535Q; 655F, 589V; 655F, 589I; 655F, 589A; 655F, 573F; 655F, 573W; 655F, 204I; 655F, 647F; 655F, 647I; 655F, 647M; 655M, 535N; 655M, 535Q; 655M, 589V; 655M, 589I; 655M, 589A; 655M, 573F; 655M, 573W; 655M, 204I; 655M, 647F; 655M, 647I; 655M, 647M; 655W, 535N; 655W, 535Q; 655W, 589V; 655W, 589I; 655W, 589A; 655W, 573F; 655W, 573W; 655W, 204I; 655W, 647F; 655W, 647I; 655W, 647M; 535N, 589V; 535N, 589I; 535N, 589A; 535N, 573F; 535N, 573W; 535N, 204I; 535N, 647F; 535N, 647I; 535N, 647M; 535Q, 589V; 535Q, 589I; 535Q, 589A; 535Q, 573F; 535Q, 573W; 535Q, 204I; 535Q, 647F; 535Q, 647I; 535Q, 647M; 589V, 573F; 589V, 573W; 589V, 204I; 589V, 647F; 589V, 647I; 589V, 647M; 589I, 573F; 589I, 573W; 589I, 204I; 589I, 647F; 589I, 647I; 589I, 647M; 589A, 573F; 589A, 573W; 589A, 204I; 589A, 647F; 589A, 647I; 589A, 647M; 573F, 204I; 573F, 647F; 573F, 647I; 573F, 647M; 573W, 204I; 573W, 647F; 573W, 647I; 573W, 647M; 204I, 647F; 204I, 647I; 201I, 647M. Each of those embodiments can be present according to the invention in any HIV Env sequence, such as a wild-type isolate, or a SOSIP mutant HIV Env protein, or a consensus HIV Env protein, or a synthetic HIV Env protein. Each of those embodiments can be combined with one of the preferred amino acids according to the invention at a third position of one of the other indicated positions from (i)-(vii) according to the invention. Such embodiments, having preferred amino acid residues at three positions of the indicated positions (i)-(vii) can be combined with one of the preferred amino acids at a fourth position of one of the other indicated positions from (i)-(vii) according to the invention. Such embodiments, having preferred amino acid residues at four positions of the indicated postions (i)-(vii) can be combined with one of the preferred amino acids at a fifth position of one of the other indicated positions from (i)-(vii) according to the invention. Such embodiments, having preferred amino acid residues at five positions of the indicated postions (i)-(vii) can be combined with one of the preferred amino acids at a sixth position of one of the other indicated positions from (i)-(vii) according to the invention. Such embodiments, having preferred amino acid residues at six positions of the indicated postions (i)-(vii) can be combined with one of the preferred amino acids at a seventh position of one of the other indicated positions from (i)-(vii) according to the invention, such that the Env protein has a preferred amino acid according to the invention at all seven positions (i)-(vii) according to the invention. Any of these further embodiments having preferred amino acids according to the invention at three, four, five, six or seven of the positions (v)-(vii) of the invention, can be present in any HIV Env protein, such as from a wild-type isolate, a SOSIP variant, a consensus HIV Env protein, a synthetic HIV Env protein, and the like.

Preferred Env proteins according to the invention with the indicated amino acids at two positions are: 651F, 655I; 651F, 535N; 651F, 589V; 651F, 589I; 651F, 573F; 651F, 204I; 651F, 647F; 655I, 535N; 655I, 589V; 655I, 589I; 655I, 573F; 655I, 204I; 655I, 647F; 535N, 589V; 535N, 589I; 535N, 573F; 535N, 204I; 535N, 647F; 589V, 573F; 589V, 204I; 589V, 647F; 589I, 573F; 589I, 204I; 589I, 647F; 573F, 204I; 573F, 647F; 204I, 647F. Particularly preferred Env proteins having preferred amino acids at at least two positions according to the invention include: 651F, 655I; 655I, 535N; 655I, 589V; 535N, 589V; 535N, 647F.

Some preferred HIV Env proteins having preferred amino acid residues at three positions are: 651F, 655I, 535N; 651F, 589V, 535N; 651F, 589I, 535N; 651F, 573F, 535N; 651F, 204I, 535N; 651F, 647F, 535N; 655I, 589V, 535N; 655I, 589I, 535N; 655I, 573F, 535N; 655I, 204I, 535N; 655I, 647F, 535N; 589V, 573F, 535N; 589V, 204I, 535N; 589V, 647F, 535N; 589I, 573F, 535N; 589I, 204I, 535N; 589I, 647F, 535N; 573F, 204I, 535N; 573F, 647F, 535N; 204I, 647F, 535N; 651F, 655I, 589V; 651F, 573F, 589V; 651F, 204I, 589V; 651F, 647F, 589V; 655I, 573F, 589V; 655I, 204I, 589V; 655I, 647F, 589V; 573F, 204I, 589V; 573F, 647F, 589V; 204I, 647F, 589V; 651F, 655I, 589I; 651F, 647F, 589I; 655I, 573F, 589I; 655I, 204I, 589I; 655I, 647F, 589I; 573F, 204I, 589I; 573F, 647F, 589I; 204I, 647F, 589I; 651F, 655I, 573F; 651F, 204I, 573F; 651F, 647F, 573F; 655I, 204I, 573F; 655I, 647F, 573F; 204I, 647F, 573F; 651F, 655I, 204I; 651F, 647F, 204I; 655I, 647F, 204I; 651F, 655I, 647F; 655I, 651F, 647F; 655I, 651F, 535N; 655I, 589V, 573F; 655I, 589V, 204I. Particularly preferred Env proteins having preferred amino acids at at least three positions according to the invention include: 651F, 655I, 535N; 655I, 589V, 535N; 655I, 573F, 589V; 655I, 204I, 589V; 651F, 655I, 647F.

Some preferred HIV Env proteins having preferred amino acid residues at four positions are: 651F, 655I, 535N, 589V; 651F, 655I, 535N, 573F; 651F, 655I, 589V, 573F; 651F, 535N, 589V, 573F; 655I, 535N, 589V, 573F; 651F, 655I, 535N, 204I; 651F, 655I, 589V, 204I; 651F, 535N, 589V, 204I; 655I, 535N, 589V, 204I; 651F, 655I, 573F, 204I; 651F, 535N, 573F, 204I; 655I, 535N, 573F, 204I; 651F, 589V, 573F, 204I; 655I, 589V, 573F, 204I; 535N, 589V, 573F, 204I; 651F, 655I, 535N, 647F; 651F, 655I, 589V, 647F; 651F, 535N, 589V, 647F; 655I, 535N, 589V, 647F; 651F, 655I, 573F, 647F; 651F, 535N, 573F, 647F; 655I, 535N, 573F, 647F; 651F, 589V, 573F, 647F; 655I, 589V, 573F, 647F; 535N, 589V, 573F, 647F; 651F, 655I, 204I, 647F; 651F, 535N, 204I, 647F; 655I, 535N, 204I, 647F; 651F, 589V, 204I, 647F; 655I, 589V, 204I, 647F; 535N, 589V, 204I, 647F; 651F, 573F, 204I, 647F; 655I, 573F, 204I, 647F; 535N, 573F, 204I, 647F; and 589V, 573F, 204I, 647F.

Some examples of preferred HIV Env proteins having preferred amino acid residues at at least four positions include: 651F, 655I, 647F, I535N; 651F, 655I, 573F, 589V. A preferred example of an HIV Env protein comprising the indicated amino acid residues at at least four positions comprises 535N, 589V, 651F, 655I. Non-limiting examples of such HIV Env proteins are provided in SEQ ID NOs: 20, 22, 24, 26, 27, 28, 29, 30, 31, and 32. Preferably such HIV Env protein is a clade C HIV Env protein or a clade A HIV Env protein, most preferably a clade C HIV Env protein. In certain embodiments, said HIV Env protein further comprises 588E, i.e. it comprises at least 535N, 588E, 589V, 651F, 655I. Non-limiting examples of such HIV Env protein are provided in SEQ ID NOs: 20, 24, 26, 27, 28, 29, 30, 31, and 32. In certain embodiments, said HIV Env further comprises 556P, i.e. it comprises at least 535N, 556P, 589V, 651F, 655I or at least 535N, 556P, 588E, 589V, 651F, 655I. Non-limiting examples of such HIV Env protein are provided in SEQ ID NOs: 22, 24, 26, 27, 29, 30, 31 and 32.

In one embodiment, a recombinant HIV Env protein according to the invention comprises the amino acid sequence of an HIV Env protein having the indicated amino acid residues at at least two of the indicated positions selected from the group consisting of:
  (i) Phe, Leu, Met, or Trp at position 651;
  (ii) Phe, Ile, Met, or Trp at position 655;
  (iii) Asn or Gln at position 535;
  (iv) Val, Ile, or Ala at position 589;
  (v) Phe or Trp at position 573;
  (vi) Ile at position 204; and
  (vii) Phe, Met, or Ile at position 647.

For example, the recombinant HIV Env protein can have one of Phe, Leu, Met, or Trp at position 651, and Asn or Gln at position 535, optionally, additional indicated amino acid residues at the additional indicated positions. Preferably, at least one of the amino acids in (i)-(vii) is introduced into the recombinant HIV Env protein by amino acid substitution. For example, the recombinant HIV Env protein can be produced from an HIV Env protein that contains none or only one of the amino acid residues in (i)-(vii) above such that all or one or more of the at least two indicated amino acid residues are introduced into the recombinant HIV Env protein by amino acid substitution.

In certain embodiments, the recombinant HIV Env protein of the invention further comprises (viii) Gln, Glu, Ile, Met, Val, Trp, or Phe at position 588, wherein Gln or Glu are preferred.

The amino acid sequence of the HIV Env protein into which the above described substitutions are introduced can be any HIV Env protein known in the art in view of the present disclosure, such as, for instance a naturally occurring sequence from HIV clade A, clade B, clade C, etc.; a mosaic sequence; a consensus sequence, e.g., clade B or clade C consensus sequence; a synthetic sequence; or any derivative or fragment thereof. In certain embodiments of the invention, the amino acid sequence of the HIV Env protein comprises additional mutations, such as, for instance, the so-called SOSIP mutations, and/or a mutation in the furin cleavage site.

In one particular embodiment, the HIV Env backbone protein is a SOSIP mutant HIV Env protein comprising at least one mutation selected from the group consisting of Cys at positions 501 and 605; Pro at position 559. In a preferred embodiment, the SOSIP mutant HIV Env protein comprises Cys at positions 501 and 605, and Pro at position 559. According to this embodiment, a recombinant HIV Env protein comprises the amino acid sequence of the SOSIP mutant HIV Env protein and an amino acid substitution by the indicated amino acid residue at at least one of the indicated positions selected from the group consisting of:

(i) Phe, Leu, Met, or Trp at position 651;
(ii) Phe, Ile, Met, or Trp at position 655;
(iii) Asn or Gln at position 535;
(iv) Val, Ile, or Ala at position 589;
(v) Phe or Trp at position 573;
(vi) Ile at position 204; and
(vii) Phe, Met, or Ile at position 647.

The SOSIP mutant HIV Env protein can further comprise a mutation in the furin cleavage site, such as a replacement at positions 608-511 by SEQ ID NO: 10.

In another embodiment, a recombinant HIV Env protein according to the invention comprises the amino acid sequence of an HIV Env protein and an amino acid substitution by the indicated amino acid residue at at least one of the indicated positions selected from the group consisting of:

(i) Phe, Leu, Met, or Trp at position 651;
(ii) Phe, Ile, Met, or Trp at position 655;
(iii) Asn or Gln at position 535;
(iv) Val, Ile, or Ala at position 589;
(v) Phe or Trp at position 573;
(vi) Ile at position 204; and
(vii) Phe, Met, or Ile at position 647, wherein the HIV Env protein is selected from the group consisting of:

(1) an HIV Env consensus sequence, such as a clade C or clade B consensus sequence, e.g. comprising the amino acid sequence of SEQ ID NO: 2, 3, 4 or 5;
(2) a synthetic HIV Env protein, e.g. comprising the amino acid sequence of (a) SEQ ID NO: 6; (b) SEQ ID NO: 6 with a mutation of Glu to Arg at position 166; (c) SEQ ID NO: 7; (d) SEQ ID NO: 8 or 9, (a), (b) or (d) optionally having further SOSIP and/or furin cleavage site mutations as described above.

Preferably, the recombinant HIV Env protein comprises the amino acid sequence of an HIV Env protein and an amino acid substitution by the indicated amino acid residue at at least two of the indicated positions selected from the group consisting of (i)-(vii) above, such as two positions or three positions. However, the recombinant HIV Env protein can comprise an amino acid substitution by the indicated amino acid residue at one or more of the indicated positions, such as one, two, three, four, five, six, or seven of the indicated positions.

In one particular embodiment, the HIV Env backbone protein is an HIV Env consensus clade C comprising an amino acid sequence that is at least 95%, 96%, 97%, 98%, 99% or 100% identical to the amino acid sequence of SEQ ID NO: 2. Preferably, the HIV consensus clade C sequence of SEQ ID NO: 2 further comprises the so-called SOSIP mutations, i.e., Cys at positions 501 and 605, and Pro at position 559, and more preferably further comprises the so-called SOSIP mutations and a mutation in the furin cleavage site, such as for instance a replacement at positions 508-511 by SEQ ID NO: 10. In a particularly preferred embodiment, the HIV Env backbone protein comprises the sequence shown in SEQ ID NO: 3, or a sequence at least 95% identical thereto, wherein preferably amino acids at positions 501, 559, 605, and 508-511 as replaced by SEQ ID NO: 10, are not mutated as compared to SEQ ID NO: 3.

In another particular embodiment, the HIV Env backbone protein is an HIV Env consensus clade B comprising an amino acid sequence that is at least 95%, 96%, 97%, 98%, 99% or 100% identical to the amino acid sequence of SEQ ID NO: 4. Preferably, the HIV consensus clade B sequence of SEQ ID NO: 4 further comprises the so-called SOSIP mutations, i.e., Cys at positions 501 and 605, and Pro at position 559, and more preferably further comprises the so-called SOSIP mutations and a mutation in the furin cleavage site, such as for instance a replacement at positions 508-511 by SEQ ID NO: 10. In a particularly preferred embodiment, the HIV Env backbone protein comprises the sequence shown in SEQ ID NO: 5, or a sequence at least 95% identical thereto, wherein preferably amino acids at positions 501, 559, 605, and 508-511 as replaced by SEQ ID NO: 10, are not mutated as compared to SEQ ID NO: 5.

In yet another particular embodiment, the HIV Env backbone protein is a synthetic HIV Env protein, e.g. comprising the amino acid sequence of (a) SEQ ID NO: 6; (b) SEQ ID NO: 6 with a mutation of Glu to Arg at position 166; (c) SEQ ID NO: 7; or (d) SEQ ID NO: 8 or 9, (a) (b) or (d) optionally having further SOSIP (501C, 605C, 559P) and/or furin cleavage site mutations (508-511RRRRRR) as described above.

In yet other particular embodiments, the HIV Env backbone protein is a HIV Env protein from a wild-type clade A or clade C HIV virus, optionally comprising mutations to repair the sequence according to methods described herein.

Exemplary combinations of two positions in the HIV Env protein that can be simultaneously substituted include residues 535,589; 535,647; and 589,655; such as for instance in double mutants I535N, D589V; I535N, E647F; and D589V, K655I. Other double mutants include K655I, I535N; N651F, K655I; and K655I, I573F. An exemplary combination of three positions in the HIV Env protein that can be simultaneously substituted includes 535,589,655, such as for instance in triple mutant I535N, D589V, K655I. Other triple mutants include K655I, D589V, I573F; and K655I, N651F, I535N.

In certain embodiments of the invention, a recombinant HIV Env protein according to the invention can further comprise an indicated amino acid residue (e.g. via substitution) at one or more additional indicated positions selected from the group consisting of positions (viii) 588, (ix) 64 or 66, (x) 316, (xi) 201/433, (xii) 556 or 558 or 556 and 558, (xiii) 548-568, (xiv) 568, 569 and 636, or (xv) 302, 519 or 520, as shown in Table 2 below. Certain of these amino acid substitutions (e.g. (viii)) were found by the present inventors to combine very well with (combinations of) mutations (i)-(vii) according to the invention as described above. Other of these amino acid substitutions have been previously reported in the literature. For example, De Taeye et al. (*Cell* (2015) 163(7), 1702-15) reported an HIV envelope protein having an E64K and T316W double mutation, and an HIV Env protein having a 66R mutation; and Kwon et al. (*Nat. Struct. Mol. Biol.* (2015) 22(7) 522-31) reported an HIV envelope protein having an I204C, A433C disulfide substitution; and Guenaga et al. (*Immunity* (2017) 46, 792-803) reported an HIV envelope protein having L568G, T569G or N636G, and N302Y, F519R, L520R triple substitution. However, to the best of the knowledge of the inventors, these previously described mutations were not described in combination with any of the novel substitutions described herein, e.g., the substitutions listed in Table 1. These amino acid mutations in combination with the amino acid substitutions of the invention can further increase trimer yield and/or the percentage of trimer formation. These amino acid substitutions can be introduced into any of the recombinant HIV Env proteins described herein in addition to substitution by the indicated amino acid residue at one or more of the indicated positions as described in Table 1.

TABLE 2

Additional Positions of Amino Acid Substitution and Residue of Substitution

| No. | Position[1] | Indicated Amino Acid Residue |
|---|---|---|
| (viii) | 588 | Gln, Glu, Ile, Met, Val, Trp, or Phe (preferably Gln or Glu) |
| (ix) | 64 or 66 | Lys at position 64; or Arg at position 66 |
| (x) | 316 | Trp |
| (xi) | 201 and 433 | Cys at both positions |
| (xii) | 556 or 558 or 556 and 558 | Pro at either or both positions |
| (xiii) | 548-568 (HR1 loop) | Replacement by shorter and less flexible loop having 7-10 amino acids, preferably a loop of 8 amino acids, e.g. having a sequence chosen from any one of (SEQ ID NOs: 12-17) |
| (xiv) | 568, 569, 636 | Gly at any one of these positions, or Gly at both positions 568 and 636, or Gly at both positions 569 and 636 |
| (xv) | 302, 519, 520 | Tyr at position 302, or Arg at position 519, or Arg at position 520; or Tyr at position 302 and Arg at position 519; or Tyr at position 302 and Arg at position 520; or Tyr at position 302 and Arg at both positions 519 and 520 |

[1]According to the numbering in gp160 of HIV-1 isolate HXB2

The substitutions identified at the indicated positions of the present invention [(i)-(vii), see e.g. Table 1] are not or rarely present in natural sequences, are not found in combination in previously reported HIV Env protein sequences, and were not previously suggested to result in improved trimerization of the HIV Env protein, improved trimer yield and/or increased trimer stability. The mutations (ix)-(xi) in Table 2 (that were previously reported by others) are all in the gp120 region, to which the trimer specific antibody PGT145 binds. These mutations keep the trimer closed at the apex (which is at the top of the molecule). The substitutions (xii) and (xiii) are all in the HR1 of gp41. Except for position 204, the mutations of the present invention in Table 1 are all in the gp41 region (at the bottom part of the molecule), but outside the HR1 region. Clearly, the previously described mutations did not provide any suggestion for introduction of the mutations of the present invention, let alone the surprising effects thereof on trimer formation with a closed apex as measured by PGT145 binding. Apart from the point mutations (viii)-(xii) in Table 2, it is also possible to replace the HR1 loop of the Env protein (amino acid residues 548-568 in a wild-type sequence, with numbering according to gp160 of the HXB2 isolate) by a shorter and less flexible loop having 7-10 amino acids, preferably a loop of 8 amino acids, e.g. having a sequence chosen from any one of (SEQ ID NOs: 12-17), see e.g. Kong et al (Nat Commun. 2016 Jun. 28; 7:12040. doi: 10.1038/ncomms12040) that describes such shorter loops replacing the HR1 loop. Such an Env variant, further having the indicated amino acid residues at at least one and preferably at at least two of the indicated positions (i)-(vii) according to the invention, is also an embodiment of the invention. Mutations listed in (viii)-(xiii) can in certain embodiments of the invention be added to HIV Env proteins of the invention, i.e. having one or more of the indicated amino acids at positions (i)-(vii). Also, combinations within the groups (viii)-(xiii) can be made, a non-limiting example being a combination of mutations (in addition to at least one mutation of (i)-(vii)) at (viii) and (xii) (e.g. I535N, A556P, K588E). Some non-limiting examples of double mutants that were made in an HIV Env background with SOSIP mutations and combining mutations at at least one of positions (i)-(vii) and at at least one of positions (viii)-(xiii) include: 535,588; 588,589; 655,588; 558,535; and 655,556; such as for instance I535N, K588E; 588Q, D589V; K655I, K588E; A558P, I535N; and K655I, L556P. Some non-limiting examples of such triple mutants include 558,535,588; 558,535,589; 558,535,655; and 558,535,651, such as for instance A558P, I535N, K588E; A558P, 1535, D589V; A558P, I535N, K655I; and A558P, I535N, N651F.

Further non-limiting examples of combinations according to the invention include 655I, 573F, 589V, 588E; 651F, 655I, 573F, 589V, 588E; 651F, 655I, 573F, 589V, 588E, 535N; 651F, 655I, 573F, 589V, 588E, 535N, 204I; 651F, 655I, 556P; 651F, 535N, 556P; 651F, 589V, 556P; 651F, 589I, 556P; 651F, 573F, 556P; 651F, 204I, 556P; 651F, 647F, 556P; 655I, 535N, 556P; 655I, 589V, 556P; 655I, 589I, 556P; 655I, 573F, 556P; 655I, 204I, 556P; 655I, 647F, 556P; 535N, 589V, 556P; 535N, 589I, 556P; 535N, 573F, 556P; 535N, 204I, 556P; 535N, 647F, 556P; 589V, 573F, 556P; 589V, 204I, 556P; 589V, 647F, 556P; 589I, 573F, 556P; 589I, 204I, 556P; 589I, 647F, 556P; 573F, 204I, 556P; 573F, 647F, 556P; 651F, 655I, 558P; 651F, 535N, 558P; 651F, 589V, 558P; 651F, 589I, 558P; 651F, 573F, 558P; 651F, 204I, 558P; 651F, 647F, 558P; 655I, 535N, 558P; 655I, 589V, 558P; 655I, 589I, 558P; 655I, 573F, 558P; 655I, 204I, 558P; 655I, 647F, 558P; 535N, 589V, 558P; 535N, 589I, 558P; 535N, 573F, 558P; 535N, 204I, 558P; 535N, 647F, 558P; 589V, 573F, 558P; 589V, 204I, 558P; 589V, 647F, 558P; 589I, 573F, 558P; 589I, 204I, 558P; 589I, 647F, 558P; 573F, 204I, 558P; 573F, 647F, 558P; 655I, 589V, 535N, 556P; 651F, 655I, 535N, 556P; 556P, 651F; 556P, 651F, 655I, 535N; 655I, 589V, 573F, 651F, 588E, 556P; 556P, 651F, 655I, 535N, 573F; 556P, 651F, 655I, 535N, 573F, 589V; 556P, 651F, 655I, 535N, 573F, 589V, 204I; 556P, 651F, 655I, 535N, 573F, 589V, 204I, 588Q; 556P, 651F, 655I, 535N, 573F, 589V, 204I, 588Q, 647F; 556P, 651F, 535N, 573F; 556P, 651F, 535N, 573F, 589V; 556P, 651F, 535N, 573F, 589V, 204I; 556P, 651F, 535N, 573F, 589V, 204I, 588Q; 556P, 651F, 535N, 573F, 589V, 204I, 588Q, 647F; 556P, 655I, 535N, 573F; 556P, 655I, 535N, 573F, 589V; 556P, 655I, 535N, 573F, 589V, 204I; 556P, 655I, 535N, 573F, 589V, 204I, 588Q; 556P, 655I, 535N, 573F, 589V, 204I, 588Q, 647F. Again, any of those embodiments can be in any HIV Env protein, e.g. a wild-type isolate, a consensus Env, a synthetic Env protein, a SOSIP mutant Env protein, a wild-type isolate containing repair mutations according to the concept described herein, etc. Some preferred combinations according to the invention include 655I, 589V, 573F, 651F, 588E, 535N, 204I; 556P, 655I, 535N, 573F, 589V, 204I, 588Q; 204I, 535N, 556P, 588E, 589V, 651F, 655I; 535N, 556P, 589V, 651F, 655I; and 535N, 556P, 588E, 589V, 651F, 655I.

In certain preferred embodiments, the HIV Env protein comprises a sequence that is at least 95% identical to, preferably at least 96%, 97%, 98%, 99% identical to, preferably 100% identical to, any one of SEQ ID NOs: 20, 22, 24, 26, 27, 28, 29, 30, 31 and 32. For determination of the % identity, preferably the positions (i)-(xv) of Tables 1 and 2, and preferably also positions 501, 559 and 605 are not taken into account. Preferably the amino acid residues at those positions are the ones in the sequences of SEQ ID NO: 20, 22, 24, 26, 27, 28, 29, 30, 31 or 32, respectively.

In certain embodiments, the HIV Env protein of the invention further comprises: (xvi) an amino acid residue chosen from Val, Ile, Phe, Met, Ala, or Leu at position 658. Preferably the amino acid at position 658 is Val or Ile, most preferably Val. It was found that this strongly increased trimer percentage and trimer yield of the Env protein, either alone or in combination with mutations chosen from (i)-(vii) of Table 1 and/or (viii)-(xv) of Table 2 described herein.

According to embodiments of the invention, a recombinant HIV Env protein has at least one of (a) an improved percentage of trimer formation and (b) an improved trimer yield compared to an HIV Env protein not having the indicated amino acid residues at one or more of positions 651, 655, 535, 589, 573, 204, and 647 as shown in Table 1.

As used herein "improved percentage of trimer formation" means that a greater percentage of trimer is formed when the backbone sequence of the HIV envelope protein contains one or more of the amino acid substitutions of the invention as compared to the percentage of trimer that is formed when the backbone sequence of the HIV envelope sequence does not contain such amino acid substitutions. As used herein "improved trimer yield" means that a greater total amount of the trimer form of the envelope protein is obtained when the backbone sequence of the HIV envelope protein contains one or more of the amino acid substitutions of the invention as compared to the total amount of trimer form of the envelope protein that is obtained when the backbone sequence of the HIV envelope sequence does not contain such amino acid substitutions.

Trimer formation can be measured by an antibody binding assay using antibodies that bind specifically to the trimer form of the HIV Env protein. Examples of trimer specific antibodies that can be used to detect the trimer form include, but are not limited to, the monoclonal antibodies (mAbs) PGT145, PGDM1400, PG16, and PGT151. Preferably, the trimer specific antibody is mAb PGT145. Any antibody binding assay known in the art in view of the present disclosure can be used to measure the percentage of trimer formation of a recombinant HIV Env protein of the invention, such as ELISA, AlphaLISA, etc.

In a particular embodiment, trimer formation is measured by AlphaLISA. AlphaLISA is a bead-based proximity assay in which singlet oxygen molecules, generated by high energy irradiation of donor beads, are transferred to acceptor beads that are within a distance of approximately 200 nm with respect to the donor beads. The transfer of singlet oxygen molecules to the acceptor beads initiates a cascading series of chemical reactions resulting in a chemiluminescent signal that can then be detected (Eglen et al. *Curr. Chem. Genomics,* 2008, 25(1): 2-10). For example, recombinant HIV envelope proteins labeled with a Flag-His tag can be incubated with a trimer specific mAb, donor beads conjugated to the antibody that binds to the trimer specific mAb, nickel-conjugated donor beads, acceptor beads conjugated to an anti-His antibody, and acceptor beads conjugated to an anti-Flag antibody. The amount of trimer formed can be determined by measuring the chemiluminescent signal generated from the pair of donor beads conjugated to the antibody that binds to the trimer specific mAb and the acceptor beads conjugated to the anti-His antibody. The total amount of HIV envelope protein expressed can be determined by measuring the chemiluminescent signal generated from the pair of nickel-conjugated donor beads and anti-Flag-conjugated acceptor beads. For example, the amount of trimer and the total envelope protein expressed can be measured by an AlphaLISA assay as described in detail in Example 3. The percentage of trimer formation can be calculated by dividing the amount of trimer formed by the total amount of expressed envelope protein.

The amount of trimer formed and the total amount of envelope protein expressed can also be determined using chromatographic techniques that are capable of separating the trimer form from other forms of the HIV envelope protein, e.g., the monomer form. Examples of such techniques that can be used include, but are not limited to size exclusion chromatography multi-angle light scattering (SEC-MALS). According to certain embodiments, the percentage of trimer formation is determined using SEC-MALS. According to certain embodiments, the trimer yield is determined using SEC-MALS.

Nucleic Acid, Vectors, and Cells

In another general aspect, the invention provides a nucleic acid molecule encoding a recombinant HIV Env protein according to the invention, and a vector comprising the nucleic acid molecule. The nucleic acid molecules of the invention can be in the form of RNA or in the form of DNA obtained by cloning or produced synthetically. The DNA can be double-stranded or single-stranded. The DNA can for example comprise cDNA, genomic DNA, or combinations thereof. The nucleic acid molecules and vectors can be used for recombinant protein production, expression of the protein in a host cell, or the production of viral particles.

According to embodiments of the invention, the nucleic acid encoding the recombinant HIV envelope protein is operably linked to a promoter, meaning that the nucleic acid is under the control of a promoter. The promoter can be a homologous promoter (i.e., derived from the same genetic source as the vector) or a heterologous promoter (i.e., derived from a different vector or genetic source). Examples of suitable promoters include the human cytomegalovirus immediate early (hCMV IE, or shortly "CMV") promoter and the Rous Sarcoma virus (RSV) promoter. Preferably, the promoter is located upstream of the nucleic acid within an expression cassette.

According to embodiments of the invention, a vector can be an expression vector. Expression vectors include, but are not limited to, vectors for recombinant protein expression and vectors for delivery of nucleic acid into a subject for expression in a tissue of the subject, such as a viral vector. Examples of viral vectors suitable for use with the invention include, but are not limited to adenoviral vectors, adeno-associated virus vectors, pox virus vectors, Modified Vaccinia Ankara (MVA) vectors, enteric virus vectors, Venezuelan Equine Encephalitis virus vectors, Semliki Forest Virus vectors, Tobacco Mosaic Virus vectors, lentiviral vectors, etc. The vector can also be a non-viral vector. Examples of non-viral vectors include, but are not limited to plasmids, bacterial artificial chromosomes, yeast artificial chromosomes, bacteriophages, etc.

In certain embodiments of the invention, the vector is an adenovirus vector, e.g., a recombinant adenovirus vector. A recombinant adenovirus vector may for instance be derived from a human adenovirus (HAdV, or AdHu), or a simian adenovirus such as chimpanzee or gorilla adenovirus (ChAd, AdCh, or SAdV) or rhesus adenovirus (rhAd). Preferably, an adenovirus vector is a recombinant human adenovirus vector, for instance a recombinant human adenovirus serotype 26, or any one of recombinant human adenovirus serotype 5, 4, 35, 7, 48, etc. In other embodiments, an adenovirus vector is a rhAd vector, e.g. rhAd51, rhAd52 or rhAd53.

The preparation of recombinant adenoviral vectors is well known in the art. For example, preparation of recombinant adenovirus 26 vectors is described, in, e.g., WO 2007/104792 and in Abbink et al., (2007) *Virol.* 81(9): 4654-63. Exemplary genome sequences of adenovirus 26 are found in GenBank Accession EF 153474 and in SEQ ID NO: 1 of WO 2007/104792. Exemplary genome sequences for rhAd51, rhAd52 and rhAd53 are provided in US 2015/0291935.

According to embodiments of the invention, any of the recombinant HIV Env proteins described herein can be expressed and/or encoded by any of the vectors described herein. In view of the degeneracy of the genetic code, the skilled person is well aware that several nucleic acid sequences can be designed that encode the same protein, according to methods entirely routine in the art. The nucleic acid encoding the recombinant HIV Env protein of the invention can optionally be codon-optimized to ensure proper expression in the host cell (e.g., bacterial or mammalian cells). Codon-optimization is a technology widely applied in the art.

The invention also provides cells, preferably isolated cells, comprising any of the nucleic acid molecules and vectors described herein. The cells can for instance be used for recombinant protein production, or for the production of viral particles.

Embodiments of the invention thus also relate to a method of making a recombinant HIV Env protein. The method comprises transfecting a host cell with an expression vector comprising nucleic acid encoding a recombinant HIV Env protein according to an embodiment of the invention operably linked to a promoter, growing the transfected cell under conditions suitable for expression of the recombinant HIV Env protein, and optionally purifying or isolating the recombinant HIV Env protein expressed in the cell. The recombinant HIV Env protein can be isolated or collected from the cell by any method known in the art including affinity chromatography, size exclusion chromatography, etc. Techniques used for recombinant protein expression will be well known to one of ordinary skill in the art in view of the present disclosure. The expressed recombinant HIV Env protein can also be studied without purifying or isolating the expressed protein, e.g., by analyzing the supernatant of cells transfected with an expression vector encoding the recombinant HIV Env protein and grown under conditions suitable for expression of the HIV Env protein.

In a preferred embodiment, the expressed recombinant HIV Env protein is purified under conditions that permit association of the protein so as to form the stabilized trimeric complex. For example, mammalian cells transfected with an expression vector encoding the recombinant HIV Env protein operably linked to a promoter (e.g. CMV promoter) can be cultured at 33-39° C., e.g. 37° C., and 2-12% $CO_2$, e.g. 8% $CO_2$. Expression can also be performed in alternative expression systems such as insect cells or yeast cells, all conventional in the art. The expressed HIV Env protein can then be isolated from the cell culture for instance by lectin affinity chromatography, which binds glycoproteins. The HIV Env protein bound to the column can be eluted with mannopyranoside. The HIV Env protein eluted from the column can be subjected to further purification steps, such as size exclusion chromatography, as needed, to remove any residual contaminants, e.g., cellular contaminants, but also Env aggregates, gp140 monomers and gp120 monomers. Alternative purification methods, non-limiting examples including antibody affinity chromatography, negative selection with non-bNAbs, anti-tag purification, or other chromatography methods such as ion exchange chromatography etc, as well as other methods known in the art, could also be used to isolate the expressed HIV Env protein.

The nucleic acid molecules and expression vectors encoding the recombinant HIV Env proteins of the invention can be made by any method known in the art in view of the present disclosure. For example, nucleic acid encoding the recombinant HIV Env protein can be prepared by introducing at least one of the amino acid substitutions at the indicated positions into the backbone HIV envelope sequence using genetic engineering technology and molecular biology techniques, e.g., site directed mutagenesis, polymerase chain reaction (PCR), etc., which are well known to those skilled in the art. The nucleic acid molecule can then be introduced or "cloned" into an expression vector also using standard molecular biology techniques. The recombinant HIV envelope protein can then be expressed from the expression vector in a host cell, and the expressed protein purified from the cell culture by any method known in the art in view of the present disclosure.

Trimeric Complex

In another general aspect, the invention relates to a trimeric complex comprising a noncovalent oligomer of three of the recombinant HIV Env proteins according to the invention. The trimeric complex can comprise any of the recombinant HIV Env proteins described herein. Preferably the trimeric complex comprises three identical monomers (or identical heterodimers if gp140 is cleaved) of the recombinant HIV Env proteins according to the invention. The trimeric complex can be separated from other forms of the HIV envelope protein, such as the monomer form, or the trimeric complex can be present together with other forms of the HIV envelope protein, such as the monomer form.

Compositions and Methods

In another general aspect, the invention relates to a composition comprising a recombinant HIV Env protein, trimeric complex, isolated nucleic acid, vector, or host cell, and a pharmaceutically acceptable carrier. The composition can comprise any of the recombinant HIV Env proteins, trimeric complexes, isolated nucleic acid molecules, vectors, or host cells described herein.

A carrier can include one or more pharmaceutically acceptable excipients such as binders, disintegrants, swelling agents, suspending agents, emulsifying agents, wetting agents, lubricants, flavorants, sweeteners, preservatives, dyes, solubilizers and coatings. The precise nature of the carrier or other material can depend on the route of administration, e.g., intramuscular, intradermal, subcutaneous, oral, intravenous, cutaneous, intramucosal (e.g., gut), intranasal or intraperitoneal routes. For liquid injectable preparations, for example, suspensions and solutions, suitable carriers and additives include water, glycols, oils, alcohols, preservatives, coloring agents and the like. For solid oral preparations, for example, powders, capsules, caplets, gelcaps and tablets, suitable carriers and additives include starches, sugars, diluents, granulating agents, lubricants, binders, disintegrating agents and the like. For nasal sprays/inhalant mixtures, the aqueous solution/suspension can comprise water, glycols, oils, emollients, stabilizers, wetting agents, preservatives, aromatics, flavors, and the like as suitable carriers and additives.

Compositions of the invention can be formulated in any matter suitable for administration to a subject to facilitate administration and improve efficacy, including, but not limited to, oral (enteral) administration and parenteral injections. The parenteral injections include intravenous injection or infusion, subcutaneous injection, intradermal injection, and intramuscular injection. Compositions of the invention can also be formulated for other routes of administration including transmucosal, ocular, rectal, long acting implantation, sublingual administration, under the tongue, from oral mucosa bypassing the portal circulation, inhalation, or intranasal.

Embodiments of the invention also relate to methods of making the composition. According to embodiments of the invention, a method of producing a composition comprises mixing a recombinant HIV Env protein, trimeric complex, isolated nucleic acid, vector, or host cell of the invention with one or more pharmaceutically acceptable carriers. One of ordinary skill in the art will be familiar with conventional techniques used to prepare such compositions.

HIV antigens (e.g., proteins or fragments thereof derived from HIV gag, pol, and/or env gene products) and vectors, such as viral vectors, expressing the HIV antigens have previously been used in immunogenic compositions and vaccines for vaccinating a subject against an HIV infection, or for generating an immune response against an HIV infection in a subject. As used herein, "subject" means any animal, preferably a mammal, most preferably a human, to who will be or has been administered an immunogenic composition according to embodiments of the invention. The term "mammal" as used herein, encompasses any mammal. Examples of mammals include, but are not limited to, mice, rats, rabbits, guinea pigs, monkeys, humans, etc., preferably a human. The recombinant HIV Env proteins of the invention can also be used as antigens to induce an immune response against human immunodeficiency virus (HIV) in a subject in need thereof. The immune response can be against one or more HIV clades, such as clade A, clade B, clade C, etc. The compositions can comprise a vector from which the recombinant HIV Env protein is expressed, or the composition can comprise an isolated recombinant HIV Env protein according to an embodiment of the invention.

For example, compositions comprising a recombinant HIV protein or a trimeric complex thereof can be administered to a subject in need thereof to induce an immune response against an HIV infection in the subject. A composition comprising a vector, such as an adenovirus vector, encoding a recombinant HIV Env protein of the invention, wherein the recombinant HIV Env protein is expressed by the vector, can also be administered to a subject in need thereof to induce an immune response against an HIV infection in the subject. The methods described herein also include administering a composition of the invention in combination with one or more additional HIV antigens (e.g., proteins or fragments thereof derived from HIV gag, pol, and/or env gene products) that are preferably expressed from one or more vectors, such as adenovirus vectors or MVA vectors, including methods of priming and boosting an immune response.

In certain embodiments, the HIV Env protein can be displayed on a particle, such as a liposome, virus-like particle (VLP), nanoparticle, virosome, or exosome, optionally in combination with endogenous and/or exogenous adjuvants. When compared to soluble or monomeric Env protein on its own, such particles typically display enhanced efficacy of antigen presentation in vivo.

Examples of VLPs that display HIV Env protein can be prepared e.g. by co-expressing the HIV Env protein with self-assembling viral proteins such as HIV Gag core or other retroviral Gag proteins. VLPs resemble viruses, but are non-infectious because they contain no viral genetic material. The expression of viral structural proteins, such as envelope or capsid, can result in self-assembly of VLPs. VLPs are well known to the skilled person, and their use in vaccines is for instance described in (Kushnir et al, 2012).

In certain preferred embodiments, the particle is a liposome. A liposome is a spherical vesicle having at least one lipid bilayer. The HIV Env trimer proteins can for instance be non-covalently coupled to such liposomes by electrostatic interactions, e.g. by adding a His-tag to the C-terminus of the HIV Env trimer and a bivalent chelating atom such as $Ni^{2+}$ or $Co^{2+}$ incorporated into the head group of derivatized lipids in the liposome. In certain non-limiting and exemplary embodiments, the liposome comprises 1,2-distearoyl-sn-glycero-3-phosphocholine (DSPC), cholesterol, and the Nickel or Cobalt salt of 1,2-dioleoyl-sn-glycero-3-[(N-(5-amino-1-carboxypentyl)iminodiacetic acid)succinyl] (DGS-NTA($Ni^{2+}$) or DGS-NTA($Co^{2+}$)) at 60:36:4 molar ratio. In preferred embodiments, the HIV Env trimer proteins are covalently coupled to the liposomal surface, e.g. via a maleimide functional group integrated in the liposome surface. In certain non-limiting exemplary embodiments thereof, the liposome comprises DSPC, cholesterol, and 1,2-dipalmitoyl-sn-glycero-3-phosphoethanolamine-N-[4-(p-maleimidomethyl)cyclohexane-carboxamide] lipid in a molar ratio of 54:30:16. The HIV Env protein can be coupled thereto e.g. via an added C-terminal cysteine in the HIV Env protein. The covalently coupled variants are more stable, elicit high antigen specific IgG titers and epitopes at the antigenically less relevant 'bottom' of the Env trimer are masked. Methods for preparing HIV Env trimers coupled to liposomes, as well as their characterization, are known and have for instance been described in (Bale et al, 2017), incorporated by reference herein. The invention also provides an HIV Env protein of the invention fused to and/or displayed on a liposome.

In certain embodiments, a HIV Env protein of the invention is fused to self-assembling particles, or displayed on nanoparticles. Antigen nanoparticles are assemblies of polypeptides that present multiple copies of antigens, e.g. the HIV Env protein of the instant invention, which result in multiple binding sites (avidity) and can provide improved antigen stability and immunogenicity. Preparation and use of self-assembling protein nanoparticles for use in vaccines is well-known to the skilled person, see e.g. (Zhao et al, 2014), (López-Sagaseta et al, 2016). As non-limiting examples, self-assembling nanoparticles can be based on ferritin, bacterioferritin, or DPS. DPS nanoparticles displaying proteins on their surface are for instance described in WO2011/082087. Description of trimeric HIV-1 antigens on such particles has for instance been described in (He et al, 2016). Other self-assembling protein nanoparticles as well as preparation thereof, are for instance disclosed in WO 2014/124301, and US 2016/0122392, incorporated by reference herein. The invention also provides an HIV Env protein of the invention fused to and/or displayed on a self-assembling nanoparticle. The invention also provides compositions comprising VLPs, liposomes, or self-assembling nanoparticles according to the invention.

In certain embodiments, an adjuvant is included in a composition of the invention or co-administered with a composition of the invention. Use of adjuvant is optional, and may further enhance immune responses when the composition is used for vaccination purposes. Adjuvants suitable for co-administration or inclusion in compositions in accordance with the invention should preferably be ones that are potentially safe, well tolerated and effective in people. Such adjuvants are well known to the skilled person, and non-limiting examples include QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Aluminium salts such as Aluminium Phosphate (e.g. AdjuPhos) or Aluminium Hydroxide, and MF59.

Other aspects of the invention relate to recombinant HIV envelope proteins comprising an amino acid sequence that is at least 95%, 96%, 97%, 98%, 99% or 100% identical to the amino acid sequence of SEQ ID NO: 2 or SEQ ID NO: 4, which represent the HIV envelope consensus clade C and consensus clade B sequences, respectively. These consensus sequences have not been found in any naturally occurring sequences, and are thus believed to be novel HIV envelope proteins. A recombinant HIV envelope protein comprising an amino acid sequence that is at least 95%, 96%, 97%, 98%, 99% or 100% identical to the amino acid sequence of SEQ ID NO: 2 or SEQ ID NO: 4 can optionally further comprise the so-called SOSIP mutations and/or a mutation in the furin cleavage site, such as, for instance in those sequences shown in SEQ ID NO: 3, or SEQ ID NO: 3 further comprising Pro at position 558 and/or position 556; and SEQ ID NO: 5, or SEQ ID NO: 5 further comprising Pro at position 558 and/or position 556. When determining the % identity for these sequences, the amino acids at the mutated furin cleavage site and at positions 501, 605, 559, 556 and 558 are preferably not taken into account. It was surprisingly found that such proteins are expressed at high levels and have a high level of stability and trimer formation. Such HIV Env proteins can in certain embodiments be used as backbone proteins, wherein the mutations described above can be made to obtain a molecule of the invention. Isolated nucleic acid molecules encoding these sequences, vectors comprising these sequences operably linked to a promoter, and compositions comprising the protein, isolated nucleic acid molecule, or vector are also contemplated by the invention.

EMBODIMENTS

Embodiment 1 is a recombinant HIV Env protein, comprising the amino acid sequence of an HIV Env protein having the indicated amino acid residues at at least two of the indicated positions selected from the group consisting of:

(i) Phe, Leu, Met, or Trp, preferably Phe, at position 651;
(ii) Phe, Ile, Met, or Trp, preferably Ile, at position 655;
(iii) Asn or Gln, preferably Asn, at position 535;
(iv) Val, Ile or Ala, preferably Val or Ile, at position 589;
(v) Phe or Trp, preferably Phe, at position 573;
(vi) Ile at position 204; and
(vii) Phe, Met, or Ile, preferably Phe, at position 647,
wherein the numbering of the positions is according to the numbering in gp160 of HIV-1 isolate HXB2.

Embodiment 2 is a recombinant HIV Env protein, comprising the amino acid sequence of an HIV Env protein and an amino acid substitution by the indicated amino acid residue at at least one of the indicated position selected from the group consisting of:

(i) Phe, Leu, Met, or Trp, preferably Phe, at position 651;
(ii) Phe, Ile, Met, or Trp, preferably Ile, at position 655;
(iii) Asn or Gln, preferably Asn, at position 535;
(iv) Val, Ile or Ala, preferably Val or Ile, at position 589;
(v) Phe or Trp, preferably Phe at position 573;
(vi) Ile at position 204; and
(vii) Phe, Met, or Ile, preferably Phe, at position 647,
wherein the HIV Env protein is selected from the group consisting of:
(1) an HIV Env protein having a consensus sequence, for instance from clade C or from clade B, e.g. comprising the amino acid sequence of (SEQ ID NO: 2, 3, 4 or 5); or
(2) a synthetic HIV Env protein, for instance comprising the amino acid sequence of (a) SEQ ID NO: 6; (b) SEQ ID NO: 6 with a mutation of Glu to Arg at position 166; (c) SEQ ID NO: 7; or (d) SEQ ID NO: 8 or SEQ ID NO: 9), wherein (a), (b) or (d) optionally may have further SOSIP (Cys at positions 501 and 605 and Pro at position 559) and/or furin cleavage site mutations (e.g. SEQ ID NO: 10 replacing amino acids 508-511); or
(3) a wild-type HIV Env protein, preferably of clade C, comprising at least one repair mutation at an amino acid residue that is present at the corresponding position at a frequency of less than 7.5%, preferably less than 2%, of HIV Env sequences in a collection of at least 100, preferably at least 1000, preferably at least 10000, wild-type HIV Env sequences, wherein the repair mutation is a substitution by an amino acid residue that is present at the corresponding position at a frequency of at least 10% of HIV Env sequences in said collection and preferably the repair mutation is a substitution by the amino acid residue that is present at the corresponding position most frequently in said collection; and
wherein the numbering of the positions is according to the numbering in gp160 of HIV-1 isolate HXB2.

Embodiment 3 is a recombinant HIV Env protein, comprising the amino acid sequence of an HIV Env protein and an amino acid substitution by the indicated amino acid residue at at least one of the indicated position selected from the group consisting of:

(i) Phe, Leu, Met, or Trp, preferably Phe, at position 651;
(ii) Phe, Ile, Met, or Trp, preferably Ile, at position 655;
(iii) Asn or Gln, preferably Asn, at position 535;
(iv) Val, Ile or Ala, preferably Val or Ile, at position 589;
(v) Phe or Trp, preferably Phe, at position 573;
(vi) Ile at position 204; and
(vii) Phe, Met, or Ile, preferably Phe, at position 647,
wherein the HIV Env protein is a SOSIP mutant HIV Env protein comprising at least one mutation selected from the group consisting of:
(a) Cys at positions 501 and 605;
(b) Pro at position 559;

(c) Cys at positions 501 and 605 and Pro at position 559;
and the numbering of the positions is according to the numbering in gp160 of HIV-1 isolate HXB2.

Embodiment 4 is the recombinant HIV Env protein of embodiment 2, comprising the indicated amino acid residues at at least two of the indicated positions selected from the group consisting of (i) to (vii).

Embodiment 5 is the recombinant HIV Env protein of embodiment 3, comprising the indicated amino acid residues at at least two of the indicated positions selected from the group consisting of (i) to (vii).

Embodiment 6 is the recombinant HIV Env protein of any of embodiments 1, 2 and 4, further comprising Cys at positions 501 and 605 or Pro at position 559, preferably Cys at positions 501 and 605 and Pro at position 559.

Embodiment 7 is the recombinant HIV Env protein of any of embodiments 1 to 6, comprising the indicated amino acid residues at at least three of the indicated positions selected from the group consisting of (i) to (vii).

Embodiment 8 is the recombinant HIV Env protein of any of embodiments 1 to 6, comprising the indicated amino acid residues at at least four of the indicated positions selected from the group consisting of (i) to (vii).

Embodiment 9 is the recombinant HIV Env protein of any of embodiments 1 to 6, comprising the indicated amino acid residues at at least five of the indicated positions selected from the group consisting of (i) to (vii).

Embodiment 10 is the recombinant HIV Env protein of any of embodiments 1 to 6, comprising the indicated amino acid residues at at least six of the indicated positions selected from the group consisting of (i) to (vii).

Embodiment 11 is the recombinant HIV Env protein of any of embodiments 1 to 6, comprising the indicated amino acid residues at seven of the indicated positions selected from the group consisting of (i) to (vii).

Embodiment 12 is the recombinant HIV Env protein of any of embodiments 1, 4, and 5, wherein the at least two indicated positions and residues are a combination selected from the group consisting of: 651F, 655I; 651F, 535N; 651F, 589V; 651F, 589I; 651F, 573F; 651F, 204I; 651F, 647F; 655I, 535N; 655I, 589V; 655I, 589I; 655I, 573F; 655I, 204I; 655I, 647F; 535N, 589V; 535N, 589I; 535N, 573F; 535N, 204I; 535N, 647F; 589V, 573F; 589V, 204I; 589V, 647F; 589I, 573F; 589I, 204I; 589I, 647F; 573F, 204I; 573F, 647F; and 204I, 647F.

Embodiment 13 is the recombinant HIV Env protein of embodiment 7, wherein the at least three indicated positions and residues are a combination selected from the group consisting of: 651F, 655I, 535N; 651F, 589V, 535N; 651F, 589I, 535N; 651F, 573F, 535N; 651F, 204I, 535N; 651F, 647F, 535N; 655I, 589V, 535N; 655I, 589I, 535N; 655I, 573F, 535N; 655I, 204I, 535N; 655I, 647F, 535N; 589V, 573F, 535N; 589V, 204I, 535N; 589V, 647F, 535N; 589I, 573F, 535N; 589I, 204I, 535N; 589I, 647F, 535N; 573F, 204I, 535N; 573F, 647F, 535N; 204I, 647F, 535N; 651F, 655I, 589V; 651F, 573F, 589V; 651F, 204I, 589V; 651F, 647F, 589V; 655I, 573F, 589V; 655I, 204I, 589V; 655I, 647F, 589V; 573F, 204I, 589V; 573F, 647F, 589V; 204I, 647F, 589V; 651F, 655I, 589I; 651F, 573F, 589I; 651F, 204I, 589I; 651F, 647F, 589I; 655I, 573F, 589I; 655I, 204I, 589I; 655I, 647F, 589I; 573F, 204I, 589I; 573F, 647F, 589I; 204I, 647F, 589I; 651F, 655I, 573F; 651F, 204I, 573F; 651F, 647F, 573F; 655I, 204I, 573F; 655I, 647F, 573F; 204I, 647F, 573F; 651F, 655I, 204I; 651F, 647F, 204I; 655I, 647F, 204I; 651F, 655I, 647F; 655I, 651F, 647F; 655I, 651F, 535N; 655I, 589V, 573F; and 655I, 589V, 204I.

Embodiment 14 is the recombinant HIV Env protein of embodiment 8, wherein the at least four indicated positions and residues are a combination selected from the group consisting of: 651F, 655I, 535N, 589V; 651F, 655I, 535N, 573F; 651F, 655I, 589V, 573F; 651F, 535N, 589V, 573F; 655I, 535N, 589V, 573F; 651F, 655I, 535N, 204I; 651F, 655I, 589V, 204I; 651F, 535N, 589V, 204I; 655I, 535N, 589V, 204I; 651F, 655I, 573F, 204I; 651F, 535N, 573F, 204I; 655I, 535N, 573F, 204I; 651F, 589V, 573F, 204I; 655I, 589V, 573F, 204I; 535N, 589V, 573F, 204I; 651F, 655I, 535N, 647F; 651F, 655I, 589V, 647F; 651F, 535N, 589V, 647F; 655I, 535N, 589V, 647F; 651F, 655I, 573F, 647F; 651F, 535N, 573F, 647F; 655I, 535N, 573F, 647F; 651F, 589V, 573F, 647F; 655I, 589V, 573F, 647F; 535N, 589V, 573F, 647F; 651F, 655I, 204I, 647F; 651F, 535N, 204I, 647F; 655I, 535N, 204I, 647F; 651F, 589V, 204I, 647F; 655I, 589V, 204I, 647F; 535N, 589V, 204I, 647F; 651F, 573F, 204I, 647F; 655I, 573F, 204I, 647F; 535N, 573F, 204I, 647F; and 589V, 573F, 204I, 647F.

Embodiment 15 is the recombinant HIV Env protein of embodiment 9, wherein the at least five indicated positions and residues are a combination selected from the group consisting of: 651F, 655I, 535N, 589V, 573F; 651F, 655I, 535N, 589V, 204I; 651F, 655I, 535N, 573F, 204I; 651F, 655I, 589V, 573F, 204I; 651F, 535N, 589V, 573F, 204I; 655I, 535N, 589V, 573F, 204I; 651F, 655I, 535N, 589V, 647F; 651F, 655I, 535N, 573F, 647F; 651F, 655I, 589V, 573F, 647F; 651F, 535N, 589V, 573F, 647F; 655I, 535N, 589V, 573F, 647F; 651F, 655I, 535N, 204I, 647F; 651F, 655I, 589V, 204I, 647F; 651F, 535N, 589V, 204I, 647F; 655I, 535N, 589V, 204I, 647F; 651F, 655I, 573F, 204I, 647F; 651F, 535N, 573F, 204I, 647F; 655I, 535N, 573F, 204I, 647F; 651F, 589V, 573F, 204I, 647F; 655I, 589V, 573F, 204I, 647F; and 535N, 589V, 573F, 204I, 647F.

Embodiment 16 is the recombinant HIV Env protein of embodiment 10, wherein the at least six indicated positions and residues are a combination selected from the group consisting of: 651F, 655I, 535N, 589V, 573F, 204I; 651F, 655I, 535N, 589V, 573F, 647F; 651F, 655I, 535N, 589V, 204I, 647F; 651F, 655I, 535N, 573F, 204I, 647F; 651F, 655I, 589V, 573F, 204I, 647F; 651F, 535N, 589V, 573F, 204I, 647F; and 655I, 535N, 589V, 573F, 204I, 647F.

Embodiment 17 is the recombinant HIV Env protein of any of embodiments 1 to 16, further comprising an amino acid substitution by the indicated amino acid residue at at least one of the indicated position selected from the group consisting of:
(viii) Gln, Glu, Ile, Met, Val, Trp, or Phe, preferably Gln or Glu, at position 588;
(ix) Lys at position 64 or Arg at position 66 or both Lys at position 64 and Arg at position 66;
(x) Trp at position 316;
(xi) Cys at both positions 201 and 433;
(xii) Pro at position 556 or 558 or at both positions 556 and 558; and
(xiii) replacement of the loop at amino acid positions 548-568 (HR1-loop) by a loop having 7-10 amino acids, preferably a loop of 8 amino acids, e.g. having a sequence chosen from any one of (SEQ ID NOs: 12-17);
(xiv) Gly at position 568, or Gly at position 569, or Gly at position 636, or Gly at both positions 568 and 636, or Gly at both positions 569 and 636; and/or
(xv) Tyr at position 302, or Arg at position 519, or Arg at position 520, or Tyr at position 302 and Arg at position 519, or Tyr at position 302 and Arg at position 520, or Tyr at position 302 and Arg at both positions 519 and 520, wherein the numbering of the positions is according to the numbering in gp160 of HIV-1 isolate HXB2.

Embodiment 18 is the recombinant HIV Env protein of any of embodiments 1 to 17, further comprising a mutation in a furin cleavage sequence of the HIV Env protein.

Embodiment 19 is the recombinant HIV Env protein of embodiment 18, wherein the mutation in the furin cleavage site is a replacement at positions 508-511 by RRRRRR (SEQ ID NO: 10).

Embodiment 20 is the recombinant HIV Env protein of any of embodiments 1 to 19, being a gp140 or gp160.

Embodiment 21 is the recombinant HIV Env protein of any of embodiments 1 to 20, wherein the recombinant HIV Env protein has at least one of an improved percentage of trimer formation and an improved trimer yield compared to an HIV Env protein not having the one or more of the indicated amino acid residues at the indicated positions selected from the group consisting of (i) to (vii).

Embodiment 22 is the recombinant HIV Env protein of embodiment 21, wherein trimer formation is measured by size exclusion chromatography with multi-angle light scattering (SEC-MALS).

Embodiment 23 is the recombinant HIV Env protein of any of embodiments 1 to 22, further comprising an amino acid residue chosen from Val, Ile, Phe, Met, Ala, or Leu, preferably Val or Ile, most preferably Val, at position 658.

Embodiment 24 is the recombinant HIV Env protein of any of embodiments 1 to 23, comprising the combination of amino acids chosen from the group consisting of:
(a) 655I, 589V, 573F, 651F, 588E, 535N, 204I;
(b) 556P, 655I, 535N, 573F, 589V, 204I, 588Q;
(c) 204I, 535N, 556P, 588E, 589V, 651F, 655I;
(d) 535N, 556P, 589V, 651F, 655I; and
(e) 535N, 556P, 588E, 589V, 651F, 655I.

Embodiment 25 is the recombinant HIV Env protein of any of embodiments 1 to 24, comprising an amino acid sequence that is at least 95%, 96%, 97%, 98%, 99% identical to, or 100% identical to, any one of SEQ ID NOs: 3, 5, 20, 22, 24, 26, 27, 28, 29, 30, 31, or 32, preferably at least 98% identical to any one of SEQ ID NOs: 20, 22, 24, 26, 27, 28, 29, 30, 31, or 32.

Embodiment 26 is a trimeric complex comprising a noncovalent oligomer of three of the recombinant HIV Env proteins of any of embodiments 1 to 25.

Embodiment 27 is a particle, e.g. liposome or nanoparticle, e.g. self-assembling nanoparticle, displaying the recombinant HIV Env protein of any one of embodiments 1-25 or the trimeric complex of embodiment 26.

Embodiment 28 is an isolated nucleic acid molecule encoding a recombinant HIV Env protein of any of embodiments 1 to 25.

Embodiment 29 is a vector comprising the isolated nucleic acid molecule of embodiment 28 operably linked to a promoter.

Embodiment 30 is the vector of embodiment 29, which is an adenovirus vector.

Embodiment 31 is a host cell comprising the isolated nucleic acid molecule of embodiment 28 or the vector of embodiment 29 or 30.

Embodiment 32 is a method of producing a recombinant HIV Env protein, comprising growing the host cell of embodiment 31 under conditions suitable for production of the recombinant HIV Env protein.

Embodiment 33 is a method of producing a recombinant HIV Env protein comprising obtaining an expression vector comprising the isolated nucleic acid of embodiment 28 operably linked to a promoter; transfecting a cell with the expression vector; growing the transfected cell under conditions suitable for expression of the recombinant HIV Env protein; and purifying the recombinant HIV Env protein under conditions that permit formation of a stabilized trimeric complex.

Embodiment 34 is a method of producing a recombinant HIV Env protein according to any one of embodiments 1 to 25, comprising introducing at least one amino acid substitution resulting in the indicated amino acid residue at a position selected from the group consisting of (i)-(vii) into a backbone HIV envelope protein sequence.

Embodiment 35 is the method according to embodiment 34, wherein a nucleotide sequence encoding the amino acid substitution is introduced into nucleic acid encoding the backbone HIV envelope protein sequence.

Embodiment 36 is the method of embodiments 34 or 35, wherein the backbone HIV envelope protein sequence is selected from the group consisting of: SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 6 having a mutation of Glu to Arg at position 166; SEQ ID NO: 6 having Cys at positions 501 and 605 and Pro at position 559 and/or having SEQ ID NO: 10 replacing amino acids 508-511; SEQ ID NO: 6 having a mutation of Glu to Arg at position 166, further having Cys at positions 501 and 605 and Pro at position 559 and/or having SEQ ID NO: 10 replacing amino acids 508-511; SEQ ID NO: 8 having Cys at positions 501 and 605 and Pro at position 559 and/or having SEQ ID NO: 10 replacing amino acids 508-511; SEQ ID NO: 9 having Cys at positions 501 and 605 and Pro at position 559 and/or having SEQ ID NO: 10 replacing amino acids 508-511; and a wild-type HIV Env protein having mutations that result in at least (a), (b) or (c), preferably at least two of (a), (b) and (c), most preferably (a), (b) and (c) of the following:
(a) Cys at positions 501 and 506 and Pro at position 559,
(b) having SEQ ID NO: 10 replacing amino acids 508-511, and/or
(c) at least one repair mutation at an amino acid residue that is present at the corresponding position at a frequency of less than 7.5%, preferably less than 2%, of HIV Env sequences in a collection of at least 100, preferably at least 1000, preferably at least 10000, wild-type HIV Env sequences, wherein the repair mutation is a substitution by an amino acid residue that is present at the corresponding position at a frequency of at least 10% of HIV Env sequences in said collection and preferably the repair mutation is a substitution by the amino acid residue that is present at the corresponding position most frequently in said collection.

Embodiment 37 is a composition comprising the recombinant HIV Env protein of any of embodiments 1 to 25, the trimeric complex of embodiment 26, the particle of embodiment 27, the isolated nucleic acid molecule of embodiment 28, the vector of embodiment 29 or 30, or the host cell of embodiment 31, and a pharmaceutically acceptable carrier.

Embodiment 38 is a composition of embodiment 37, further comprising an adjuvant.

Embodiment 39 is a method of producing the composition of embodiment 37, comprising mixing the recombinant HIV Env protein, trimeric complex, particle, isolated nucleic acid, vector, or host cell with one or more pharmaceutically acceptable carriers.

Embodiment 40 is a method of vaccinating a subject against an HIV infection comprising administering to the subject a composition comprising the recombinant HIV envelope protein of any one of embodiments 1 to 25, the trimeric complex of embodiment 26, the particle of embodiment 27, or the vector of embodiment 29 or 30.

Embodiment 41 is a method of producing an immune response against an HIV infection in a subject in need thereof, comprising administering to the subject a composition comprising the recombinant HIV envelope protein of any one of embodiments 1 to 25, the trimeric complex of embodiment 26, the particle of embodiment 27, or the vector of embodiment 29 or 30.

Embodiment 42 is a recombinant HIV Env protein comprising the amino acid sequence of SEQ ID NO: 2, or a sequence that is at least 95% identical thereto.

Embodiment 43 is a recombinant HIV Env protein comprising the amino acid sequence of SEQ ID NO: 3, or a sequence that is at least 95% identical thereto.

Embodiment 44 is a recombinant HIV Env protein comprising the amino acid sequence of SEQ ID NO: 4, or a sequence that is at least 95% identical thereto.

Embodiment 45 is a recombinant HIV Env protein comprising the amino acid sequence of SEQ ID NO: 5, or a sequence that is at least 95% identical thereto.

Embodiment 46 is an isolated nucleic acid molecule encoding the recombinant HIV Env protein of any of embodiments 42 to 45.

Embodiment 47 is a vector comprising the isolated nucleic acid molecule of embodiment 46 operably linked to a promoter.

Embodiment 48 is the vector of embodiment 47, which is an adenovirus vector.

Embodiment 49 is a host cell comprising the isolated nucleic acid molecule of embodiment 46 or the vector of embodiment 47 or 48.

Embodiment 50 is a composition comprising the recombinant HIV Env protein of any of embodiments 42 to 45, the isolated nucleic acid molecule of embodiment 46, the vector of embodiment 47 or 48, or the host cell of embodiment 49, and a pharmaceutically acceptable carrier.

Embodiment 51 is a method to improve the trimer percentage and/or trimer yield (representing folding and stability) of a parent HIV Env protein, the method comprising repairing the amino acid sequence of the parent HIV Env protein by introducing at least one repair mutation, preferably at least 3 repair mutations in the parent HIV Env protein, wherein a repair mutation is an amino acid substitution at an amino acid residue that is found at the corresponding position at a frequency of less than 7.5%, preferably less than 2%, of HIV Env sequences in a collection of at least 100, preferably at least 500, preferably at least 1000, preferably at least 10000, wild-type HIV Env sequences, wherein the substitution is by an amino acid residue that is found at the corresponding position at a frequency of at least 10% of HIV Env sequences in said collection and preferably the substitution is by the amino acid residue that is found at the corresponding position most frequently in said collection.

Embodiment 52 is the method of embodiment 51, wherein at least 50%, preferably at least 80%, of the amino acid residues in the parent HIV Env protein that are found at corresponding positions at a frequency of less than 7.5% of HIV Env sequences in said collection are repaired.

Embodiment 53 is the method of embodiment 51, wherein at least 50%, preferably at least 80%, of the amino acid residues in the parent HIV Env protein that are found at corresponding positions at a frequency of less than 2% of HIV Env sequences in said collection are repaired.

Embodiment 54 is the method of any one of embodiments 51 to 53, wherein the parent HIV Env protein is from clade C.

Embodiment 55 is the method of any one of embodiments 51 to 54, wherein the parent HIV Env protein is a wild-type HIV Env protein.

Embodiment 56 is the method of any one of embodiments 51 to 54, wherein the parent HIV Env protein comprises one or more of the following:
(a) Cys at positions 501 and 506 and Pro at position 559;
(b) a mutation in a furin cleavage sequence of the HIV Env protein, e.g. having SEQ ID NO: 10 replacing amino acids 508-511;
(c) Phe at position 651;
(d) Ile at position 655;
(e) Asn at position 535;
(f) Val at position 589;
(g) Phe at position 573;
(h) Ile at position 204;
(i) Phe at position 647;
(j) Val at position 658;
(k) Gln or Glu at position 588; and/or
(l) Pro at position 556, 558, or 556 and 558.

Embodiment 57 is a recombinant HIV Env protein obtainable by the method of any of embodiments 51 to 56.

EXAMPLES

Example 1: Generation of HIV Envelope Clade C and Clade B Consensus Sequence

HIV Envelope Clade C Consensus Sequence

An HIV clade C envelope (Env) protein consensus sequence was developed as the backbone sequence for studying the effects of various mutations on trimer formation of the HIV Env proteins. A sequence alignment of 3,434 envelope protein sequences from known HIV viral isolates was downloaded from the Los Alamos Database (http://www.hiv.lanl.gov/content/index). From the 3,434 sequences, 1,252 sequences of clade C only were selected to generate the HIV clade C Env protein consensus sequence. At positions for which a consensus residue could not be clearly identified based on the alignment, the consensus sequence was used to identify the closest wild-type sequences by a BLAST search. The consensus residue at these positions was then selected as the amino acid in the closest wild-type sequences identified from the BLAST search. The HIV Env clade C consensus sequence is shown in SEQ ID NO: 2. The two sequences with the highest homology to SEQ ID NO: 2 using BLAST were the sequences with Genbank numbers ADM30337.1 and ADM30340.1, both having 90% sequence identity to SEQ ID NO: 2.

The HIV Env clade C consensus sequence was further modified by introducing the so-called SOSIP mutations, which include cysteine residues at positions 501 and 605 and a proline residue at position 559, as well as optimizing the furin cleavage site by replacing the furin site at residues 508-511 with 6 arginine residues. Further, Val at position 295 was mutated into an Asn (V295N), to create an N-linked glycosylation site present in the majority of HIV strains and that can improve binding to certain antibodies used in some experiments. Additionally, the C-terminus was truncated at residue 664, resulting in a sequence encoding a soluble HIV gp140 protein. All positions of substitution/modification described above are relative to the numbering in gp160 of HIV-1 isolate HXB2. The resulting HIV gp140 sequence, referred to as "ConC_SOSIP," is shown in (SEQ ID NO: 3). The ConC_SOSIP sequence was used as the backbone or parent HIV envelope sequence into which additional mutations, e.g., single and double amino acid substitutions, were introduced to produce recombinant HIV Env proteins according to embodiments of the invention.

HIV Envelope Clade B Consensus Sequence

An HIV Env clade B consensus sequence was generated using a similar procedure as that described above for generating the HIV Env clade C consensus sequence. The clade B consensus sequence was generated using 1,708 clade B envelope protein sequences from known clade B viral isolates. The HIV Env clade B consensus sequence is shown in SEQ ID NO: 4.

The HIV Env clade B consensus sequence was further modified by introducing the so-called SOSIP mutations, optimizing the furin cleavage site by replacing the furin site with 6 arginine residues, and truncating the C-terminus at residue 664, as described above, resulting in a sequence encoding a soluble HIV gp140 clade B consensus sequence. The resulting HIV gp140 Env protein sequence, referred to as "ConB_SOSIP" is shown in (SEQ ID NO: 5).

It was surprisingly found that the consensus-based molecules had improved expression levels over molecules based on natural isolates, and moreover already had improved trimerization levels. Hence, the molecules having SEQ ID NOs: 2-5 already have surprisingly advantageous properties.

Example 2: Expression and Purification of Recombinant HIV Env Protein

Recombinant HIV Env proteins were expressed and purified as soluble gp140 proteins. Single mutations (amino acid substitutions) and combinations thereof (e.g., double and triple mutations) were introduced into the ConC_SOSIP backbone consensus sequence to generate a series of recombinant HIV Env protein variants.

Generation and Expression of HIV gp140 Env Constructs and Variants

DNA encoding the HIV clade C Env consensus sequence ConC_SOSIP shown in SEQ ID NO: 3 was synthesized and codon-optimized at GenScript (Piscataway, N.J. 08854) or Gene Art (Life Technologies, Carlsbad, Calif.). The codon-optimized sequence was then cloned into the vector pcDNA2004 to generate an HIV clade C gp140 Env construct, which was used as the backbone HIV envelope sequence for introducing further mutations. Mutations were introduced into the ConC_SOSIP backbone sequence by site directed mutagenesis and polymerase chain reaction (PCR) performed on the pcDNA2004 HIV clade C gp140 Env construct. HEK-Expi293F cells or HEK293F cells were transiently transfected with 90% of the pcDNA2004 vector encoding the ConC_SOSIP sequence or variant thereof and 10% of a pcDNA2004 vector encoding the furin protease (furin-pCDNA2004) according to the manufacturer's instructions. The transfected cells were cultured for 5 days at 37° C. and 10% $CO_2$. Culture supernatants were spun for 10 minutes at 1250×g. The spun supernatant was subsequently sterile filtered using a 0.22 μm vacuum filter and stored at 4° C. until further use. For expressions in 96-well format the cells were cultured for 3 days at 37° C. and 10% $CO_2$. 4 uL of Optimem (culture medium) was mixed with 4 uL 100 ng/uL DNA and 8 uL Expi293F mix (54 uL/mL Optimem) as added and incubated for 20 minutes. Subsequently 200 uL/well Expi293F cells were added at 2.5×10E6 cells/mL. The culture supernatant was harvested and spun for 5 minutes at 300 g to remove cells and cellular debris. The spun supernatant was subsequently sterile filtered using a 0.22 μm vacuum filter and stored at 4° C. until further use.

Purification of HIV gp140 Env Protein

HIV gp140 Env protein expressed from the pcDNA2004 vector was purified according to a two-step purification protocol using a *Galantus nivalis*-lectin column (Vectorlabs, AL-1243) for the initial purification, and a Superdex200 Increase column (GE) in a subsequent step to remove residual contaminants. For the initial step using the *Galantus nivalis*-lectin column, culture supernatant was diluted with buffer (40 mM Tris, 500 mM NaCl pH 7.5) and passed over a 4 mL CV Tricorn 10-50 Lectin Agarose Column at a rate of 4 mL per minute. Subsequently, the column was washed with four column volumes buffer (40 mM Tris, 500 mM NaCl pH 7.5) and eluted with four column volumes of 40 mM Tris, 500 mM NaCl, and 1 M mannopyranoside pH 7.5 with an upflow of 1.6 mL/min, meaning that the direction of flow has been changed from down to up to increase the rate of elution of envelope protein and decrease the elution volume. The eluate was concentrated using a spin concentrator (50K, Amicon Ultra, Millipore).

The HIV gp140 Env protein was further purified on a Superdex200 column using 50 mM Tris, 150 mM NaCl pH 7.4 as running buffer. The second peak that eluted from the column contained the HIV gp140 Env protein. The fractions containing this peak were pooled, and the identity of the peak confirmed as HIV gp140 Env protein using Western blot and SDS-PAGE, and/or SEC-MALS analysis. The concentration of the purified HIV gp140 Env protein was determined by measuring the optical density at 280 nm, and the purified HIV gp140 Env protein was stored at 4° C. until further use.

SDS-PAGE and Western Blotting Analysis

Cell culture supernatants containing expressed HIV gp140 Env protein and purified HIV gp140 Env protein samples were analyzed on 4-12% (w/v) Bis-Tris NuPAGE gels, 1× MOPS (Life Technologies) under reducing or non-reducing conditions, and blotted using the iBlot technology (Life Technologies). All procedures were performed according to the manufacturer's instructions. For purity analysis, the gels were stained with Krypton Infrared Protein Stain (Thermo Scientific) or SYPRO *Rubi* protein stain (Bio-Rad). For Western blotting analysis, membranes were probed with an anti-6x-Histidine-Tag antibody (anti-His-HRP). The gels and the blot membranes were scanned on an Odyssey instrument (Li-Cor), and images were analyzed using Odyssey 3.0 software (Li-Cor).

Imaging of HIV Env Trimer Formation by Negative Stain Electron Microscopy Negative stain electron microscopy (NS-EM) was used to image trimers of the envelope protein having the ConC_SOSIP backbone sequence, which were purified using *Galanthus nivalis* lectin followed by size exclusion chromatography, and was performed as described in Julien et al. 2015 (*Proc. Natl. Acad. Sci.* (2015) 112(38) 11947-52). Trimer samples were diluted to between 0.01-0.5 mg/mL in Tris-buffered saline (TBS), pH 7.4 and adhered onto a carbon-coated 200 Cu mesh grid (EMS CF200-Cu) that had been glow discharged in air 2*10-1 mbar, 25 mA, 30 seconds, just before use. Subsequently, a 3 μL drop of the diluted trimer sample was applied to the grid for 1 min followed by blotting with filter paper (Whatman no. 1 or 4). The grids were dried for one minute, then stained with 3 μL of 2.3% uranyl acetate (UAc) for 60 seconds. Data were collected using an FEI Tecnai F20 electron microscope operating at 120 keV, with a magnification of 25,000× that resulted in a pixel size of 4.68 Å at the specimen plane. Images were acquired with a Gatan BM ultrascan.

Almost all particles in the images (of this trimer-enriched material) were well-formed closed trimers (data not shown).

Example 3: Screening of Recombinant HIV gp140 Env Variants for Trimer Yield and Percentage of Trimer Formation The recombinant HIV Env protein variants generated in Example 2 were screened for trimer formation to identify those mutations that improved the percentage of trimer formed and/or improved trimer yields relative to the ConC_SOSIP backbone sequence. High throughput screening of trimer percentage and trimer yields was conducted using an AlphaLISA assay to evaluate the binding of a panel of broadly neutralizing HIV antibodies (bNAbs) and non-bNAbs to the recombinant HIV Env proteins. The results of the AlphaLISA assay were confirmed by size exclusion chromatography and multi-angle light scattering (SEC-MALS).

AlphaLISA® Assay Analysis

Total expression of the HIV gp140 Env protein and the total amount of correctly folded native trimer of over 200 HIV gp140 variants with single amino acid substitutions introduced into the ConC_SOSIP sequence generated as described in Example 2 were measured in cell culture supernatant by AlphaLISA assay. HIV gp140 variants containing double and triple mutations were also tested. The HIV Env protein having the ConC_SOSIP sequence without any additional mutations was tested for comparison.

The following monoclonal antibodies (mAbs) were inter alia used for analysis: mAb PGT145, mAb PGDM1400, mAb PG16, mAb PGT151, mAb 35022, mAb PGT128, mAb PG9, mAb F105, mAb B6, mAb 447-52d, mAb 14e, and mAb 17b. MAbs 447-52D (AB014), PG9 (AB015), and PG16 (AB016) were purchased from Polymun Scientific Immunbiologische Forschung GmbH (Klosterneuburg, Austria). The non-neutralizing antibody b6 was obtained from Dennis R. Burton (The Scripps Research Institue, La Jolla, Calif.), and the non-neutralizing antibody 14e was obtained from James E. Robinson (Tulane University, New Orleans, La.). For mAbs PGT145 (PDB: 3U1S), PGDM1400 (PDB: 4RQQ), PGT151 (PDB: 4NUG), 35022 (PDB: 4TVP), F105 (PDB: 1U6A), PGT128 (PDB: 3TYG), and 17b (PDB: 4RQS) nucleic acids encoding the published sequences were cloned into an expression vector and produced for evaluation of the HIV Env proteins. With the exception of mAbs F105, B6, 447-52d, 14e, and 17b, the antibodies used for analysis are broadly neutralizing antibodies (bNAbs). bNAbs are capable of neutralizing multiple HIV viral strains. Of the bNAbs, PGT145, PGDM1400, and PG16 are apex binders and are trimer specific. PGT151 is also trimer specific, but binds at the interface of two protomers of gp120 and gp41, and is cleavage dependent. Binding of non-bNAbs is indicative of incorrect folding or an open trimer conformation.

Protein folding was also tested by measuring the binding of soluble HIV gp140 Env protein variants to an antibody (mAb 17b) known to bind the co-receptor binding site of the HIV envelope protein, which is exposed only after binding of CD4 (data not shown). In particular, soluble receptor CD4 (sCD4) was used in combination with mAb 17 to evaluate CD4-induced conformational change. Binding of mAb 17b to the HIV gp140 Env protein variant without prior CD4 binding to the envelope protein is an indication of partially unfolded or pre-triggered envelope protein (i.e., an unstable Env that adopts the "open" conformation in the absence of CD4 binding).

For the AlphaLISA assay, HIV gp140 Env constructs in the pcDNA2004 vector containing a linker followed by a sortase A tag followed by a Flag-tag followed by a flexible $(G_4S)_7$ linker and ending with a His-tag, were prepared (the sequence of the tag, which was placed at the C-terminus of the HIV Env protein, is provided in SEQ ID NO: 19). The HIV gp140 Env constructs were expressed in HEK-Expi293 cells, which were cultured for three days in 96 well plates (200 µL/well). Crude supernatants were diluted 120 times in AlphaLISA buffer (PBS+0.05% Tween-20+0.5 mg/mL BSA). For mAb 17b based assays, supernatants were diluted 12 times. Then, 10 µL of each dilution were transferred to a 96-well plate and mixed with 40 µL acceptor beads, donor beads, and one of the above listed mAbs. The donor beads were conjugated to ProtA (Cat #: AS102M, Lot #1831829, Perkin Elmer), which binds to the mAb. The acceptor beads were conjugated to an anti-His antibody (Cat #: AL128M, Perkin Elmer), which binds to the His-tag of the construct. For quantification of the total protein yield, including all forms of the envelope protein, a combination of Nickel-conjugated donor beads (Cat #: AS101M, Perkin Elmer) for detection of the His-tag together with anti-Flag antibody-conjugated acceptor beads (Cat #: AL112R, Perkin Elmer) for detection of the Flag tag were used. For the tests using mAb 17b in combination with sCD4-His, a combination of ProtA donor beads and anti-Flag acceptor beads were used (data not shown). One sample was mixed with donor and acceptor beads to detect trimer formation, and a second sample of the same Env variant was mixed with nickel-conjugated donor beads and anti-Flag conjugated acceptor bead to measure the total amount of protein expressed (i.e., total protein yield).

The mixture of the supernatant containing the expressed HIV gp140 Env protein, the mAb, donor beads, and acceptor beads was incubated at room temperature for 2 hours without shaking. Subsequently, the chemiluminescent signal was measured with a Synergy NEO plate reader instrument (BioTek). The average background signal attributed to mock transfected cells was subtracted from the AlphaLISA counts measured for each the HIV gp140 Env variants. Then, the whole data set was divided by signal measured for the HIV Env protein having the ConC_SOSIP backbone sequence signal to normalize the signal for each of the HIV gp140 Env variants tested to the backbone. Binding data for each of the HIV gp140 Env variants to the trimer specific mAb PGT145 was used to determine the percentage of trimer formation and trimer yield for each of the variants. Binding to the other mAbs was used to evaluate the general binding pattern of the HIV Env variants to bNAbs and non-bNAbs (not shown).

The percentage of trimer formation for each of the HIV Env variants was calculated by dividing the normalized chemiluminescent signal obtained from sample mixture of HIV Env variant, the mAb PGT145, ProtA-conjugated donor beads, and anti-His-conjugated acceptor beads, by the normalized chemiluminescent signal obtained from the sample mixture of the HIV Env variant, anti-His-conjugated donor beads and anti-Flag-conjugated acceptor beads.

Trimer yield for each of the HIV Env variants was determined relative to the trimer yield for the HIV Env protein having ConC_SOSIP backbone sequence without any additional mutations. The normalized chemiluminescent signal obtained from the binding of mAb PGT145 to the ConC_SOSIP envelope protein was set to 1, and the normalized chemiluminescent signal obtained from the binding of mAb PGT145 to each of the HIV gp140 proteins was normalized to this value.

Results of AlphaLISA Assay Analysis—Trimer Percentage and Trimer Yields

Figure 2A:
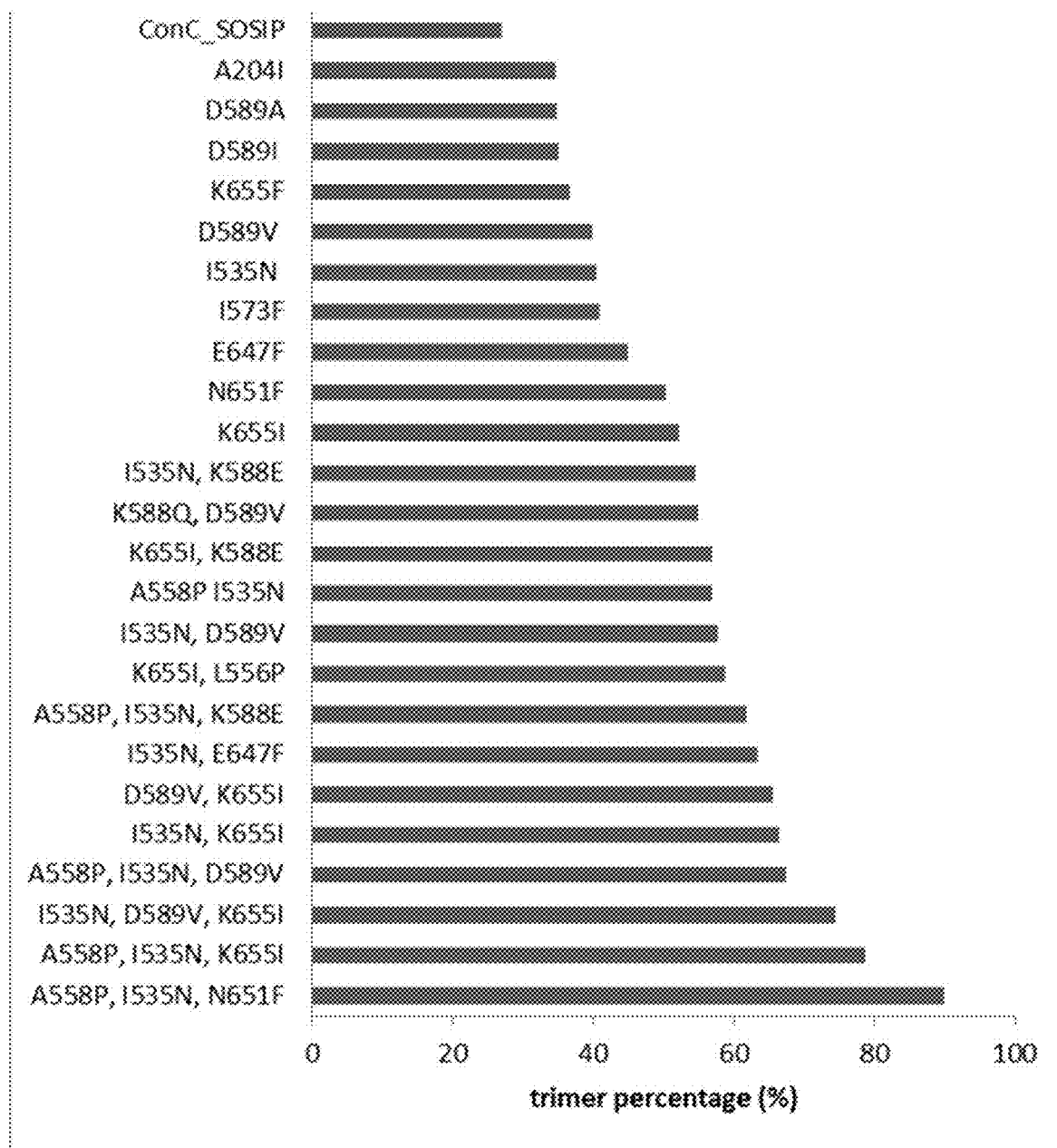
FIGS. 2A and 2B show the percentage of trimer formation (FIG. 2A) and the trimer yield (FIG. 2B) for recombinant HIV Env proteins according to embodiments of the invention as measured by AlphaLISA assay as described in Example 3; the recombinant HIV Env proteins tested contained a single, double, or triple amino acid substitution introduced into the backbone HIV Env consensus clade C sequence ConC_SOSIP (SEQ ID NO: 3); trimer percentage and trimer yield were determined based on the binding of the trimer specific monoclonal antibody (mAb) PGT145 to each of the recombinant HIV Env proteins; the trimer yield and percentage of trimer formation for each of the recombinant HIV Env proteins of the invention is compared to that of an envelope protein having the backbone ConC_SOSIP sequence without any additional trimer stabilizing mutations described herein.

The percentage of trimer formation as determined by the AlphaLISA assay for several single, double, and triple amino acid substitutions from the list of (i)-(vii) in Table 1 above in the ConC_SOSIP backbone sequence is shown in FIG. 2A. Of the about 200 HIV gp140 Env variants containing single amino acid substitutions that were tested, seven positions of substitution were identified for which the percentage of trimer formed increased by at least 25% relative to the percentage of trimer formed for the ConC_SOSIP backbone sequence without any additional amino acid substitutions.

The results shown in FIG. 2A demonstrate that the seven preferred positions of substitution for which a significant increase in the percentage of trimer formation was observed include N651, K655, I535, D589, I573, A204, and E647 according to the numbering in gp160 of HIV-1 isolate HXB2. In particular, the single amino acid substitutions that resulted in the most improved percentage of trimer formation included N651F, K655I (/F/W) (although there was also one experiment in which K654F did not appear to result in improvement), I534N, D588V(/A), I572F, A204I, E647F. Some mutations that were tested in combination with several of these mutations, included K588Q/E, I556P and A558P, and these further improved the trimer percentage of mutants with preferred amino acids at positions of the invention ((i)-(vii) of Table 1) in this experiment.

All double substitutions tested in this experiment had a higher percentage of trimer formation than the corresponding single substitutions, and all triple substitutions tested had a higher percentage of trimer formation than the corresponding single and double mutations (FIG. 2A). These unpredictable and surprising results indicate that these mutations could display a form of synergy in these experiments with respect to trimerization of the envelope protein.

Figure 2B:
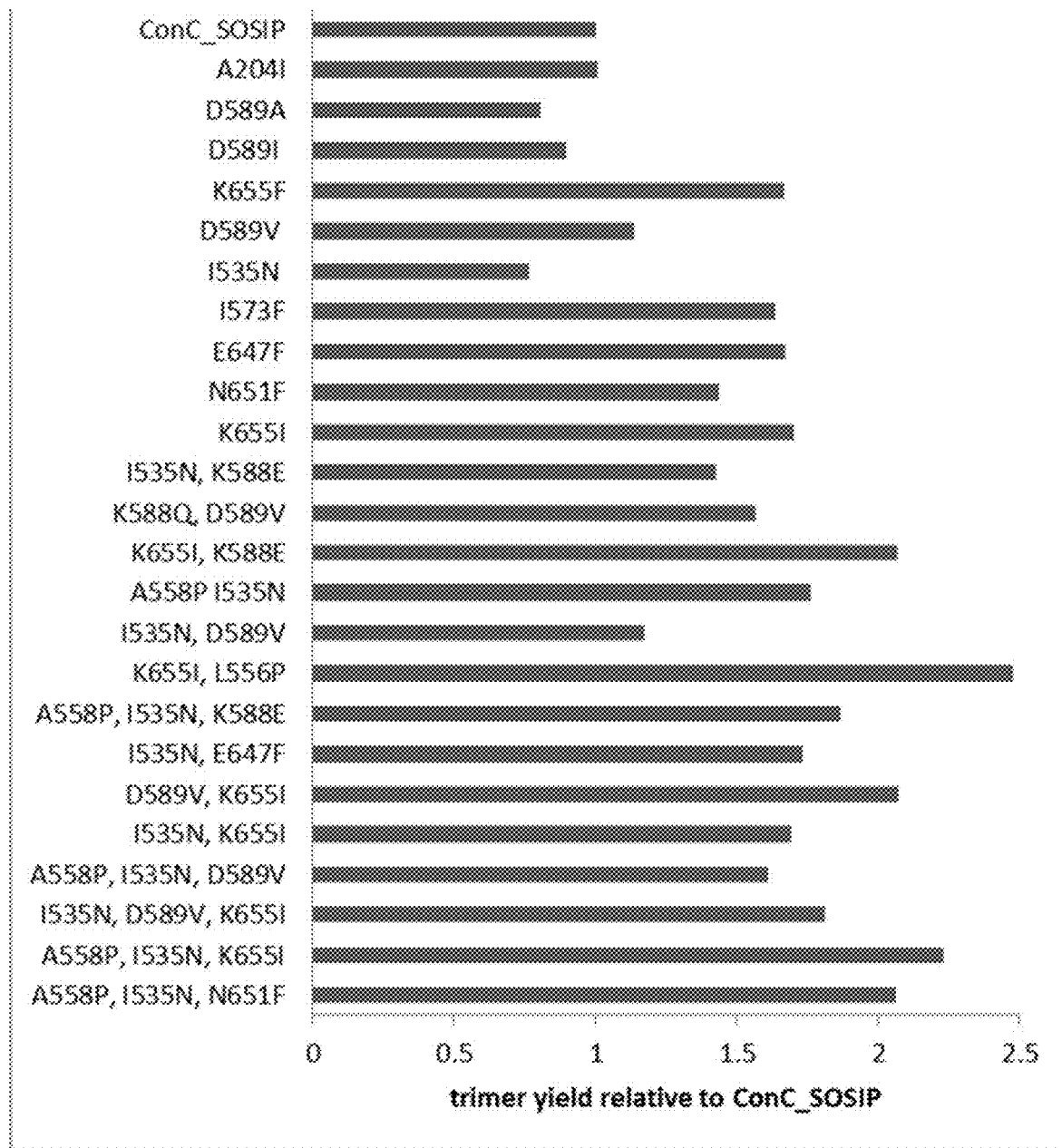
Figure 3A:
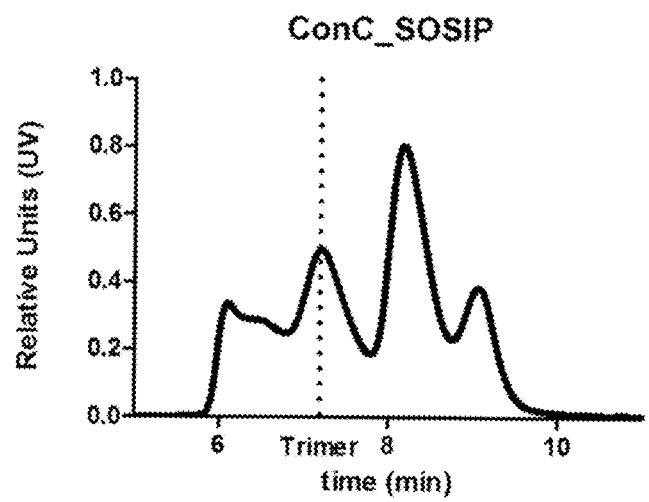
FIGS. 3A-3G show the chromatograms from size exclusion chromatography with multi-angle light scattering (SEC-MALS) analysis of recombinant HIV Env proteins according to embodiments of the invention (ConC_SOSIP (FIG. 3A); N651F (FIG. 3B); K655I (FIG. 3C); I535N (FIG. 3D); D589V (FIG. 3E); A204I (FIG. 3F); and I573F (FIG. 3G)); the recombinant HIV Env proteins tested contained a single amino acid substitution introduced into the backbone HIV Env consensus clade C sequence ConC_SOSIP (SEQ ID NO: 3) (FIG. 3A), and were purified by lectin affinity chromatography as described in Example 2; SEC-MALS analysis was performed as described in Example 3; the peak corresponding to the trimer form is indicated in each of the chromatograms.
Figure 3B:
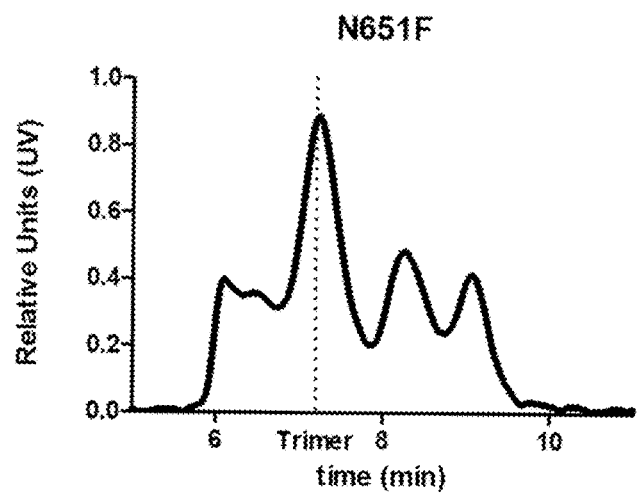
Figure 3C:
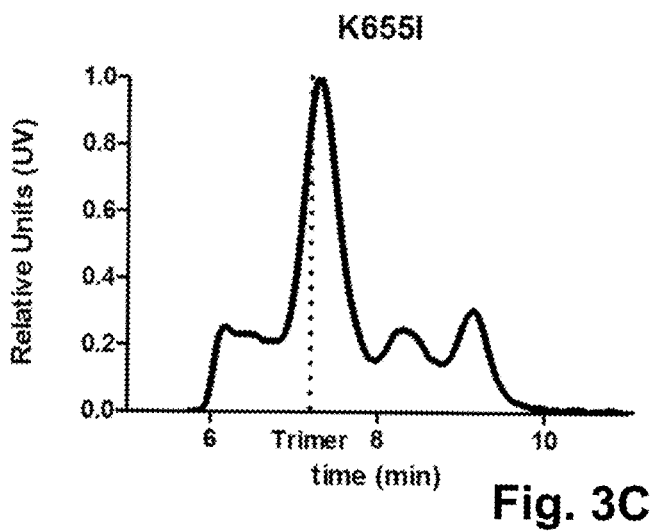
Figure 3D:
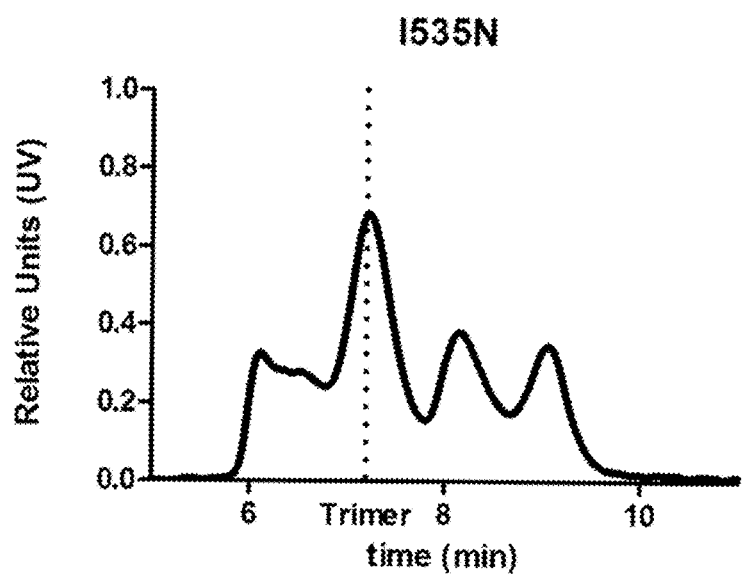
Figure 3E:
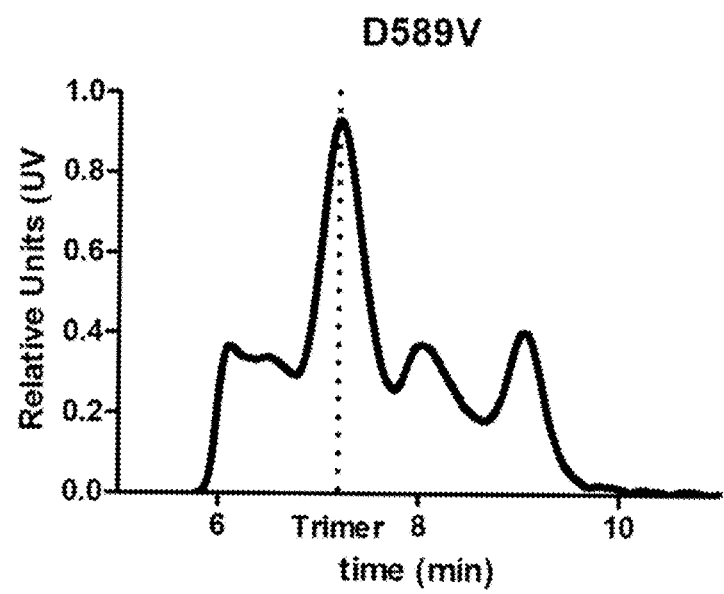
Figure 3F:
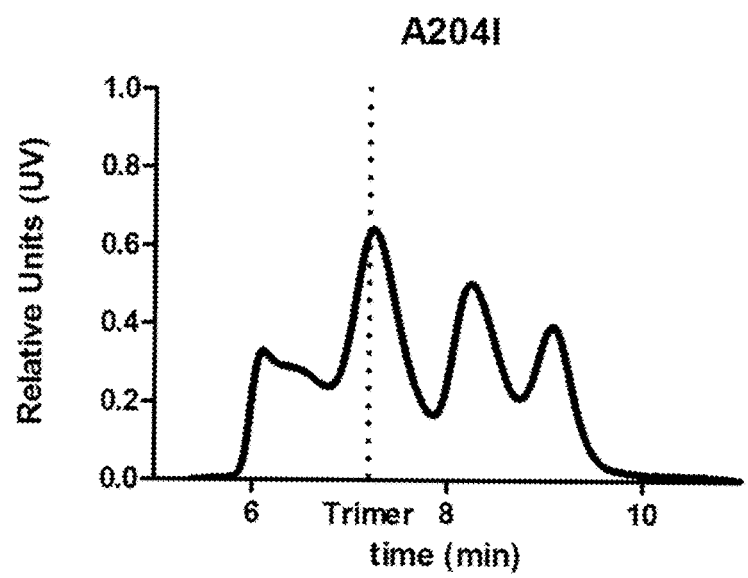
Figure 3G:
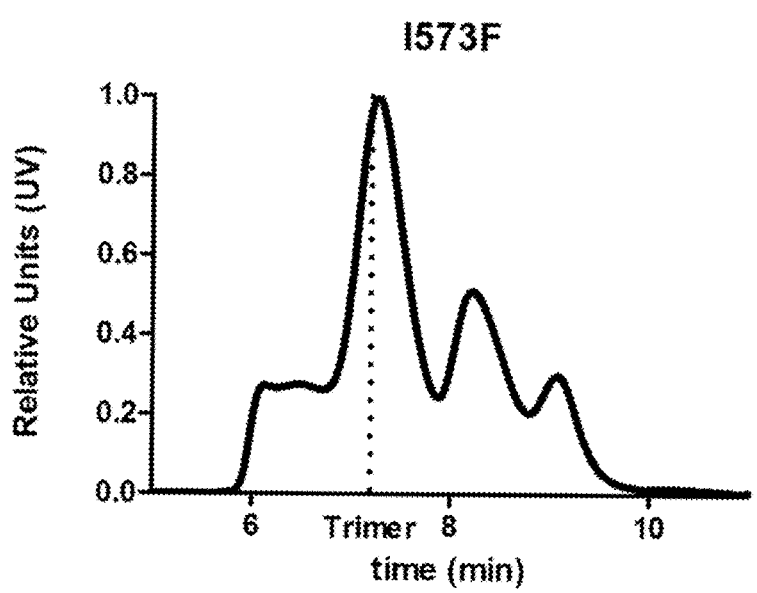

In addition to improved percentage of trimer formation, an increased trimer yield is also desirable. Therefore, the trimer yield of HIV gp140 variants containing single, double, and triple mutations in the ConC_SOSIP backbone sequence was also determined by the AlphaLISA assay. The results are shown in FIG. 2B. Most HIV gp140 variants containing single mutations (exceptions were I535N, D589A and D589I), had a higher trimer yield than the ConC_SOSIP envelope protein. However, the more accurate SEC-MALS analysis of the I535N mutant, as described below, showed an increase in trimer yield. Moreover, additional mutations in combination with I535N, such as D589V, resulted in the same trimer yield observed for the envelope protein having that particular additional substitution in the absence of the I535N mutation. The trimer yield of the variants with double mutations was also increased where each of the single mutation variants had a higher trimer yield than the ConC_SOSIP envelope protein (FIG. 2B).

The percentage of trimer formation for HIV gp140 variants with double mutations in the ConC_SOSIP backbone that were previously described in the literature was also tested, including the E64K, T316W double substitution described by (De Taeye et al., supra), and the disulfide double substitution I204C, A433C described by (Kwon et al., supra). The E64K, T316W double substitution resulted in a lower percentage of trimer formation than the ConC_SOSIP envelope protein, i.e., 15% (data not shown). Although the disulfide double substitution I204C, A433C increased the trimer percentage to 43% (data not shown), the novel double substitutions described herein, such as I535N/K588E, K588Q/D589V, K655I/K588E, I535N/D589V, I535N/E647F, D589V/K655I, and I535N/K655I (FIG. 2A) resulted in an even greater percentage of trimer formation in the AlphaLISA experiment.

Additional mutations (proline at residues 558 and/or 556) were also introduced into the ConC_SOSIP backbone, and the percentage of trimer formation and trimer yield measured for these HIV gp140 Env proteins. Both the single substitutions of Pro at position 558 or 556, and the double substitution of proline at both positions 556 and 558 in addition to the SOSIP mutations already contained in the ConC_SOSIP backbone (i.e., Cys at positions 501 and 605, and Pro at position 559) increased the percentage of trimer formation and trimer yield (data not shown). Indeed, introduction of one or more of the novel amino acid stabilizing substitutions of the invention in the ConC_SOSIP backbone further comprising Pro residues at positions 558 and/or 556 further improves the percentage of trimer formation and/or trimer yield (e.g. FIG. 2A, e.g. A558P/I535N, K655I/L556P, and several triple mutants including the A558P mutation).

Binding data of the HIV gp140 Env variants to the other bNAbs and non-bNAbs demonstrated that most of the single, double and triple mutations tested which increased trimer yield and the percentage of trimer formation, such as those listed in FIGS. 2A and 2B, also had increased binding to bNAbs, and the same or decreased binding to non-bNAbs relative to the amount of binding observed to the bNAbs and non-bNAbs for the HIV envelope protein having the ConC_SOSIP backbone sequence (data not shown). For vaccine development, increased binding to bNAbs and reduced binding to non-bNAbs is preferred. The data thus demonstrates that the HIV envelope proteins comprising the amino acid substitutions at positions (i)-(vii) indicated in Table 1 above have desirable properties with respect to binding patterns to broadly neutralizing and non-broadly neutralizing antibodies.

SEC-MALS Analysis

SEC-MALS analysis was also used to verify the trimer yield and percentage of trimer formation for the HIV gp140 variants screened using the AlphaLISA assay. The HIV gp140 variants were expressed in 30 mL scale cultures and purified by applying the cell free supernatants on 200 µl *Galanthus nivalis* lectin beads (Vectorlab Cat # AL-1243) in Polyprep gravity flow columns (Biorad Cat #731-1550). The beads were washed with 2 ml binding buffer (40 mM Tris, 500 mM NaCl pH 7.4). The proteins were eluted using 250-500 µl of 40 mM Tris, 500 mM NaCl, 1 M mannopyranoside pH 7.4. A high-performance liquid chromatography system (Agilent Technologies) and MiniDAWN TREOS instrument (Wyatt) coupled to an Optilab T-rEX Refractive Index Detector (Wyatt) was used for performing the SEC-MALS experiment. In total, either 100 µl of lectin elution or approximately 30 µg of protein was applied to a TSK-Gel G3000SWx1 column (Tosoh Bioscience) equilibrated in running buffer (150 mM sodium phosphate, 50 mM NaCl, pH 7.0) at 1 mL/min. The data were analyzed using the Astra 6 software package, and molecular weight calculations were derived from the refractive index signal.

The SEC-MALS chromatograms of the ConC_SOSIP envelope protein and the HIV gp140 variants containing single mutations are shown in FIGS. 3A-3G. In general, the results obtained from the SEC-MALS analysis were comparable to and consistent with the results obtained from the AlphaLISA analysis. The chromatogram of the ConC_SOSIP envelope protein has four major peaks, with the second peak that eluted at about 7.3 minutes being the trimer peak. The ConC_SOSIP envelope protein was determined to be about 27% trimeric. The formation of aggregates and monomers indicates that there is some misfolding and instability associated with HIV gp140 Env protein having the ConC_SOSIP consensus sequence. As demonstrated by the chromatograms shown in FIGS. 3A-3G, all single substitutions resulted in a relatively higher trimer peak as compared to the trimer peak for the ConC_SOSIP envelope protein, indicating that trimer yield was increased for each of the HIV gp140 variants.

Taken together, the results demonstrate that the amino acid substitutions identified in (i)-(vii) of Table 1 herein provide recombinant HIV Env proteins with improved percentage of trimer formation and/or improved trimer yield. In particular, HIV Env protein variants having multiple substitutions at the identified positions of (i)-(vii) of Table 1, such as combinations of two or more of the identified mutations typically exhibited even more improved trimer yield and/or percentage of trimer formation over HIV Env protein variants having only a single mutation, which shows a possible synergistic effect of combinations mutations (i)-(vii) of Table 1. To the best of the knowledge of the inventors, none of these combinations of amino acid substitutions have been reported in naturally occurring HIV envelope protein sequences, and all combinations (between (i)-(vii)) are thus believed to be novel combinations of trimer stabilizing mutations. HIV envelope proteins having an increased percentage of trimer formation, such as the recombinant HIV envelope proteins of the invention, are advantageous from a manufacturing perspective, such as for vaccines, because less purification and removal of the envelope protein present in the preparation in the undesired non-native conformations will be required. Also, an increased total expression yield of the trimer is advantageous for manufacturing a vaccine product.

Example 4: Stability of Trimeric HIV Envelope Proteins

The thermal stability of recombinant HIV Env proteins according to embodiments of the invention was tested by AlphaLISA and differential scanning calorimetry (DSC).

Thermal Stability Measurements Using AlphaLISA

Heat stability was tested by measuring the loss of intact trimer upon heat treatment based on binding to the trimer-specific mAb PGT145. Crude supernatant (20 µl) was heated at 60° C. for 1 hour. The samples were then centrifuged at maximum speed for five minutes to remove aggregates. The AlphaLISA assay was performed as described above in Example 3.

Figure 4:
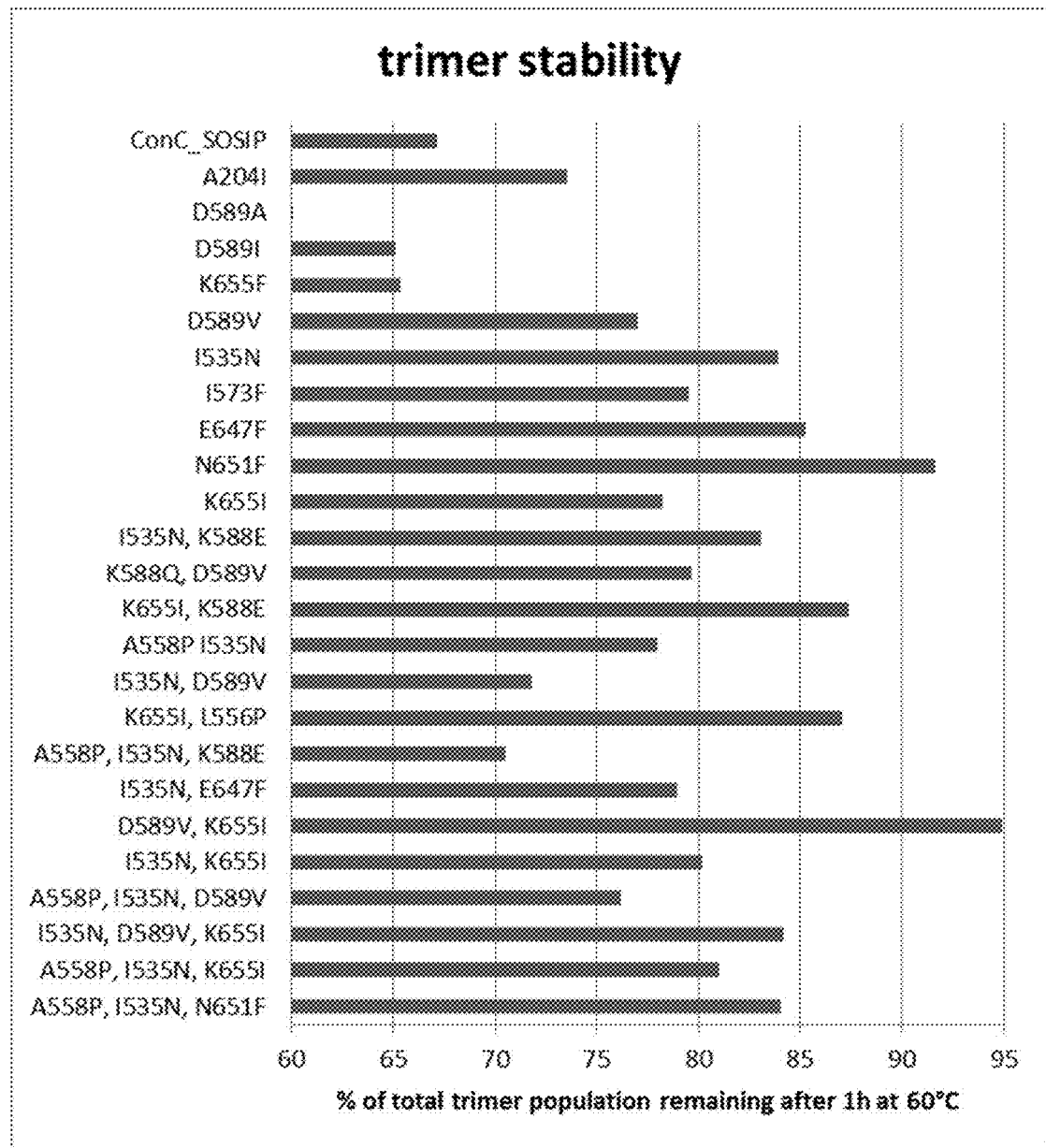
FIG. 4 shows the thermal stability of recombinant HIV Env proteins according to embodiments of the invention reported as percentage of trimers remaining after heat treatment; the recombinant HIV Env proteins tested contained a single, double, or triple amino acid substitution introduced into the backbone HIV Env consensus clade C sequence ConC_SOSIP (SEQ ID NO: 3); the recombinant HIV Env proteins were subjected to heat treatment, and the percentage of trimers remaining after the heat treatment was determined by AlphaLISA assay as described in Example 4; the thermal stability of the envelope protein having the backbone ConC_SOSIP sequence without any additional trimer stabilizing mutations is also shown.

The results are shown in FIG. 4, and the data is reported as the percentage of trimers left intact after the heat treatment. From the results, it can be seen that most of the single mutant recombinant HIV gp140 Env proteins of the invention tested had higher heat stability than the ConC_SOSIP envelope protein. The HIV envelope proteins having the trimer stabilizing double and triple substitutions identified herein that were tested were also found to have higher heat stability than the ConC_SOSIP envelope protein.

Thermal Stability Measurements Using DSC

The melting temperature ($T_m$) of the HIV gp140 Env variants was determined by DSC using a MicroCal capillary DSC system. Each measurement was performed with a start temperature of 20° C. and a final temperature of 110° C. at a scan rate of 100° C./hour. A protein sample with a concentration of 0.5 mg/mL (400 µL) was used for each measurement. The data were analyzed using the Origin J. Software (MicroCal VP-analysis tool).

The melting temperature ($T_m$) of the ConC_SOSIP envelope protein measured using DSC was determined to be 69.8° C. and the onset temperature of melting was 60.1° C. The $T_m$ measured for the ConC_SOSIP envelope protein was higher than that for the BG505_SOSIP envelope protein (HIV envelope protein of the BG505 viral isolate having the so-called SOSIP mutations), which was reported to have a $T_m$ of 67.0° C. (Kwon et al, 2015). This indicates that an HIV envelope protein having the ConC_SOSIP backbone sequence has more favorable properties with respect to heat stability than another known HIV envelope sequence with trimer stabilizing mutations.

The $T_m$ of the K655I mutant of ConC_SOSIP was measured to be 72.3° C. and the onset temperature of melting was 63.7° C., which is even higher than the $T_m$ of ConC_SOSIP envelope protein. The Tm of the A558P, N651F, I535N mutant of ConC_SOSIP was measured to be 77.29° C. with an onset temperature of 74.87° C. The DSC results thus confirm the heat stability results determined by the AlphaLISA assay.

Taken together, the results demonstrate that HIV Env proteins comprising at least one of the amino substitutions described herein typically have higher heat stability than envelope proteins lacking such mutations. The results also demonstrate that all double substitution HIV Env protein variants had higher heat stability than the ConC_SOSIP envelope protein. Triple substitution HIV Env protein variants were also more stable than the ConC_SOSIP envelope protein.

Example 5: Recombinant HIV Envelope Protein Variants Based on a Clade B Envelope Protein Consensus Sequence Recombinant HIV Env proteins according to embodiments of the invention comprising a single amino acid substitution (I535N, D589V, N651F or K655I) introduced into the clade B consensus sequence ConB_SOSIP (SEQ ID NO: 5) were generated and purified as described in Example 2. The trimer yield and percentage of trimer formation were measured by AlphaLISA assay as described in Example 3.

Figure 5B:
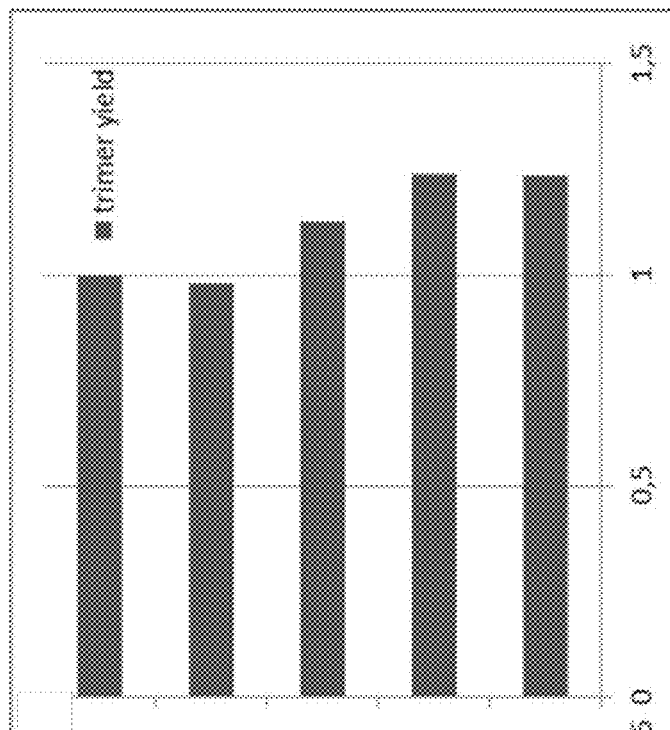
FIGS. 5A-5B show the percentage of trimer formation (FIG. 5A) and the trimer yield (FIG. 5B) for recombinant HIV Env proteins having a single amino acid substitution introduced into the backbone HIV Env consensus clade B sequence ConB_SOSIP (SEQ ID NO: 5) according to embodiments of the invention compared to that of the envelope protein having the backbone ConB_SOSIP sequence without any additional trimer stabilizing mutations of the invention as described in Example 5; trimer yield and the percentage of trimer formation was measured by AlphaLISA assay.
Figure 5A:
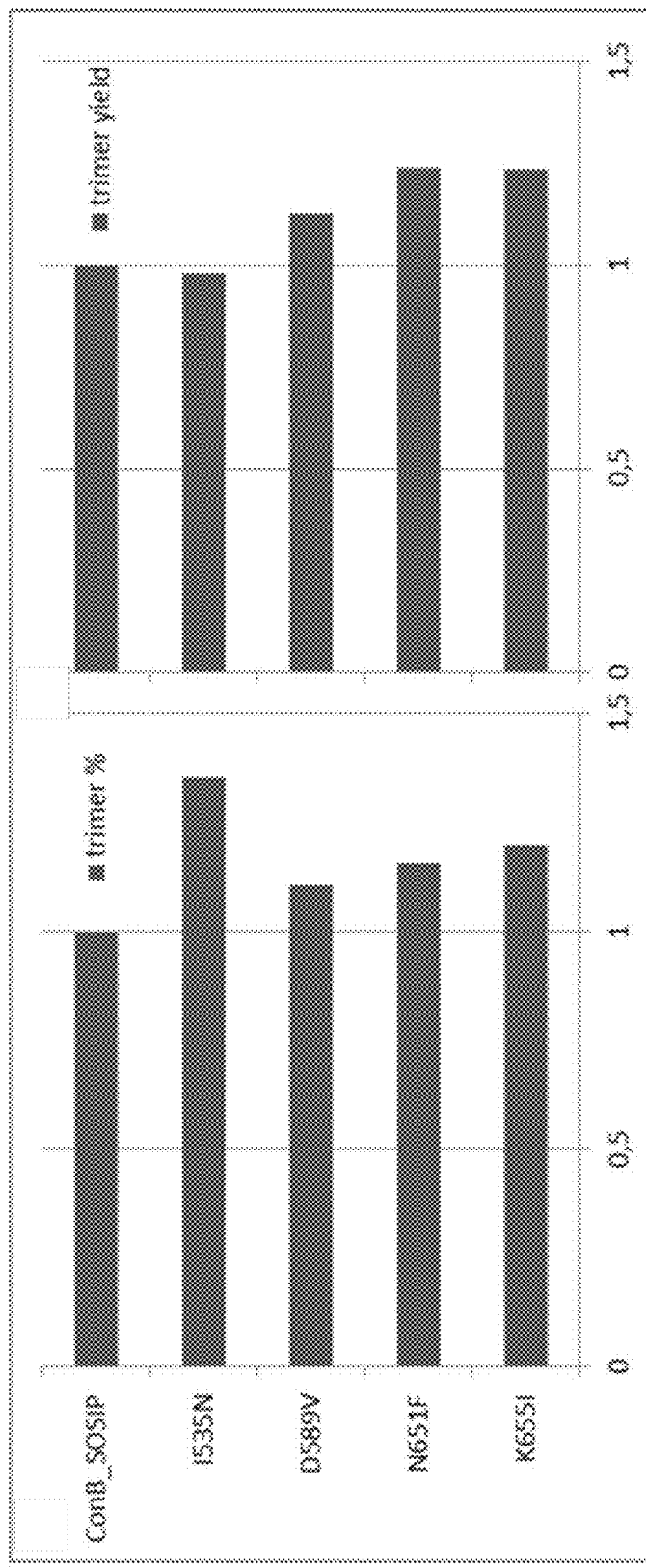

The results are shown in FIG. 5A (percentage of trimer formation) and FIG. 5B (trimer yield). The values reported are relative to the value measured for the ConB_SOSIP envelope protein, which was set to 1 for both the percentage of trimer formation and trimer yield. The results show that all of the mutations tested increased the percentage of trimer formation. The trimer yield was about the same or improved relative to the ConB_SOSIP envelope protein for all of the mutations tested.

These results demonstrate that these mutations also had a stabilizing effect on the envelope protein, e.g., improved trimer yield, improved percentage of trimer formation, etc., when introduced into a different backbone HIV envelope protein sequence, in this case a Clade B derived consensus sequence.

Example 6: Recombinant HIV Envelope Protein Variants Based on a Synthetic Envelope Protein Sequence Recombinant HIV Env proteins according to embodiments of the invention comprising amino acid substitutions introduced into a synthetic HIV envelope protein (named 'DS_sC4_SOSIP_E166R') having the sequence shown in SEQ ID NO: 7 were prepared and purified as described in Example 2. The synthetic HIV envelope protein DS_sC4_SOSIP_E166R has the so-called SOSIP mutations (Cys at residues 501 and 605, and Pro at residue 559), Cys at residues 201 and 433 resulting in the introduction of a disulfide (DS) bond, and Arg at position 166 to stabilize the apex. In addition, the protein is truncated at position 655. The percentage of trimer formation and trimer yield were measured by AlphaLISA assay as described in Example 3.

Figure 6A:
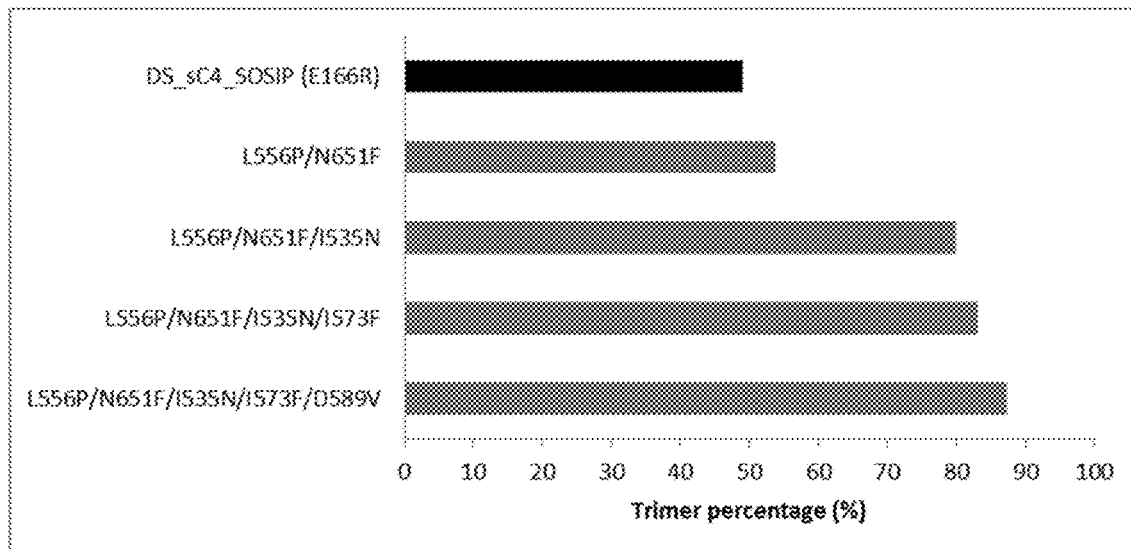
FIGS. 6A-6B show the percentage of trimer formation and trimer yield for recombinant HIV Env proteins having amino acid substitutions introduced into the backbone synthetic HIV envelope protein sequence DS_sC4_SOSIP_E166R according to embodiments of the invention as described in Example 6; the percentage of trimer formation and trimer yield were measured by AlphaLISA assay.
Figure 6B:
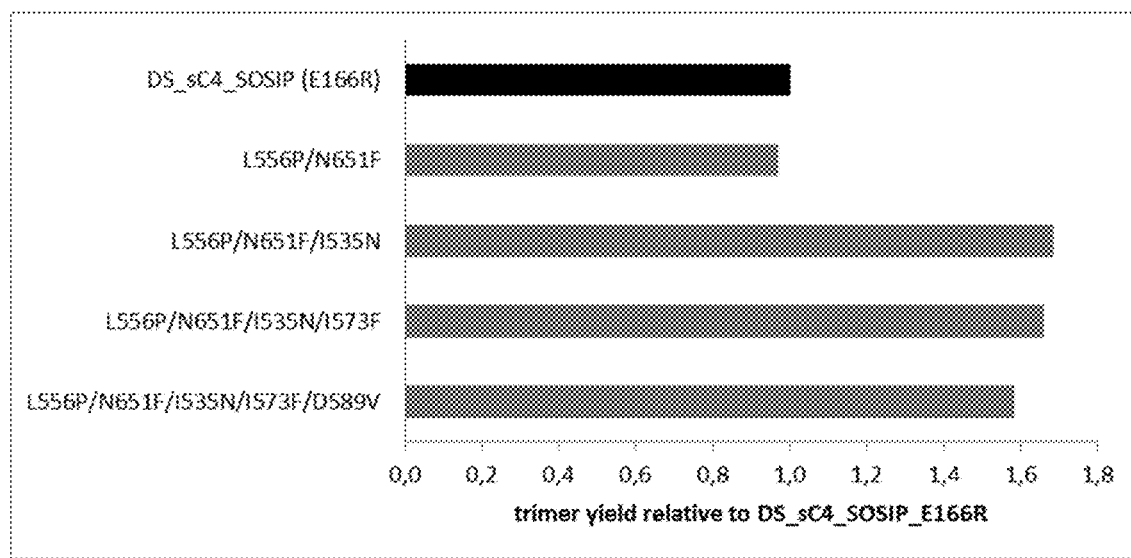

The results are shown in FIG. 6, which compares the percentage of trimer formation for each of the variants tested to the percentage of trimer formation (FIG. 6A) and trimer yield (FIG. 6B) for the DS_sC4_SOSIP_E166R backbone. A greater percentage of trimer formation was observed for each of the variants tested as compared to the backbone sequence.

Figure 12:
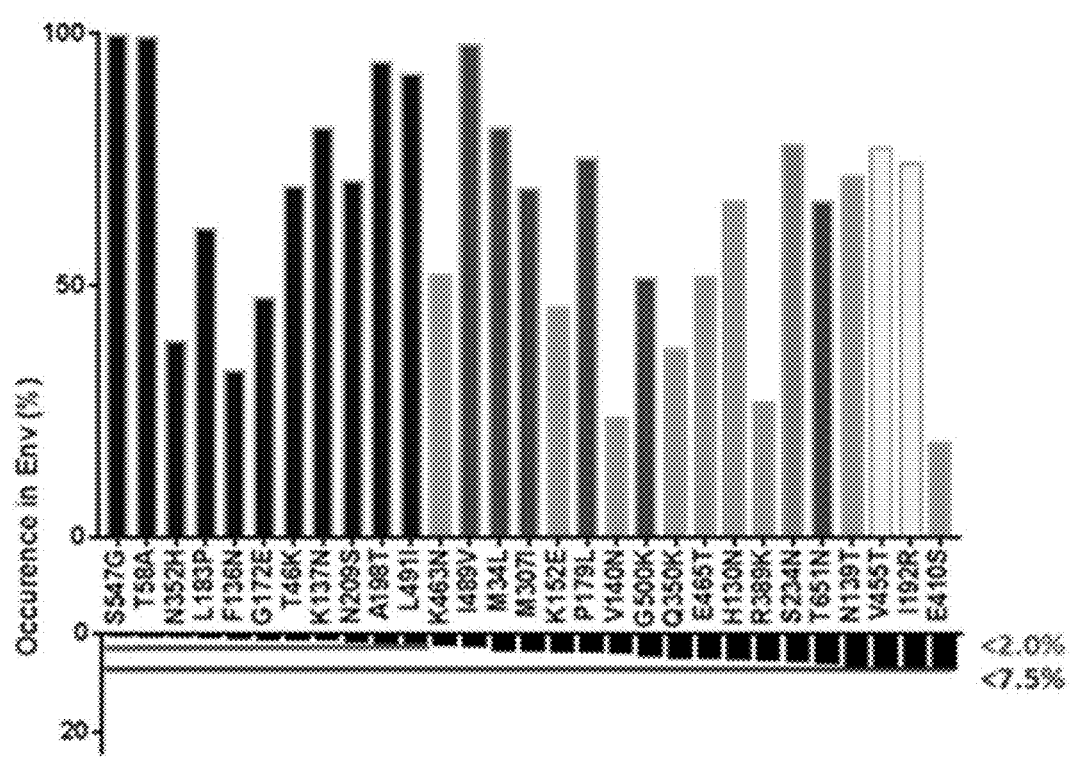
FIG. 12 shows the universal concept for repairing HIV-1 Env sequence illustrated for strain C97ZA. The residue with the highest frequency of occurrence (referred to herein as 'consensus residue') in the total HIV-1 database (top bars) and strain C97ZA residue (bottom bars) sorted from low to high occurrence percentage of C97ZA residue position. C97ZA sequence positions to be substituted to consensus residue were selected based on the following criteria: Positions with a C97ZA residue that occurs less than 2% in Env database sequences (black bars). Positions with a C97ZA residue that occur between 2% and 7.5% in Env database sequences and are buried or partly buried (dark grey bars). Positions that are exposed and hydrophobic in C97ZA and hydrophilic consensus residues (two lightest grey bars) and a position that is a potential N-glycosylation site (PNGS) consensus residue (S234N).
Figure 13:
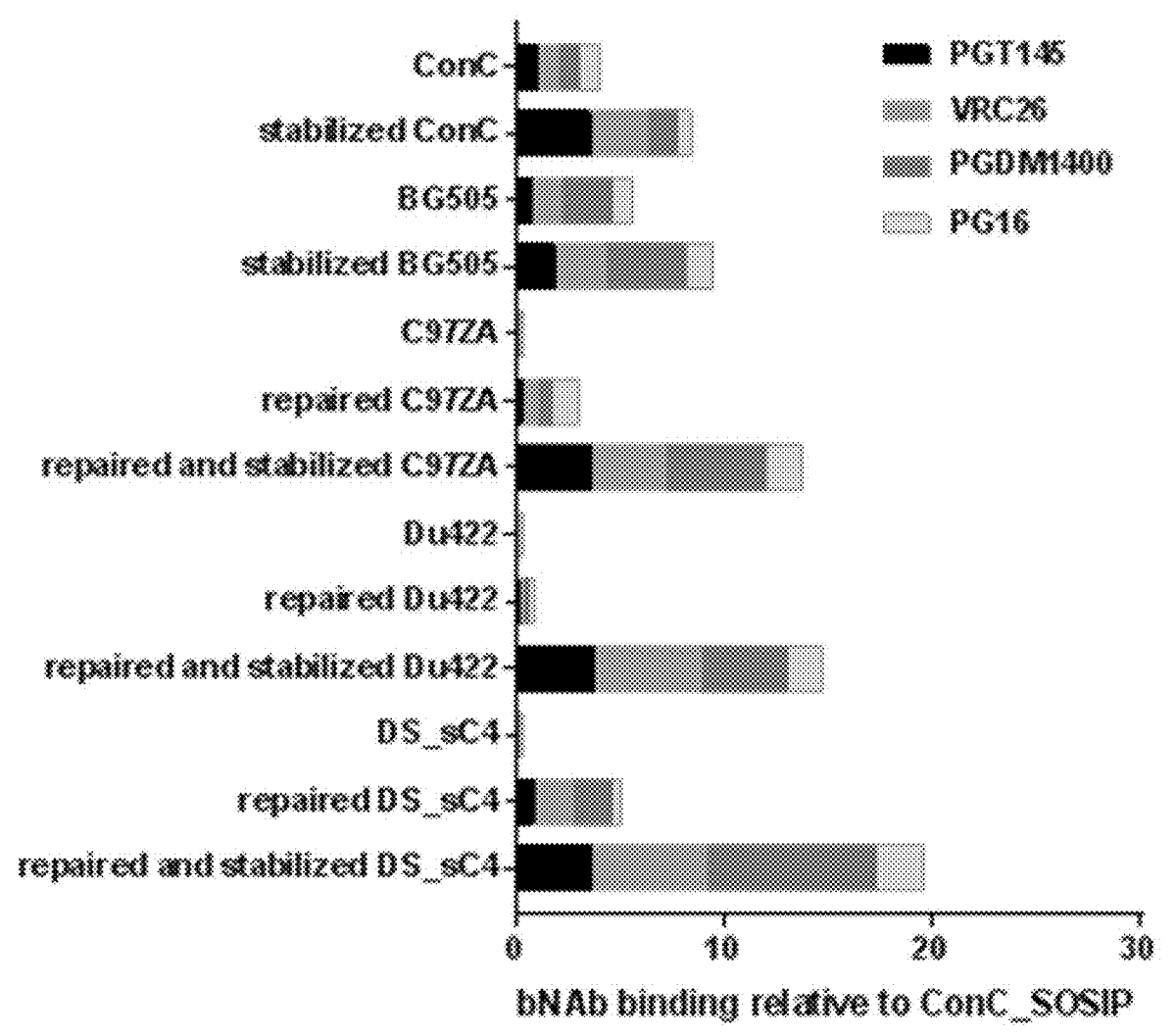

Besides E166R, some other rarely occurring amino acids were changed into more prevalent ones at the corresponding position in a collection of wild-type HIV Env proteins (A114Q, E117K, T375S and I434M), to 'repair' the protein according to a framework explained in more detail in example 12 below and FIG. 12. In this 'repaired' protein, the stabilizing mutations A204I, and K655I improve sC4_SOSIP even further (FIG. 13).

The results of this Example are consistent with those of Example 5 in demonstrating that the mutations described herein also have a stabilizing effect on the envelope protein, e.g., improved percentage of trimer formation, and/or improved trimer yield, etc., when introduced into different backbone HIV envelope protein sequences, in this case a non-consensus, synthetic, Env sequence.

Example 7: Further Combinations of HIV Env Mutations

Recombinant HIV Env proteins according to embodiments of the invention comprising amino acid substitutions introduced in ConC_SOSIP (having the sequence shown in SEQ ID NO: 3) were prepared and purified as described in Example 2. The percentage of trimer formation was measured by AlphaLISA assay as described in Example 3. Subsequently, a smaller selection of combinations (the ones depicted below in italic and additionally K655I; I535N, D589V; I535N, K655I; D589V, K655I) were purified using *Galanthus nivalis* lectin and trimer content was analyzed using SEC-MALS as described in Example 3. Stability was measured as described in Example 4.

The following mutants were prepared for this experiment:
K655I, N651F;
K655I, N651F, E647F;
K655I, N651F, E647F, I535N;
K655I, N651F, I535N;
K655I, I573F;
K655I, D589V, I573F;
K655I, D589V, I573F, N651F;
K655I, D589V, I573F, K588E;
K655I, D589V, I573F, N651F, K588E;
K655I, D589V, I573F, N651F, K588E, I535N;
K655I, D589V, I573F, N651F, K588E, I535N, A204I;
K655I, D589V, I535N, L556P;
K655I, D589V, I573F, N651F, K588E, L556P;
K655I, D589V, A204I;
L556P, N651F;
L556P, N651F, K655I;
L556P, N651F, K655I, I535N;
L556P, N651F, K655I, I535N, I573F;
L556P, N651F, K655I, I535N, I573F, D589V;
L556P, N651F, K655I, I535N, I573F, D589V, A204I;
L556P, N651F, K655I, I535N, I573F, D589V, A204I, K588Q;
L556P, N651F, K655I, I535N, I573F, D589V, A204I, K588Q, E647F;
L556P, N651F, I535N;
L556P, N651F, I535N, I573F;
L556P, N651F, I535N, I573F, D589V;
L556P, N651F, I535N, I573F, D589V, A204I;
L556P, N651F, I535N, I573F, D589V, A204I, K588Q;
L556P, N651F, I535N, I573F, D589V, A204I, K588Q, E647F;
L556P, K655I, I535N;
L556P, K655I, I535N, I573F;
L556P, K655I, I535N, I573F, D589V;
L556P, K655I, I535N, I573F, D589V, A204I;
L556P, K655I, I535N, I573F, D589V, A204I, K588Q;
L556P, K655I, I535N, I573F, D589V, A204I, K588Q, E647F;
L556P, N651F, I535N, I573F, D589V, A204I, K588Q with the SOS mutation removed.

All tested combinations of substitutions in the ConC_SOSIP backbone showed higher trimer percentage, higher trimer yield and higher trimer stability at 60° C. compared to the backbone in AlphaLISA (data not shown). SEC_MALS confirmed improved trimer percentage for all tested mutations in the backbone (data not shown).

Figure 7:
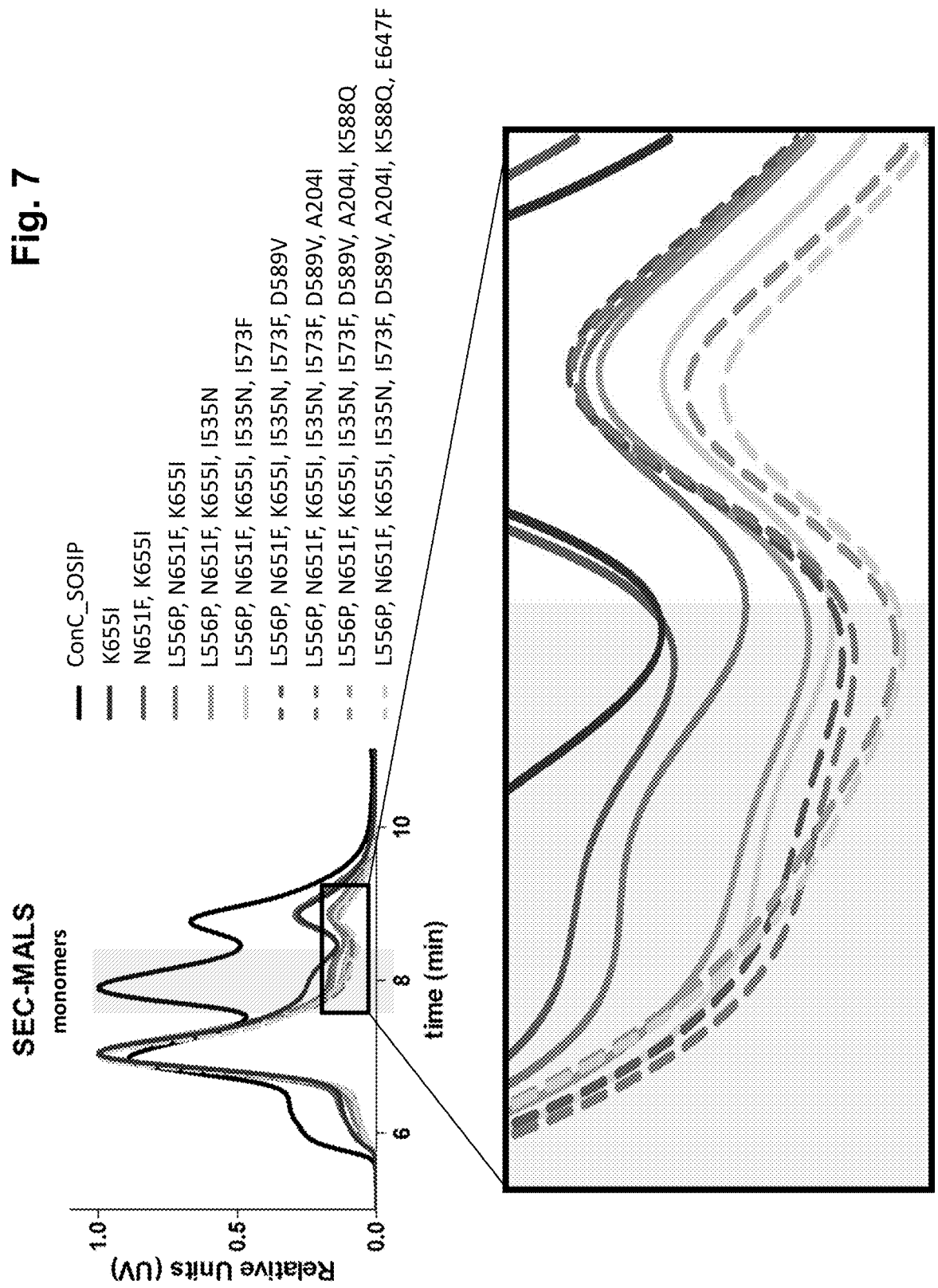
FIG. 7 shows the chromatograms from size exclusion chromatography with multi-angle light scattering (SEC-MALS) analysis of recombinant HIV Env proteins according to embodiments of the invention; the recombinant HIV Env proteins tested contained the single K655I mutation with in each next variant an additional mutation introduced into the backbone HIV Env consensus clade C sequence ConC_SOSIP (SEQ ID NO: 3), and were purified by lectin affinity chromatography as described in example 2; SEC-MALS analysis was performed as described in example 3; the peak representing the gp140 monomers in ConC_SOSIP are indicated by a shaded box, at the right side of the trimer peak. The lower panel shows a zoom in on the lower part of the graph, such that it can be seen that each additional mutation causes a further drop in the height of the gp140 monomer peak.

For a set comprising one by one additional mutations up to nine mutations, SEC-MALS showed that by the introduction of each next mutation the ratio trimer/monomer increased, as the height of the monomer peak decreased, while the height of the trimer peak stayed the same in the SEC graph (FIG. 7). Of all the variants tested in SEC-MALS, the variant with L556P, N651F, K655I, I535N, I573F, D589V, A204I, K588Q, E647F substitutions showed the highest trimer percentage (the least gp140 monomers and the least gp120 monomers), the highest total protein yield and one of the higher temperature stabilities. This means that these mutations can be combined without loss of trimer compared to the backbone. In addition, this suggests that, in general, addition of mutations described in (i)-(vii) of Table 1, optionally combined with mutations described in Table 2, results in further improved trimerization.

A construct with the L556P, N651F, I535N, I573F, D589V, A204I, K588Q mutations wherein the 'SOS mutations' were removed (i.e. the two cysteine residues at positions 501 and 605 were reverted back into the amino acid residues that were originally present in the consensus clade C sequence), was also tested. Even though its temperature stability was lower, the mutant had comparable trimer percentage and yield as its corresponding mutant that did comprise the SOS mutation. The mutant wherein the SOS mutation was removed even had an advantage in that it bound less non-bNAbs than its corresponding SOS-containing counterpart (having the L556P, N651F, I535N, I573F, D589V, A204I, K588Q mutations). This demonstrates that advantageous properties of the instant invention, such as high trimerization percentage, can also be obtained in HIV Env proteins that do not have all the SOSIP mutations.

One mutant (tested in the ConC_SOSIP backbone), based upon a combination of favorable properties in expression level, trimer formation and binding to broadly neutralizing antibody PGT151, has the following mutations: L556P, N651F, I535N, I573F, D589V, A204I, K588Q.

In the ConC_SOSIP background, the 9 most successful substitutions were L556P, E647F, N651F, K655I, I535N, D589V, I573F, and K588E in gp41 and A204I in gp120. The combination of all these 9 substitutions led to increased stability, trimer content and trimer yield. Since addition of L556P in this variant with 9 substitutions had a relatively limited effect on improved trimer percentage, and the E647F substitution in this context appeared to hamper PGT151 binding, these two mutations were not always used in further variants, and a variant with 7 substitutions (named ConC_SOSIP_7mut, sometimes also referred to herein as 'stabilized ConC_SOSIP' or 'ConC_base'; including N651F, K655I, I535N, D589V, I573F, K588E, and A204I) was found to be slightly more stable (increased melting temperature) than the variant with the 9 substitutions indicated above. The complete sequence of this variant (stabilized ConC_SOSIP Env, HIV 160544) is provided in SEQ ID NO: 20.

At this moment, a particularly preferred mutant [tested in the ConC_SOSIP backbone with the following additional mutations: (a) D279N, A281V, A362Q (increase similarity to transmitted founder viruses, as described by others); (b) Del139-152 (deletion of a variable loop to reduce chance of inducing antibodies to this loop); and (c) V295N (introduction of a glycan site that is present in the majority of HIV strains)], based upon a combination of favorable properties in expression level, trimer formation and binding to a broadly neutralizing antibody, has the following stabilizing mutations of the invention: N651F, K655I, I535N, I573F, D589V, A204I, K588E. The complete sequence of this variant (Stabilized ConC_SOSIP.v3 Env (HIV170654, ConC_SOSIP.v3)) is provided in SEQ ID NO: 28.

In a further variant, a K658V mutation was added to this construct (see also example 15 below), which further improved the results.

Example 8: Self-Assembling Particles Displaying Stabilized HIV Env Protein

Ferritin and DPS self-assembling particles were prepared that display stabilized Env proteins in a similar fashion as described in (He et al, 2016). In order to do this the gp140 protein was fused to the N-terminus of the particles via a short amino acid linker (e.g. GSG or AAAGS, but other linkers can also be used, see e.g. He et al, 2016) at DNA level and expressed the fusion protein in Expi293F cells. One example of a particle that was prepared in this manner was based on ferritin fused to a ConC_SOSIP (SEQ ID NO: 3) HIV Env protein with the following mutations: I535N, A558P, D589V, K655I. Ferritin particles with this Env protein having an additional V570D mutation, which has been reported to improve trimerization (Kesavardhana et al, 2014), were also prepared, but it was observed that this mutation leads to a strong increase in binding of a non-neutralizing antibody (17b), which is undesired. Env with these five mutations was also fused to two types of DPS particles, from *Helicobacter pylori* and from *Mycobacterium smegmatis* (see e.g. WO2011/082087 for preparation of DPS particles). Env with these five mutations and in addition the disulfide bridge introducing double mutation I201C-A433C was also fused to ferritin.

The particles were purified from cell free supernatant with PGDM140 affinity beads and the particles were analyzed using SEC-MALS with a TSKgel G6000PWCL column. SEC-MALS, as well as Native PAGE (3-12%), confirmed that particles with approximately the expected sizes were formed.

In a similar manner, ferritin and DPS self-assembling nanoparticles displaying HIV Env having a ConC_SOSIP sequence with the following combination of mutations: (L556P, N651F, I535N, I573F, D589V, A204I, K588Q), are also prepared.

Further liposomes and/or self-assembling nanoparticles displaying other HIV Env variants described herein, e.g. HIV Env having SEQ ID NO: 20, 22, 24, 26, 27, 28, 29, 30, 31, or 32, are also prepared.

Example 9: Recombinant HIV Envelope Protein Variants Based on a Clade a Envelope Protein Sequence Recombinant HIV Env proteins according to embodiments of the invention comprising single amino acid substitutions (I535N, D589V, N651F, K655I, I573F, A204I or E647F) were introduced into a wild type clade A HIV envelope protein with the SOSIP modification (named 'BG505_SOSIP') as described in Example 2. The HIV envelope protein BG505_SOSIP has the so-called SOSIP mutations (Cys at residues 501 and 605, and Pro at residue 559), as well as further Cys at residues 201 and 433 resulting in the introduction of a disulfide (DS) bond, and a potential N-glycosylation site on position 332 (T332N mutation). The protein is truncated at position 664. The sequence of BG505_SOSIP is shown in SEQ ID NO: 21.

Figure 8A:
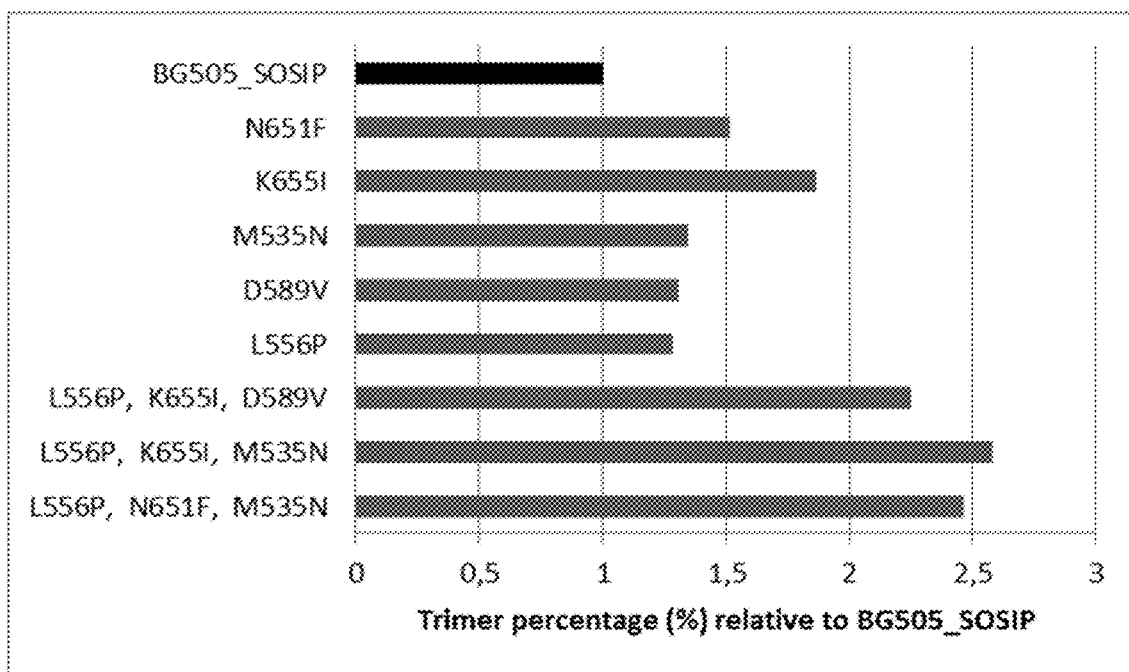
FIGS. 8A-8B show the percentage of trimer formation (FIG. 8A) and the trimer yield (FIG. 8B) for BG505_SOSIP (derived from a wild-type clade A strain) having single amino acid substitutions and combinations of substitutions introduced according to embodiments of the invention compared to that of the envelope protein having the backbone BG505_SOSIP sequence without any additional trimer stabilizing mutations of the invention as described in Example 9. Trimer yield and the percentage of trimer formation was measured by AlphaLISA assay.
Figure 8B:
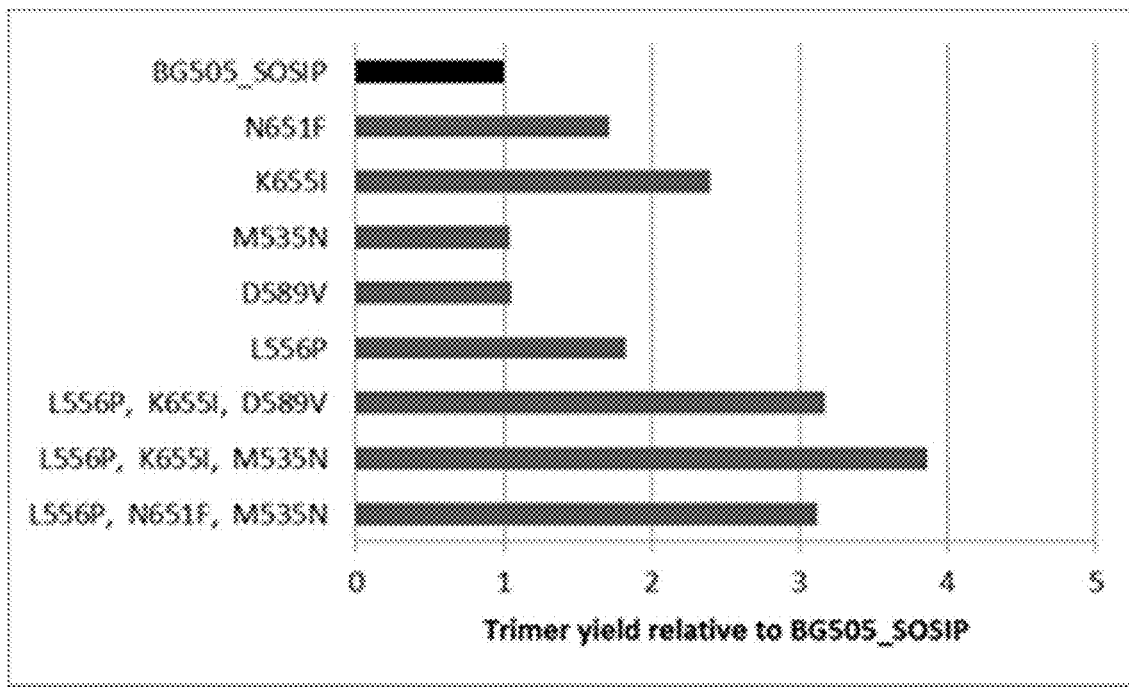

The percentage of trimer formation and trimer yield were measured by AlphaLISA assay as described in Example 3. The percentage of trimer formation and trimer yield for each of the variants tested was compared to BG505_SOSIP. A higher percentage of trimer formation was observed for the M535N, D589V, N651F or K655I substitutions as compared to the backbone sequence (e.g. FIG. 8A). Combination of e.g. L556P, K655I and M535N showed an even more increased trimer yield and percentage (e.g. FIGS. 8A and 8B). Combination of N651F and D589V improved the trimer yield and percentage even more (data not shown). The results of this Example for a clade A virus are consistent with those of examples 10 and 11 (clade C) below and Example 5 (clade B), in which the mutations I535N, D589V, N651F and K655I also showed a stabilizing effect on the envelope protein derived from wild-type strains, e.g., improved percentage of trimer formation, and/or improved trimer yield. Clearly, these mutations of the invention also improve trimerization of HIV Env derived from a wild-type clade A strain.

Figure 9:
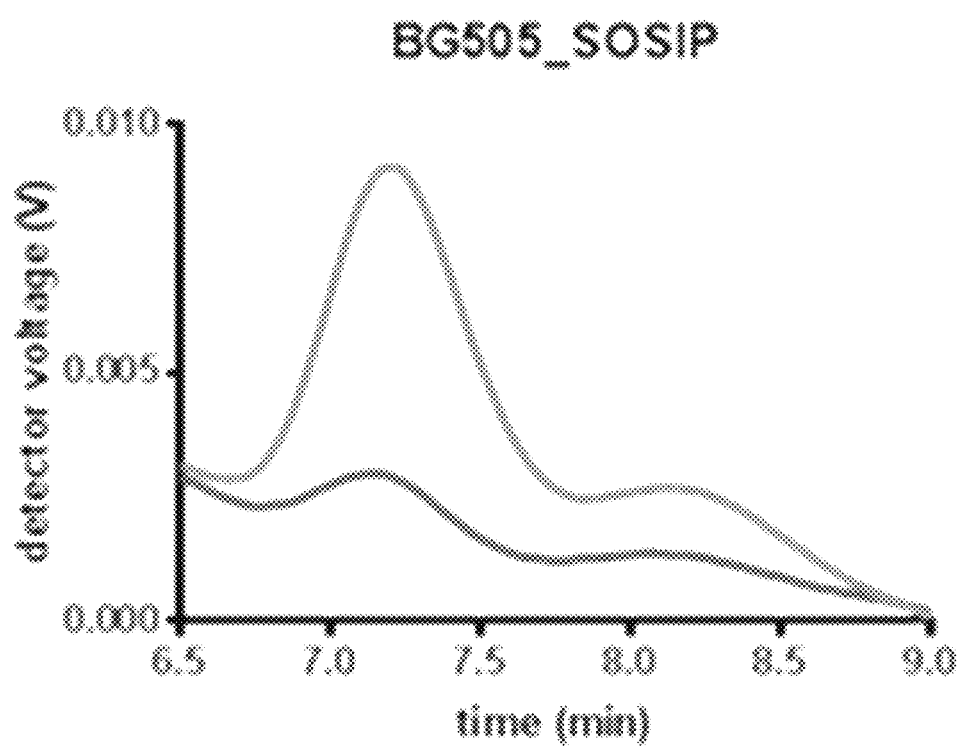
FIG. 9 shows the chromatograms from size exclusion chromatography with multi-angle light scattering (SEC-MALS) analysis of recombinant HIV Env proteins according to embodiments of the invention; SEC-MALS analysis was performed on culture supernatant of Env transfected cells. The peak corresponding to the trimer form elutes between 7 and 7.5 minutes. The dark grey line is BG505_SOSIP (derived from a wild-type clade A strain) and the light grey line is BG505_SOSIP with L556P, K655I, M535N, N651F, D589V, K588E substitutions.

At this moment, a particularly preferred mutant (tested in the BG505_SOSIP backbone, based upon a combination of favorable properties in expression level, trimer formation and binding to a broadly neutralizing antibody, is the one having the following mutations: L556P, K655I, M535N, N651F, D589V, (see e.g. FIG. 9, showing a strongly improved trimer formation of such mutant in a SEC-MALS analysis, and FIG. 13, showing a clearly improved binding of broadly neutralizing antibodies of such mutant). The sequence of this stabilized BG505_SOSIP Env (HIV170863) is shown in SEQ ID NO: 22.

Addition of mutation Q658V provided a small further improvement.

A further preferred construct contains the L556P, K655I, M535N, N651F, D589V mutations, as well as the 'DS' mutations (Cys at positions 201 and 433 resulting in introduction of a disulfide bond), R588E, and Q658V. The sequence of that variant (BG505_SOSIP.v2 Env, HIV171814) is provided in SEQ ID NO: 29.

Example 10: Recombinant HIV Envelope Protein Variants Based on Clade C Wild Type Envelope Protein Sequence Recombinant HIV Env proteins according to embodiments of the invention comprising the single amino acid substitution T651F, the double amino acid substitution T651F, M535N introduced into a WT C97ZA_SOSIP Env sequence (SEQ ID NO: 23) with the additional substitution L556P (C97ZA_SOSIP_L556P) were generated and expressed as described in Example 2. The trimer yield and percentage of trimer formation were measured by AlphaLISA assay as described in Example 3.

Figure 10A:
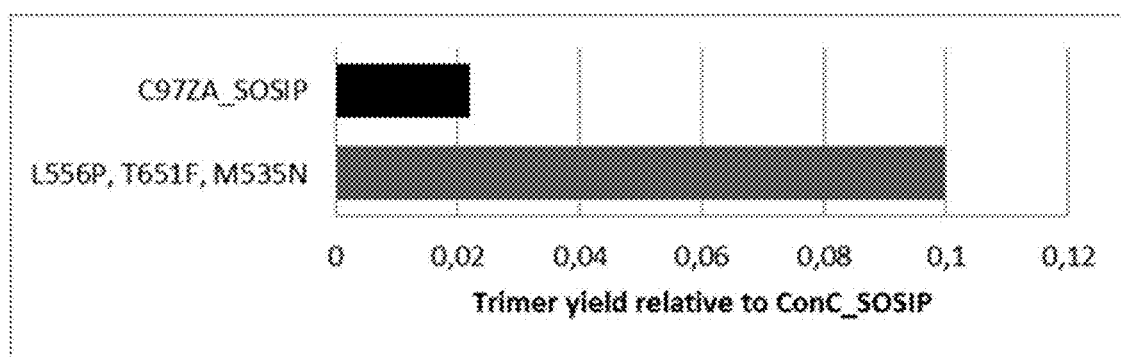
FIGS. 10A-10B show the trimer yield for C97ZA_SOSIP variants, described in Example 10. Trimer yield of C97ZA with three stabilizing substitutions (L556P, T651F and M535N) (FIG. 10A and FIG. 10B).
Figure 10B:
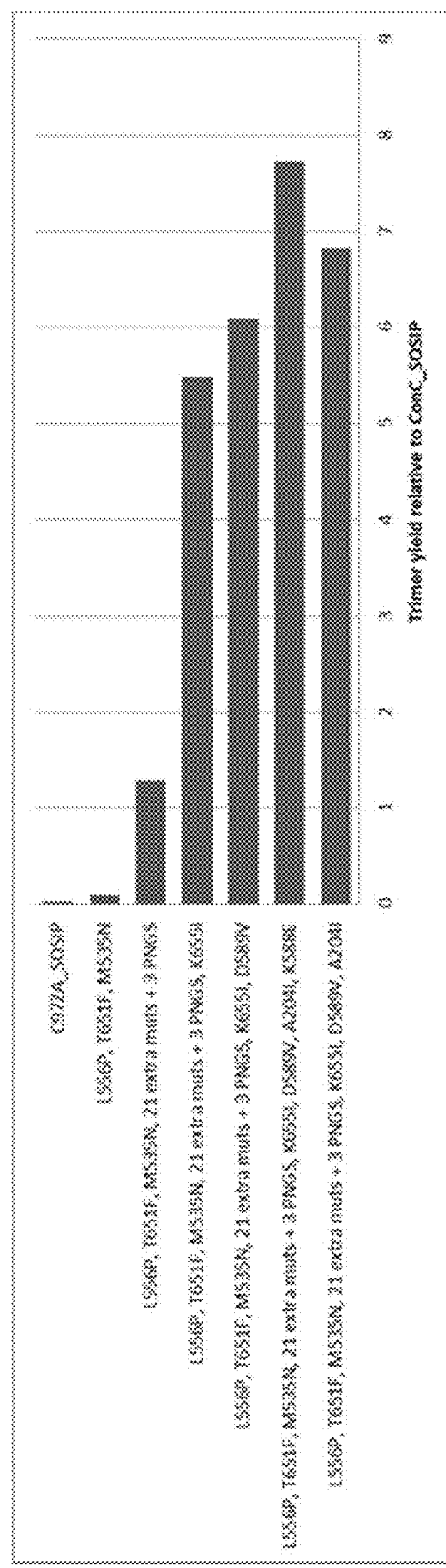

The results are shown in FIGS. 10A and B. The trimer yield of C97ZA_SOSIP_L556P_T651F_M535N is five times higher than that of the C97ZA_SOSIP backbone.

The L556P, T651F and M535N substitutions thus gave a large improvement of C97ZA_SOSIP, but binding to bNAbs and trimer percentage for this clade C wild-type derived variant was still much lower than for the ConC_SOSIP backbone. Because a wt Env may be adapted to its host, possibly reducing its general fitness, and thereby the folding may be corrupted, the Env sequence was 'repaired' according to the conceptual framework described below in Example 12 and in FIG. 12. A total of 21 residues were changed, to repair the sequence, and three potential N-glycosylation sites (PNGS) were added to fill the so-called "glycan holes" (positions where in at least 50% of the wild-type HIV strains Env protein a potential N-glycosylation site is present). The mutations introduced by following this framework for C97ZA_SOSIP are indicated in Table 3 in the column 'repairing mutations'. Addition of stabilizing mutation K655I disclosed herein increased the trimer percentage and yield even further, as did D589V, A204I and K588E.

These results demonstrate that the T651F, M535N and K655I, D589V, A204I and K588E mutations described herein also had a stabilizing effect on the envelope protein, e.g., improved trimer yield, improved percentage of trimer formation when introduced into C97ZA_SOSIP (derived from a clade C wild-type strain Env protein) and variants thereof.

At this moment, a particularly preferred variant (tested in the C97ZA_SOSIP backbone), based upon a combination of favorable properties in expression level, trimer formation and binding to a broadly neutralizing antibody, is the one having the following mutations: Q567K (described by others before); A198T, S243N, K236T, V295N (to fill glycan holes); M34L, T46K, T58A, Q171K, G172V, P179L, L183Q, I192R, N209T, M307I, Q350R, N352H, Y353F, D412N, G429E, V455T, I489V, L491I, G500K, S547G, T578A, T651N (to repair the sequence); V505N, E507T, T663N (added potential N-glycosylation sites at base of molecule); and A204I, M535N, L556P, K588E, D589V, T651F, K655I (stabilizing mutations of invention). Data for this variant are for instance shown in FIG. 13, see in particular 'stabilized and repaired C97ZA' therein), showing a huge increase in broadly neutralizing antibody binding as compared to the original wt C97ZA Env molecule. The sequence of this variant (stabilized and repaired C97ZA_SOSIP Env (HIV170690)) is provided in SEQ ID NO: 24.

Addition of mutation K658V stabilized this protein even further.

A further preferred variant includes the 'DS' mutation and K658V, and the sequence of this variant (C97ZA_SOSIP.v2 Env, HIV171810) is provided in SEQ ID NO: 30.

Figure 11:
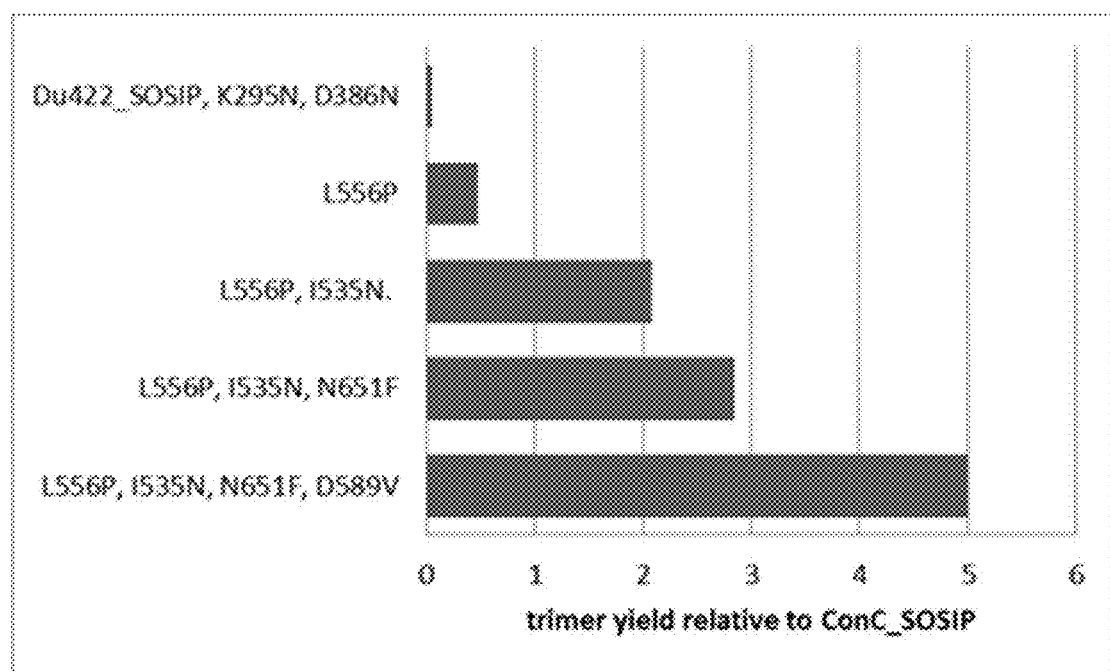
FIG. 11 shows the trimer yield of HIV-1 Env strain DU422 with four stabilizing substitutions (see Example 11 for details). All numbers were normalized to ConC_SOSIP (not shown) which was set to 1.

Example 11: Recombinant HIV Envelope Protein Variants Based on Another Clade C Wild Type Envelope Protein Sequence In the Env protein from clade C strain Du422, SOSIP mutations were introduced and two glycan holes were filled at position 295 and 386 by K295N and D386N mutations. In addition, some residues were repaired according to the conceptual framework described in Example 12 and FIG. 12 (V272I, W456R, G466E and F643Y), and stabilizing substitutions L556P, I535N, N651F and D589V were introduced. All additional substitutions resulted in higher trimer yields and trimer percentages (e.g. FIG. 11).

In a specific tested variant with these four stabilizing mutations (SEQ ID NO: 25), the additional K655I substitution further increased trimer yield and trimer percentage by a factor 1.3 and 1.4 respectively (data not shown).

At this moment, a particularly preferred Du422_SOSIP Env variant, based upon a combination of favorable properties in expression level, trimer formation and binding to a broadly neutralizing antibody, is the one having the following mutations: L556P, K655I, M535N, N651F, D589V, K588E, I201C, A433C, V272I, W456R, G466E, F643Y, D386N, and K295N. The sequence of this variant (stabilized and repaired Du422_SOSIP Env (HIV170859) is provided in SEQ ID NO: 26. Data for this variant are for instance shown in FIG. 13 (see stabilized and repaired Du422 therein), showing a huge increase in broadly neutralizing antibody binding compared to the original wt Du422 Env molecule.

A further preferred variant additionally comprises the 'DS' mutation and K658V, and the sequence of this variant (Du422_SOSIP.v1 Env, HIV171812) is provided in SEQ ID NO: 31.

Example 12: Repairing and Stabilizing Various HIV-1 Env Sequences

Because wt sequences from viruses isolated from infected patients may have acquired destabilizing mutations that impede correct folding, wt Env sequences of clade C C97ZA, DU422 and the mosaic sC4 were first repaired.

To search for non-optimal mutations in wild type sequences an alignment of all HIV-1 Env sequences in the UniProt database and the Los Alamos HIV database (~90.000 sequences) was made and the amino acid distribution was calculated for each amino acid. In general, a number of relatively rarely occurring amino acids in wt Env sequences were substituted into more common amino acids (based upon frequency in the database at the corresponding position) according to the conceptual framework described in FIG. 12.

Furthermore, two additional substitutions Y353F and Q171K at the apex of C97ZA_SOSIP were introduced to possibly improve the binding of apex targeting antibodies, and extra glycan sites were introduced by the substitution of D411N, K236T and V295N because these potential N-glycosylation sites (PNGS) were conserved >50%. Next, stabilizing substitutions described in previous examples were transferred to the repaired sequence.

The stabilized ConC_SOSIP contains the substitutions A204I, I535N, I573F, K588E, D589V, N651F and K655I (stabilized ConC_SOSIP). The complete sequence of stabilized ConC_SOSIP is provided in SEQ ID NO: 20.

An overview of some of the variant Env proteins and their mutations is provided in Table 3.

TABLE 3

HIV Env protein variants.

| Protein | mutations from literature | added PNGS | leader sequence (SEQ ID NO:) | repairing mutations | stabilizing mutations | other mutations | terminus |
|---|---|---|---|---|---|---|---|
| ConC_SOSIP | | V295N | 11 | | | | 664 |
| Stabilized ConC_SOSIP | | V295N | 11 | | A204I, I535N, I573F, K588E, D589V, N651F, K655I | | 664 |
| BG505_SOSIP | | T332N | 34 | | | | 664 |
| stabilized BG505_SOSIP | | T332N | 34 | | M535N, L556P, D589V, N651F, K655I | | 664 |
| C97ZA_SOSIP | L535M, Q567K | | native | | | | 664 |
| repaired C97ZA_SOSIP | L535M, Q567K | A198T, S243N, K236T, V295N | 11 | M34L, T46K, T58A, Q171K, G172V, P179L, L183Q, I192R, N209T, M307I, Q350R, N352H, Y353F, D412N, G429E, V455T, I489V, L491I, G500K, S547G, T578A, T651N | | V505N, E507T, T663N | 664 |
| repaired and stabilized C97ZA_SOSIP | Q567K | A198T, S243N, K236T, V295N | 11 | M34L, T46K, T58A, Q171K, G172V, P179L, L183Q, I192R, N209T, M307I, Q350R, N352H, Y353F, D412N, G429E, V455T, I489V, L491I, G500K, S547G, T578A, T651N | A204I, M535N, L556P, D589V, T651F, K655I | V505N, E507T, T663N | 664 |
| Du422_SOSIP | | D386N, K295N | 11 | | | | 664 |
| repaired Du422_SOSIP | | D386N, K295N | 11 | V272I, W456R, G466E, F643Y | | | 664 |
| repaired and stabilized Du422_SOSIP | | D386N, K295N | 11 | V272I, W456R, G466E, F643Y | M535N, L556P, K588E, D589V, N651F, K655I | | 664 |
| DS_sC4_SOSIP | I201C-A433C | V295N | 33 | | | | 655 |
| repaired DS_sC4_SOSIP | I201C-A433C | V295N | 33 | A114Q, E117K, E166R, T375S, I434M | | | 655 |
| repaired and stabilized DS_sC4_SOSIP | I201C-A433C | V295N | 33 | A114Q, E117K, E166R, T375S, I434M | A204I, I535N, L556P, Q588E, D589V, N651F, K655I | delta138-152 (SSNGTYNII HNETYK), delta191 (SEKSSENSSE), delta 463 (GVP) | 655 |

Table 3. Several of HIV Env protein variants described herein. The column 'mutations from literature' describes mutations that were used in these constructs and previously described by others. The column 'added PNGS' describes mutations that add a potential N-glycosylation site (at positions where many wild type Env proteins comprise such a site). The column 'leader sequence' describes which leader sequence was used for expression if it was not the original (native) leader sequence. The column 'repairing mutations' describes the mutations that improve folding and stability (measured as trimer yield and percentage, based on binding to bNAbs) of some of the wild-type Env proteins, as described in Example 12 and FIG. 12. The column 'stabilizing mutations' describes mutations of the invention that stabilize the protein and improve trimerization as disclosed herein. The column 'further mutations' describes additional mutations made for some constructs. The column 'terminus' describes the position of the last amino acid (numbering throughout the table is with respect to HXB2 Env sequence).

Supernatants of cells transiently transfected with wild-type (wt), repaired, and stabilized Env variants were tested for binding to several trimer-specific broadly neutralizing antibodies directed to the apex. The repair substitutions and especially the stabilizing substitutions had a dramatic impact on trimer content (FIGS. 13 and 14A-E), determined with AlphaLISA (FIG. 13) and SEC-MALS (FIGS. 14A-E).

The sequence of a preferred variant of the repaired and stabilized DS_sC4 Env protein (repaired and stabilized DS_sC4_SOSIP Env (HIV170686)) is provided in SEQ ID NO: 27.

Another preferred variant thereof is provided in SEQ ID NO: 32 (repaired and stabilized sC4_SOSIP.v4 Env.

Example 13: Stabilizing Mutations of the Invention Function in the Absence of the SOSIP Mutations As shown in previous examples, the 7 mutations (A204I, I535N, I573F, K588E, D589V, N651F and K655I) improved the trimer yield and percentage in the ConC_SOSIP (resulting in 'ConC_base' or 'stabilized ConC_SOSIP' or 'ConC_SOSIP 7mut') (e.g. FIGS. 13 and 15).

This example demonstrates that the different SOSIP mutations (i.e. the 'SOS' mutation: 2 substitutions by Cys residues at positions 501 and 605; and the 'IP mutation': substitution by Pro residue at position 559) contribute to further stabilization, but are not required to obtain benefits from the mutations of the invention.

Figure 15:
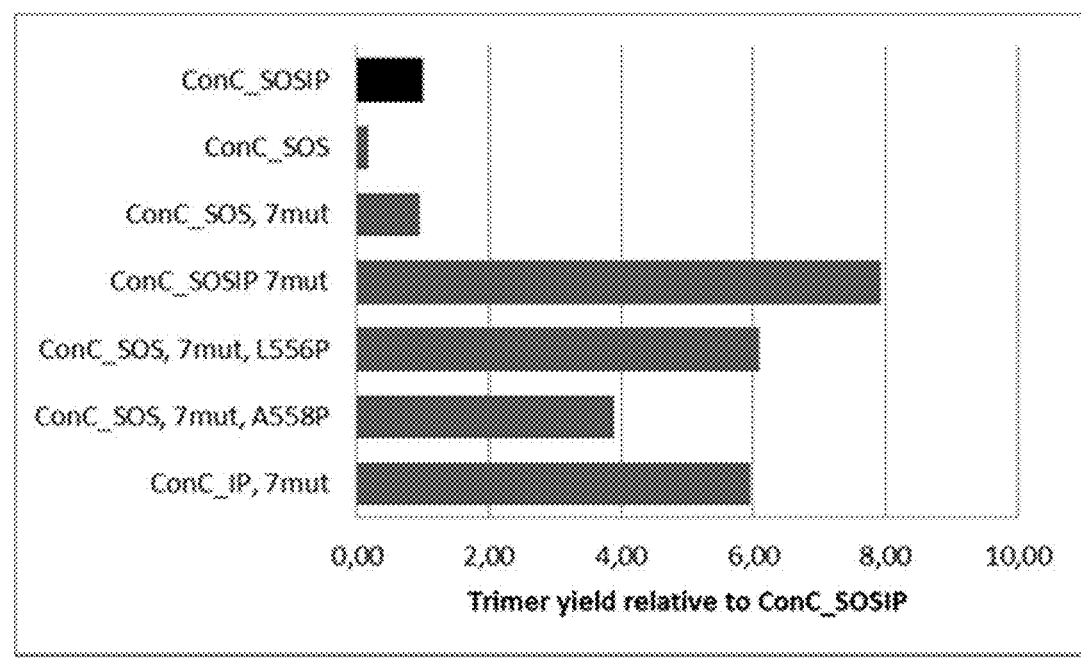
FIG. 15 shows a graph demonstrating trimer yield of HIV-1 Env ConC variants without the stabilizing SOSIP modifications.

The 7 mutations were shown to also improve trimer yield in the so-called ConC_SOS, which does not contain the stabilizing I559P mutation (IP' mutation), as shown in FIG. 15 (compare ConC_SOS vs ConC_SOS, 7mut). Hence, the 'IP' mutation is not essential for obtaining a benefit from the mutations described herein. Addition of the I559P mutation resulted in a big increase, showing that the 'IP' mutation is beneficial in this construct in addition to the 7 mutations of the invention. The stabilizing IP mutation (I559P) could also be replaced by A558P or L556P, both of these also resulting in a big increase over the variant lacking the I559P mutation.

Also the ConC_IP, 7 mut, which contains the 7 mutations of the invention described above, but lacks the 'SOS' mutations, still showed a very high trimer yield, demonstrating that also the 'SOS' mutations are not essential for obtaining benefit from the mutations described herein (e.g. compare ConC_SOSIP vs ConC_IP, 7 mut), in line with observations in example 7. Addition of the 'SOS' mutation does further increase the trimer yield.

Thus, while Env trimers containing the stabilizing mutations described herein can benefit from further stabilization with the SOSIP mutations, none of the 3 SOSIP mutations is required for obtaining benefits (e.g. improved trimer yield) of the stabilizing mutations described herein.

Figure 16A:
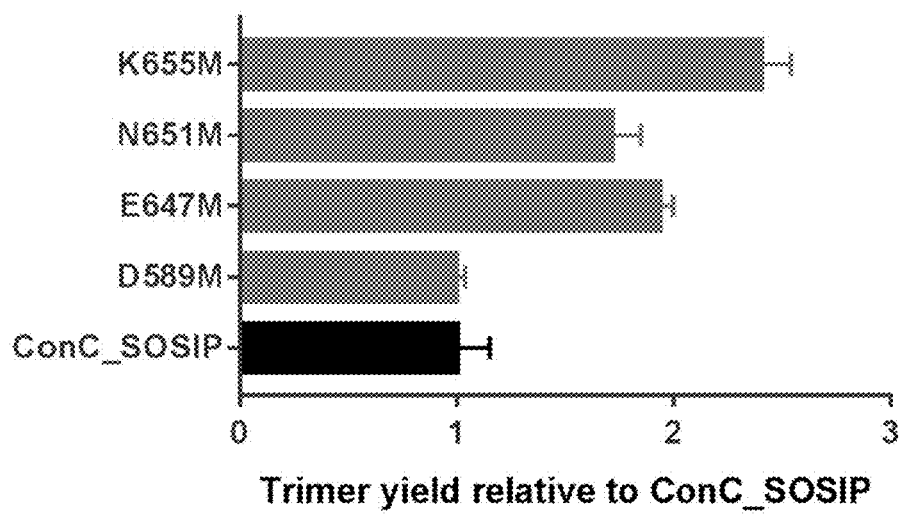
FIGS. 16A and 16B show graphs demonstrating trimer yield (FIG. 16A) and trimer percentage (FIG. 16B) of ConC_SOSIP with mutations at positions 589, 647, 651 and 655 to methionines. All numbers were normalized to ConC_SOSIP (not shown) which was set to 1. An error bar is shown at the right end of the bars.
Figure 16B:
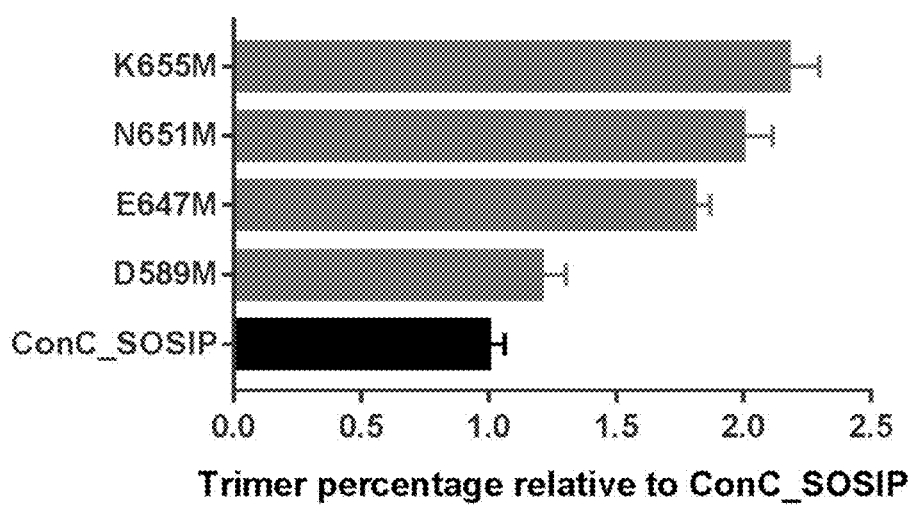

Example 14: Methionine Substitution at Positions 647, 651 or 655 Improves Trimer Quality Further to the mutations described in example 2, positions 589, 647, 651 and 655 were individually substituted by a Met residue in a ConC_SOSIP (SEQ ID NO: 3) backbone, and tested for trimerization percentage and yield using methods as described above. It was shown that a Met at positions 647, 651, or 655, like the mutations described in example 2, improved the quality of the trimer (higher trimer percentage and yield, increased bNAb binding), as can be seen in FIG. 16.

Thus, apart from substitution by Phe, Ala, or Trp at position 651, substitution by Met at position 651 also improves trimer formation; apart from substitution by Phe, Ile, or Trp at position 655, substitution by Met at position 655 also improves trimer formation; and apart from substitution by Phe, or Ile at position 647, substitution by Met at position 647 also improves trimer formation.

Example 15: HIV Env Protein with Trimer Stabilizing Mutation at Position 658

Recombinant HIV Env proteins with substitution mutations at position 658 (numbering according to gp160 of HIV-1 isolate HXB2) were prepared, in the ConC_SOSIP (SEQ ID NO: 3) backbone. K658 was mutated into Val, Ile, Phe, Leu, Met, or Ala. In addition, some double mutants were made wherein these mutations were combined with one of the stabilizing mutations described above, K655I. The percentage of trimer formation was determined by the AlphaLISA assay as described in Example 3.

Figure 17A:
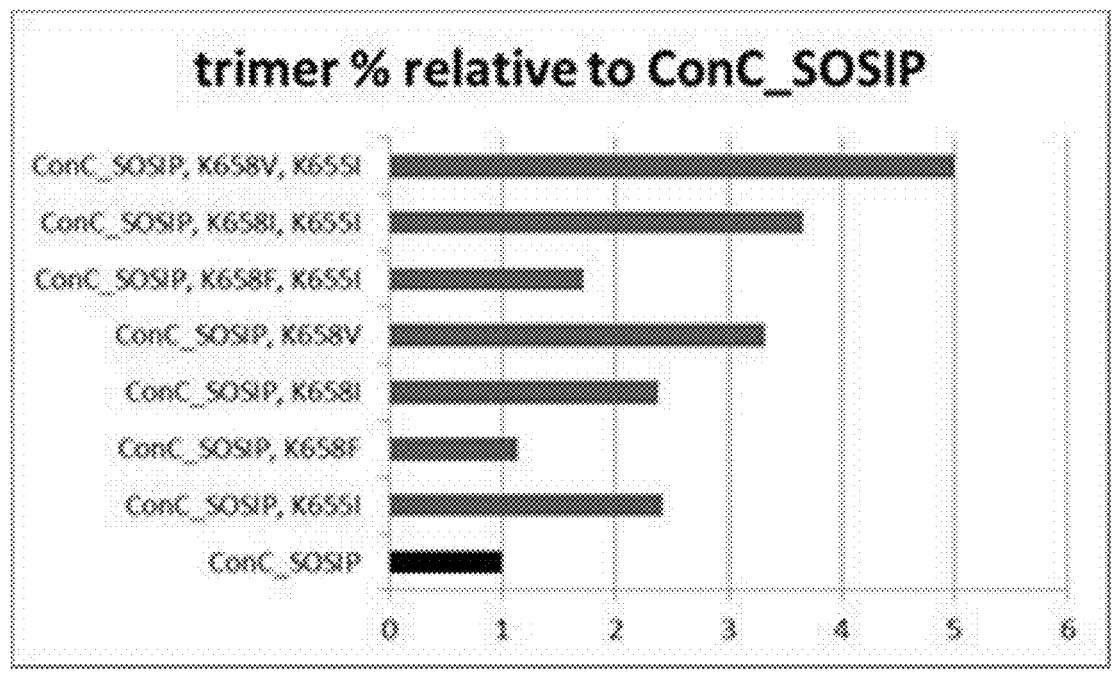
FIGS. 17A-17D show the percentage of trimer formation (FIG. 17A, B for different experiments) and the trimer yield (FIG. 17C, D for different experiments) for recombinant HIV Env proteins with the indicated mutations as described in Example 15, measured by AlphaLISA assay.
Figure 17B:
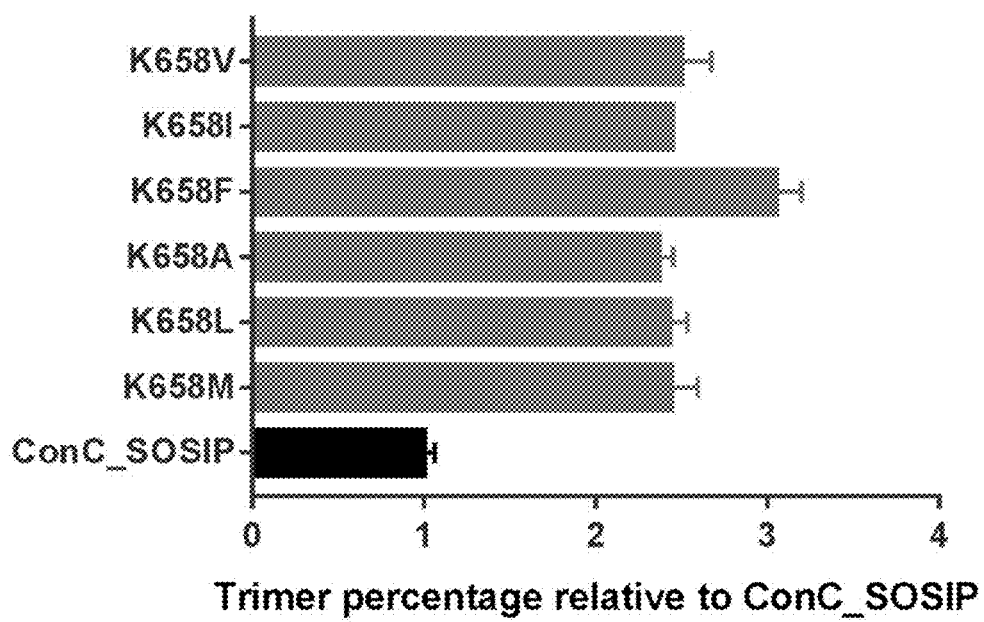
Figure 17C:
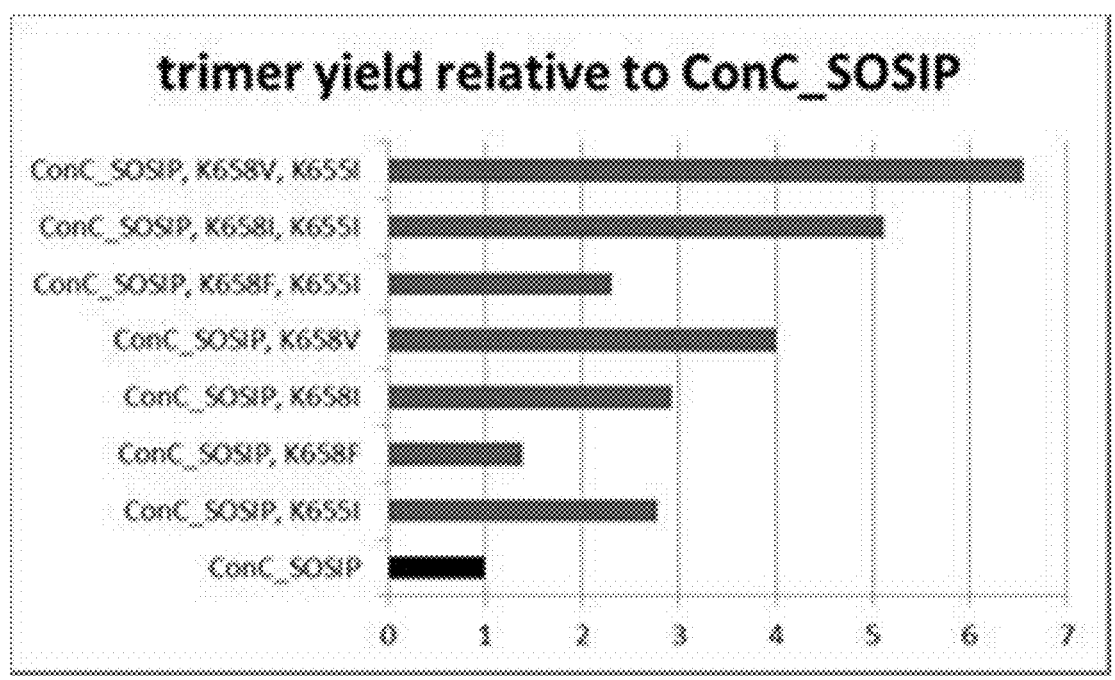
Figure 17D:
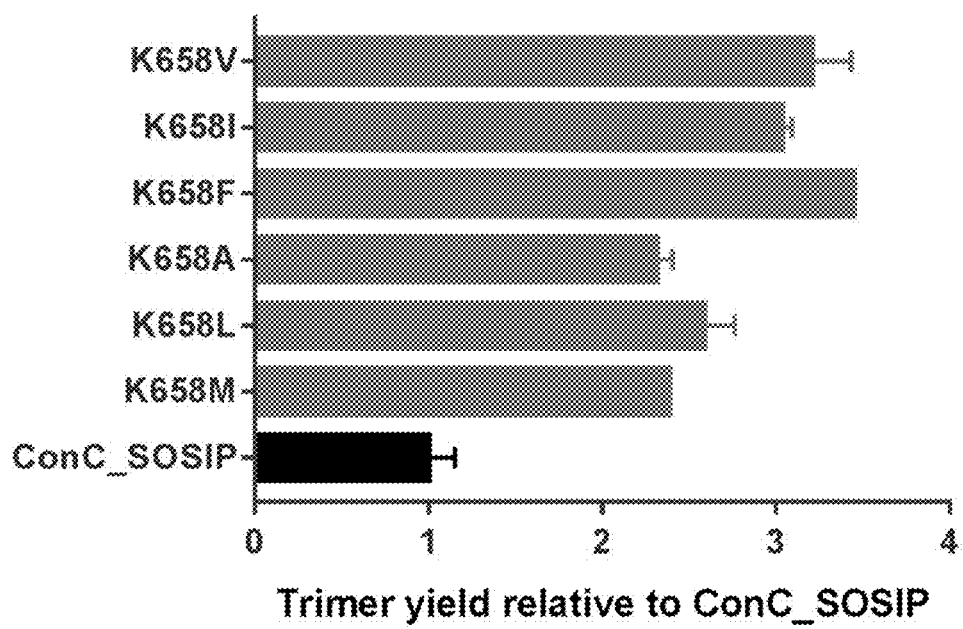

Results are shown in FIGS. 17A and B (trimer percentage, measured in different experiments, hence two panels) and FIGS. 17C and D (trimer yield, measured in different experiments, hence two panels). These results demonstrate that substitution at position 658 by Ile, Phe, Met, Leu, Ala, or Val resulted in improved percentage of trimer formation and improved trimer yield. Substitution with Ile at position 658 resulted in increases that are in about the same range as the K655I mutation (FIGS. 17A, C), which was the best performing single mutant from the mutations (i)-(vii) in Table 1 described above (see e.g. FIG. 2A). Substitution with Val at position 658 resulted in even higher improvement (FIGS. 17A, C).

The results also demonstrated that substitution at position 658 by Ile or Val could be combined with mutation K655I that was described above, and that this resulted in a further improvement over each of the corresponding single mutants (FIGS. 17A, C).

Figure 18:
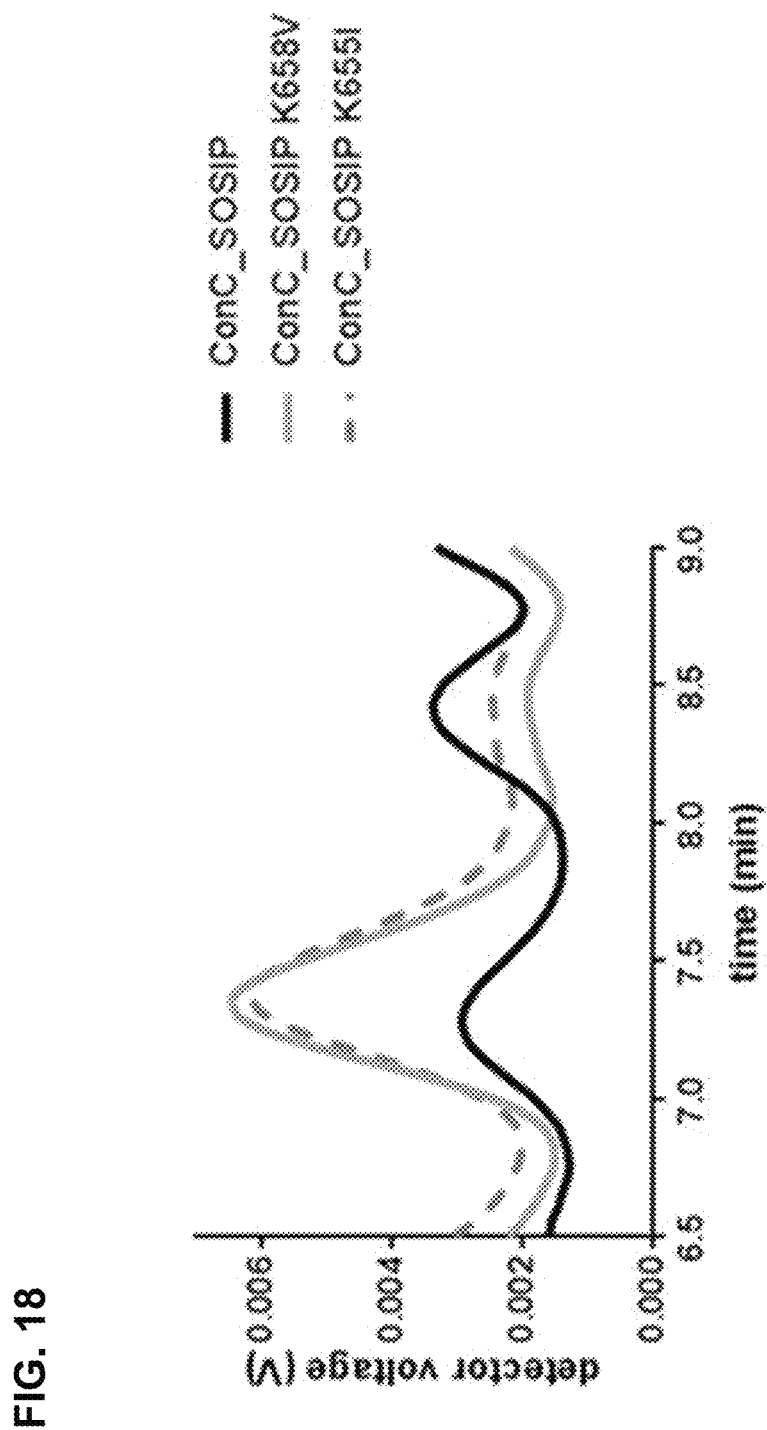
FIG. 18 shows the SEC-MALS chromatograms of recombinant HIV Env proteins with the indicated mutations, as described in Example 15.

The K658V mutant was also tested using SEC-MALS. 96-well cultures were grown for three days as was done for the AlphaLISA. Supernatant was directly loaded on a SEC-MALS column. The chromatograms obtained for the mock supernatant (with furin expression) was subtracted from the chromatograms of the supernatant with Env proteins. The trimeric protein eluted from the column between 7 and 8 minutes. The results are shown in FIG. 18, and confirmed that the K658V mutant showed improved trimerization over the background Env protein, and over the K655I mutant Env protein.

This example demonstrates that substitution of the amino acid at position 658 in HIV Env protein by Val, Ile, Phe, Met, Leu, or Ala results in improved trimer percentage and trimer yield.

Further experiments to measure trimer formation of variants using AlphaLISA and/or SEC-MALS are performed in HIV Env variants wherein the K658V mutation is present in combination with other mutations from Tables 1 and/or 2 as described herein, as well as in HIV strains from clade A and B. For example, the 658V mutation has already been shown to improve the ConC_SOSIP,7mut variant as described above (example 7), as well as BG505_SOSIP with L556P, K655I, M535N, N651F, D589V, K588E (example 9), as well as the repaired and stabilized C97ZA_SOSIP (example 10).

Based on the results described above, it is expected that the mutation of the amino acid at position 658 into a Valine, Isoleucine, Phenylalanine, Leucine, Methionine or Alanine, preferably into a Valine, residue will improve trimer formation and/or trimer yield in different background HIV Env proteins.

Example 16. Immunization with Stabilized HIV Env Proteins

A rabbit immunization study is conducted with soluble Env protein and with Env proteins coupled to liposomes. The prime is performed with stabilized ConC_SOSIP.v3

(SEQ ID NO: 28), and followed by four boosts, each with another protein, i.e. with 1) repaired and stabilized sC4_SOSIP.v4 (SEQ ID NO: 32); 2) repaired and stabilized C97ZA_SOSIP.v2 (SEQ ID NO: 30); 3) repaired and stabilized Du422_SOSIP.v1 (SEQ ID NO: 31); and 4) stabilized BG505_SOSIP.v2 (SEQ ID NO: 29).

Serum is isolated after successive immunizations, and analyzed for induced antibodies that particularly bind to the stable, closed, pre-fusion conformation of Env (using ELISA), as well as for induction of bNAbs (using virus neutralization assays).

The examples above demonstrate that the invention provides a universal approach to optimize the folding and stability of prefusion-closed HIV envelope trimer proteins.

It is understood that the examples and embodiments described herein are for illustrative purposes only, and that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

---

LIST OF SEQUENCES

SEQ ID NO: 1 gp160 of HIV-1 isolate HXB2 (signal sequence in italics; amino acids at positions (i)-(vii) for mutations according to the invention indicated by grey shading)
*MRVKEKYQHLWRWGWRWGTMLLGMLMIC*SATEKLWVTVYYGVPVWKEATTTLFCASDAKAYDTEVHNVWATHACVPTD
PNPQEVVLVNVTENFNMWKNDMVEQMHEDIISLWDQSLKPCVKLTPLCVSLKCTDLKNDTNTNSSSGRMIMEKGEIKN
CSFNISTSIRGKVQKEYAFFYKLDIIPIDNDTTSYKLTSCNTSVITQACPKVSFEPIPIHYCAPAGFAILKCNNKTFN GTGPCTNVSTVQCTHGIRPVVSTQLLLNGSLAEEEVVIRSVNFTDNAKTIIVQLNTSVEINCTRPNNNTRKRIRIQRG
PGRAFVTIGKIGNMRQAHCNISRAKWNNTLKQIASKLREQFGNNKTIIFKQSSGGDPEIVTHSFNCGGEFFYCNSTQL
FNSTWFNSTWSTEGSNNTEGSDTITLPCRIKQIINMWQKVGKAMYAPPISGQIRCSSNITGLLLTRDGGNSNNESEIF
RPGGGDMRDNWRSELYKYKVVKIEPLGVAPTKAKRRVVQREKRAVGIGALFLGFLGAAGSTMGAASMTLTVQARQLLS

GIVQQQNNLLRAIEAQQHLLQLTVWGIKQLQARILAVERYLKDQQLLGIWGCSGKLICTTAVPWNASWSNKSLEQIWN

HTTWMEWDREINNYTSLIHSLIEESQNQQEKNEQELLELDKWASLWNWFNITNWLWYIKLFIMIVGGLVGLRIVFAVL

SIVNRVRQGYSPLSFQTHLPTPRGPDRPEGIEEEGGERDRDRSIRLVNGSLALIWDDLRSLCLFSYHRLRDLLLIVTR
IVELLGRRGWEALKYWWNLLQYWSQELKNSAVSLLNATAIAVAEGTDRVIEVVQGACRAIRHIPRRIRQGLERILL

SEQ ID NO: 2 HIV Env consensus clade C (consensus sequence only, not including any signal sequence, transmembrane domain (664 is last amino acid), SOSIP mutations, and/or furin cleavage site mutations; amino acids at positions (i)-(vii) for mutations according to the invention indicated by grey shading)
NLWVTVYYGVPVWKEAKTTLFCASDAKAYEKEVHNVWATHACVPTDPNPQEMVLENVTENFNMWKNDMVDQMHEDIIS
LWDQSLKPCVKLTPLCVTLNCTNVNVTNTNNNNMKEEMKNCSFNTTTEIRDKKQKEYALFYRLDIVPLNENSSEYRLI
NCNTSTITQACPKVSFDPIPIHYCAPAGYAILKCNNKTFNGTGPCNNVSTVQCTHGIKPVVSTQLLLNGSLAEEEIII RSENLTDNAKTIIVHLNESVEINCTRPNNNTRKSIRIGPGQTFYATGDIIGDIRQAHCNISEAKWNKTLQRVKKKLKE
HFPNKTIKFAPSSGGDLEITTHSFNCRGEFFYCNTSKLFNSTYNNTTSNSTITLPCRIKQIINMWQEVGRAMYAPPIA
GNITCKSNITGLLLTRDGGNNNNNTETFRPGGGDMRDNWRSELYKYKVVEIKPLGIAPTKAKRRVVEREKRRAVGIGA
VFLGFLGAAGSTMGAASITLTVQARQLLSGIVQQQSNLLRAIEAQQHMLQLTVWGIKQLQARVLAIERYLKDQQLLGI

WGCSGKLICTTAVPWNSSWSNKSQEDIWDNMTWMQWDREISNYTDTIYRLLEESQNQQEKNEKDLLALD

SEQ ID NO: 3 ConC_SOSIP (mature clade C consensus sequence with SOSIP mutations and furin cleavage site (in italics), and C-terminal truncation; amino acids at (positions i)-(vii) for mutations according to the invention indicated by grey shading)
NLWVTVYYGVPVWKEAKTTLFCASDAKAYEKEVHNVWATHACVPTDPNPQEMVLENVTENFNMWKNDMVDQMHEDII
SLWDQSLKPCVKLTPLCVTLNCTNVNVTNTNNNNMKEEMKNCSFNTTTEIRDKKQKEYALFYRLDIVPLNENSSEYR
LINCNTSTITQACPKVSFDPIPIHYCAPAGYAILKCNNKTFNGTGPCNNVSTVQCTHGIKPVVSTQLLLNGSLAEEE IIIRSENLTDNAKTIIVHLNESVEINCTRPNNNTRKSIRIGPGQTFYATGDIIGDIRQAHCNISEAKWNKTLQRVKK
KLKEHFPNKTIKFAPSSGGDLEITTHSFNCRGEFFYCNTSKLFNSTYNNTTSNSTITLPCRIKQIINMWQEVGRAMY
APPIAGNITCKSNITGLLLTRDGGNNNNNTETFRPGGGDMRDNWRSELYKYKVVEIKPLGIAPTKCKRRVV*ERRRR
R*AVGIGAVFLGFLGAAGSTMGAASITLTVQARQLLSGIVQQQSNLLRAPEAQQHMLQLTVWGIKQLQARVLAIERYL

KDQQLLGIWGCSGKLICCTAVPWNSSWSNKSQEDIWDNMTWMQWDREISNYTDTIYRLLEESQNQQEKNEKDLLALD

SEQ ID NO: 4 HIV Env consensus clade B (consensus sequence only, not including any signal, sequence, transmembrane domain (664 is last amino acid), SOSIP mutations, and/or furin cleavage site mutations; amino acids at positions (i)-(vii) for mutations according to the invention indicated by grey shading)
AEKLWVTVYYGVPVWKEATTTLFCASDAKAYDTEVHNVWATHACVPTDPNPQEVVLENVTENFNMWKNNMVEQMHEDI
ISLWDQSLKPCVKLTPLCVTLNCTDLNNNTTNNNSSSEKMEKGEIKNCSFNITTSIRDKVQKEYALFYKLDVVPIDNN
NTSYRLISCNTSVITQACPKVSFEPIPIHYCAPAGFAILKCNDKKFNGTGPCTNVSTVQCTHGIRPVVSTQLLLNGSL AEEEVVIRSENFTDNAKTIIVQLNESVEINCTRPNNNTRKSIHIGPGRAFYATGDIIGDIRQAHCNISRTKWNNTLKQ
IVKKLREQFGNKTIVFNQSSGGDPEIVMHSFNCGGEFFYCNTTQLFNSTWNSNGTWNNTTGNDTITLPCRIKQIINMW
QEVGKAMYAPPIRGQIRCSSNITGLLLTRDGGNNNNNTTETFRPGGGDMRDNWRSELYKYKVVKIEPLGVAPTKCKRR -continued

LIST OF SEQUENCES

VVQRRRRRRAVGIGAMFLGFLGAAGSTMGAASJTLTVQARQLLSGIVQQQNNLLRAPEAQQHLLQLTVWGIKQLQARV

LAVERYLKDQQLLGIWGCSGKLICCTAVPWNTSWSNKSLDEIWDNMTWMQWEREIDNYTGLIYTLIESQNQQEKNEQ

ELLELD

SEQ ID NO: 5 ConB_SOSIP (mature clade B consensus sequence with SOSIP mutations and furin cleavage site (in italics), and C-terminal truncation; amino acids at positions (i)-(vii) for mutations according to the invention indicated by grey shading)
AEKLWVTVYYGVPVWKEATTTLFCASDAKAYDTEVHNVWATHACVPTDPNPQEVVLENVTENFNMWKNNMVEQMHED
IISLWDQSLKPCVKLTPLCVTLNCTDLNNNTTNNNSSSEKMEKGEIKNCSFNITTSIRDKVQKEYALFYKLDVVPID
NNNTSYRLISCNTSVITQACPKVSFEPIPIHYCAPAGFAILKCNDKKFNGTGPCTNVSTVQCTHGIRPVVSTQLLLN GSLAEEEVVIRSENFTDNAKTIIVQLNESVEINCTRPNNNTRKSIHIGPGRAFYATGDIIGDIRQAHCNISRTKWNN
TLKQIVKKLREQFGNKTIVFNQSSGGDPEIVMHSFNCGGEFFYCNTTQLFNSTWNSNGTWNNTTGNDTITLPCRIKQ
IINMWQEVGKAMYAPPIRGQIRCSSNITGLLLTRDGGNNNNNTTETFRPGGGDMRDNWRSELYKYKVVKIEPLGVAP
TKCKRRVVQRRRRRAVGIGAMFLGFLGAAGSTMGAASJTLTVQARQLLSGIVQQQNNLLRAPEAQQHLLQLTVWGI

KQLQARVLAVERYLKDQQLLGIWGCSGKLICCTAVPWNTSWSNKSLDEIWDNMTWMQWEREIDNYTGLIYTLIESQ

NQQEKNEQELLELD

SEQ ID NO: 6 synthetic HIV envelope protein Mos2S Env C4 fragment; amino acids at positions (i)-(vii) for mutations according to the invention indicated by grey shading)
MGNLWVTVYYGVPVWKDAKTTLFCASDAKAYEKEVHNVWATHACVPTDPNPQEIVLGNVTENFNMWKNDMVDQMHEDI
ISLWDASLEPCVKLTPLCVTLNCRNVRNVSSNGTYNIIHNETYKEMKNCSFNATTVVEDRKQKVHALFYRLDIVPLDE
NNSSEKSSENSSEYYRLINCNTSAITQACPKVSFDPIPIHYCAPAGYAILKCNNKTFNGTGPCNNVSTVQCTHGIKPV VSTQLLLNGSLAEEEIIRSENLTNNAKTIIVHLNETVNITCTRPNNNTRKSIRIGPGQTFYATGDIIGDIRQAHCNL
SRDGWNKTLQGVKKKLAEHFPNKTIKFAPHSGGDLEITTHTFNCRGEFFYCNTSNLFNESNIERNDSIITLPCRIKQI
INMWQEVGRAIYAPPIAGNITCRSNITGLLLTRDGGSNNGVPNDTETFRPGGGDMRNNWRSELYKYKVVEVKPLGVAP
TEAKRRVVEREKRAVGIGAVFLGILGAAGSTMGAASJTLTVQARQLLSGIVQQQSNLLRAIEAQQHMLQLTVWGIKQL

QTRVLAIERYLQDQQLLGLWGCSGKLICTTAVPWNTSWSNKSQTDIWDNMTWMQWDKEIGNYTGEIYRLLEESQNQQE

K

SEQ ID NO: 7 (DS_sC4_SOSIP_E166R sequence; amino acids at positions (i)-(vii) for mutations according to the invention indicated by grey shading)
MGNLWVTVYYGVPVWKDAKTTLFCASDAKAYEKEVHNVWATHACVPTDPNPQEIVLGNVTENFNMWKNDMVDQMHED
IISLWDASLEPCVKLTPLCVTLNCRNVRNVSSNGTYNIIHNETYKEMKNCSFNATTVVRDRKQKVHALFYRLDIVPL
DENNSSEKSSENSSEYYRLINCNTSACTQACPKVSFDPIPIHYCAPAGYAILKCNNKTFNGTGPCNNVSTVQCTHGI KPVVSTQLLLNGSLAEEEIIRSENLTNNAKTIIVHLNETVNINCTRPNNNTRKSIRIGPGQTFYATGDIIGDIRQA
HCNLSRDGWNKTLQGVKKKLAEHFPNKTIKFAPHSGGDLEITTHTFNCRGEFFYCNTSNLFNESNIERNDSIITLPC
RIKQIINMWQEVGRCIYAPPIAGNITCRSNITGLLLTRDGGSNNGVPNDTETFRPGGGDMRNNWRSELYKYKVVEVK
PLGVAPTECKRRVVERRRRRAVGIGAVFLGILGAAGSTMGAASJTLTVQARQLLSGIVQQQSNLLRAPEAQQHMLQ

LTVWGIKQLQTRVLAIERYLQDQQLLGLWGCSGKLICCTAVPWNTSWSNKSQTDIWDNMTWMQWDKEIGNYTGEIYR

LLEESQNQQEK

SEQ ID NO: 8 (Mos1.Env, mosaic HIV envelope protein sequence; amino acids at positions (i)-(vii) for mutations according to the invention indicated by grey shading)
AGKLWVTVYYGVPVWKEATTTLFCASDAKAYDTEVHNVWATHACVPTDPNPQEVVLENVTENFNMWKNNMVEQMHED
IISLWDQSLKPCVKLTPLCVTLNCTDDVRNVTNNATNTNSSWGEPMEKGEIKNCSFNITTSIRNKVQKQYALFYKLD
VVPIDNDSNNTNYRLISCNTSVITQACPKVSFEPIPIHYCAPAGFAILKCNDKKFNGTGPCTNVSTVQCTHGIRPVV STQLLLNGSLAEEEVVIRSENFTNNAKTIMVQLNVSVEINCTRPNNNTRKSIHIGPGRAFYTAGDIIGDIRQAHCNI
SRANWNNTLRQIVEKLGKQFGNNKTIVFNHSSGGDPEIVMHSFNCGGEFFYCNSTKLFNSTWTWNNSTWNNTKRSND
TEEHITLPCRIKQIINMWQEVGKAMYAPPIRGQIRCSSNITGLLLTRDGGNDTSGTEIFRPGGGDMRDNWRSELYKY
KVVKIEPLGVAPTKAKRRVVQSEKSAVGIGAVFLGFLGAAGSTMGAASMTLTVQARLLLSGIVQQQNNLLRAIEAQQ

HLLQLTVWGIKQLQARVLAVERYLKDQQLLGIWGCSGKLICTTTVPWNASWSNKSLDKIWNNMTWMEWEREINNYTS

LIYTLIEESQNQQEK

LIST OF SEQUENCES

SEQ ID NO: 9 (Mos2.Env, mosaic HIV envelope protein sequence; amino acids at positions (i)-(vii) for mutation according to the invention indicated by grey shading)
MGNLWVTVYYGVPVWKEAKTTLFCASDAKAYEKEVHNVWATHACVPTDPNPQEMVLENVTENFNMWKNDMVDQMHED
IIRLWDQSLKPCVKLTPLCVTLECRNVRNVSSNGTYNIIHNETYKEMKNCSFNATTVVEDRKQKVHALFYRLDIVPL
DENNSSEKSSENSSEYYRLINCNTSAITQACPKVSFDPIPIHYCAPAGYAILKCNNKTFNGTGPCNNVSTVQCTHGI KPVVSTQLLLNGSLAEEEIIIRSENLTNNAKTIIVHLNETVNITCTRPNNNTRKSIRIGPGQTFYATGDIIGDIRQA
HCNLSRDGWNKTLQGVKKKLAEHFPNKTINFTSSSGGDLEITTHSFNCRGEFFYCNTSGLFNGTYMPNGTNSNSSSN
ITLPCRIKQIINMWQEVGRAMYAPPIAGNITCRSNITGLLLTRDGGSNNGVPNDTETFRPGGGDMRNNWRSELYKYK
VVEVKPLGVAPTEAKRRVVEREKRAVGIGAVFLGILGAAGSTMGAASITLTVQARQLLSGIVQQQSNLLRAIEAQQH

MLQLTVWGIKQLQTRVLAIERYLQDQQLLGLWGCSGKLICTTAVPWNTSWSNKSQTDIWDNMTWMQWDKEIGNYTGE

IYRLLEESQNQQEK

SEQ ID NO: 10 (furin cleavage site mutant sequence)
RRRRRR

SEQ ID NO: 11 (example of a signal sequence (e.g. used for ConC_SOSIP, and some wild-type derived variants))
MRVRGILRNWQQWWIWGILGFWMLMICNVVG (note: the last VG could be the beginning of the mature protein or the end of the signal sequence)

SEQ ID NO: 12 (example of 8 amino acid sequence that can replace HR1 loop)
NPDWLPDM SEQ ID NO: 13 (example of 8 amino acid sequence that can replace HR1 loop)
GSGSGSGS SEQ ID NO: 14 (example of 8 amino acid sequence that can replace HR1 loop)
DDVGPDWD SEQ ID NO: 15 (example of 8 amino acid sequence that can replace HR1 loop)
RDTFALMM SEQ ID NO: 16 (example of 8 amino acid sequence that can replace HR1 loop)
DEEKVMDF SEQ ID NO: 17 (example of 8 amino acid sequence that can replace HR1 loop)
DEDPHWDP SEQ ID NO: 18 (example of a signal sequence (e.g. used for ConB_SOSIP)
MRVKGIRKNYQHLWRWGTMLLGMLMICSA SEQ ID NO: 19 (tag used for HIV gp140 constructs in AlphaLISA assay)
AAALPETGGGSDYKDDDDKPGGGGSGGGGSGGGGSGGGGSGGGGSGGGGSGGGGSHHHHHH SEQ ID NO: 20 (stabilized ConC_SOSIP, 'ConC_SOSIP_7mut', (HIV160544))
NLWVTVYYGVPVWKEAKTTLFCASDAKAYEKEVHNVWATHACVPTDPNPQEMVLENVTENFNMWKNDMVDQMHEDII
SLWDQSLKPCVKLTPLCVTLNCTNVNVTNTNNNNMKEEMKNCSFNTTTEIRDKKQKEYALFYRLDIVPLNENSSEYR
LINCNTSTITQiCPKVSFDPIPIHYCAPAGYAILKCNNKTFNGTGPCNNVSTVQCTHGIKPVVSTQLLLNGSLAEEE
IIIRSENLTDNAKTIIVHLNESVEINCTRPNNNTRKSIRIGPGQTFYATGDIIGDIRQAHCNISEAKWNKTLQRVKK
KLKEHFPNKTIKFAPSSGGDLEITTHSFNCRGEFFYCNTSKLFNSTYNNTTSNSTITLPCRIKQIINMWQEVGRAMY
APPIAGNITCKSNITGLLLTRDGGNNNNNTETFRPGGGDMRDNWRSELYKYKVVEIKPLGIAPTKCKRRVVERRRRR
RAVGIGAVFLGFLGAAGSTMGAASnTLTVQARQLLSGIVQQQSNLLRAPEAQQHMLQLTVWGfKQLQARVLAIERYL
evQQLLGIWGCSGKLICCTAVPWNSSWSNKSQEDIWDNMTWMQWDREISNYTDTIYRLLEESQfQQEiNEKDLLALD SEQ ID NO: 21 (BG505_SOSIP Env protein (HIV150673)
AENLWVTVTYGVPVWKDAETTLFCASDAKAYETEKHNVWATHACVPTDPNPQEIHLENVTEEFNMWKNNMVEQMHTD
IISLWDQSLKPCVKLTPLCVTLQCTNVTNNITDDMRGELKNCSFNMTTELRDKKQKVYSLFYRLDVVQINENQGNRS
NNSNKEYRLINCNTSAITQACPKVSFEPIPIHYCAPAGFAILKCKDKKFNGTGPCPSVSTVQCTHGIKPVVSTQLLL
NGSLAEEEVMIRSENITNNAKNILVQFNTPVQINCTRPNNNTRKSIRIGPGQAFYATGDIIGDIRQAHCNVSKATWN
ETLGKVVKQLRKHFGNNTIIRFANSSGGDLEVTTHSFNCGGEFFYCNTSGLFNSTWISNTSVQGSNSTGSNDSITLP
CRIKQIINMWQRIGQAMYAPPIQGVIRCVSNITGLILTRDGGSTNSTTETFRPGGGDMRDNWRSELYKYKVVKIEPL
GVAPTRCKRRVVGRRRRRRAVGIGAVFLGFLGAAGSTMGAASMTLTVQARNLLSGIVQQQSNLLRAPEAQQHLLKLT
VWGIKQLQARVLAVERYLRDQQLLGIWGCSGKLICCTNVPWNSSWSNRNLSEIWDNMTWLQWDKEISNYTQIIYGLL
EESQNQQEKNEQDLLALD SEQ ID NO: 22 (stabilized BG505_SOSIP Env protein (HIV170863))
AENLWVTVYYGVPVWKDAETTLFCASDAKAYETEKHNVWATHACVPTDPNPQEIHLENVTEEFNMWKNNMVEQMHTD
IISLWDQSLKPCVKLTPLCVTLQCTNVTNNITDDMRGELKNCSFNMTTELRDKKQKVYSLFYRLDVVQINENQGNRS
NNSNKEYRLINCNTSAITQACPKVSFEPIPIHYCAPAGFAILKCKDKKFNGTGPCPSVSTVQCTHGIKPVVSTQLLL
NGSLAEEEVMIRSENITNNAKNILVQFNTPVQINCTRPNNNTRKSIRIGPGQAFYATGDIIGDIRQAHCNVSKATWN
ETLGKVVKQLRKHFGNNTIIRFANSSGGDLEVTTHSFNCGGEFFYCNTSGLFNSTWISNTSVQGSNSTGSNDSITLP
CRIKQIINMWQRIGQAMYAPPIQGVIRCVSNITGLILTRDGGSTNSTTETFRPGGGDMRDNWRSELYKYKVVKIEPL

LIST OF SEQUENCES

GVAPTRCKRRVVGRRRRRRAVGIGAVFLGFLGAAGSTMGAASnTLTVQARNLLSGIVQQQSNLpRAPEAQQHLLKLT
VWGIKQLQARVLAVERYLRvQQLLGIWGCSGKLICCTNVPWNSSWSNRNLSEIWDNMTWLQWDKEISNYTQIIYGLL
EESQfQQEiNEQDLLALD

SEQ ID NO: 23 (wt C97Z2_SOSIP Env protein with L535M and Q567K (HIV150673))
NMWVTVYYGVPVWTDAKTTLFCASDTKAYDREVHNVWATHACVPTDPNPQEIVLENVTENFNMWKNDMVDQMHEDII
SLWDQSLKPCVKLTPLCVTLHCTNATFKNNVTNDMNKEIRNCSFNTTTEIRDKKQQGYALFYRPDIVLLKENRNNSN
NSEYILINCNASTITQACPKVNFDPIPIHYCAPAGYAILKCNNKTFSGKGPCNNVSTVQCTHGIKPVVSTQLLLNGS
LAEKEIIRSENLTDNVKTIIVHLNKSVEIVCTRPNNNTRKSMRIGPGQTFYATGDIIGDIRQAYCNISGSKWNETL
KRVKEKLQENYNNNKTIKFAPSSGGDLEITTHSFNCRGEFFYCNTTRLFNNNATEDETITLPCRIKQXINMWQGVGR
AMYAPPIAGNITCKSNITGLLLVRDGGEDNKTEEIFRPGGGNMKDNWRSELYKYKVIELKPLGIAPTGcKRRVVERr
rrrRAVGIGAVFLGFLGAAGSTMGAASmTLTVQARQLLSSIVQQQSNLLRApEAQQHMLkLTVWGIKQLQTRVLAIE
RYLKDQQLLGIWGCSGKLICcTNVPWNSSWSNKSQTDIWNNMTWMEWDREISNYTDTIYRLLEDSQTQQEKNEKDLL
ALD SEQ ID NO: 24 (repaired and stabilized C97ZA_SOSIP Env protein (HIV170690))
NlWVTVYYGVPVWkDAKTTLFCASDaKAYDREVHNVWATHACVPTDPNPQEIVLENVTENFNMWKNDMVDQMHEDII
SLWDQSLKPCVKLTPLCVTLHCTNATFKNNVTNDMNKEIRNCSFNTTTEIRDKKQkVYALFYRlDIVqLKENRNNSN
NSEYrLINCNtSTITQiCPKVtFDPIPIHYCAPAGYAILKCNNKTFnGtGPCNNVSTVQCTHGIKPVVSTQLLLNGS
LAEKEIIRSENLTDNVKTIIVHLNKSVEInCTRPNNNTRKSiRIGPGQTFYATGDIIGDIRQAYCNISGSKWNETL
KRVKEKLrEhfNNNKTIKFAPSSGGDLEITTHSFNCRGEFFYCNTTRLFNNNATEnETITLPCRIKQIINMWQeVGR
AMYAPPIAGNITCKSNITGLLLtRDGGEDNKTEEIFRPGGGNMKDNWRSELYKYKVvEiKPLGIAPTkcKRRnVtRr
rrrRAVGIGAVFLGFLGAAGSTMGAASnTLTVQARQLLSgIVQQQSNLpRApEAQQHMLkLTVWGIKQLQaRVLAIE
RYLevQQLLGIWGCSGKLICcTNVPWNSSWSNKSQTDIWNNMTWMEWDREISNYTDTIYRLLEDSQfQQEiNEKDLL
AnD SEQ ID NO: 25 (variant of repaired and stabilized Du422 construct (HIV161818))
NLWVTVYYGVPVWKEAKTTLFCASDAKAYDKEVHNVWATHACVPTDPNPQEIVLENVTENFNMWKNDMVDQMHEDII
SLWDQSLKPCVKLTPLCVTLNCKNVNISANANATATLNSSMNGEIKNCSFNTTTELRDKKQKVYALFYKPDVVPLNG
GEHNETGEYILINCNSSTcTQACPKVSFDPIPIHYCAPAGYAILKCNNKTFNGTGPCNNVSTVQCTHGIKPVVSTQL
LLNGSLAEEEIIRSENLTNNIKTIIVHLNKSVEINCTRPNNNTRKSVRIGPGQTFYATGEIIGDIREAHCNISRET
WNSTLIQVKEKLREHYNKTIKFEPSSGGDLEVTTHSFNCRGEFFYCNTTKLFNETKLFNESEYVDNKTIILPCRIKQ
IINMWQEVGRcMYAPPIEGNITCKSNITGLLLTRDGGENSTEEVFRPGGGNMKDNWRSELYKYKVVEIKPLGVAPTK
CKRKnVtRRRRRRAVGLGAVLLGFLGAAGSTMGAASnTLTVQARQLLSGIVQQQSNLpRAPEAQQHLLQLTVWGIKQ
LQTRVLAIERYLKvQQLGLWGCSGKLICCTAVPWNSSWSNKSLGDIWDNMTWMQWDREISNYTNTIYRLLEDSQfQ
QEKNEKDLLAnD SEQ ID NO: 26 (repaird and stabilized Du422_SOSIP (HIV170859))
NLWVTVYYGVPVWKEAKTTLFCASDAKAYDKEVHNVWATHACVPTDPNPQEIVLENVTENFNMWKNDMVDQMHEDII
SLWDQSLKPCVKLTPLCVTLNCKNVNISANANATATLNSSMNGEIKNCSFNTTTELRDKKQKVYALFYKPDVVPLNG
GEHNETGEYILINCNSSTITQACPKVSFDPIPIHYCAPAGYAILKCNNKTFNGTGPCNNVSTVQCTHGIKPVVSTQL
LLNGSLAEEEIIRSENLTNNIKTIIVHLNKSVEINCTRPNNNTRKSVRIGPGQTFYATGEIIGDIREAHCNISRET
WNSTLIQVKEKLREHYNKTIKFEPSSGGDLEVTTHSFNCRGEFFYCNTTKLFNETKLFNESEYVDNKTIILPCRIKQ
IINMWQEVGRAMYAPPIEGNITCKSNITGLLLTRDGGENSTEEVFRPGGGNMKDNWRSELYKYKVVEIKPLGVAPTK
CKRKVVGRRRRRRAVGLGAVLLGFLGAAGSTMGAASnTLTVQARQLLSGIVQQQSNLpRAPEAQQHLLQLTVWGIKQ
LQTRVLAIERYLevQQLLGLWGCSGKLICCTAVPWNSSWSNKSLGDIWDNMTWMQWDREISNYTNTIYRLLEDSQfQ
QEiNEKDLLALD SEQ ID NO: 27 (repaired and stabilized DS_sC4_SOSIP (HIV170686))
MGNLWVTVYYGVPVWKDAKTTLFCASDAKAYEKEVHNVWATHACVPTDPNPQEIVLGNVTENFNMWKNDMVDQMHED
IISLWDqSLkPCVKLTPLCVTLNCRNVRNVEMKNCSFNATTVVrDRKQKVHALFYRLDIVPLDENNSSYRLINCNTS
AcTQiCPKVSFDPIPIHYCAPAGYAILKCNNKTFNGTGPCNNVSTVQCTHGIKPVVSTQLLLNGSLAEEEIIRSEN
LTNNAKTIIVHLNETVNINCTRPNNNTRKSIRIGPGQTFYATGDIIGDIRQAHCNLSRDGWNKTLQGVKKKLAEHFP
NKTIKFAPHSGGDLEITTHsFNCRGEFFYCNTSNLFNESNIERLDLPCRIKQIIINMWQEVGRcmYAPPIAGNI
TCRSNITGLLLTRDGGSNNNDTETFRPGGGDMRNNWRSELYKYKVVEVKPLGVAPTECKRRVVERRRRRRAVGIGAV
FLGILGAAGSTMGAASnTLTVQARQLLSGIVQQQSNLpRAPEAQQHMLQLTVWGIKQLQTRVLAIERYLevQQLLGL
WGCSGKLICCTAVPWNTSWSNKSQTDIWDNMTWMQWDKEIGNYTGEIYRLLEESQfQQEi SEQ ID NO: 28 (Stabilized ConC_SOSIP.v3) (HIV170654))
NLWVTVYYGVPVWKEAKTTLFCASDAKAYEKEVHNVWATHACVPTDPNPQEMVLENVTENFNMWKNDMVDQMHEDII
SLWDQSLKPCVKLTPLCVTLNCTNVNVTEMKNCSFNTTTEIRDKKQKEYALFYRLDIVPLNENSSEYRLINCNTSTI
TQICPKVSFDPIPIHYCAPAGYAILKCNNKTFNGTGPCNNVSTVQCTHGIKPVVSTQLLLNGSLAEEEIIRSENLT
NNVKTIIVHLNESVEIVCTRPNNNTRKSIRIGPGQTFYATGDIIGDIRQAHCNISEAKWNKTLQRVKKKLKEHFPNK
TIKFQPSSGGDLEITTHSFNCRGEFFYCNTSKLFNSTYNNTTSNSTITLPCRIKQIINMWQEVGRAMYAPPIAGNIT
CKSNITGLLLTRDGGNNNNNNTETFRPGGGDMRDNWRSELYKYKVVEIKPLGIAPTKCKRRVVERRRRRRAVGIGAVF
LGFLGAAGSTMGAASNTLTVQARQLLSGIVQQQSNLLRAPEAQQHMLQLTVWGFKQLQARVLAIERYLEVQQLLGIW
GCSGKLICCTAVPWNSSWSNKSQEDIWDNMTWMQWDREISNYTDTIYRLLEESQFQQEINEKDLLALD SEQ ID NO: 29 (Stabilized BG505_SOSIP.v2 (HIV171814)
AENLWVTVYYGVPVWKDAETTLFCASDAKAYETEKHNVWATHACVPTDPNPQEIHLENVTEEFNMWKNNMVEQMHTD
IISLWDQSLKPCVKLTPLCVTLQCTNVTNNITDDMRGELKNCSFNMTTELRDKKQKVYSLFYRLDVVQINENQGNRS
NNSNKEYRLINCNTSAcTQACPKVSFEPIPIHYCAPAGFAILKCKDKKFNGTGPCPSVSTVQCTHGIKPVVSTQLLL
NGSLAEEEVMIRSENITNNAKNILVQFNTPVQINCTRPNNNTRKSIRIGPGQAFYATGDIIGDIRQAHCNVSKATWN
ETLGKVVKQLRKHFGNNTIIRFANSSGGDLEVTTHSFNCGGEFFYCNTSGLFNSTWISNTSVQGSNSTGSNDSITLP
CRIKQIINMWQRIGQcMYAPPIQGVIRCVSNITGLILTRDGGSTNSTTETFRPGGGDMRDNWRSELYKYKVVKIEPL

LIST OF SEQUENCES

```
GVAPTRCKRRVVGRRRRRRAVGIGAVFLGFLGAAGSTMGAASnTLTVQARNLLSGIVQQQSNLpRAPEAQQHLLKLT
VWGIKQLQARVLAVERYLevQQLLGIWGCSGKLICCTNVPWNSSWSNRNLSEIWDNMTWLQWDKEISNYTQIIYGLL
EESQfQQEiNEvDLLALD

SEQ ID NO: 30 (Repaired and stabilized C97ZA_SOSIP.v2 (HIV171810))
NlWVTVYYGVPVWkDAKTTLFCASDaKAYDREVHNVWATHACVPTDPNPQEIVLENVTENFNMWKNDMVDQMHEDII
SLWDQSLKPCVKLTPLCVTLHCTNATFKNNVTNDMNKEIRNCSFNTTTEIRDKKQKvYALFYR1DIVqLKENRNNSN
NSEYrLINCNtSTcTQiCPKVtFDPIPIHYCAPAGYAILKCNNKTFnGtGPCNNVSTVQCTHGIKPVVSTQLLLNGS
LAEKEIIIRSENLTDNVKTIIVHLNKSVEInCTRPNNNTRKSiRIGPGQTFYATGDIIGDIRQAYCNISGSKWNETL
KRVKEKLrEhfNNNKTIKFAPSSGGDLEITTHSFNCRGEFFYCNTTRLFNNNATEnETITLPCRIKQIINMWQeVGR
cMYAPPIAGNITCKSNITGLLLtRDGGEDNKTEEIFRPGGGNMKDNWRSELYKYKVvEiKPLGIAPTkcKRRnVtRr
rrrRAVGIGAVFLGFLGAAGSTMGAASnTLTVQARQLLSgIVQQQSNLpRApEAQQHMLkLTVWGIKQLQaRVLAIE
RYLevQQLLGIWGCSGKLICcTNVPWNSSWSNKSQTDIWNNMTWMEWDREISNYTDTIYRLLEDSQfQQEiNEvDLL
AnD SEQ ID NO: 31 (Repaired and stabilized Du422_SOSIP.v1 (HIV171812))
NLWVTVYYGVPVWKEAKTTLFCASDAKAYDKEVHNVWATHACVPTDPNPQEIVLENVTENFNMWKNDMVDQMHEDII
SLWDQSLKPCVKLTPLCVTLNCKNVNISANANATATLNSSMNGEIKNCSFNTTTELRDKKQKVYALFYKPDVVPLNG
GEHNETGEYILINCNSSTcTQACPKVSFDPIPIHYCAPAGYAILKCNNKTFNGTGPCNNVSTVQCTHGIKPVVSTQL
LLNGSLAEEEIIIRSENLTNNIKTIIVHLNKSVEINCTRPNNNTRKSVRIGPGQTFYATGEIIGDIREAHCNISRET
WNSTLIQVKEKLREHYNKTIKFEPSSGGDLEVTTHSFNCRGEFFYCNTTKLFNETKLFNESEYVDNKTIILPCRIKQ
IINMWQEVGRcMYAPPIEGNITCKSNITGLLLTRDGGENSTEEVFRPGGGNMKDNWRSELYKYKVVEIKPLGVAPTK
CKRKVVGRRRRRRAVGLGAVLLGFLGAAGSTMGAASnTLTVQARQLLSGIVQQQSNLpRAPEAQQHLLQLTVWGIKQ
LQTRVLAIERYLevQQLLGLWGCSGKLICCTAVPWNSSWSNKSLGDIWDNMTWMQWDREISNYTNTIYRLLEDSQfQ
QEiNEvDLLALD SEQ ID NO: 32 (Stabilized and repaired sC4_SOSIP.v4)
MGNLWVTVYYGVPVWKDAKTTLFCASDAKAYEKEVHNVWATHACVPTDPNPQEIVLGNVTENFNMWKNDMVDQMHED
IISLWDqSLkPCVKLTPLCVTLNCRNVRNVEMKNCSFNATTVVrDRKQKVHALFYRLDIVPLDENNSSYRLINCNTS
AcTQiCPKVSFDPIPIHYCAPAGYAILKCNNKTFNGTGPCNNVSTVQCTHGIKPVVSTQLLLNGSLAEEEIIIRSEN
LTNNAKTIIVHLNETVNIVCTRPNNNTRKSIRIGPGQTFYATGDIIGDIRQAHCNLSRDGWNKTLQGVKKKLAEHFP
NKTIKFAPHSGGDLEITTHsFNCRGEFFYCNTSNLFNESNIERNDSIITLPCRIKQIINMWQEVGRcmYAPPIAGNI
TCRSNITGLLLTRDGGSNNNDTETFRPGGGDMRNNWRSELYKYKVVEVKPLGVAPTECKRRnVtRRRRRRAVGIGAV
FLGILGAAGSTMGAASnTLTVQARQLLSGIVQQQSNLpRAPEAQQHMLQLTVWGIKQLQTRVLAIERYLeDQQLLGL
WGCSGKLICCTAVPWNTSWSNKSQTDIWDNMTWMQWDKEIGNYTGEIYRLLEESQfQQEi SEQ ID NO: 33 (example of a signal sequence (e.g. used for DS_sC4_SOSIP variants)
MRVRGMLRNWQQWWIWSSLGFWMLMIYSV SEQ ID NO: 34 (example of a signal sequence (e.g. used for BG505_SOSIP variants)
MRVMGIQRNCQHLFRWGTMILGMIIICSA
```

REFERENCES

1. Sanders et al. J. Virol. (2002) 76(17), 8875-89
2. Sanders et al. Science (2015) 349(6224), 139-140
3. Julien et al. Proc. Nat. Acad. Sci. (2015) 112(38), 11947-52
4. de Taeye et al. Cell (2015) 163(7), 1702-15
5. Kwon et al. (2015) Nat. Struct. Mol. Biol. 22(7) 522-31
6. Eglen et al. Curr. Chem. Genomics, (2008) 25(1), 2-10
7. Kong et al, Nat Commun. 2016 Jun. 28; 7:12040. doi: 10.1038/ncomms12040
8. Julien et al. Proc. Natl. Acad. Sci. (2015) 112(38) 11947-52
9. Barouch et al, Nat Med 2010, 16: 319-323
10. WO 2010/059732
11. European Patent Application EP15200138.4
12. Sharma S K, et al. Cell Rep. (2015) 11(4):539-50. doi: 10.1016/j.celrep.2015.03.047.
13. Georgiev I S, et al. J Virol. (2015) 89(10):5318-29. doi: 10.1128/JVI.03451-14.
14. López-Sagaseta J, et al (2016) Computational and Struct Biotechnol J 14: 58-68.
15. Zhao L, et al (2014) Vaccine 32: 327-337
16. He L, et al (2016) Nat Commun. 2016 Jun. 28; 7:12041. doi: 10.1038/ncomms12041
17. WO 2011/082087
18. Kesavardhana A and Varadarajan R (2014) J Virol 88: 9590-9604
19. Guenaga J, et al (2015) Immunity 46: 792-803
20. Bale S, et al (2017) J. Virol. doi:10.1128/JVI.00443-17
21. Abbink et al (2007) *Virol.* 81(9): 4654-64
22. Altschul S F et al (1997) *Nucleic Acid Res.* 25: 3389-3402
23. Harris et al (2011) *PNAS* 108 (28): 11440-11445
24. Kushnir et al (2012) Vaccine (31): 58-83
25. WO 2007/104792
26. WO 2014/124301
27. US 2016/0122392

What is claimed is:

1. A recombinant human immunodeficiency virus (HIV) envelope (Env) protein, comprising two or more of the following amino acid residues:
   (i) Phe, Leu, Met, or Trp at position 651;
   (ii) Phe, Ile, Met, or Trp at position 655;
   (iii) Asn or Gln at position 535;
   (iv) Val, Ile or Ala at position 589;
   (v) Phe or Trp at position 573;
   (vi) Ile at position 204; and/or
   (vii) Phe, Met, or Ile at position 647,
wherein the numbering of the positions is according to the numbering in gp160 of HIV-1 isolate HXB2 having the amino acid sequence of SEQ ID NO: 1.

2. A recombinant HIV Env protein, comprising one or more of the following amino acid residues:
   (i) Phe, Leu, Met, or Trp at position 651;
   (ii) Phe, Ile, Met, or Trp at position 655;
   (iii) Asn or Gln at position 535;
   (iv) Val, Ile or Ala at position 589;
   (v) Phe or Trp at position 573;
   (vi) Ile at position 204; and/or
   (vii) Phe, Met, or Ile at position 647,
wherein the HIV Env protein is selected from the group consisting of:
   (1) an HIV Env protein comprising an HIV Env consensus sequence;
   (2) a synthetic HIV Env protein; and
   (3) a parent HIV Env protein comprising at least one repair mutation at an amino acid residue that is present at the corresponding position at a frequency of less than 7.5% of HIV Env sequences in a collection of at least 1000 HIV Env sequences, wherein the repair mutation is a substitution by an amino acid residue that is present at the corresponding position at a frequency of at least 10% of HIV Env sequences in said collection; and wherein the numbering of the positions is according to the numbering in gp160 of HIV-1 isolate HXB2 having the amino acid sequence of SEQ ID NO: 1.

3. A recombinant HIV Env protein, comprising one or more of the following amino acid residues:
(i) Phe, Leu, Met, or Trp at position 651;
(ii) Phe, Ile, Met, or Trp at position 655;
(iii) Asn or Gln at position 535;
(iv) Val, Ile or Ala at position 589;
(v) Phe or Trp at position 573;
(vi) Ile at position 204; and/or
(vii) Phe, Met, or Ile at position 647,
wherein the HIV Env protein is a HIV Env protein further comprising at least one of the following:
(a) Cys at positions 501 and 605;
(b) Pro at position 559; or
(c) Cys at positions 501 and 605 and Pro at position 559; and
the numbering of the positions is according to the numbering in gp160 of HIV-1 isolate HXB2 having the amino acid sequence of SEQ ID NO: 1.

4. The recombinant HIV Env protein of claim 2, comprising two or more of the amino acid residues indicated in (i) to (vii).

5. The recombinant HIV Env protein of claim 1, comprising Cys at positions 501 and 605 and/or Pro at position 559.

6. The recombinant HIV Env protein of claim 1, comprising three or more of the amino acid residues indicated in (i) to (vii).

7. The recombinant HIV Env protein of claim 1, comprising four or more of the amino acid residues indicated in (i) to (vii).

8. The recombinant HIV Env protein of claim 1, comprising Phe at position 651, Ile at position 655, Asn at position 535, and Val at position 589.

9. The recombinant HIV Env protein of claim 1, comprising five or more of the amino acid residues indicated in (i) to (vii).

10. The recombinant HIV Env protein of claim 1, further comprising one or more of the following:
(viii) Gln, Glu, Ile, Met, Val, Trp, or Phe at position 588;
(ix) Lys at position 64 or Arg at position 66 or Lys at position 64 and Arg at position 66;
(x) Trp at position 316;
(xi) Cys at both positions 201 and 433;
(xii) Pro at position 556 or 558 or at both positions 556 and 558;
(xiii) replacement of the loop at amino acid positions 548-568 (HR1-loop) by a loop having 7-10 amino acids;
(xiv) Gly at position 568, or Gly at position 569, or Gly at position 636, or Gly at both positions 568 and 636, or Gly at both positions 569 and 636; and/or
(xv) Tyr at position 302, or Arg at position 519, or Arg at position 520, or Tyr at position 302 and Arg at position 519, or Tyr at position 302 and Arg at position 520, or Tyr at position 302 and Arg at both positions 519 and 520.

11. The recombinant HIV Env protein of claim 1, further comprising a mutation in a furin cleavage sequence of the HIV Env protein.

12. The recombinant HIV Env protein of claim 1, further comprising:
(xvi) an amino acid residue chosen from Val, Ile, Phe, Met, Ala, or Leu at position 658.

13. The recombinant HIV Env protein of claim 1, being a gp140 or gp160 protein.

14. The recombinant HIV Env protein of claim 1, which is from clade C, clade B or clade A.

15. A trimeric complex comprising a noncovalent oligomer of three of the recombinant HIV Env proteins of claim 1.

16. A particle displaying on its surface a recombinant HIV Env protein of claim 1.

17. A composition comprising the recombinant HIV Env protein of claim 1 and a pharmaceutically acceptable carrier.

18. The recombinant HIV Env protein of claim 1, comprising two or more of the following amino acid residues:
(i) Phe at position 651;
(ii) Ile at position 655;
(iii) Asn at position 535;
(iv) Val at position 589;
(v) Phe at position 573;
(vi) Ile at position 204; and/or
(vii) Phe at position 647.

19. The recombinant HIV Env protein of claim 2, comprising one or more of the following amino acid residues:
(i) Phe at position 651;
(ii) Ile at position 655;
(iii) Asn at position 535;
(iv) Val at position 589;
(v) Phe at position 573;
(vi) Ile at position 204; and/or
(vii) Phe at position 647.

20. The recombinant HIV Env protein of claim 3, comprising one or more of the following amino acid residues:
(i) Phe at position 651;
(ii) Ile at position 655;
(iii) Asn at position 535;
(iv) Val at position 589;
(v) Phe at position 573;
(vi) Ile at position 204; and/or
(vii) Phe at position 647.

21. The recombinant HIV Env protein of claim 20, comprising Cys at positions 501 and 605 and Pro at position 559.

22. The recombinant HIV Env protein of claim 10, comprising one or more of the following:
(viii) Gln or Glu at position 588;
(xi) Cys at both positions 201 and 433; and/or
(xii) Pro at position 556 or 558 or at both positions 556 and 558.

23. The recombinant HIV Env protein of claim 12, comprising Val at position 658.

* * * * *

SEQUENCE LISTING

```
<160> NUMBER OF SEQ ID NOS: 34

<210> SEQ ID NO 1
<211> LENGTH: 856
<212> TYPE: PRT
```

<213> ORGANISM: HIV-1
<220> FEATURE:
<221> NAME/KEY: misc_feature
<223> OTHER INFORMATION: gp160 of HIV-1 isolate HXB2

<400> SEQUENCE: 1

```
Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
    290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
    370                 375                 380
```

-continued

```
Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
            405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
            435                 440                 445

Ile Thr Gly Leu Leu Leu Thr Arg Asp Gly Gly Asn Ser Asn Asn Glu
            450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
            485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
            515                 520                 525

Thr Met Gly Ala Ala Ser Met Thr Leu Thr Val Gln Ala Arg Gln Leu
530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
            565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
            595                 600                 605

Pro Trp Asn Ala Ser Trp Ser Asn Lys Ser Leu Glu Gln Ile Trp Asn
            610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
            645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
            675                 680                 685

Val Gly Gly Leu Val Gly Leu Arg Ile Val Phe Ala Val Leu Ser Ile
            690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
            725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
            755                 760                 765

His Arg Leu Arg Asp Leu Leu Leu Ile Val Thr Arg Ile Val Glu Leu
            770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
```

```
                    805                 810                 815
Ala Thr Ala Ile Ala Val Ala Glu Gly Thr Asp Arg Val Ile Glu Val
                820                 825                 830

Val Gln Gly Ala Cys Arg Ala Ile Arg His Ile Pro Arg Arg Ile Arg
            835                 840                 845

Gln Gly Leu Glu Arg Ile Leu Leu
        850                 855

<210> SEQ ID NO 2
<211> LENGTH: 615
<212> TYPE: PRT
<213> ORGANISM: Artificial Sequence
<220> FEATURE:
<223> OTHER INFORMATION: HIV Env consensus clade C sequence

<400> SEQUENCE: 2

Asn Leu Trp Val Thr Val Tyr Tyr Gly Val Pro Val Trp Lys Glu Ala
1               5                   10                  15

Lys Thr Thr Leu Phe Cys Ala Ser Asp Ala Lys Ala Tyr Glu Lys Glu
            20                  25                  30

Val His Asn Val Trp Ala Thr His Ala Cys Val Pro Thr Asp Pro Asn
        35                  40                  45

Pro Gln Glu Met Val Leu Glu Asn Val Thr Glu Asn Phe Asn Met Trp
    50                  55                  60

Lys Asn Asp Met Val Asp Gln Met His Glu Asp Ile Ile Ser Leu Trp
65                  70                  75                  80

Asp Gln Ser Leu Lys Pro Cys Val Lys Leu Thr Pro Leu Cys Val Thr
                85                  90                  95

Leu Asn Cys Thr Asn Val Asn Val Thr Asn Thr Asn Asn Asn Asn Met
            100                 105                 110

Lys Glu Glu Met Lys Asn Cys Ser Phe Asn Thr Thr Thr Glu Ile Arg
        115                 120                 125

Asp Lys Lys Gln Lys Glu Tyr Ala Leu Phe Tyr Arg Leu Asp Ile Val
    130                 135                 140

Pro Leu Asn Glu Asn Ser Ser Glu Tyr Arg Leu Ile Asn Cys Asn Thr
145                 150                 155                 160

Ser Thr Ile Thr Gln Ala Cys Pro Lys Val Ser Phe Asp Pro Ile Pro
                165                 170                 175

Ile His Tyr Cys Ala Pro Ala Gly Tyr Ala Ile Leu Lys Cys Asn Asn
            180                 185                 190

Lys Thr Phe Asn Gly Thr Gly Pro Cys Asn Asn Val Ser Thr Val Gln
        195                 200                 205

Cys Thr His Gly Ile Lys Pro Val Val Ser Thr Gln Leu Leu Leu Asn
    210                 215                 220

Gly Ser Leu Ala Glu Glu Glu Ile Ile Ile Arg Ser Glu Asn Leu Thr
225                 230                 235                 240

Asp Asn Ala Lys Thr Ile Ile Val His Leu Asn Glu Ser Val Glu Ile
                245                 250                 255

Asn Cys Thr Arg Pro Asn Asn Asn Thr Arg Lys Ser Ile Arg Ile Gly
            260                 265                 270

Pro Gly Gln Thr Phe Tyr Ala Thr Gly Asp Ile Ile Gly Asp Ile Arg
        275                 280                 285

Gln Ala His Cys Asn Ile Ser Glu Ala Lys Trp Asn Lys Thr Leu Gln
    290                 295                 300

Arg Val Lys Lys Lys Leu Lys Glu His Phe Pro Asn Lys Thr Ile Lys
```

```
            305                 310                 315                 320
        Phe Ala Pro Ser Ser Gly Gly Asp Leu Glu Ile Thr Thr His Ser Phe
                        325                 330                 335

Asn Cys Arg Gly Glu Phe Phe Tyr Cys Asn Thr Ser Lys Leu Phe Asn
                        340                 345                 350

Ser Thr Tyr Asn Asn Thr Thr Ser Asn Ser Thr Ile Thr Leu Pro Cys
                        355                 360                 365

Arg Ile Lys Gln Ile Ile Asn Met Trp Gln Glu Val Gly Arg Ala Met
                        370                 375                 380

Tyr Ala Pro Pro Ile Ala Gly Asn Ile Thr Cys Lys Ser Asn Ile Thr
        385                 390                 395                 400

Gly Leu Leu Leu Thr Arg Asp Gly Gly Asn Asn Asn Asn Thr Glu
                        405                 410                 415

Thr Phe Arg Pro Gly Gly Gly Asp Met Arg Asp Asn Trp Arg Ser Glu
                        420                 425                 430

Leu Tyr Lys Tyr Lys Val Val Glu Ile Lys Pro Leu Gly Ile Ala Pro
                        435                 440                 445

Thr Lys Ala Lys Arg Arg Val Val Glu Arg Glu Lys Arg Ala Val
                        450                 455                 460

Gly Ile Gly Ala Val Phe Leu Gly Phe Leu Gly Ala Ala Gly Ser Thr
        465                 470                 475                 480

Met Gly Ala Ala Ser Ile Thr Leu Thr Val Gln Ala Arg Gln Leu Leu
                        485                 490                 495

Ser Gly Ile Val Gln Gln Gln Ser Asn Leu Leu Arg Ala Ile Glu Ala
                        500                 505                 510

Gln Gln His Met Leu Gln Leu Thr Val Trp Gly Ile Lys Gln Leu Gln
                        515                 520                 525

Ala Arg Val Leu Ala Ile Glu Arg Tyr Leu Lys Asp Gln Gln Leu Leu
                        530                 535                 540

Gly Ile Trp Gly Cys Ser Gly Lys Leu Ile Cys Thr Thr Ala Val Pro
        545                 550                 555                 560

Trp Asn Ser Ser Trp Ser Asn Lys Ser Gln Glu Asp Ile Trp Asp Asn
                        565                 570                 575

Met Thr Trp Met Gln Trp Asp Arg Glu Ile Ser Asn Tyr Thr Asp Thr
                        580                 585                 590

Ile Tyr Arg Leu Leu Glu Glu Ser Gln Asn Gln Gln Glu Lys Asn Glu
                        595                 600                 605

Lys Asp Leu Leu Ala Leu Asp
            610                 615

<210> SEQ ID NO 3
<211> LENGTH: 616
<212> TYPE: PRT
<213> ORGANISM: Artificial Sequence
<220> FEATURE:
<223> OTHER INFORMATION: ConC_SOSIP sequence

<400> SEQUENCE: 3

Asn Leu Trp Val Thr Val Tyr Tyr Gly Val Pro Val Trp Lys Glu Ala
        1               5                   10                  15

Lys Thr Thr Leu Phe Cys Ala Ser Asp Ala Lys Ala Tyr Glu Lys Glu
                        20                  25                  30

Val His Asn Val Trp Ala Thr His Ala Cys Val Pro Thr Asp Pro Asn
                        35                  40                  45

Pro Gln Glu Met Val Leu Glu Asn Val Thr Glu Asn Phe Asn Met Trp
```

```
            50                  55                  60
Lys Asn Asp Met Val Asp Gln Met His Glu Asp Ile Ile Ser Leu Trp
 65                  70                  75                  80

Asp Gln Ser Leu Lys Pro Cys Val Lys Leu Thr Pro Leu Cys Val Thr
                 85                  90                  95

Leu Asn Cys Thr Asn Val Asn Val Thr Asn Thr Asn Asn Asn Asn Met
             100                 105                 110

Lys Glu Glu Met Lys Asn Cys Ser Phe Asn Thr Thr Thr Glu Ile Arg
         115                 120                 125

Asp Lys Lys Gln Lys Glu Tyr Ala Leu Phe Tyr Arg Leu Asp Ile Val
     130                 135                 140

Pro Leu Asn Glu Asn Ser Ser Glu Tyr Arg Leu Ile Asn Cys Asn Thr
145                 150                 155                 160

Ser Thr Ile Thr Gln Ala Cys Pro Lys Val Ser Phe Asp Pro Ile Pro
                 165                 170                 175

Ile His Tyr Cys Ala Pro Ala Gly Tyr Ala Ile Leu Lys Cys Asn Asn
             180                 185                 190

Lys Thr Phe Asn Gly Thr Gly Pro Cys Asn Asn Val Ser Thr Val Gln
         195                 200                 205

Cys Thr His Gly Ile Lys Pro Val Val Ser Thr Gln Leu Leu Leu Asn
     210                 215                 220

Gly Ser Leu Ala Glu Glu Glu Ile Ile Ile Arg Ser Glu Asn Leu Thr
225                 230                 235                 240

Asp Asn Ala Lys Thr Ile Ile Val His Leu Asn Glu Ser Val Glu Ile
                 245                 250                 255

Asn Cys Thr Arg Pro Asn Asn Asn Thr Arg Lys Ser Ile Arg Ile Gly
             260                 265                 270

Pro Gly Gln Thr Phe Tyr Ala Thr Gly Asp Ile Ile Gly Asp Ile Arg
         275                 280                 285

Gln Ala His Cys Asn Ile Ser Glu Ala Lys Trp Asn Lys Thr Leu Gln
     290                 295                 300

Arg Val Lys Lys Lys Leu Lys Glu His Phe Pro Asn Lys Thr Ile Lys
305                 310                 315                 320

Phe Ala Pro Ser Ser Gly Gly Asp Leu Glu Ile Thr Thr His Ser Phe
                 325                 330                 335

Asn Cys Arg Gly Glu Phe Phe Tyr Cys Asn Thr Ser Lys Leu Phe Asn
             340                 345                 350

Ser Thr Tyr Asn Asn Thr Thr Ser Asn Ser Thr Ile Thr Leu Pro Cys
         355                 360                 365

Arg Ile Lys Gln Ile Ile Asn Met Trp Gln Glu Val Gly Arg Ala Met
370                 375                 380

Tyr Ala Pro Pro Ile Ala Gly Asn Ile Thr Cys Lys Ser Asn Ile Thr
385                 390                 395                 400

Gly Leu Leu Leu Thr Arg Asp Gly Gly Asn Asn Asn Asn Asn Thr Glu
                 405                 410                 415

Thr Phe Arg Pro Gly Gly Gly Asp Met Arg Asp Asn Trp Arg Ser Glu
             420                 425                 430

Leu Tyr Lys Tyr Lys Val Val Glu Ile Lys Pro Leu Gly Ile Ala Pro
         435                 440                 445

Thr Lys Cys Lys Arg Arg Val Val Glu Arg Arg Arg Arg Arg Arg Ala
     450                 455                 460

Val Gly Ile Gly Ala Val Phe Leu Gly Phe Leu Gly Ala Ala Gly Ser
465                 470                 475                 480
```

```
Thr Met Gly Ala Ala Ser Ile Thr Leu Thr Val Gln Ala Arg Gln Leu
            485                 490                 495

Leu Ser Gly Ile Val Gln Gln Ser Asn Leu Leu Arg Ala Pro Glu
        500                 505                 510

Ala Gln Gln His Met Leu Gln Leu Thr Val Trp Gly Ile Lys Gln Leu
        515                 520                 525

Gln Ala Arg Val Leu Ala Ile Glu Arg Tyr Leu Lys Asp Gln Gln Leu
        530                 535                 540

Leu Gly Ile Trp Gly Cys Ser Gly Lys Leu Ile Cys Cys Thr Ala Val
545                 550                 555                 560

Pro Trp Asn Ser Ser Trp Ser Asn Lys Ser Gln Glu Asp Ile Trp Asp
                565                 570                 575

Asn Met Thr Trp Met Gln Trp Asp Arg Glu Ile Ser Asn Tyr Thr Asp
                580                 585                 590

Thr Ile Tyr Arg Leu Leu Glu Glu Ser Gln Asn Gln Gln Glu Lys Asn
            595                 600                 605

Glu Lys Asp Leu Leu Ala Leu Asp
        610                 615

<210> SEQ ID NO 4
<211> LENGTH: 630
<212> TYPE: PRT
<213> ORGANISM: Artificial Sequence
<220> FEATURE:
<223> OTHER INFORMATION: HIV Env consensus Clade B sequence

<400> SEQUENCE: 4

Ala Glu Lys Leu Trp Val Thr Val Tyr Tyr Gly Val Pro Val Trp Lys
1               5                   10                  15

Glu Ala Thr Thr Thr Leu Phe Cys Ala Ser Asp Ala Lys Ala Tyr Asp
            20                  25                  30

Thr Glu Val His Asn Val Trp Ala Thr His Ala Cys Val Pro Thr Asp
        35                  40                  45

Pro Asn Pro Gln Glu Val Val Leu Glu Asn Val Thr Glu Asn Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Thr Asp Leu Asn Asn Asn Thr Asn Asn Asn
            100                 105                 110

Ser Ser Ser Glu Lys Met Glu Lys Gly Glu Ile Lys Asn Cys Ser Phe
        115                 120                 125

Asn Ile Thr Thr Ser Ile Arg Asp Lys Val Gln Lys Glu Tyr Ala Leu
    130                 135                 140

Phe Tyr Lys Leu Asp Val Val Pro Ile Asp Asn Asn Thr Ser Tyr
145                 150                 155                 160

Arg Leu Ile Ser Cys Asn Thr Ser Val Ile Thr Gln Ala Cys Pro Lys
                165                 170                 175

Val Ser Phe Glu Pro Ile Pro Ile His Tyr Cys Ala Pro Ala Gly Phe
            180                 185                 190

Ala Ile Leu Lys Cys Asn Asp Lys Lys Phe Asn Gly Thr Gly Pro Cys
        195                 200                 205

Thr Asn Val Ser Thr Val Gln Cys Thr His Gly Ile Arg Pro Val Val
    210                 215                 220
```

```
Ser Thr Gln Leu Leu Leu Asn Gly Ser Leu Ala Glu Glu Val Val
225                 230                 235                 240

Ile Arg Ser Glu Asn Phe Thr Asp Asn Ala Lys Thr Ile Ile Val Gln
            245                 250                 255

Leu Asn Glu Ser Val Glu Ile Asn Cys Thr Arg Pro Asn Asn Asn Thr
                260                 265                 270

Arg Lys Ser Ile His Ile Gly Pro Gly Arg Ala Phe Tyr Ala Thr Gly
            275                 280                 285

Asp Ile Ile Gly Asp Ile Arg Gln Ala His Cys Asn Ile Ser Arg Thr
            290                 295                 300

Lys Trp Asn Asn Thr Leu Lys Gln Ile Val Lys Lys Leu Arg Glu Gln
305                 310                 315                 320

Phe Gly Asn Lys Thr Ile Val Phe Asn Gln Ser Ser Gly Gly Asp Pro
                325                 330                 335

Glu Ile Val Met His Ser Phe Asn Cys Gly Glu Phe Phe Tyr Cys
                340                 345                 350

Asn Thr Thr Gln Leu Phe Asn Ser Thr Trp Asn Ser Asn Gly Thr Trp
            355                 360                 365

Asn Asn Thr Thr Gly Asn Asp Thr Ile Thr Leu Pro Cys Arg Ile Lys
370                 375                 380

Gln Ile Ile Asn Met Trp Gln Glu Val Gly Lys Ala Met Tyr Ala Pro
385                 390                 395                 400

Pro Ile Arg Gly Gln Ile Arg Cys Ser Ser Asn Ile Thr Gly Leu Leu
                405                 410                 415

Leu Thr Arg Asp Gly Gly Asn Asn Asn Asn Thr Thr Glu Thr Phe
                420                 425                 430

Arg Pro Gly Gly Gly Asp Met Arg Asp Asn Trp Arg Ser Glu Leu Tyr
                435                 440                 445

Lys Tyr Lys Val Val Lys Ile Glu Pro Leu Gly Val Ala Pro Thr Lys
    450                 455                 460

Cys Lys Arg Arg Val Val Gln Arg Arg Arg Arg Arg Ala Val Gly
465                 470                 475                 480

Ile Gly Ala Met Phe Leu Gly Phe Leu Gly Ala Ala Gly Ser Thr Met
                485                 490                 495

Gly Ala Ala Ser Ile Thr Leu Thr Val Gln Ala Arg Gln Leu Leu Ser
            500                 505                 510

Gly Ile Val Gln Gln Gln Asn Asn Leu Leu Arg Ala Pro Glu Ala Gln
        515                 520                 525

Gln His Leu Leu Gln Leu Thr Val Trp Gly Ile Lys Gln Leu Gln Ala
        530                 535                 540

Arg Val Leu Ala Val Glu Arg Tyr Leu Lys Asp Gln Gln Leu Leu Gly
545                 550                 555                 560

Ile Trp Gly Cys Ser Gly Lys Leu Ile Cys Cys Thr Ala Val Pro Trp
                565                 570                 575

Asn Thr Ser Trp Ser Asn Lys Ser Leu Asp Glu Ile Trp Asp Asn Met
            580                 585                 590

Thr Trp Met Gln Trp Glu Arg Glu Ile Asp Asn Tyr Thr Gly Leu Ile
        595                 600                 605

Tyr Thr Leu Ile Glu Glu Ser Gln Asn Gln Gln Glu Lys Asn Glu Gln
        610                 615                 620

Glu Leu Leu Glu Leu Asp
625                 630
```

<210> SEQ ID NO 5
<211> LENGTH: 630
<212> TYPE: PRT
<213> ORGANISM: Artificial Sequence
<220> FEATURE:
<223> OTHER INFORMATION: ConB_SOSIP sequence

<400> SEQUENCE: 5

```
Ala Glu Lys Leu Trp Val Thr Val Tyr Tyr Gly Val Pro Val Trp Lys
1               5                   10                  15

Glu Ala Thr Thr Thr Leu Phe Cys Ala Ser Asp Ala Lys Ala Tyr Asp
            20                  25                  30

Thr Glu Val His Asn Val Trp Ala Thr His Ala Cys Val Pro Thr Asp
        35                  40                  45

Pro Asn Pro Gln Glu Val Val Leu Glu Asn Val Thr Glu Asn Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Thr Asp Leu Asn Asn Thr Thr Asn Asn
            100                 105                 110

Ser Ser Ser Glu Lys Met Glu Lys Gly Glu Ile Lys Asn Cys Ser Phe
            115                 120                 125

Asn Ile Thr Thr Ser Ile Arg Asp Lys Val Gln Lys Glu Tyr Ala Leu
130                 135                 140

Phe Tyr Lys Leu Asp Val Val Pro Ile Asp Asn Asn Thr Ser Tyr
145                 150                 155                 160

Arg Leu Ile Ser Cys Asn Thr Ser Val Ile Thr Gln Ala Cys Pro Lys
                165                 170                 175

Val Ser Phe Glu Pro Ile Pro Ile His Tyr Cys Ala Pro Ala Gly Phe
            180                 185                 190

Ala Ile Leu Lys Cys Asn Asp Lys Lys Phe Asn Gly Thr Gly Pro Cys
        195                 200                 205

Thr Asn Val Ser Thr Val Gln Cys Thr His Gly Ile Arg Pro Val Val
    210                 215                 220

Ser Thr Gln Leu Leu Leu Asn Gly Ser Leu Ala Glu Glu Val Val
225                 230                 235                 240

Ile Arg Ser Glu Asn Phe Thr Asp Asn Ala Lys Thr Ile Ile Val Gln
                245                 250                 255

Leu Asn Glu Ser Val Glu Ile Asn Cys Thr Arg Pro Asn Asn Asn Thr
            260                 265                 270

Arg Lys Ser Ile His Ile Gly Pro Gly Arg Ala Phe Tyr Ala Thr Gly
        275                 280                 285

Asp Ile Ile Gly Asp Ile Arg Gln Ala His Cys Asn Ile Ser Arg Thr
    290                 295                 300

Lys Trp Asn Asn Thr Leu Lys Gln Ile Val Lys Lys Leu Arg Glu Gln
305                 310                 315                 320

Phe Gly Asn Lys Thr Ile Val Phe Asn Gln Ser Ser Gly Gly Asp Pro
                325                 330                 335

Glu Ile Val Met His Ser Phe Asn Cys Gly Gly Glu Phe Phe Tyr Cys
            340                 345                 350

Asn Thr Thr Gln Leu Phe Asn Ser Thr Trp Asn Ser Asn Gly Thr Trp
        355                 360                 365
```

```
Asn Asn Thr Thr Gly Asn Asp Thr Ile Thr Leu Pro Cys Arg Ile Lys
        370                 375                 380
Gln Ile Ile Asn Met Trp Gln Glu Val Gly Lys Ala Met Tyr Ala Pro
385                 390                 395                 400
Pro Ile Arg Gly Gln Ile Arg Cys Ser Ser Asn Ile Thr Gly Leu Leu
                405                 410                 415
Leu Thr Arg Asp Gly Asn Asn Asn Asn Thr Thr Glu Thr Phe
            420                 425                 430
Arg Pro Gly Gly Gly Asp Met Arg Asp Asn Trp Arg Ser Glu Leu Tyr
                435                 440                 445
Lys Tyr Lys Val Val Lys Ile Glu Pro Leu Gly Val Ala Pro Thr Lys
            450                 455                 460
Cys Lys Arg Arg Val Val Gln Arg Arg Arg Arg Arg Ala Val Gly
465                 470                 475                 480
Ile Gly Ala Met Phe Leu Gly Phe Leu Gly Ala Ala Gly Ser Thr Met
                485                 490                 495
Gly Ala Ala Ser Ile Thr Leu Thr Val Gln Ala Arg Gln Leu Leu Ser
            500                 505                 510
Gly Ile Val Gln Gln Gln Asn Asn Leu Leu Arg Ala Pro Glu Ala Gln
        515                 520                 525
Gln His Leu Leu Gln Leu Thr Val Trp Gly Ile Lys Gln Leu Gln Ala
    530                 535                 540
Arg Val Leu Ala Val Glu Arg Tyr Leu Lys Asp Gln Gln Leu Leu Gly
545                 550                 555                 560
Ile Trp Gly Cys Ser Gly Lys Leu Ile Cys Cys Thr Ala Val Pro Trp
                565                 570                 575
Asn Thr Ser Trp Ser Asn Lys Ser Leu Asp Glu Ile Trp Asp Asn Met
            580                 585                 590
Thr Trp Met Gln Trp Glu Arg Glu Ile Asp Asn Tyr Thr Gly Leu Ile
        595                 600                 605
Tyr Thr Leu Ile Glu Glu Ser Gln Asn Gln Gln Glu Lys Asn Glu Gln
    610                 615                 620
Glu Leu Leu Glu Leu Asp
625                 630

<210> SEQ ID NO 6
<211> LENGTH: 625
<212> TYPE: PRT
<213> ORGANISM: Artificial Sequence
<220> FEATURE:
<223> OTHER INFORMATION: synthetic HIV envelope protein

```
Val Thr Leu Asn Cys Arg Asn Val Arg Asn Val Ser Ser Asn Gly Thr
            100                 105                 110

Tyr Asn Ile Ile His Asn Glu Thr Tyr Lys Glu Met Lys Asn Cys Ser
            115                 120                 125

Phe Asn Ala Thr Thr Val Val Glu Asp Arg Lys Gln Lys Val His Ala
            130                 135                 140

Leu Phe Tyr Arg Leu Asp Ile Val Pro Leu Asp Glu Asn Asn Ser Ser
145                 150                 155                 160

Glu Lys Ser Ser Glu Asn Ser Ser Glu Tyr Tyr Arg Leu Ile Asn Cys
                165                 170                 175

Asn Thr Ser Ala Ile Thr Gln Ala Cys Pro Lys Val Ser Phe Asp Pro
            180                 185                 190

Ile Pro Ile His Tyr Cys Ala Pro Ala Gly Tyr Ala Ile Leu Lys Cys
            195                 200                 205

Asn Asn Lys Thr Phe Asn Gly Thr Gly Pro Cys Asn Asn Val Ser Thr
            210                 215                 220

Val Gln Cys Thr His Gly Ile Lys Pro Val Val Ser Thr Gln Leu Leu
225                 230                 235                 240

Leu Asn Gly Ser Leu Ala Glu Glu Ile Ile Ile Arg Ser Glu Asn
                245                 250                 255

Leu Thr Asn Asn Ala Lys Thr Ile Ile Val His Leu Asn Glu Thr Val
            260                 265                 270

Asn Ile Thr Cys Thr Arg Pro Asn Asn Asn Thr Arg Lys Ser Ile Arg
            275                 280                 285

Ile Gly Pro Gly Gln Thr Phe Tyr Ala Thr Gly Asp Ile Ile Gly Asp
            290                 295                 300

Ile Arg Gln Ala His Cys Asn Leu Ser Arg Asp Gly Trp Asn Lys Thr
305                 310                 315                 320

Leu Gln Gly Val Lys Lys Leu Ala Glu His Phe Pro Asn Lys Thr
                325                 330                 335

Ile Lys Phe Ala Pro His Ser Gly Gly Asp Leu Glu Ile Thr Thr His
            340                 345                 350

Thr Phe Asn Cys Arg Gly Glu Phe Phe Tyr Cys Asn Thr Ser Asn Leu
            355                 360                 365

Phe Asn Glu Ser Asn Ile Glu Arg Asn Asp Ser Ile Ile Thr Leu Pro
            370                 375                 380

Cys Arg Ile Lys Gln Ile Ile Asn Met Trp Gln Glu Val Gly Arg Ala
385                 390                 395                 400

Ile Tyr Ala Pro Pro Ile Ala Gly Asn Ile Thr Cys Arg Ser Asn Ile
                405                 410                 415

Thr Gly Leu Leu Leu Thr Arg Asp Gly Gly Ser Asn Asn Gly Val Pro
            420                 425                 430

Asn Asp Thr Glu Thr Phe Arg Pro Gly Gly Gly Asp Met Arg Asn Asn
            435                 440                 445

Trp Arg Ser Glu Leu Tyr Lys Tyr Lys Val Val Glu Val Lys Pro Leu
            450                 455                 460

Gly Val Ala Pro Thr Glu Ala Lys Arg Arg Val Val Glu Arg Glu Lys
465                 470                 475                 480

Arg Ala Val Gly Ile Gly Ala Val Phe Leu Gly Ile Leu Gly Ala Ala
                485                 490                 495

Gly Ser Thr Met Gly Ala Ala Ser Ile Thr Leu Thr Val Gln Ala Arg
            500                 505                 510
```

```
Gln Leu Leu Ser Gly Ile Val Gln Gln Ser Asn Leu Leu Arg Ala
            515                 520                 525

Ile Glu Ala Gln Gln His Met Leu Gln Leu Thr Val Trp Gly Ile Lys
530                 535                 540

Gln Leu Gln Thr Arg Val Leu Ala Ile Glu Arg Tyr Leu Gln Asp Gln
545                 550                 555                 560

Gln Leu Leu Gly Leu Trp Gly Cys Ser Gly Lys Leu Ile Cys Thr Thr
                565                 570                 575

Ala Val Pro Trp Asn Thr Ser Trp Ser Asn Lys Ser Gln Thr Asp Ile
            580                 585                 590

Trp Asp Asn Met Thr Trp Met Gln Trp Asp Lys Glu Ile Gly Asn Tyr
            595                 600                 605

Thr Gly Glu Ile Tyr Arg Leu Leu Glu Glu Ser Gln Asn Gln Gln Glu
    610                 615                 620

Lys
625

<210> SEQ ID NO 7
<211> LENGTH: 627
<212> TYPE: PRT
<213> ORGANISM: Artificial Sequence
<220> FEATURE:
<223> OTHER INFORMATION: DS_sC4_SOSIP_E166R sequence

<400> SEQUENCE: 7

Met Gly Asn Leu Trp Val Thr Val Tyr Tyr Gly Val Pro Val Trp Lys
1               5                   10                  15

Asp Ala Lys Thr Thr Leu Phe Cys Ala Ser Asp Ala Lys Ala Tyr Glu
            20                  25                  30

Lys Glu Val His Asn Val Trp Ala Thr His Ala Cys Val Pro Thr Asp
        35                  40                  45

Pro Asn Pro Gln Glu Ile Val Leu Gly Asn Val Thr Glu Asn Phe Asn
    50                  55                  60

Met Trp Lys Asn Asp Met Val Asp Gln Met His Glu Asp Ile Ile Ser
65                  70                  75                  80

Leu Trp Asp Ala Ser Leu Glu Pro Cys Val Lys Leu Thr Pro Leu Cys
                85                  90                  95

Val Thr Leu Asn Cys Arg Asn Val Arg Asn Val Ser Ser Asn Gly Thr
            100                 105                 110

Tyr Asn Ile Ile His Asn Glu Thr Tyr Lys Glu Met Lys Asn Cys Ser
        115                 120                 125

Phe Asn Ala Thr Thr Val Val Arg Asp Arg Lys Gln Lys Val His Ala
    130                 135                 140

Leu Phe Tyr Arg Leu Asp Ile Val Pro Leu Asp Glu Asn Asn Ser Ser
145                 150                 155                 160

Glu Lys Ser Ser Glu Asn Ser Ser Glu Tyr Tyr Arg Leu Ile Asn Cys
                165                 170                 175

Asn Thr Ser Ala Cys Thr Gln Ala Cys Pro Lys Val Ser Phe Asp Pro
            180                 185                 190

Ile Pro Ile His Tyr Cys Ala Pro Ala Gly Tyr Ala Ile Leu Lys Cys
        195                 200                 205

Asn Asn Lys Thr Phe Asn Gly Thr Gly Pro Cys Asn Asn Val Ser Thr
    210                 215                 220

Val Gln Cys Thr His Gly Ile Lys Pro Val Val Ser Thr Gln Leu Leu
225                 230                 235                 240
```

Leu Asn Gly Ser Leu Ala Glu Glu Ile Ile Arg Ser Asn
            245                 250                 255

Leu Thr Asn Asn Ala Lys Thr Ile Ile Val His Leu Asn Glu Thr Val
        260                 265                 270

Asn Ile Asn Cys Thr Arg Pro Asn Asn Asn Thr Arg Lys Ser Ile Arg
    275                 280                 285

Ile Gly Pro Gly Gln Thr Phe Tyr Ala Thr Gly Asp Ile Ile Gly Asp
290                 295                 300

Ile Arg Gln Ala His Cys Asn Leu Ser Arg Asp Gly Trp Asn Lys Thr
305                 310                 315                 320

Leu Gln Gly Val Lys Lys Leu Ala Glu His Phe Pro Asn Lys Thr
                325                 330                 335

Ile Lys Phe Ala Pro His Ser Gly Gly Asp Leu Glu Ile Thr Thr His
            340                 345                 350

Thr Phe Asn Cys Arg Gly Glu Phe Phe Tyr Cys Asn Thr Ser Asn Leu
        355                 360                 365

Phe Asn Glu Ser Asn Ile Glu Arg Asn Asp Ser Ile Ile Thr Leu Pro
370                 375                 380

Cys Arg Ile Lys Gln Ile Ile Asn Met Trp Gln Glu Val Gly Arg Cys
385                 390                 395                 400

Ile Tyr Ala Pro Pro Ile Ala Gly Asn Ile Thr Cys Arg Ser Asn Ile
                405                 410                 415

Thr Gly Leu Leu Leu Thr Arg Asp Gly Gly Ser Asn Asn Gly Val Pro
            420                 425                 430

Asn Asp Thr Glu Thr Phe Arg Pro Gly Gly Gly Asp Met Arg Asn Asn
        435                 440                 445

Trp Arg Ser Glu Leu Tyr Lys Tyr Lys Val Val Glu Val Lys Pro Leu
450                 455                 460

Gly Val Ala Pro Thr Glu Cys Lys Arg Arg Val Val Glu Arg Arg
465                 470                 475                 480

Arg Arg Arg Ala Val Gly Ile Gly Ala Val Phe Leu Gly Ile Leu Gly
                485                 490                 495

Ala Ala Gly Ser Thr Met Gly Ala Ala Ser Ile Thr Leu Thr Val Gln
            500                 505                 510

Ala Arg Gln Leu Leu Ser Gly Ile Val Gln Gln Ser Asn Leu Leu
        515                 520                 525

Arg Ala Pro Glu Ala Gln Gln His Met Leu Gln Leu Thr Val Trp Gly
530                 535                 540

Ile Lys Gln Leu Gln Thr Arg Val Leu Ala Ile Glu Arg Tyr Leu Gln
545                 550                 555                 560

Asp Gln Gln Leu Leu Gly Leu Trp Gly Cys Ser Gly Lys Leu Ile Cys
                565                 570                 575

Cys Thr Ala Val Pro Trp Asn Thr Ser Trp Ser Asn Lys Ser Gln Thr
            580                 585                 590

Asp Ile Trp Asp Asn Met Thr Trp Met Gln Trp Asp Lys Glu Ile Gly
        595                 600                 605

Asn Tyr Thr Gly Glu Ile Tyr Arg Leu Leu Glu Glu Ser Gln Asn Gln
610                 615                 620

Gln Glu Lys
625

<210> SEQ ID NO 8
<211> LENGTH: 631
<212> TYPE: PRT

<213> ORGANISM: Artificial Sequence
<220> FEATURE:
<223> OTHER INFORMATION: Mos1.Env sequence

<400> SEQUENCE: 8

```
Ala Gly Lys Leu Trp Val Thr Val Tyr Tyr Gly Val Pro Val Trp Lys
1               5                   10                  15

Glu Ala Thr Thr Thr Leu Phe Cys Ala Ser Asp Ala Lys Ala Tyr Asp
            20                  25                  30

Thr Glu Val His Asn Val Trp Ala Thr His Ala Cys Val Pro Thr Asp
        35                  40                  45

Pro Asn Pro Gln Glu Val Val Leu Glu Asn Val Thr Glu Asn Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Thr Asp Asp Val Arg Asn Val Thr Asn Asn Ala
            100                 105                 110

Thr Asn Thr Asn Ser Ser Trp Gly Glu Pro Met Glu Lys Gly Glu Ile
        115                 120                 125

Lys Asn Cys Ser Phe Asn Ile Thr Thr Ser Ile Arg Asn Lys Val Gln
130                 135                 140

Lys Gln Tyr Ala Leu Phe Tyr Lys Leu Asp Val Val Pro Ile Asp Asn
145                 150                 155                 160

Asp Ser Asn Asn Thr Asn Tyr Arg Leu Ile Ser Cys Asn Thr Ser Val
                165                 170                 175

Ile Thr Gln Ala Cys Pro Lys Val Ser Phe Glu Pro Ile Pro Ile His
            180                 185                 190

Tyr Cys Ala Pro Ala Gly Phe Ala Ile Leu Lys Cys Asn Asp Lys Lys
        195                 200                 205

Phe Asn Gly Thr Gly Pro Cys Thr Asn Val Ser Thr Val Gln Cys Thr
    210                 215                 220

His Gly Ile Arg Pro Val Val Ser Thr Gln Leu Leu Leu Asn Gly Ser
225                 230                 235                 240

Leu Ala Glu Glu Glu Val Val Ile Arg Ser Glu Asn Phe Thr Asn Asn
                245                 250                 255

Ala Lys Thr Ile Met Val Gln Leu Asn Val Ser Val Glu Ile Asn Cys
            260                 265                 270

Thr Arg Pro Asn Asn Asn Thr Arg Lys Ser Ile His Ile Gly Pro Gly
        275                 280                 285

Arg Ala Phe Tyr Thr Ala Gly Asp Ile Ile Gly Asp Ile Arg Gln Ala
    290                 295                 300

His Cys Asn Ile Ser Arg Ala Asn Trp Asn Asn Thr Leu Arg Gln Ile
305                 310                 315                 320

Val Glu Lys Leu Gly Lys Gln Phe Gly Asn Asn Lys Thr Ile Val Phe
                325                 330                 335

Asn His Ser Ser Gly Gly Asp Pro Glu Ile Val Met His Ser Phe Asn
            340                 345                 350

Cys Gly Gly Glu Phe Phe Tyr Cys Asn Ser Thr Lys Leu Phe Asn Ser
        355                 360                 365

Thr Trp Thr Trp Asn Asn Ser Thr Trp Asn Asn Thr Lys Arg Ser Asn
    370                 375                 380

Asp Thr Glu Glu His Ile Thr Leu Pro Cys Arg Ile Lys Gln Ile Ile
```

```
385                 390                 395                 400
Asn Met Trp Gln Glu Val Gly Lys Ala Met Tyr Ala Pro Pro Ile Arg
            405                 410                 415

Gly Gln Ile Arg Cys Ser Ser Asn Ile Thr Gly Leu Leu Leu Thr Arg
        420                 425                 430

Asp Gly Gly Asn Asp Thr Ser Gly Thr Glu Ile Phe Arg Pro Gly Gly
        435                 440                 445

Gly Asp Met Arg Asp Asn Trp Arg Ser Glu Leu Tyr Lys Tyr Lys Val
    450                 455                 460

Val Lys Ile Glu Pro Leu Gly Val Ala Pro Thr Lys Ala Lys Arg Arg
465                 470                 475                 480

Val Val Gln Ser Glu Lys Ser Ala Val Gly Ile Gly Ala Val Phe Leu
                485                 490                 495

Gly Phe Leu Gly Ala Ala Gly Ser Thr Met Gly Ala Ala Ser Met Thr
            500                 505                 510

Leu Thr Val Gln Ala Arg Leu Leu Leu Ser Gly Ile Val Gln Gln Gln
        515                 520                 525

Asn Asn Leu Leu Arg Ala Ile Glu Ala Gln Gln His Leu Leu Gln Leu
    530                 535                 540

Thr Val Trp Gly Ile Lys Gln Leu Gln Ala Arg Val Leu Ala Val Glu
545                 550                 555                 560

Arg Tyr Leu Lys Asp Gln Gln Leu Leu Gly Ile Trp Gly Cys Ser Gly
                565                 570                 575

Lys Leu Ile Cys Thr Thr Thr Val Pro Trp Asn Ala Ser Trp Ser Asn
            580                 585                 590

Lys Ser Leu Asp Lys Ile Trp Asn Asn Met Thr Trp Met Glu Trp Glu
        595                 600                 605

Arg Glu Ile Asn Asn Tyr Thr Ser Leu Ile Tyr Thr Leu Ile Glu Glu
    610                 615                 620

Ser Gln Asn Gln Gln Glu Lys
625                 630

<210> SEQ ID NO 9
<211> LENGTH: 630
<212> TYPE: PRT
<213> ORGANISM: Artificial Sequence
<220> FEATURE:
<223> OTHER INFORMATION: Mos2.Env sequence

<400> SEQUENCE: 9

Met Gly Asn Leu Trp Val Thr Val Tyr Tyr Gly Val Pro Val Trp Lys
1               5                   10                  15

Glu Ala Lys Thr Thr Leu Phe Cys Ala Ser Asp Ala Lys Ala Tyr Glu
            20                  25                  30

Lys Glu Val His Asn Val Trp Ala Thr His Ala Cys Val Pro Thr Asp
        35                  40                  45

Pro Asn Pro Gln Glu Met Val Leu Glu Asn Val Thr Glu Asn Phe Asn
    50                  55                  60

Met Trp Lys Asn Asp Met Val Asp Gln Met His Glu Asp Ile Ile Arg
65                  70                  75                  80

Leu Trp Asp Gln Ser Leu Lys Pro Cys Val Lys Leu Thr Pro Leu Cys
                85                  90                  95

Val Thr Leu Glu Cys Arg Asn Val Arg Asn Val Ser Ser Asn Gly Thr
            100                 105                 110

Tyr Asn Ile Ile His Asn Glu Thr Tyr Lys Glu Met Lys Asn Cys Ser
```

-continued

```
            115                 120                 125
Phe Asn Ala Thr Thr Val Val Glu Asp Arg Lys Gln Lys Val His Ala
130                 135                 140
Leu Phe Tyr Arg Leu Asp Ile Val Pro Leu Asp Glu Asn Asn Ser Ser
145                 150                 155                 160
Glu Lys Ser Ser Glu Asn Ser Ser Glu Tyr Tyr Arg Leu Ile Asn Cys
                165                 170                 175
Asn Thr Ser Ala Ile Thr Gln Ala Cys Pro Lys Val Ser Phe Asp Pro
                180                 185                 190
Ile Pro Ile His Tyr Cys Ala Pro Ala Gly Tyr Ala Ile Leu Lys Cys
                195                 200                 205
Asn Asn Lys Thr Phe Asn Gly Thr Gly Pro Cys Asn Asn Val Ser Thr
210                 215                 220
Val Gln Cys Thr His Gly Ile Lys Pro Val Val Ser Thr Gln Leu Leu
225                 230                 235                 240
Leu Asn Gly Ser Leu Ala Glu Glu Ile Ile Ile Arg Ser Glu Asn
                245                 250                 255
Leu Thr Asn Asn Ala Lys Thr Ile Ile Val His Leu Asn Glu Thr Val
                260                 265                 270
Asn Ile Thr Cys Thr Arg Pro Asn Asn Asn Thr Arg Lys Ser Ile Arg
            275                 280                 285
Ile Gly Pro Gly Gln Thr Phe Tyr Ala Thr Gly Asp Ile Ile Gly Asp
290                 295                 300
Ile Arg Gln Ala His Cys Asn Leu Ser Arg Asp Gly Trp Asn Lys Thr
305                 310                 315                 320
Leu Gln Gly Val Lys Lys Leu Ala Glu His Phe Pro Asn Lys Thr
                325                 330                 335
Ile Asn Phe Thr Ser Ser Ser Gly Gly Asp Leu Glu Ile Thr Thr His
                340                 345                 350
Ser Phe Asn Cys Arg Gly Glu Phe Phe Tyr Cys Asn Thr Ser Gly Leu
            355                 360                 365
Phe Asn Gly Thr Tyr Met Pro Asn Gly Thr Asn Ser Asn Ser Ser Ser
370                 375                 380
Asn Ile Thr Leu Pro Cys Arg Ile Lys Gln Ile Ile Asn Met Trp Gln
385                 390                 395                 400
Glu Val Gly Arg Ala Met Tyr Ala Pro Pro Ile Ala Gly Asn Ile Thr
                405                 410                 415
Cys Arg Ser Asn Ile Thr Gly Leu Leu Leu Thr Arg Asp Gly Gly Ser
                420                 425                 430
Asn Asn Gly Val Pro Asn Asp Thr Glu Thr Phe Arg Pro Gly Gly Gly
            435                 440                 445
Asp Met Arg Asn Asn Trp Arg Ser Glu Leu Tyr Lys Tyr Lys Val Val
            450                 455                 460
Glu Val Lys Pro Leu Gly Val Ala Pro Thr Glu Ala Lys Arg Arg Val
465                 470                 475                 480
Val Glu Arg Glu Lys Arg Ala Val Gly Ile Gly Ala Val Phe Leu Gly
                485                 490                 495
Ile Leu Gly Ala Ala Gly Ser Thr Met Gly Ala Ala Ser Ile Thr Leu
                500                 505                 510
Thr Val Gln Ala Arg Gln Leu Leu Ser Gly Ile Val Gln Gln Gln Ser
            515                 520                 525
Asn Leu Leu Arg Ala Ile Glu Ala Gln Gln His Met Leu Gln Leu Thr
            530                 535                 540
```

-continued

Val Trp Gly Ile Lys Gln Leu Gln Thr Arg Val Leu Ala Ile Glu Arg
545                 550                 555                 560

Tyr Leu Gln Asp Gln Gln Leu Gly Leu Trp Gly Cys Ser Gly Lys
                565                 570                 575

Leu Ile Cys Thr Thr Ala Val Pro Trp Asn Thr Ser Trp Ser Asn Lys
            580                 585                 590

Ser Gln Thr Asp Ile Trp Asp Asn Met Thr Trp Met Gln Trp Asp Lys
        595                 600                 605

Glu Ile Gly Asn Tyr Thr Gly Glu Ile Tyr Arg Leu Leu Glu Glu Ser
    610                 615                 620

Gln Asn Gln Gln Glu Lys
625                 630

<210> SEQ ID NO 10
<211> LENGTH: 6
<212> TYPE: PRT
<213> ORGANISM: Artificial Sequence
<220> FEATURE:
<223> OTHER INFORMATION: furin cleavage site mutant sequence

<400> SEQUENCE: 10

Arg Arg Arg Arg Arg Arg
1               5

<210> SEQ ID NO 11
<211> LENGTH: 31
<212> TYPE: PRT
<213> ORGANISM: Artificial Sequence
<220> FEATURE:
<223> OTHER INFORMATION: signal sequence

<400> SEQUENCE: 11

Met Arg Val Arg Gly Ile Leu Arg Asn Trp Gln Gln Trp Trp Ile Trp
1               5                   10                  15

Gly Ile Leu Gly Phe Trp Met Leu Met Ile Cys Asn Val Val Gly
            20                  25                  30

<210> SEQ ID NO 12
<211> LENGTH: 8
<212> TYPE: PRT
<213> ORGANISM: Artificial Sequence
<220> FEATURE:
<223> OTHER INFORMATION: example of 8 amino acid sequence that can
      replace HR1 loop

<400> SEQUENCE: 12

Asn Pro Asp Trp Leu Pro Asp Met
1               5

<210> SEQ ID NO 13
<211> LENGTH: 8
<212> TYPE: PRT
<213> ORGANISM: Artificial Sequence
<220> FEATURE:
<223> OTHER INFORMATION: example of 8 amino acid sequence that can
      replace HR1 loop

<400> SEQUENCE: 13

Gly Ser Gly Ser Gly Ser Gly Ser
1               5

<210> SEQ ID NO 14
<211> LENGTH: 8

```
<212> TYPE: PRT
<213> ORGANISM: Artificial Sequence
<220> FEATURE:
<223> OTHER INFORMATION: example of 8 amino acid sequence that can
      replace HR1 loop

<400> SEQUENCE: 14

Asp Asp Val His Pro Asp Trp Asp
1               5

<210> SEQ ID NO 15
<211> LENGTH: 8
<212> TYPE: PRT
<213> ORGANISM: Artificial Sequence
<220> FEATURE:
<223> OTHER INFORMATION: example of 8 amino acid sequence that can
      replace HR1 loop

<400> SEQUENCE: 15

Arg Asp Thr Phe Ala Leu Met Met
1               5

<210> SEQ ID NO 16
<211> LENGTH: 8
<212> TYPE: PRT
<213> ORGANISM: Artificial Sequence
<220> FEATURE:
<223> OTHER INFORMATION: example of 8 amino acid sequence that can
      replace HR1 loop Ala Ala Ala Leu Pro Glu Thr Gly Gly Gly Ser Asp Tyr Lys Asp Asp
1               5                   10                  15

Asp Asp Lys Pro Gly Gly Gly Ser Gly Gly Gly Ser Gly Gly
            20              25              30

Gly Gly Ser Gly Gly Gly Ser Gly Gly Gly Ser Gly Gly Gly
        35              40              45

Gly Ser Gly Gly Gly Ser His His His His His His
    50              55              60

<210> SEQ ID NO 20
<211> LENGTH: 616
<212> TYPE: PRT
<213> ORGANISM: Artificial Sequence
<220> FEATURE:
<223> OTHER INFORMATION: stabilized ConC_SOSIP Env protein (HIV160544)

<400> SEQUENCE: 20

Asn Leu Trp Val Thr Val Tyr Tyr Gly Val Pro Val Trp Lys Glu Ala
1               5                   10                  15

Lys Thr Thr Leu Phe Cys Ala Ser Asp Ala Lys Ala Tyr Glu Lys Glu
            20                  25                  30

Val His Asn Val Trp Ala Thr His Ala Cys Val Pro Thr Asp Pro Asn
        35                  40                  45

Pro Gln Glu Met Val Leu Glu Asn Val Thr Glu Asn Phe Asn Met Trp
    50                  55                  60

Lys Asn Asp Met Val Asp Gln Met His Glu Asp Ile Ile Ser Leu Trp
65                  70                  75                  80

Asp Gln Ser Leu Lys Pro Cys Val Lys Leu Thr Pro Leu Cys Val Thr
                85                  90                  95

Leu Asn Cys Thr Asn Val Asn Val Thr Asn Thr Asn Asn Asn Asn Met
            100                 105                 110

Lys Glu Glu Met Lys Asn Cys Ser Phe Asn Thr Thr Glu Ile Arg
        115                 120                 125

Asp Lys Lys Gln Lys Glu Tyr Ala Leu Phe Tyr Arg Leu Asp Ile Val
    130                 135                 140

Pro Leu Asn Glu Asn Ser Ser Glu Tyr Arg Leu Ile Asn Cys Asn Thr
145                 150                 155                 160

Ser Thr Ile Thr Gln Ile Cys Pro Lys Val Ser Phe Asp Pro Ile Pro
                165                 170                 175

Ile His Tyr Cys Ala Pro Ala Gly Tyr Ala Ile Leu Lys Cys Asn Asn
            180                 185                 190

Lys Thr Phe Asn Gly Thr Gly Pro Cys Asn Asn Val Ser Thr Val Gln
        195                 200                 205

Cys Thr His Gly Ile Lys Pro Val Val Ser Thr Gln Leu Leu Leu Asn
    210                 215                 220

Gly Ser Leu Ala Glu Glu Ile Ile Ile Arg Ser Glu Asn Leu Thr
225                 230                 235                 240

Asp Asn Ala Lys Thr Ile Ile Val His Leu Asn Glu Ser Val Glu Ile
                245                 250                 255

Asn Cys Thr Arg Pro Asn Asn Asn Thr Arg Lys Ser Ile Arg Ile Gly
            260                 265                 270

Pro Gly Gln Thr Phe Tyr Ala Thr Gly Asp Ile Ile Gly Asp Ile Arg
        275                 280                 285

Gln Ala His Cys Asn Ile Ser Glu Ala Lys Trp Asn Lys Thr Leu Gln
    290                 295                 300

Arg Val Lys Lys Lys Leu Lys Glu His Phe Pro Asn Lys Thr Ile Lys
305                 310                 315                 320

Phe Ala Pro Ser Ser Gly Gly Asp Leu Glu Ile Thr Thr His Ser Phe
            325                 330                 335

Asn Cys Arg Gly Glu Phe Phe Tyr Cys Asn Thr Ser Lys Leu Phe Asn
            340                 345                 350

Ser Thr Tyr Asn Asn Thr Thr Ser Asn Ser Thr Ile Thr Leu Pro Cys
        355                 360                 365

Arg Ile Lys Gln Ile Ile Asn Met Trp Gln Glu Val Gly Arg Ala Met
370                 375                 380

Tyr Ala Pro Pro Ile Ala Gly Asn Ile Thr Cys Lys Ser Asn Ile Thr
385                 390                 395                 400

Gly Leu Leu Leu Thr Arg Asp Gly Gly Asn Asn Asn Asn Asn Thr Glu
                405                 410                 415

Thr Phe Arg Pro Gly Gly Gly Asp Met Arg Asp Asn Trp Arg Ser Glu
            420                 425                 430

Leu Tyr Lys Tyr Lys Val Val Glu Ile Lys Pro Leu Gly Ile Ala Pro
        435                 440                 445

Thr Lys Cys Lys Arg Arg Val Val Glu Arg Arg Arg Arg Arg Arg Ala
450                 455                 460

Val Gly Ile Gly Ala Val Phe Leu Gly Phe Leu Gly Ala Ala Gly Ser
465                 470                 475                 480

Thr Met Gly Ala Ala Ser Asn Thr Leu Thr Val Gln Ala Arg Gln Leu
                485                 490                 495

Leu Ser Gly Ile Val Gln Gln Gln Ser Asn Leu Leu Arg Ala Pro Glu
            500                 505                 510

Ala Gln Gln His Met Leu Gln Leu Thr Val Trp Gly Phe Lys Gln Leu
        515                 520                 525

Gln Ala Arg Val Leu Ala Ile Glu Arg Tyr Leu Glu Val Gln Gln Leu
530                 535                 540

Leu Gly Ile Trp Gly Cys Ser Gly Lys Leu Ile Cys Cys Thr Ala Val
545                 550                 555                 560

Pro Trp Asn Ser Ser Trp Ser Asn Lys Ser Gln Glu Asp Ile Trp Asp
                565                 570                 575

Asn Met Thr Trp Met Gln Trp Asp Arg Glu Ile Ser Asn Tyr Thr Asp
            580                 585                 590

Thr Ile Tyr Arg Leu Leu Glu Glu Ser Gln Phe Gln Gln Glu Ile Asn
        595                 600                 605

Glu Lys Asp Leu Leu Ala Leu Asp
610                 615

<210> SEQ ID NO 21
<211> LENGTH: 634
<212> TYPE: PRT
<213> ORGANISM: Artificial Sequence
<220> FEATURE:
<223> OTHER INFORMATION: BG505_SOSIP Env protein (HIV150673)

<400> SEQUENCE: 21

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

```
Pro Asn Pro Gln Glu Ile His Leu Glu Asn Val Thr Glu Glu Phe Asn
    50              55                  60
Met Trp Lys Asn Asn Met Val Glu Gln Met His Thr Asp Ile Ile Ser
 65              70                  75                      80
Leu Trp Asp Gln Ser Leu Lys Pro Cys Val Lys Leu Thr Pro Leu Cys
                 85                  90                  95
Val Thr Leu Gln Cys Thr Asn Val Thr Asn Asn Ile Thr Asp Asp Met
            100                 105                 110
Arg Gly Glu Leu Lys Asn Cys Ser Phe Asn Met Thr Thr Glu Leu Arg
            115                 120                 125
Asp Lys Lys Gln Lys Val Tyr Ser Leu Phe Tyr Arg Leu Asp Val Val
130                 135                 140
Gln Ile Asn Glu Asn Gln Gly Asn Arg Ser Asn Asn Ser Asn Lys Glu
145                 150                 155                 160
Tyr Arg Leu Ile Asn Cys Asn Thr Ser Ala Ile Thr Gln Ala Cys Pro
                165                 170                 175
Lys Val Ser Phe Glu Pro Ile Pro Ile His Tyr Cys Ala Pro Ala Gly
            180                 185                 190
Phe Ala Ile Leu Lys Cys Lys Asp Lys Lys Phe Asn Gly Thr Gly Pro
            195                 200                 205
Cys Pro Ser Val Ser Thr Val Gln Cys Thr His Gly Ile Lys Pro Val
            210                 215                 220
Val Ser Thr Gln Leu Leu Leu Asn Gly Ser Leu Ala Glu Glu Glu Val
225                 230                 235                 240
Met Ile Arg Ser Glu Asn Ile Thr Asn Asn Ala Lys Asn Ile Leu Val
                245                 250                 255
Gln Phe Asn Thr Pro Val Gln Ile Asn Cys Thr Arg Pro Asn Asn Asn
                260                 265                 270
Thr Arg Lys Ser Ile Arg Ile Gly Pro Gly Gln Ala Phe Tyr Ala Thr
                275                 280                 285
Gly Asp Ile Ile Gly Asp Ile Arg Gln Ala His Cys Asn Val Ser Lys
            290                 295                 300
Ala Thr Trp Asn Glu Thr Leu Gly Lys Val Val Lys Gln Leu Arg Lys
305                 310                 315                 320
His Phe Gly Asn Asn Thr Ile Ile Arg Phe Ala Asn Ser Ser Gly Gly
                325                 330                 335
Asp Leu Glu Val Thr Thr His Ser Phe Asn Cys Gly Gly Glu Phe Phe
                340                 345                 350
Tyr Cys Asn Thr Ser Gly Leu Phe Asn Ser Thr Trp Ile Ser Asn Thr
            355                 360                 365
Ser Val Gln Gly Ser Asn Ser Thr Gly Ser Asn Asp Ser Ile Thr Leu
            370                 375                 380
Pro Cys Arg Ile Lys Gln Ile Ile Asn Met Trp Gln Arg Ile Gly Gln
385                 390                 395                 400
Ala Met Tyr Ala Pro Pro Ile Gln Gly Val Ile Arg Cys Val Ser Asn
                405                 410                 415
Ile Thr Gly Leu Ile Leu Thr Arg Asp Gly Gly Ser Thr Asn Ser Thr
            420                 425                 430
Thr Glu Thr Phe Arg Pro Gly Gly Gly Asp Met Arg Asp Asn Trp Arg
            435                 440                 445
Ser Glu Leu Tyr Lys Tyr Lys Val Val Lys Ile Glu Pro Leu Gly Val
            450                 455                 460
Ala Pro Thr Arg Cys Lys Arg Arg Val Val Gly Arg Arg Arg Arg Arg
```

```
                465                 470                 475                 480
Arg Ala Val Gly Ile Gly Ala Val Phe Leu Gly Phe Leu Gly Ala Ala
                    485                 490                 495
Gly Ser Thr Met Gly Ala Ala Ser Met Thr Leu Thr Val Gln Ala Arg
                500                 505                 510
Asn Leu Leu Ser Gly Ile Val Gln Gln Gln Ser Asn Leu Leu Arg Ala
                515                 520                 525
Pro Glu Ala Gln Gln His Leu Leu Lys Leu Thr Val Trp Gly Ile Lys
530                 535                 540
Gln Leu Gln Ala Arg Val Leu Ala Val Glu Arg Tyr Leu Arg Asp Gln
545                 550                 555                 560
Gln Leu Leu Gly Ile Trp Gly Cys Ser Gly Lys Leu Ile Cys Cys Thr
                    565                 570                 575
Asn Val Pro Trp Asn Ser Ser Trp Ser Asn Arg Asn Leu Ser Glu Ile
                580                 585                 590
Trp Asp Asn Met Thr Trp Leu Gln Trp Asp Lys Glu Ile Ser Asn Tyr
                595                 600                 605
Thr Gln Ile Ile Tyr Gly Leu Leu Glu Glu Ser Gln Asn Gln Gln Glu
                610                 615                 620
Lys Asn Glu Gln Asp Leu Leu Ala Leu Asp
625                 630
```

<210> SEQ ID NO 22
<211> LENGTH: 634
<212> TYPE: PRT
<213> ORGANISM: Artificial Sequence
<220> FEATURE:
<223> OTHER INFORMATION: stabilized BG505_SOSIP Env protein (HIV170863)

<400> SEQUENCE: 22

```
Ala Glu Asn Leu Trp Val Thr Val Tyr Tyr Gly Val Pro Val Trp Lys
1               5                   10                  15
Asp Ala Glu Thr Thr Leu Phe Cys Ala Ser Asp Ala Lys Ala Tyr Glu
                20                  25                  30
Thr Glu Lys His Asn Val Trp Ala Thr His Ala Cys Val Pro Thr Asp
                35                  40                  45
Pro Asn Pro Gln Glu Ile His Leu Glu Asn Val Thr Glu Glu Phe Asn
        50                  55                  60
Met Trp Lys Asn Asn Met Val Glu Gln Met His Thr Asp Ile Ile Ser
65                  70                  75                  80
Leu Trp Asp Gln Ser Leu Lys Pro Cys Val Lys Leu Thr Pro Leu Cys
                85                  90                  95
Val Thr Leu Gln Cys Thr Asn Val Thr Asn Asn Ile Thr Asp Asp Met
                100                 105                 110
Arg Gly Glu Leu Lys Asn Cys Ser Phe Asn Met Thr Thr Glu Leu Arg
                115                 120                 125
Asp Lys Lys Gln Lys Val Tyr Ser Leu Phe Tyr Arg Leu Asp Val Val
        130                 135                 140
Gln Ile Asn Glu Asn Gln Gly Asn Arg Ser Asn Asn Ser Asn Lys Glu
145                 150                 155                 160
Tyr Arg Leu Ile Asn Cys Asn Thr Ser Ala Ile Thr Gln Ala Cys Pro
                165                 170                 175
Lys Val Ser Phe Glu Pro Ile Pro Ile His Tyr Cys Ala Pro Ala Gly
                180                 185                 190
Phe Ala Ile Leu Lys Cys Lys Asp Lys Lys Phe Asn Gly Thr Gly Pro
```

```
            195                 200                 205
Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Val
225                 230                 235                 240

Met Ile Arg Ser Glu Asn Ile Thr Asn Asn Ala Lys Asn Ile Leu Val
                245                 250                 255

Gln Phe Asn Thr Pro Val Gln Ile Asn Cys Thr Arg Pro Asn Asn Asn
            260                 265                 270

Thr Arg Lys Ser Ile Arg Ile Gly Pro Gly Gln Ala Phe Tyr Ala Thr
        275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Asn Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
        355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
        435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Phe Leu Gly Phe Leu Gly Ala Ala
                485                 490                 495

Gly Ser Thr Met Gly Ala Ala Ser Asn Thr Leu Thr Val Gln Ala Arg
            500                 505                 510

Asn Leu Leu Ser Gly Ile Val Gln Gln Gln Ser Asn Leu Pro Arg Ala
        515                 520                 525

Pro Glu Ala Gln Gln His Leu Leu Lys Leu Thr Val Trp Gly Ile Lys
    530                 535                 540

Gln Leu Gln Ala Arg Val Leu Ala Val Glu Arg Tyr Leu Arg Val Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
            580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Phe Gln Gln Glu
    610                 615                 620
```

Ile Asn Glu Gln Asp Leu Leu Ala Leu Asp
625                 630

<210> SEQ ID NO 23
<211> LENGTH: 619
<212> TYPE: PRT
<213> ORGANISM: Artificial Sequence
<220> FEATURE:
<223> OTHER INFORMATION: wt C97ZA_SOSIP Env protein with L535M and Q567K
      (HIV150673)

<400> SEQUENCE: 23

Asn Met Trp Val Thr Val Tyr Tyr Gly Val Pro Val Trp Thr Asp Ala
1               5                   10                  15

Lys Thr Thr Leu Phe Cys Ala Ser Asp Thr Lys Ala Tyr Asp Arg Glu
            20                  25                  30

Val His Asn Val Trp Ala Thr His Ala Cys Val Pro Thr Asp Pro Asn
        35                  40                  45

Pro Gln Glu Ile Val Leu Glu Asn Val Thr Glu Asn Phe Asn Met Trp
    50                  55                  60

Lys Asn Asp Met Val Asp Gln Met His Glu Asp Ile Ile Ser Leu Trp
65                  70                  75                  80

Asp Gln Ser Leu Lys Pro Cys Val Lys Leu Thr Pro Leu Cys Val Thr
                85                  90                  95

Leu His Cys Thr Asn Ala Thr Phe Lys Asn Asn Val Thr Asn Asp Met
            100                 105                 110

Asn Lys Glu Ile Arg Asn Cys Ser Phe Asn Thr Thr Thr Glu Ile Arg
        115                 120                 125

Asp Lys Lys Gln Gln Gly Tyr Ala Leu Phe Tyr Arg Pro Asp Ile Val
    130                 135                 140

Leu Leu Lys Glu Asn Arg Asn Asn Ser Asn Asn Ser Glu Tyr Ile Leu
145                 150                 155                 160

Ile Asn Cys Asn Ala Ser Thr Ile Thr Gln Ala Cys Pro Lys Val Asn
                165                 170                 175

Phe Asp Pro Ile Pro Ile His Tyr Cys Ala Pro Ala Gly Tyr Ala Ile
            180                 185                 190

Leu Lys Cys Asn Asn Lys Thr Phe Ser Gly Lys Gly Pro Cys Asn Asn
        195                 200                 205

Val Ser Thr Val Gln Cys Thr His Gly Ile Lys Pro Val Val Ser Thr
    210                 215                 220

Gln Leu Leu Leu Asn Gly Ser Leu Ala Glu Lys Glu Ile Ile Ile Arg
225                 230                 235                 240

Ser Glu Asn Leu Thr Asp Asn Val Lys Thr Ile Ile Val His Leu Asn
                245                 250                 255

Lys Ser Val Glu Ile Val Cys Thr Arg Pro Asn Asn Asn Thr Arg Lys
            260                 265                 270

Ser Met Arg Ile Gly Pro Gly Gln Thr Phe Tyr Ala Thr Gly Asp Ile
        275                 280                 285

Ile Gly Asp Ile Arg Gln Ala Tyr Cys Asn Ile Ser Gly Ser Lys Trp
    290                 295                 300

Asn Glu Thr Leu Lys Arg Val Lys Glu Lys Leu Gln Glu Asn Tyr Asn
305                 310                 315                 320

Asn Asn Lys Thr Ile Lys Phe Ala Pro Ser Ser Gly Gly Asp Leu Glu
                325                 330                 335

Ile Thr Thr His Ser Phe Asn Cys Arg Gly Glu Phe Phe Tyr Cys Asn

```
                    340                 345                 350
Thr Thr Arg Leu Phe Asn Asn Asn Ala Thr Glu Asp Glu Thr Ile Thr
            355                 360                 365
Leu Pro Cys Arg Ile Lys Gln Ile Ile Asn Met Trp Gln Gly Val Gly
        370                 375                 380
Arg Ala Met Tyr Ala Pro Pro Ile Ala Gly Asn Ile Thr Cys Lys Ser
385                 390                 395                 400
Asn Ile Thr Gly Leu Leu Leu Val Arg Asp Gly Gly Glu Asp Asn Lys
                405                 410                 415
Thr Glu Glu Ile Phe Arg Pro Gly Gly Gly Asn Met Lys Asp Asn Trp
            420                 425                 430
Arg Ser Glu Leu Tyr Lys Tyr Lys Val Ile Glu Leu Lys Pro Leu Gly
        435                 440                 445
Ile Ala Pro Thr Gly Cys Lys Arg Arg Val Val Glu Arg Arg Arg Arg
450                 455                 460
Arg Arg Ala Val Gly Ile Gly Ala Val Phe Leu Gly Phe Leu Gly Ala
465                 470                 475                 480
Ala Gly Ser Thr Met Gly Ala Ala Ser Met Thr Leu Thr Val Gln Ala
                485                 490                 495
Arg Gln Leu Leu Ser Ser Ile Val Gln Gln Ser Asn Leu Leu Arg
            500                 505                 510
Ala Pro Glu Ala Gln Gln His Met Leu Lys Leu Thr Val Trp Gly Ile
            515                 520                 525
Lys Gln Leu Gln Thr Arg Val Leu Ala Ile Glu Arg Tyr Leu Lys Asp
        530                 535                 540
Gln Gln Leu Leu Gly Ile Trp Gly Cys Ser Gly Lys Leu Ile Cys Cys
545                 550                 555                 560
Thr Asn Val Pro Trp Asn Ser Ser Trp Ser Asn Lys Ser Gln Thr Asp
                565                 570                 575
Ile Trp Asn Asn Met Thr Trp Met Glu Trp Asp Arg Glu Ile Ser Asn
            580                 585                 590
Tyr Thr Asp Thr Ile Tyr Arg Leu Leu Glu Asp Ser Gln Thr Gln Gln
        595                 600                 605
Glu Lys Asn Glu Lys Asp Leu Leu Ala Leu Asp
    610                 615

<210> SEQ ID NO 24
<211> LENGTH: 619
<212> TYPE: PRT
<213> ORGANISM: Artificial Sequence
<220> FEATURE:
<223> OTHER INFORMATION: repaired and stabilized C97ZA_SOSIP Env protein
      (HIV170690)

<400> SEQUENCE: 24

Asn Leu Trp Val Thr Val Tyr Tyr Gly Val Pro Val Trp Lys Asp Ala
1               5                   10                  15
Lys Thr Thr Leu Phe Cys Ala Ser Asp Ala Lys Ala Tyr Asp Arg Glu
            20                  25                  30
Val His Asn Val Trp Ala Thr His Ala Cys Val Pro Thr Asp Pro Asn
        35                  40                  45
Pro Gln Glu Ile Val Leu Glu Asn Val Thr Glu Asn Phe Asn Met Trp
    50                  55                  60
Lys Asn Asp Met Val Asp Gln Met His Glu Asp Ile Ile Ser Leu Trp
65                  70                  75                  80
```

```
Asp Gln Ser Leu Lys Pro Cys Val Lys Leu Thr Pro Leu Cys Val Thr
                85                  90                  95
Leu His Cys Thr Asn Ala Thr Phe Lys Asn Asn Val Thr Asn Asp Met
            100                 105                 110
Asn Lys Glu Ile Arg Asn Cys Ser Phe Asn Thr Thr Thr Glu Ile Arg
        115                 120                 125
Asp Lys Lys Gln Lys Val Tyr Ala Leu Phe Tyr Arg Leu Asp Ile Val
    130                 135                 140
Gln Leu Lys Glu Asn Arg Asn Asn Ser Asn Asn Ser Glu Tyr Arg Leu
145                 150                 155                 160
Ile Asn Cys Asn Thr Ser Thr Ile Thr Gln Ile Cys Pro Lys Val Thr
                165                 170                 175
Phe Asp Pro Ile Pro Ile His Tyr Cys Ala Pro Ala Gly Tyr Ala Ile
            180                 185                 190
Leu Lys Cys Asn Asn Lys Thr Phe Asn Gly Thr Gly Pro Cys Asn Asn
        195                 200                 205
Val Ser Thr Val Gln Cys Thr His Gly Ile Lys Pro Val Val Ser Thr
    210                 215                 220
Gln Leu Leu Leu Asn Gly Ser Leu Ala Glu Lys Glu Ile Ile Ile Arg
225                 230                 235                 240
Ser Glu Asn Leu Thr Asp Asn Val Lys Thr Ile Ile Val His Leu Asn
                245                 250                 255
Lys Ser Val Glu Ile Asn Cys Thr Arg Pro Asn Asn Asn Thr Arg Lys
            260                 265                 270
Ser Ile Arg Ile Gly Pro Gly Gln Thr Phe Tyr Ala Thr Gly Asp Ile
        275                 280                 285
Ile Gly Asp Ile Arg Gln Ala Tyr Cys Asn Ile Ser Gly Ser Lys Trp
    290                 295                 300
Asn Glu Thr Leu Lys Arg Val Lys Glu Lys Leu Arg Glu His Phe Asn
305                 310                 315                 320
Asn Asn Lys Thr Ile Lys Phe Ala Pro Ser Ser Gly Gly Asp Leu Glu
                325                 330                 335
Ile Thr Thr His Ser Phe Asn Cys Arg Gly Glu Phe Phe Tyr Cys Asn
            340                 345                 350
Thr Thr Arg Leu Phe Asn Asn Asn Ala Thr Glu Asn Glu Thr Ile Thr
        355                 360                 365
Leu Pro Cys Arg Ile Lys Gln Ile Ile Asn Met Trp Gln Glu Val Gly
    370                 375                 380
Arg Ala Met Tyr Ala Pro Pro Ile Ala Gly Asn Ile Thr Cys Lys Ser
385                 390                 395                 400
Asn Ile Thr Gly Leu Leu Leu Thr Arg Asp Gly Gly Glu Asp Asn Lys
                405                 410                 415
Thr Glu Glu Ile Phe Arg Pro Gly Gly Gly Asn Met Lys Asp Asn Trp
            420                 425                 430
Arg Ser Glu Leu Tyr Lys Tyr Lys Val Val Glu Ile Lys Pro Leu Gly
        435                 440                 445
Ile Ala Pro Thr Lys Cys Lys Arg Arg Asn Val Thr Arg Arg Arg Arg
    450                 455                 460
Arg Arg Ala Val Gly Ile Gly Ala Val Phe Leu Gly Phe Leu Gly Ala
465                 470                 475                 480
Ala Gly Ser Thr Met Gly Ala Ala Ser Asn Thr Leu Thr Val Gln Ala
                485                 490                 495
Arg Gln Leu Leu Ser Gly Ile Val Gln Gln Gln Ser Asn Leu Pro Arg
```

```
              500                 505                 510
Ala Pro Glu Ala Gln Gln His Met Leu Lys Leu Thr Val Trp Gly Ile
            515                 520                 525

Lys Gln Leu Gln Ala Arg Val Leu Ala Ile Glu Arg Tyr Leu Glu Val
            530                 535                 540

Gln Gln Leu Leu Gly Ile Trp Gly Cys Ser Gly Lys Leu Ile Cys Cys
545                 550                 555                 560

Thr Asn Val Pro Trp Asn Ser Ser Trp Ser Asn Lys Ser Gln Thr Asp
                565                 570                 575

Ile Trp Asn Asn Met Thr Trp Met Glu Trp Asp Arg Glu Ile Ser Asn
            580                 585                 590

Tyr Thr Asp Thr Ile Tyr Arg Leu Leu Glu Asp Ser Gln Phe Gln Gln
            595                 600                 605

Glu Ile Asn Glu Lys Asp Leu Leu Ala Asn Asp
            610                 615

<210> SEQ ID NO 25
<211> LENGTH: 628
<212> TYPE: PRT
<213> ORGANISM: Artificial Sequence
<220> FEATURE:
<223> OTHER INFORMATION: variant of repaired and stabilized Du422
      construct (HIV161818)

<400> SEQUENCE: 25

Asn Leu Trp Val Thr Val Tyr Tyr Gly Val Pro Val Trp Lys Glu Ala
1               5                   10                  15

Lys Thr Thr Leu Phe Cys Ala Ser Asp Ala Lys Ala Tyr Asp Lys Glu
            20                  25                  30

Val His Asn Val Trp Ala Thr His Ala Cys Val Pro Thr Asp Pro Asn
        35                  40                  45

Pro Gln Glu Ile Val Leu Glu Asn Val Thr Glu Asn Phe Asn Met Trp
    50                  55                  60

Lys Asn Asp Met Val Asp Gln Met His Glu Asp Ile Ile Ser Leu Trp
65                  70                  75                  80

Asp Gln Ser Leu Lys Pro Cys Val Lys Leu Thr Pro Leu Cys Val Thr
                85                  90                  95

Leu Asn Cys Lys Asn Val Asn Ile Ser Ala Asn Ala Asn Ala Thr Ala
            100                 105                 110

Thr Leu Asn Ser Ser Met Asn Gly Glu Ile Lys Asn Cys Ser Phe Asn
        115                 120                 125

Thr Thr Thr Glu Leu Arg Asp Lys Lys Gln Lys Val Tyr Ala Leu Phe
    130                 135                 140

Tyr Lys Pro Asp Val Val Pro Leu Asn Gly Gly Glu His Asn Glu Thr
145                 150                 155                 160

Gly Glu Tyr Ile Leu Ile Asn Cys Asn Ser Ser Thr Cys Thr Gln Ala
                165                 170                 175

Cys Pro Lys Val Ser Phe Asp Pro Ile Pro Ile His Tyr Cys Ala Pro
            180                 185                 190

Ala Gly Tyr Ala Ile Leu Lys Cys Asn Asn Lys Thr Phe Asn Gly Thr
        195                 200                 205

Gly Pro Cys Asn Asn Val Ser Thr Val Gln Cys Thr His Gly Ile Lys
    210                 215                 220

Pro Val Val Ser Thr Gln Leu Leu Leu Asn Gly Ser Leu Ala Glu Glu
225                 230                 235                 240
```

-continued

Glu Ile Ile Ile Arg Ser Glu Asn Leu Thr Asn Asn Ile Lys Thr Ile
            245                 250                 255

Ile Val His Leu Asn Lys Ser Val Glu Ile Asn Cys Thr Arg Pro Asn
        260                 265                 270

Asn Asn Thr Arg Lys Ser Val Arg Ile Gly Pro Gly Gln Thr Phe Tyr
        275                 280                 285

Ala Thr Gly Glu Ile Ile Gly Asp Ile Arg Glu Ala His Cys Asn Ile
    290                 295                 300

Ser Arg Glu Thr Trp Asn Ser Thr Leu Ile Gln Val Lys Glu Lys Leu
305                 310                 315                 320

Arg Glu His Tyr Asn Lys Thr Ile Lys Phe Glu Pro Ser Ser Gly Gly
                325                 330                 335

Asp Leu Glu Val Thr Thr His Ser Phe Asn Cys Arg Gly Glu Phe Phe
            340                 345                 350

Tyr Cys Asn Thr Thr Lys Leu Phe Asn Glu Thr Lys Leu Phe Asn Glu
        355                 360                 365

Ser Glu Tyr Val Asp Asn Lys Thr Ile Ile Leu Pro Cys Arg Ile Lys
    370                 375                 380

Gln Ile Ile Asn Met Trp Gln Glu Val Gly Arg Cys Met Tyr Ala Pro
385                 390                 395                 400

Pro Ile Glu Gly Asn Ile Thr Cys Lys Ser Asn Ile Thr Gly Leu Leu
                405                 410                 415

Leu Thr Arg Asp Gly Gly Glu Asn Ser Thr Glu Glu Val Phe Arg Pro
            420                 425                 430

Gly Gly Gly Asn Met Lys Asp Asn Trp Arg Ser Glu Leu Tyr Lys Tyr
        435                 440                 445

Lys Val Val Glu Ile Lys Pro Leu Gly Val Ala Pro Thr Lys Cys Lys
    450                 455                 460

Arg Lys Asn Val Thr Arg Arg Arg Arg Ala Val Gly Leu Gly
465                 470                 475                 480

Ala Val Leu Leu Gly Phe Leu Gly Ala Ala Gly Ser Thr Met Gly Ala
                485                 490                 495

Ala Ser Asn Thr Leu Thr Val Gln Ala Arg Gln Leu Leu Ser Gly Ile
            500                 505                 510

Val Gln Gln Gln Ser Asn Leu Pro Arg Ala Pro Glu Ala Gln Gln His
        515                 520                 525

Leu Leu Gln Leu Thr Val Trp Gly Ile Lys Gln Leu Gln Thr Arg Val
    530                 535                 540

Leu Ala Ile Glu Arg Tyr Leu Lys Val Gln Gln Leu Leu Gly Leu Trp
545                 550                 555                 560

Gly Cys Ser Gly Lys Leu Ile Cys Cys Thr Ala Val Pro Trp Asn Ser
                565                 570                 575

Ser Trp Ser Asn Lys Ser Leu Gly Asp Ile Trp Asp Asn Met Thr Trp
            580                 585                 590

Met Gln Trp Asp Arg Glu Ile Ser Asn Tyr Thr Asn Thr Ile Tyr Arg
        595                 600                 605

Leu Leu Glu Asp Ser Gln Phe Gln Gln Glu Lys Asn Glu Lys Asp Leu
    610                 615                 620

Leu Ala Asn Asp
625

<210> SEQ ID NO 26
<211> LENGTH: 628
<212> TYPE: PRT

<213> ORGANISM: Artificial Sequence
<220> FEATURE:
<223> OTHER INFORMATION: repaired and stabilized Du422_SOSIP Env protein (HIV170859)

<400> SEQUENCE: 26

| | | | | | | | | | | | | | | |
|---|---|---|---|---|---|---|---|---|---|---|---|---|---|---|
| Asn | Leu | Trp | Val | Thr | Val | Tyr | Tyr | Gly | Val | Pro | Val | Trp | Lys | Glu | Ala |
| 1 | | | | 5 | | | | | 10 | | | | | 15 | |
| Lys | Thr | Thr | Leu | Phe | Cys | Ala | Ser | Asp | Ala | Lys | Ala | Tyr | Asp | Lys | Glu |
| | | | 20 | | | | | 25 | | | | | 30 | | |
| Val | His | Asn | Val | Trp | Ala | Thr | His | Ala | Cys | Val | Pro | Thr | Asp | Pro | Asn |
| | | 35 | | | | | 40 | | | | | 45 | | | |
| Pro | Gln | Glu | Ile | Val | Leu | Glu | Asn | Val | Thr | Glu | Asn | Phe | Asn | Met | Trp |
| 50 | | | | | 55 | | | | | 60 | | | | | |
| Lys | Asn | Asp | Met | Val | Asp | Gln | Met | His | Glu | Asp | Ile | Ile | Ser | Leu | Trp |
| 65 | | | | 70 | | | | | 75 | | | | | 80 | |
| Asp | Gln | Ser | Leu | Lys | Pro | Cys | Val | Lys | Leu | Thr | Pro | Leu | Cys | Val | Thr |
| | | | 85 | | | | | 90 | | | | | 95 | | |
| Leu | Asn | Cys | Lys | Asn | Val | Asn | Ile | Ser | Ala | Asn | Ala | Asn | Ala | Thr | Ala |
| | | | 100 | | | | | 105 | | | | | 110 | | |
| Thr | Leu | Asn | Ser | Ser | Met | Asn | Gly | Glu | Ile | Lys | Asn | Cys | Ser | Phe | Asn |
| | | | 115 | | | | | 120 | | | | | 125 | | |
| Thr | Thr | Thr | Glu | Leu | Arg | Asp | Lys | Lys | Gln | Lys | Val | Tyr | Ala | Leu | Phe |
| | | 130 | | | | | 135 | | | | | 140 | | | |
| Tyr | Lys | Pro | Asp | Val | Val | Pro | Leu | Asn | Gly | Gly | Glu | His | Asn | Glu | Thr |
| 145 | | | | | 150 | | | | | 155 | | | | | 160 |
| Gly | Glu | Tyr | Ile | Leu | Ile | Asn | Cys | Asn | Ser | Ser | Thr | Ile | Thr | Gln | Ala |
| | | | | 165 | | | | | 170 | | | | | 175 | |
| Cys | Pro | Lys | Val | Ser | Phe | Asp | Pro | Ile | Pro | Ile | His | Tyr | Cys | Ala | Pro |
| | | | 180 | | | | | 185 | | | | | 190 | | |
| Ala | Gly | Tyr | Ala | Ile | Leu | Lys | Cys | Asn | Asn | Lys | Thr | Phe | Asn | Gly | Thr |
| | | | 195 | | | | | 200 | | | | | 205 | | |
| Gly | Pro | Cys | Asn | Asn | Val | Ser | Thr | Val | Gln | Cys | Thr | His | Gly | Ile | Lys |
| | | 210 | | | | | 215 | | | | | 220 | | | |
| Pro | Val | Val | Ser | Thr | Gln | Leu | Leu | Leu | Asn | Gly | Ser | Leu | Ala | Glu | Glu |
| 225 | | | | | 230 | | | | | 235 | | | | | 240 |
| Glu | Ile | Ile | Ile | Arg | Ser | Glu | Asn | Leu | Thr | Asn | Asn | Ile | Lys | Thr | Ile |
| | | | | 245 | | | | | 250 | | | | | 255 | |
| Ile | Val | His | Leu | Asn | Lys | Ser | Val | Glu | Ile | Asn | Cys | Thr | Arg | Pro | Asn |
| | | | 260 | | | | | 265 | | | | | 270 | | |
| Asn | Asn | Thr | Arg | Lys | Ser | Val | Arg | Ile | Gly | Pro | Gly | Gln | Thr | Phe | Tyr |
| | | 275 | | | | | 280 | | | | | 285 | | | |
| Ala | Thr | Gly | Glu | Ile | Ile | Gly | Asp | Ile | Arg | Glu | Ala | His | Cys | Asn | Ile |
| | | 290 | | | | | 295 | | | | | 300 | | | |
| Ser | Arg | Glu | Thr | Trp | Asn | Ser | Thr | Leu | Ile | Gln | Val | Lys | Glu | Lys | Leu |
| 305 | | | | | 310 | | | | | 315 | | | | | 320 |
| Arg | Glu | His | Tyr | Asn | Lys | Thr | Ile | Lys | Phe | Glu | Pro | Ser | Ser | Gly | Gly |
| | | | | 325 | | | | | 330 | | | | | 335 | |
| Asp | Leu | Glu | Val | Thr | Thr | His | Ser | Phe | Asn | Cys | Arg | Gly | Glu | Phe | Phe |
| | | | 340 | | | | | 345 | | | | | 350 | | |
| Tyr | Cys | Asn | Thr | Thr | Lys | Leu | Phe | Asn | Glu | Thr | Lys | Leu | Phe | Asn | Glu |
| | | | 355 | | | | | 360 | | | | | 365 | | |
| Ser | Glu | Tyr | Val | Asp | Asn | Lys | Thr | Ile | Ile | Leu | Pro | Cys | Arg | Ile | Lys |
| | | 370 | | | | | 375 | | | | | 380 | | | |

```
Gln Ile Ile Asn Met Trp Gln Glu Val Gly Arg Ala Met Tyr Ala Pro
385                 390                 395                 400

Pro Ile Glu Gly Asn Ile Thr Cys Lys Ser Asn Ile Thr Gly Leu Leu
            405                 410                 415

Leu Thr Arg Asp Gly Gly Glu Asn Ser Thr Glu Glu Val Phe Arg Pro
        420                 425                 430

Gly Gly Gly Asn Met Lys Asp Asn Trp Arg Ser Glu Leu Tyr Lys Tyr
            435                 440                 445

Lys Val Val Glu Ile Lys Pro Leu Gly Val Ala Pro Thr Lys Cys Lys
450                 455                 460

Arg Lys Val Val Gly Arg Arg Arg Arg Arg Ala Val Gly Leu Gly
465                 470                 475                 480

Ala Val Leu Leu Gly Phe Leu Gly Ala Ala Gly Ser Thr Met Gly Ala
            485                 490                 495

Ala Ser Asn Thr Leu Thr Val Gln Ala Arg Gln Leu Leu Ser Gly Ile
            500                 505                 510

Val Gln Gln Gln Ser Asn Leu Pro Arg Ala Pro Glu Ala Gln Gln His
515                 520                 525

Leu Leu Gln Leu Thr Val Trp Gly Ile Lys Gln Leu Gln Thr Arg Val
530                 535                 540

Leu Ala Ile Glu Arg Tyr Leu Glu Val Gln Gln Leu Leu Gly Leu Trp
545                 550                 555                 560

Gly Cys Ser Gly Lys Leu Ile Cys Cys Thr Ala Val Pro Trp Asn Ser
            565                 570                 575

Ser Trp Ser Asn Lys Ser Leu Gly Asp Ile Trp Asp Asn Met Thr Trp
            580                 585                 590

Met Gln Trp Asp Arg Glu Ile Ser Asn Tyr Thr Asn Thr Ile Tyr Arg
            595                 600                 605

Leu Leu Glu Asp Ser Gln Phe Gln Gln Glu Ile Asn Glu Lys Asp Leu
            610                 615                 620

Leu Ala Leu Asp
625

<210> SEQ ID NO 27
<211> LENGTH: 599
<212> TYPE: PRT
<213> ORGANISM: Artificial Sequence
<220> FEATURE:
<223> OTHER INFORMATION: repaired and stabilized DS_sC4_SOSIP Env
      protein (HIV170686)

<400> SEQUENCE: 27

Met Gly Asn Leu Trp Val Thr Val Tyr Tyr Gly Val Pro Val Trp Lys
1               5                   10                  15

Asp Ala Lys Thr Thr Leu Phe Cys Ala Ser Asp Ala Lys Ala Tyr Glu
            20                  25                  30

Lys Glu Val His Asn Val Trp Ala Thr His Ala Cys Val Pro Thr Asp
        35                  40                  45

Pro Asn Pro Gln Glu Ile Val Leu Gly Asn Val Thr Glu Asn Phe Asn
    50                  55                  60

Met Trp Lys Asn Asp Met Val Asp Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Arg Asn Val Arg Asn Val Glu Met Lys Asn Cys
            100                 105                 110
```

```
Ser Phe Asn Ala Thr Thr Val Val Arg Asp Arg Lys Gln Lys Val His
        115                 120                 125

Ala Leu Phe Tyr Arg Leu Asp Ile Val Pro Leu Asp Glu Asn Asn Ser
    130                 135                 140

Ser Tyr Arg Leu Ile Asn Cys Asn Thr Ser Ala Cys Thr Gln Ile Cys
145                 150                 155                 160

Pro Lys Val Ser Phe Asp Pro Ile Pro Ile His Tyr Cys Ala Pro Ala
                165                 170                 175

Gly Tyr Ala Ile Leu Lys Cys Asn Asn Lys Thr Phe Asn Gly Thr Gly
                180                 185                 190

Pro Cys Asn Asn Val Ser Thr Val Gln Cys Thr His Gly Ile Lys Pro
            195                 200                 205

Val Val Ser Thr Gln Leu Leu Leu Asn Gly Ser Leu Ala Glu Glu Glu
        210                 215                 220

Ile Ile Ile Arg Ser Glu Asn Leu Thr Asn Asn Ala Lys Thr Ile Ile
225                 230                 235                 240

Val His Leu Asn Glu Thr Val Asn Ile Asn Cys Thr Arg Pro Asn Asn
                245                 250                 255

Asn Thr Arg Lys Ser Ile Arg Ile Gly Pro Gly Gln Thr Phe Tyr Ala
            260                 265                 270

Thr Gly Asp Ile Ile Gly Asp Ile Arg Gln Ala His Cys Asn Leu Ser
        275                 280                 285

Arg Asp Gly Trp Asn Lys Thr Leu Gln Gly Val Lys Lys Lys Leu Ala
    290                 295                 300

Glu His Phe Pro Asn Lys Thr Ile Lys Phe Ala Pro His Ser Gly Gly
305                 310                 315                 320

Asp Leu Glu Ile Thr Thr His Ser Phe Asn Cys Arg Gly Glu Phe Phe
                325                 330                 335

Tyr Cys Asn Thr Ser Asn Leu Phe Asn Glu Ser Asn Ile Glu Arg Asn
                340                 345                 350

Asp Ser Ile Ile Thr Leu Pro Cys Arg Ile Lys Gln Ile Ile Asn Met
            355                 360                 365

Trp Gln Glu Val Gly Arg Cys Met Tyr Ala Pro Pro Ile Ala Gly Asn
        370                 375                 380

Ile Thr Cys Arg Ser Asn Ile Thr Gly Leu Leu Leu Thr Arg Asp Gly
385                 390                 395                 400

Gly Ser Asn Asn Asn Asp Thr Glu Thr Phe Arg Pro Gly Gly Gly Asp
                405                 410                 415

Met Arg Asn Asn Trp Arg Ser Glu Leu Tyr Lys Tyr Lys Val Val Glu
                420                 425                 430

Val Lys Pro Leu Gly Val Ala Pro Thr Glu Cys Lys Arg Arg Val Val
        435                 440                 445

Glu Arg Arg Arg Arg Arg Ala Val Gly Ile Gly Ala Val Phe Leu
    450                 455                 460

Gly Ile Leu Gly Ala Ala Gly Ser Thr Met Gly Ala Ala Ser Asn Thr
465                 470                 475                 480

Leu Thr Val Gln Ala Arg Gln Leu Leu Ser Gly Ile Val Gln Gln Gln
                485                 490                 495

Ser Asn Leu Pro Arg Ala Pro Glu Ala Gln Gln His Met Leu Gln Leu
            500                 505                 510

Thr Val Trp Gly Ile Lys Gln Leu Gln Thr Arg Val Leu Ala Ile Glu
        515                 520                 525
```

```
Arg Tyr Leu Glu Val Gln Gln Leu Leu Gly Leu Trp Gly Cys Ser Gly
            530                 535                 540

Lys Leu Ile Cys Cys Thr Ala Val Pro Trp Asn Thr Ser Trp Ser Asn
545                 550                 555                 560

Lys Ser Gln Thr Asp Ile Trp Asp Asn Met Thr Trp Met Gln Trp Asp
            565                 570                 575

Lys Glu Ile Gly Asn Tyr Thr Gly Glu Ile Tyr Arg Leu Leu Glu Glu
            580                 585                 590

Ser Gln Phe Gln Gln Glu Ile
        595

<210> SEQ ID NO 28
<211> LENGTH: 607
<212> TYPE: PRT
<213> ORGANISM: Artificial Sequence
<220> FEATURE:
<223> OTHER INFORMATION: Stabilized ConC_SOSIP.v3 Env protein
      (HIV170654)

<400> SEQUENCE: 28

Asn Leu Trp Val Thr Val Tyr Tyr Gly Val Pro Val Trp Lys Glu Ala
1               5                   10                  15

Lys Thr Thr Leu Phe Cys Ala Ser Asp Ala Lys Ala Tyr Glu Lys Glu
            20                  25                  30

Val His Asn Val Trp Ala Thr His Ala Cys Val Pro Thr Asp Pro Asn
        35                  40                  45

Pro Gln Glu Met Val Leu Glu Asn Val Thr Glu Asn Phe Asn Met Trp
    50                  55                  60

Lys Asn Asp Met Val Asp Gln Met His Glu Asp Ile Ile Ser Leu Trp
65                  70                  75                  80

Asp Gln Ser Leu Lys Pro Cys Val Lys Leu Thr Pro Leu Cys Val Thr
                85                  90                  95

Leu Asn Cys Thr Asn Val Asn Val Thr Glu Met Lys Asn Cys Ser Phe
            100                 105                 110

Asn Thr Thr Thr Glu Ile Arg Asp Lys Lys Gln Lys Glu Tyr Ala Leu
        115                 120                 125

Phe Tyr Arg Leu Asp Ile Val Pro Leu Asn Glu Asn Ser Ser Glu Tyr
    130                 135                 140

Arg Leu Ile Asn Cys Asn Thr Ser Thr Ile Thr Gln Ile Cys Pro Lys
145                 150                 155                 160

Val Ser Phe Asp Pro Ile Pro Ile His Tyr Cys Ala Pro Ala Gly Tyr
                165                 170                 175

Ala Ile Leu Lys Cys Asn Asn Lys Thr Phe Asn Gly Thr Gly Pro Cys
            180                 185                 190

Asn Asn Val Ser Thr Val Gln Cys Thr His Gly Ile Lys Pro Val Val
        195                 200                 205

Ser Thr Gln Leu Leu Leu Asn Gly Ser Leu Ala Glu Glu Glu Ile Ile
    210                 215                 220

Ile Arg Ser Glu Asn Leu Thr Asn Asn Val Lys Thr Ile Ile Val His
225                 230                 235                 240

Leu Asn Glu Ser Val Glu Ile Val Cys Thr Arg Pro Asn Asn Asn Thr
                245                 250                 255

Arg Lys Ser Ile Arg Ile Gly Pro Gly Gln Thr Phe Tyr Ala Thr Gly
            260                 265                 270

Asp Ile Ile Gly Asp Ile Arg Gln Ala His Cys Asn Ile Ser Glu Ala
        275                 280                 285
```

```
Lys Trp Asn Lys Thr Leu Gln Arg Val Lys Lys Leu Lys Glu His
    290                 295                 300
Phe Pro Asn Lys Thr Ile Lys Phe Gln Pro Ser Ser Gly Gly Asp Leu
305                 310                 315                 320
Glu Ile Thr Thr His Ser Phe Asn Cys Arg Gly Glu Phe Phe Tyr Cys
                325                 330                 335
Asn Thr Ser Lys Leu Phe Asn Ser Thr Tyr Asn Asn Thr Thr Ser Asn
                340                 345                 350
Ser Thr Ile Thr Leu Pro Cys Arg Ile Lys Gln Ile Ile Asn Met Trp
                355                 360                 365
Gln Glu Val Gly Arg Ala Met Tyr Ala Pro Pro Ile Ala Gly Asn Ile
    370                 375                 380
Thr Cys Lys Ser Asn Ile Thr Gly Leu Leu Leu Thr Arg Asp Gly Gly
385                 390                 395                 400
Asn Asn Asn Asn Asn Thr Glu Thr Phe Arg Pro Gly Gly Gly Asp Met
                405                 410                 415
Arg Asp Asn Trp Arg Ser Glu Leu Tyr Lys Tyr Lys Val Val Glu Ile
                420                 425                 430
Lys Pro Leu Gly Ile Ala Pro Thr Lys Cys Lys Arg Arg Val Val Glu
    435                 440                 445
Arg Arg Arg Arg Arg Ala Val Gly Ile Gly Ala Val Phe Leu Gly
450                 455                 460
Phe Leu Gly Ala Ala Gly Ser Thr Met Gly Ala Ala Ser Asn Thr Leu
465                 470                 475                 480
Thr Val Gln Ala Arg Gln Leu Leu Ser Gly Ile Val Gln Gln Ser
                485                 490                 495
Asn Leu Leu Arg Ala Pro Glu Ala Gln Gln His Met Leu Gln Leu Thr
                500                 505                 510
Val Trp Gly Phe Lys Gln Leu Gln Ala Arg Val Leu Ala Ile Glu Arg
    515                 520                 525
Tyr Leu Glu Val Gln Gln Leu Leu Gly Ile Trp Gly Cys Ser Gly Lys
    530                 535                 540
Leu Ile Cys Cys Thr Ala Val Pro Trp Asn Ser Ser Trp Ser Asn Lys
545                 550                 555                 560
Ser Gln Glu Asp Ile Trp Asp Asn Met Thr Trp Met Gln Trp Asp Arg
                565                 570                 575
Glu Ile Ser Asn Tyr Thr Asp Thr Ile Tyr Arg Leu Leu Glu Glu Ser
                580                 585                 590
Gln Phe Gln Gln Glu Ile Asn Glu Lys Asp Leu Leu Ala Leu Asp
    595                 600                 605

<210> SEQ ID NO 29
<211> LENGTH: 634
<212> TYPE: PRT
<213> ORGANISM: Artificial Sequence
<220> FEATURE:
<223> OTHER INFORMATION: Stabilized BG505_SOSIP.v2 Env protein
      (HIV171814)

<400> SEQUENCE: 29

Ala Glu Asn Leu Trp Val Thr Val Tyr Tyr Gly Val Pro Val Trp Lys
1               5                   10                  15
Asp Ala Glu Thr Thr Leu Phe Cys Ala Ser Asp Ala Lys Ala Tyr Glu
                20                  25                  30
Thr Glu Lys His Asn Val Trp Ala Thr His Ala Cys Val Pro Thr Asp
```

```
                35                  40                  45
Pro Asn Pro Gln Glu Ile His Leu Glu Asn Val Thr Glu Glu Phe Asn
 50                  55                  60
Met Trp Lys Asn Asn Met Val Glu Gln Met His Thr Asp Ile Ile Ser
 65                  70                  75                  80
Leu Trp Asp Gln Ser Leu Lys Pro Cys Val Lys Leu Thr Pro Leu Cys
                 85                  90                  95
Val Thr Leu Gln Cys Thr Asn Val Thr Asn Asn Ile Thr Asp Asp Met
                100                 105                 110
Arg Gly Glu Leu Lys Asn Cys Ser Phe Asn Met Thr Thr Glu Leu Arg
                115                 120                 125
Asp Lys Lys Gln Lys Val Tyr Ser Leu Phe Tyr Arg Leu Asp Val Val
130                 135                 140
Gln Ile Asn Glu Asn Gln Gly Asn Arg Ser Asn Asn Ser Asn Lys Glu
145                 150                 155                 160
Tyr Arg Leu Ile Asn Cys Asn Thr Ser Ala Cys Thr Gln Ala Cys Pro
                165                 170                 175
Lys Val Ser Phe Glu Pro Ile Pro Ile His Tyr Cys Ala Pro Ala Gly
                180                 185                 190
Phe Ala Ile Leu Lys Cys Lys Asp Lys Lys Phe Asn Gly Thr Gly Pro
                195                 200                 205
Cys Pro Ser Val Ser Thr Val Gln Cys Thr His Gly Ile Lys Pro Val
210                 215                 220
Val Ser Thr Gln Leu Leu Leu Asn Gly Ser Leu Ala Glu Glu Glu Val
225                 230                 235                 240
Met Ile Arg Ser Glu Asn Ile Thr Asn Asn Ala Lys Asn Ile Leu Val
                245                 250                 255
Gln Phe Asn Thr Pro Val Gln Ile Asn Cys Thr Arg Pro Asn Asn Asn
                260                 265                 270
Thr Arg Lys Ser Ile Arg Ile Gly Pro Gly Gln Ala Phe Tyr Ala Thr
                275                 280                 285
Gly Asp Ile Ile Gly Asp Ile Arg Gln Ala His Cys Asn Val Ser Lys
290                 295                 300
Ala Thr Trp Asn Glu Thr Leu Gly Lys Val Val Lys Gln Leu Arg Lys
305                 310                 315                 320
His Phe Gly Asn Asn Thr Ile Ile Arg Phe Ala Asn Ser Ser Gly Gly
                325                 330                 335
Asp Leu Glu Val Thr Thr His Ser Phe Asn Cys Gly Gly Glu Phe Phe
                340                 345                 350
Tyr Cys Asn Thr Ser Gly Leu Phe Asn Ser Thr Trp Ile Ser Asn Thr
                355                 360                 365
Ser Val Gln Gly Ser Asn Ser Thr Gly Ser Asn Asp Ser Ile Thr Leu
                370                 375                 380
Pro Cys Arg Ile Lys Gln Ile Ile Asn Met Trp Gln Arg Ile Gly Gln
385                 390                 395                 400
Cys Met Tyr Ala Pro Pro Ile Gln Gly Val Ile Arg Cys Val Ser Asn
                405                 410                 415
Ile Thr Gly Leu Ile Leu Thr Arg Asp Gly Gly Ser Thr Asn Ser Thr
                420                 425                 430
Thr Glu Thr Phe Arg Pro Gly Gly Gly Asp Met Arg Asp Asn Trp Arg
                435                 440                 445
Ser Glu Leu Tyr Lys Tyr Lys Val Val Lys Ile Glu Pro Leu Gly Val
450                 455                 460
```

Ala Pro Thr Arg Cys Lys Arg Arg Val Val Gly Arg Arg Arg Arg
465                 470                 475                 480

Arg Ala Val Gly Ile Gly Ala Val Phe Leu Gly Phe Leu Gly Ala Ala
        485                 490                 495

Gly Ser Thr Met Gly Ala Ala Ser Asn Thr Leu Thr Val Gln Ala Arg
            500                 505                 510

Asn Leu Leu Ser Gly Ile Val Gln Gln Gln Ser Asn Leu Pro Arg Ala
        515                 520                 525

Pro Glu Ala Gln Gln His Leu Leu Lys Leu Thr Val Trp Gly Ile Lys
530                 535                 540

Gln Leu Gln Ala Arg Val Leu Ala Val Glu Arg Tyr Leu Glu Val Gln
545                 550                 555                 560

Gln Leu Leu Gly Ile Trp Gly Cys Ser Gly Lys Leu Ile Cys Cys Thr
            565                 570                 575

Asn Val Pro Trp Asn Ser Ser Trp Ser Asn Arg Asn Leu Ser Glu Ile
        580                 585                 590

Trp Asp Asn Met Thr Trp Leu Gln Trp Asp Lys Glu Ile Ser Asn Tyr
        595                 600                 605

Thr Gln Ile Ile Tyr Gly Leu Leu Glu Glu Ser Gln Phe Gln Gln Glu
        610                 615                 620

Ile Asn Glu Val Asp Leu Leu Ala Leu Asp
625                 630

<210> SEQ ID NO 30
<211> LENGTH: 619
<212> TYPE: PRT
<213> ORGANISM: Artificial Sequence
<220> FEATURE:
<223> OTHER INFORMATION: Repaired and stabilized C97ZA_SOSIP.v2 Env
      protein (HIV171810)

<400> SEQUENCE: 30

Asn Leu Trp Val Thr Val Tyr Tyr Gly Val Pro Val Trp Lys Asp Ala
1               5                   10                  15

Lys Thr Thr Leu Phe Cys Ala Ser Asp Ala Lys Ala Tyr Asp Arg Glu
            20                  25                  30

Val His Asn Val Trp Ala Thr His Ala Cys Val Pro Thr Asp Pro Asn
        35                  40                  45

Pro Gln Glu Ile Val Leu Glu Asn Val Thr Glu Asn Phe Asn Met Trp
    50                  55                  60

Lys Asn Asp Met Val Asp Gln Met His Glu Asp Ile Ile Ser Leu Trp
65                  70                  75                  80

Asp Gln Ser Leu Lys Pro Cys Val Lys Leu Thr Pro Leu Cys Val Thr
                85                  90                  95

Leu His Cys Thr Asn Ala Thr Phe Lys Asn Asn Val Thr Asn Asp Met
            100                 105                 110

Asn Lys Glu Ile Arg Asn Cys Ser Phe Asn Thr Thr Thr Glu Ile Arg
        115                 120                 125

Asp Lys Lys Gln Lys Val Tyr Ala Leu Phe Tyr Arg Leu Asp Ile Val
    130                 135                 140

Gln Leu Lys Glu Asn Arg Asn Asn Ser Asn Asn Ser Glu Tyr Arg Leu
145                 150                 155                 160

Ile Asn Cys Asn Thr Ser Thr Cys Thr Gln Ile Cys Pro Lys Val Thr
                165                 170                 175

Phe Asp Pro Ile Pro Ile His Tyr Cys Ala Pro Ala Gly Tyr Ala Ile

-continued

```
             180                 185                 190
Leu Lys Cys Asn Asn Lys Thr Phe Asn Gly Thr Gly Pro Cys Asn Asn
             195                 200                 205

Val Ser Thr Val Gln Cys Thr His Gly Ile Lys Pro Val Val Ser Thr
             210                 215                 220

Gln Leu Leu Leu Asn Gly Ser Leu Ala Glu Lys Glu Ile Ile Ile Arg
225                 230                 235                 240

Ser Glu Asn Leu Thr Asp Asn Val Lys Thr Ile Val His Leu Asn
             245                 250                 255

Lys Ser Val Glu Ile Asn Cys Thr Arg Pro Asn Asn Asn Thr Arg Lys
             260                 265                 270

Ser Ile Arg Ile Gly Pro Gly Gln Thr Phe Tyr Ala Thr Gly Asp Ile
             275                 280                 285

Ile Gly Asp Ile Arg Gln Ala Tyr Cys Asn Ile Ser Gly Ser Lys Trp
             290                 295                 300

Asn Glu Thr Leu Lys Arg Val Lys Glu Lys Leu Arg Glu His Phe Asn
305                 310                 315                 320

Asn Asn Lys Thr Ile Lys Phe Ala Pro Ser Ser Gly Gly Asp Leu Glu
             325                 330                 335

Ile Thr Thr His Ser Phe Asn Cys Arg Gly Glu Phe Phe Tyr Cys Asn
             340                 345                 350

Thr Thr Arg Leu Phe Asn Asn Asn Ala Thr Glu Asn Glu Thr Ile Thr
             355                 360                 365

Leu Pro Cys Arg Ile Lys Gln Ile Ile Asn Met Trp Gln Glu Val Gly
             370                 375                 380

Arg Cys Met Tyr Ala Pro Pro Ile Ala Gly Asn Ile Thr Cys Lys Ser
385                 390                 395                 400

Asn Ile Thr Gly Leu Leu Leu Thr Arg Asp Gly Gly Glu Asp Asn Lys
             405                 410                 415

Thr Glu Glu Ile Phe Arg Pro Gly Gly Gly Asn Met Lys Asp Asn Trp
             420                 425                 430

Arg Ser Glu Leu Tyr Lys Tyr Lys Val Val Glu Ile Lys Pro Leu Gly
             435                 440                 445

Ile Ala Pro Thr Lys Cys Lys Arg Arg Asn Val Thr Arg Arg Arg Arg
             450                 455                 460

Arg Arg Ala Val Gly Ile Gly Ala Val Phe Leu Gly Phe Leu Gly Ala
465                 470                 475                 480

Ala Gly Ser Thr Met Gly Ala Ala Ser Asn Thr Leu Thr Val Gln Ala
             485                 490                 495

Arg Gln Leu Leu Ser Gly Ile Val Gln Gln Ser Asn Leu Pro Arg
             500                 505                 510

Ala Pro Glu Ala Gln Gln His Met Leu Lys Leu Thr Val Trp Gly Ile
             515                 520                 525

Lys Gln Leu Gln Ala Arg Val Leu Ala Ile Glu Arg Tyr Leu Glu Val
             530                 535                 540

Gln Gln Leu Leu Gly Ile Trp Gly Cys Ser Gly Lys Leu Ile Cys Cys
545                 550                 555                 560

Thr Asn Val Pro Trp Asn Ser Ser Trp Ser Asn Lys Ser Gln Thr Asp
             565                 570                 575

Ile Trp Asn Asn Met Thr Trp Met Glu Trp Asp Arg Glu Ile Ser Asn
             580                 585                 590

Tyr Thr Asp Thr Ile Tyr Arg Leu Leu Glu Asp Ser Gln Phe Gln Gln
             595                 600                 605
```

```
Glu Ile Asn Glu Val Asp Leu Leu Ala Asn Asp
        610             615

<210> SEQ ID NO 31
<211> LENGTH: 628
<212> TYPE: PRT
<213> ORGANISM: Artificial Sequence
<220> FEATURE:
<223> OTHER INFORMATION: Repaired and stabilized Du422_SOSIP.v1 Env
      protein (HIV171812)

<400> SEQUENCE: 31

Asn Leu Trp Val Thr Val Tyr Tyr Gly Val Pro Val Trp Lys Glu Ala
1               5                   10                  15

Lys Thr Thr Leu Phe Cys Ala Ser Asp Ala Lys Ala Tyr Asp Lys Glu
            20                  25                  30

Val His Asn Val Trp Ala Thr His Ala Cys Val Pro Thr Asp Pro Asn
        35                  40                  45

Pro Gln Glu Ile Val Leu Glu Asn Val Thr Glu Asn Phe Asn Met Trp
    50                  55                  60

Lys Asn Asp Met Val Asp Gln Met His Glu Asp Ile Ile Ser Leu Trp
65                  70                  75                  80

Asp Gln Ser Leu Lys Pro Cys Val Lys Leu Thr Pro Leu Cys Val Thr
                85                  90                  95

Leu Asn Cys Lys Asn Val Asn Ile Ser Ala Asn Ala Asn Ala Thr Ala
            100                 105                 110

Thr Leu Asn Ser Ser Met Asn Gly Glu Ile Lys Asn Cys Ser Phe Asn
        115                 120                 125

Thr Thr Thr Glu Leu Arg Asp Lys Lys Gln Lys Val Tyr Ala Leu Phe
    130                 135                 140

Tyr Lys Pro Asp Val Val Pro Leu Asn Gly Gly Glu His Asn Glu Thr
145                 150                 155                 160

Gly Glu Tyr Ile Leu Ile Asn Cys Asn Ser Ser Thr Cys Thr Gln Ala
                165                 170                 175

Cys Pro Lys Val Ser Phe Asp Pro Ile Pro Ile His Tyr Cys Ala Pro
            180                 185                 190

Ala Gly Tyr Ala Ile Leu Lys Cys Asn Asn Lys Thr Phe Asn Gly Thr
        195                 200                 205

Gly Pro Cys Asn Asn Val Ser Thr Val Gln Cys Thr His Gly Ile Lys
    210                 215                 220

Pro Val Val Ser Thr Gln Leu Leu Leu Asn Gly Ser Leu Ala Glu Glu
225                 230                 235                 240

Glu Ile Ile Ile Arg Ser Glu Asn Leu Thr Asn Asn Ile Lys Thr Ile
                245                 250                 255

Ile Val His Leu Asn Lys Ser Val Glu Ile Asn Cys Thr Arg Pro Asn
            260                 265                 270

Asn Asn Thr Arg Lys Ser Val Arg Ile Gly Pro Gly Gln Thr Phe Tyr
        275                 280                 285

Ala Thr Gly Glu Ile Ile Gly Asp Ile Arg Glu Ala His Cys Asn Ile
    290                 295                 300

Ser Arg Glu Thr Trp Asn Ser Thr Leu Ile Gln Val Lys Glu Lys Leu
305                 310                 315                 320

Arg Glu His Tyr Asn Lys Thr Ile Lys Phe Glu Pro Ser Ser Gly Gly
                325                 330                 335

Asp Leu Glu Val Thr Thr His Ser Phe Asn Cys Arg Gly Glu Phe Phe
```

```
                340               345               350
Tyr Cys Asn Thr Thr Lys Leu Phe Asn Glu Thr Lys Leu Phe Asn Glu
                355               360               365
Ser Glu Tyr Val Asp Asn Lys Thr Ile Ile Leu Pro Cys Arg Ile Lys
            370               375               380
Gln Ile Ile Asn Met Trp Gln Glu Val Gly Arg Cys Met Tyr Ala Pro
385               390               395               400
Pro Ile Glu Gly Asn Ile Thr Cys Lys Ser Asn Ile Thr Gly Leu Leu
                405               410               415
Leu Thr Arg Asp Gly Gly Glu Asn Ser Thr Glu Glu Val Phe Arg Pro
            420               425               430
Gly Gly Gly Asn Met Lys Asp Asn Trp Arg Ser Glu Leu Tyr Lys Tyr
            435               440               445
Lys Val Val Glu Ile Lys Pro Leu Gly Val Ala Pro Thr Lys Cys Lys
        450               455               460
Arg Lys Val Val Gly Arg Arg Arg Arg Arg Ala Val Gly Leu Gly
465               470               475               480
Ala Val Leu Leu Gly Phe Leu Gly Ala Ala Gly Ser Thr Met Gly Ala
                485               490               495
Ala Ser Asn Thr Leu Thr Val Gln Ala Arg Gln Leu Leu Ser Gly Ile
            500               505               510
Val Gln Gln Gln Ser Asn Leu Pro Arg Ala Pro Glu Ala Gln Gln His
        515               520               525
Leu Leu Gln Leu Thr Val Trp Gly Ile Lys Gln Leu Gln Thr Arg Val
    530               535               540
Leu Ala Ile Glu Arg Tyr Leu Glu Val Gln Gln Leu Leu Gly Leu Trp
545               550               555               560
Gly Cys Ser Gly Lys Leu Ile Cys Cys Thr Ala Val Pro Trp Asn Ser
                565               570               575
Ser Trp Ser Asn Lys Ser Leu Gly Asp Ile Trp Asp Asn Met Thr Trp
            580               585               590
Met Gln Trp Asp Arg Glu Ile Ser Asn Tyr Thr Asn Thr Ile Tyr Arg
            595               600               605
Leu Leu Glu Asp Ser Gln Phe Gln Gln Glu Ile Asn Glu Val Asp Leu
        610               615               620
Leu Ala Leu Asp
625

<210> SEQ ID NO 32
<211> LENGTH: 599
<212> TYPE: PRT
<213> ORGANISM: Artificial Sequence
<220> FEATURE:
<223> OTHER INFORMATION: Stabilized and repaired sC4_SOSIP.v4 Env
      protein

<400> SEQUENCE: 32

Met Gly Asn Leu Trp Val Thr Val Tyr Tyr Gly Val Pro Val Trp Lys
1               5                   10                  15
Asp Ala Lys Thr Thr Leu Phe Cys Ala Ser Asp Ala Lys Ala Tyr Glu
            20                  25                  30
Lys Glu Val His Asn Val Trp Ala Thr His Ala Cys Val Pro Thr Asp
        35                  40                  45
Pro Asn Pro Gln Glu Ile Val Leu Gly Asn Val Thr Glu Asn Phe Asn
    50                  55                  60
```

-continued

```
Met Trp Lys Asn Asp Met Val Asp Gln Met His Glu Asp Ile Ile Ser
 65                  70                  75                  80

Leu Trp Asp Gln Ser Leu Lys Pro Cys Val Lys Leu Thr Pro Leu Cys
                 85                  90                  95

Val Thr Leu Asn Cys Arg Asn Val Arg Asn Val Glu Met Lys Asn Cys
            100                 105                 110

Ser Phe Asn Ala Thr Thr Val Arg Asp Arg Lys Gln Lys Val His
        115                 120                 125

Ala Leu Phe Tyr Arg Leu Asp Ile Val Pro Leu Asp Glu Asn Asn Ser
    130                 135                 140

Ser Tyr Arg Leu Ile Asn Cys Asn Thr Ser Ala Cys Thr Gln Ile Cys
145                 150                 155                 160

Pro Lys Val Ser Phe Asp Pro Ile Pro Ile His Tyr Cys Ala Pro Ala
                165                 170                 175

Gly Tyr Ala Ile Leu Lys Cys Asn Asn Lys Thr Phe Asn Gly Thr Gly
            180                 185                 190

Pro Cys Asn Asn Val Ser Thr Val Gln Cys Thr His Gly Ile Lys Pro
        195                 200                 205

Val Val Ser Thr Gln Leu Leu Leu Asn Gly Ser Leu Ala Glu Glu Glu
    210                 215                 220

Ile Ile Ile Arg Ser Glu Asn Leu Thr Asn Asn Ala Lys Thr Ile Ile
225                 230                 235                 240

Val His Leu Asn Glu Thr Val Asn Ile Val Cys Thr Arg Pro Asn Asn
                245                 250                 255

Asn Thr Arg Lys Ser Ile Arg Ile Gly Pro Gly Gln Thr Phe Tyr Ala
            260                 265                 270

Thr Gly Asp Ile Ile Gly Asp Ile Arg Gln Ala His Cys Asn Leu Ser
        275                 280                 285

Arg Asp Gly Trp Asn Lys Thr Leu Gln Gly Val Lys Lys Lys Leu Ala
290                 295                 300

Glu His Phe Pro Asn Lys Thr Ile Lys Phe Ala Pro His Ser Gly Gly
305                 310                 315                 320

Asp Leu Glu Ile Thr Thr His Ser Phe Asn Cys Arg Gly Glu Phe Phe
                325                 330                 335

Tyr Cys Asn Thr Ser Asn Leu Phe Asn Glu Ser Asn Ile Glu Arg Asn
            340                 345                 350

Asp Ser Ile Ile Thr Leu Pro Cys Arg Ile Lys Gln Ile Ile Asn Met
        355                 360                 365

Trp Gln Glu Val Gly Arg Cys Met Tyr Ala Pro Pro Ile Ala Gly Asn
370                 375                 380

Ile Thr Cys Arg Ser Asn Ile Thr Gly Leu Leu Leu Thr Arg Asp Gly
385                 390                 395                 400

Gly Ser Asn Asn Asn Asp Thr Glu Thr Phe Arg Pro Gly Gly Gly Asp
                405                 410                 415

Met Arg Asn Asn Trp Arg Ser Glu Leu Tyr Lys Tyr Lys Val Val Glu
            420                 425                 430

Val Lys Pro Leu Gly Val Ala Pro Thr Glu Cys Lys Arg Arg Asn Val
        435                 440                 445

Thr Arg Arg Arg Arg Arg Ala Val Gly Ile Gly Ala Val Phe Leu
    450                 455                 460

Gly Ile Leu Gly Ala Ala Gly Ser Thr Met Gly Ala Ala Ser Asn Thr
465                 470                 475                 480

Leu Thr Val Gln Ala Arg Gln Leu Leu Ser Gly Ile Val Gln Gln Gln
```

```
                     485                 490                 495
Ser Asn Leu Pro Arg Ala Pro Glu Ala Gln Gln His Met Leu Gln Leu
                500                 505                 510

Thr Val Trp Gly Ile Lys Gln Leu Gln Thr Arg Val Leu Ala Ile Glu
            515                 520                 525

Arg Tyr Leu Glu Asp Gln Gln Leu Leu Gly Leu Trp Gly Cys Ser Gly
        530                 535                 540

Lys Leu Ile Cys Cys Thr Ala Val Pro Trp Asn Thr Ser Trp Ser Asn
545                 550                 555                 560

Lys Ser Gln Thr Asp Ile Trp Asp Asn Met Thr Trp Met Gln Trp Asp
                565                 570                 575

Lys Glu Ile Gly Asn Tyr Thr Gly Glu Ile Tyr Arg Leu Leu Glu Glu
                580                 585                 590

Ser Gln Phe Gln Gln Glu Ile
        595

<210> SEQ ID NO 33
<211> LENGTH: 29
<212> TYPE: PRT
<213> ORGANISM: Artificial Sequence
<220> FEATURE:
<223> OTHER INFORMATION: signal sequence

<400> SEQUENCE: 33

Met Arg Val Arg Gly Met Leu Arg Asn Trp Gln Gln Trp Trp Ile Trp
1               5                   10                  15

Ser Ser Leu Gly Phe Trp Met Leu Met Ile Tyr Ser Val
            20                  25

<210> SEQ ID NO 34
<211> LENGTH: 29
<212> TYPE: PRT
<213> ORGANISM: Artificial Sequence
<220> FEATURE:
<223> OTHER INFORMATION: signal sequence

<400> SEQUENCE: 34

Met Arg Val Met Gly Ile Gln Arg Asn Cys Gln His Leu Phe Arg Trp
1               5                   10                  15

Gly Thr Met Ile Leu Gly Met Ile Ile Ile Cys Ser Ala
            20                  25
```